US011459580B2

(12) United States Patent
Christensen et al.

(10) Patent No.: US 11,459,580 B2
(45) Date of Patent: Oct. 4, 2022

(54) NUCLEOTIDE SEQUENCES AND POLYPEPTIDES ENCODED THEREBY USEFUL FOR MODIFYING PLANT CHARACTERISTICS IN RESPONSE TO COLD

(71) Applicant: Ceres, Inc., Thousands Oaks, CA (US)

(72) Inventors: Cory Christensen, Simi Valley, CA (US); Jack Okamuro, Oak Park, CA (US); Shing Kwok, Woodland Hills, CA (US); Roger Pennell, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 103 days.

(21) Appl. No.: 16/855,674

(22) Filed: Apr. 22, 2020

(65) Prior Publication Data

US 2020/0255853 A1    Aug. 13, 2020

Related U.S. Application Data

(60) Division of application No. 16/275,659, filed on Feb. 14, 2019, now Pat. No. 10,696,979, which is a division of application No. 15/362,633, filed on Nov. 28, 2016, now Pat. No. 10,240,166, which is a division of application No. 11/779,266, filed on Jul. 17, 2007, now abandoned, which is a continuation-in-part of application No. 11/778,060, filed on Jul. 15, 2007, now abandoned, which is a continuation-in-part of application No. 11/248,547, filed on Oct. 12, 2005, now Pat. No. 7,244,879.

(51) Int. Cl.
| | | |
|---|---|---|
| *C12N 15/82* | (2006.01) | |
| *C07K 14/415* | (2006.01) | |
| *A01H 1/02* | (2006.01) | |
| *C12Q 1/6895* | (2018.01) | |

(52) U.S. Cl.
CPC .......... *C12N 15/8273* (2013.01); *A01H 1/02* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 5,990,387 A | 11/1999 | Tomes et al. |
| 7,244,879 B2 | 7/2007 | Christensen et al. |
| 10,240,166 B2 | 3/2019 | Christensen et al. |
| 10,508,284 B2 | 12/2019 | Christensen et al. |
| 10,696,979 B2 | 6/2020 | Christensen et al. |
| 11,021,714 B2 | 6/2021 | Christensen et al. |
| 11,034,973 B2 | 6/2021 | Christensen et al. |
| 2004/0031072 A1 | 2/2004 | La Rosa et al. |
| 2006/0107345 A1 | 5/2006 | Alexandrov et al. |
| 2006/0150283 A1 | 7/2006 | Alexandrov et al. |
| 2009/0094717 A1 | 4/2009 | Troukhan et al. |
| 2009/0241208 A1 | 9/2009 | Christensen et al. |
| 2009/0265275 A1 | 10/2009 | Alexandrov et al. |
| 2009/0265815 A1 | 10/2009 | Alexandrov et al. |
| 2010/0083407 A1 | 4/2010 | Feldmann et al. |
| 2015/0259699 A1 | 9/2015 | Nadzan et al. |
| 2016/0369294 A9* | 12/2016 | Nadzan ............. C12N 15/8241 |
| 2018/0223303 A1 | 8/2018 | Alexandrov et al. |
| 2019/0276836 A1 | 9/2019 | Christensen et al. |
| 2020/0109412 A1 | 4/2020 | Christensen et al. |
| 2020/0131525 A1 | 4/2020 | Christensen et al. |
| 2021/0324400 A1 | 10/2021 | Christensen et al. |
| 2021/0388371 A1 | 12/2021 | Christensen et al. |

FOREIGN PATENT DOCUMENTS

| EP | 1033405 A2 * | 9/2000 | ........... C07K 14/415 |
| ER | 1033405 | 9/2000 | |
| WO | WO 9902687 | 1/1999 | |
| WO | WO-9902687 A1 * | 1/1999 | ........... C07K 14/415 |
| WO | WO 2004035798 | 4/2004 | |
| WO | WO-2004035798 A2 * | 4/2004 | ......... C12N 15/8261 |

OTHER PUBLICATIONS

Wells (Biochemistry 29:8509-8517, 1990).*
Guo et al. (PNAS, 101: 9205-9210, 2004).*
Ngo et al., (The Protein Folding Problem and Tertiary Structure Prediction, K. Merz., and S. Le Grand (eds.) pp. 492-495, 1994).*
Thornton et al. (Nature structural Biology, structural genomics supplement, Nov. 2000).*
Keskin et al. (Protein Science, 13:1043-1055, 2004).*
U.S. Appl. No. 16/719,390, filed Dec. 18, 2019, Christensen et al.
Kim et al., "Molecular cloning of low temperature-inducible ribosomal proteins from soybean," *Journal of Experimental Botany* 55:1153-1155, 2004.
Lu et al., "Arabidopsis Mutants Deficient in Diacylglycerol Acyltransferase Display Increased Sensitivity to Abscisic Acid, Sugards, and Osmotic Stress during Germination and Seedling Development," *Plant Physiology* 129:1352-1358, 2002.
Ngo et al., "Computational Complexity, Protein Structure Prediction, and the Levinthal Pradox," *The Protein Folding Problem and Tertiary Structure Prediction*, K. Merz and S. Le Grand (eds.), pp. 492-495, 1994.
Guo et al., "Protein tolerance to random amino acid change," *PNAS* 101:9205-9210, 2004.
GenBank Accession No. AY117196, dated Sep. 18, 2002.
Keskin et al., "A new, structurally nonredundant, diverse data set of protein-protein interfaces and its implications," *Protein Science* 13:1043-1055, 2004.

(Continued)

*Primary Examiner* — Vinod Kumar
(74) *Attorney, Agent, or Firm* — Dentons US LLP

(57) ABSTRACT

Methods and materials for modulating cold tolerance levels in plants are disclosed. For example, nucleic acids encoding cold tolerance-modulating polypeptides are disclosed as well as methods for using such nucleic acids to transform plant cells. Also disclosed are plants having increased levels of cold tolerance and plant products produced from plants having increased cold tolerance levels.

7 Claims, 8 Drawing Sheets

Specification includes a Sequence Listing.

(56) References Cited

OTHER PUBLICATIONS

Thornton et al., "From structure to function: Approaches and limitations," *Nature Structural Biology, Structural Gemonics Supplement*, Nov. 2000.
Wells, "Additivity of Mutational Effects in Proteins," *Biochemistry* 29:8509-8517, 1990.
USPTO: Notice of Allowance and Fee(s) Due regarding U.S. Appl. No. 16/275,629, dated Aug. 2, 2019.
U.S. Appl. No. 17/222,626, filed Apr. 5, 2021, Christensen et al.
U.S. Appl. No. 17/314,977, filed May 7, 2021, Christensen et al.
Didierjean et al., Heavy-metal-responsive genes in maize: identification and comparison of their expression upon various forms of abiotic stress, Planta 199:1-8, 1996.
GenBank Accession No. AK118678.1, dated Feb. 14, 2004.

\* cited by examiner

|  |  |  |  |  |  |  |
|---|---|---|---|---|---|---|
| SEQ-ID-NO-17-CLONE-839727 | MSAAE---GA | VVFSEEKEAL | VLKSWAIMKK | DSANLGLRFF | LKIFEIAPSA | 47 |
| SEQ-ID-NO-16-CLONE-1554560 | MALAEADDGA | VVFGEEQEAL | VLKSWAVMKK | DAANLGLRFF | LKVFEIAPSA | 50 |
| SEQ-ID-NO-60-CLONE-1802327 | MALAE---GN | VIFGEEQEAL | VLKSWALMKK | DSADLGLRFF | LKIFEIAPSA | 47 |
| SEQ-ID-NO-9-CLONE-30469-FL | -MESE---GK | IVFTEEQEAL | VVKSWSVMKK | NSAELGLKLF | LKIFEIAPTA | 46 |
| SEQ-ID-NO-10-GI-30909306 | -MESE---GK | LVFTEEQEAL | VVKSWSVMKK | NSADLGLKFF | LKIFEIAPTA | 46 |
| SEQ-ID-NO-13-CLONE-546001 | -MTTTLERG- | --FSEEQEAL | VVKSWNVMKK | NSGELGLKFF | LKIFEIAPSA | 46 |
| SEQ-ID-NO-70-CLONE-1916866 | MATYE---GK | -VFTEEQEAL | VVKSWTVMKK | NAAELGLKFF | LKIFEIAPSA | 46 |

|  |  |  |  |  |  |  |
|---|---|---|---|---|---|---|
| SEQ-ID-NO-17-CLONE-839727 | RQMFPFLRDS | DVPLETNPKL | KTHAVSVFVM | TCEAAAQLRK | AGKITVRETT | 97 |
| SEQ-ID-NO-16-CLONE-1554560 | KQMFSFLRDS | DVPLEKNPKL | KTHAMSVFVM | TCEAAAQLRK | AGKVTVRETT | 100 |
| SEQ-ID-NO-60-CLONE-1802327 | KQMFSFLRDS | DVPLEKNPKL | KNHAMSVFVM | TCEAAAQLRK | AGKVTVRETT | 97 |
| SEQ-ID-NO-9-CLONE-30469-FL | KKMFSFLRDS | PIPAEQNPKL | KPHAMSVFVM | CCESAVQLRK | TGKVTVRETT | 96 |
| SEQ-ID-NO-10-GI-30909306 | KKLFSFLRDS | PIPAEQNPKL | KPHAVSVFVM | CCESAAQLRK | TGKVTVKETT | 96 |
| SEQ-ID-NO-13-CLONE-546001 | QKLFSFLRDS | TVPLEQNPKL | KPHAVSVFVM | TCDSAVQLRK | AGKVTVRESN | 96 |
| SEQ-ID-NO-70-CLONE-1916866 | KKLFSFLRDS | NVPLEQNTKL | KPHAMSVFVM | TCESAVQLRK | AGKVTVRESN | 96 |

|  |  |  |  |  |  |  |
|---|---|---|---|---|---|---|
| SEQ-ID-NO-17-CLONE-839727 | LKRLGGTHLK | YGVADGHFEV | TRFALLETIK | EALPADMWGP | EMRNAWGEAY | 147 |
| SEQ-ID-NO-16-CLONE-1554560 | LKRLGATHLR | YGVADGHFEV | TGFALLETIK | EALPADMWSL | EMKKAWAEAY | 150 |
| SEQ-ID-NO-60-CLONE-1802327 | LKRLGATHFF | YGVADGHFEV | TRFALLETIK | EALPADMWSL | EMKNAWSEAY | 147 |
| SEQ-ID-NO-9-CLONE-30469-FL | LKRLGASHSK | YGVDEHFEV | AKYALLETIK | EAVP-EMWSP | EMKVAWGQAY | 145 |
| SEQ-ID-NO-10-GI-30909306 | LKRLGANHSK | YGVVDEHFEV | TKYALLETIK | EAVP-EMWSP | EMKSAWGQAY | 145 |
| SEQ-ID-NO-13-CLONE-546001 | LKKLGATHFR | TGVANEHFEV | TKFALLETIK | EAVP-EMWSP | AMKNAWGEAY | 145 |
| SEQ-ID-NO-70-CLONE-1916866 | LKKLGATHFK | YGVVDEHFEV | TKFALLETIK | EAVP-DMWSD | EMKNAWGEAY | 145 |

|  |  |  |
|---|---|---|
| SEQ-ID-NO-17-CLONE-839727 | DQLVAAIKQE | MKPSE--- | 162 |
| SEQ-ID-NO-16-CLONE-1554560 | SQLVAAIKRE | MKPDA--- | 165 |
| SEQ-ID-NO-60-CLONE-1802327 | NQLVAAIKQE | MKPAA--- | 162 |
| SEQ-ID-NO-9-CLONE-30469-FL | DHLVAAIKAE | MNLSN--- | 160 |
| SEQ-ID-NO-10-GI-30909306 | DHLVAAIKAE | MKPSH--- | 160 |
| SEQ-ID-NO-13-CLONE-546001 | DQLVDAIKSE | MKPPSS--- | 161 |
| SEQ-ID-NO-70-CLONE-1916866 | DRLVAAIKIE | MKACSQAA | 163 |

FIGURE 3

| | | | | | | | |
|---|---|---|---|---|---|---|---|
| SEQ-ID-NO-221-CLONE-839727-T | MSAAE---GA | VVFSEEKEAL | VLKSWAIMKK | DSANLGLRFF | LKIFEIAPSA | | 47 |
| SEQ-ID-NO-207-CLONE-1554560-T | MALAEADDGA | VVFGEEQEAL | VLKSWAVMKK | DAANLGLRFF | LKVFEIAPSA | | 50 |
| SEQ-ID-NO-208-CLONE-1802327-T | MALAE---GN | VIFGEEQEAL | VLKSWALMKK | DSADLGLRFF | LKIFEIAPSA | | 47 |
| SEQ-ID-NO-7-CLONE-30469 | MESE---GK | VFTEEQEAL | VVKSWSVMKK | NSAELGLKLF | IKIFEIAPTA | | 46 |
| SEQ-ID-NO-227-GI-30909306-T | MESE---GK | VFTEEQEAL | VVKSWSVMKK | NSADLGLKLF | IKIFEIAPTA | | 46 |
| SEQ-ID-NO-219-CLONE-546001-T | MTT----LE | RGFSEEQEAL | VVKSWNVMKK | NSCELCLKFF | LKIFEIAPSA | | 46 |
| SEQ-ID-NO-212-CLONE-1916866-T | MATY---EG | KVFTEEQEAL | VVKSWTVMKK | NAAELGLKFF | LKIFEIAPSA | | 46 |

| | | | | | |
|---|---|---|---|---|---|
| SEQ-ID-NO-221-CLONE-839727-T | RQMFPFLRDS | DVPLETNPKL | KTHAVSVFVM | -- | 77 |
| SEQ-ID-NO-207-CLONE-1554560-T | KQMFSFLRDS | DVPLEKNPKL | KTHAMSVFVM | -- | 80 |
| SEQ-ID-NO-208-CLONE-1802327-T | KQMFSFLRDS | DVPLEKNPKL | KNHAMSVFVM | -- | 77 |
| SEQ-ID-NO-7-CLONE-30469 | KKMFSFLRDS | PIPAEQNPKL | KPHAMSVFVM | YN | 78 |
| SEQ-ID-NO-227-GI-30909306-T | KKLFSFLRDS | PIPAEQNPKL | KPHAMSVFVM | -- | 76 |
| SEQ-ID-NO-219-CLONE-546001-T | QKLFSFLRDS | TVPLEQNPKL | KPHAVSVFVM | -- | 76 |
| SEQ-ID-NO-212-CLONE-1916866-T | KKLFSFLRDS | NVPLEQNTKL | KPHAMSVFVM | -- | 76 |

FIGURE 4

| | | | | | | |
|---|---|---|---|---|---|---|
| SEQ-ID-NO-20-CLONE-271922  | MA KRT KK V GI | VGKYGTRYGA | SI RKQI KKME | VSQHSKYFCE | FCGKY G VKRK | 50 |
| SEQ-ID-NO-54-CLONE-1627907 | MT KRT KKAGI  | VGKYGTRYGA | SLRKQI KKME | VSQHAKYFCE | FCGKYAVKRQ   | 50 |
| SEQ-ID-NO-25-CLONE-664936  | MT KRT KKAGI  | VGKYGTRYGA | SLRKQI KKME | VSQHSKFFCE | FCGKYAVKRK   | 50 |
| SEQ-ID-NO-28-CLONE-632613  | MT KRT KKAGI  | VGKYGTRYGA | SLRKQI KKME | VSQHSKYFCE | FCGKFAVKRK   | 50 |
| SEQ-ID-NO-29-CLONE-1390976 | MT KRT KKAGI  | VGKYGTRYGA | SLRKQI KKME | VSQHSKYFCE | FCGKFAVKRK   | 50 |
| SEQ-ID-NO-58-CLONE-1783890 | MT KRT KKAGI  | VGKYGTRYGA | SLRKQI KKME | VSQHSKYFCE | FCGKFAVKRK   | 50 |

| | | | | | | |
|---|---|---|---|---|---|---|
| SEQ-ID-NO-20-CLONE-271922  | AVGI WGCKDC | GKVKAGGAYT | MNT ASAVTVR | STI RRL REQI | EG | 92 |
| SEQ-ID-NO-54-CLONE-1627907 | AVGI WGCKDC | GKVKAGGAYT | LNT ASAVTVR | STI RRL REQT | ES | 92 |
| SEQ-ID-NO-25-CLONE-664936  | AVGI WGCKDC | GKVKAGGAYT | LNT ASAVTVR | STI RRL REQT | EG | 92 |
| SEQ-ID-NO-28-CLONE-632613  | AVGI WGCKDC | GKVKAGGAYT | MNT ASAVTVR | STI RRL REQT | EA | 92 |
| SEQ-ID-NO-29-CLONE-1390976 | AVGI WGCKDC | GKVKAGGAYT | MNT ASAVTVR | STI RRL REQT | EA | 92 |
| SEQ-ID-NO-58-CLONE-1783890 | AVGI WGCKDC | GKVKAGGAYT | MNT ASAVTVR | STI RRL REQT | EA | 92 |

FIGURE 5

| SEQ-ID | 1-50 | | | | | |
|---|---|---|---|---|---|---|
| SEQ-ID-NO-34-CLONE-2403-FL | MQI FVKTLTG | KTI TLEVESS | DTI DNVKAKI | QDKEGI PPDQ | QRLI FAGKQL | 50 |
| SEQ-ID-NO-35-CLONE-1482731 | MQI FVKTLTG | KTI TLEVESS | DTI DNVKSKI | QDKEGI PPDQ | QRLI FAGKQL | 50 |
| SEQ-ID-NO-36-CLONE-522921 | MQI FVKTLTG | KTI TLEVESS | DTI DNVKAKI | QDKEGI PPDQ | QRLI FAGKQL | 50 |
| SEQ-ID-NO-37-CLONE-1036726 | MQI FVKTLTG | KTI TLEVESS | DTI DNVKAKI | QDKEGI PPDQ | QRLI FAGKQL | 50 |
| SEQ-ID-NO-68-CLONE-1884696 | MQI FVKTLTG | KTI TLEVESS | DTI DNVKAKI | QDKEGI PPDQ | QRLI FAGKQL | 50 |
| SEQ-ID-NO-80-CLONE-2034916 | MQI FVKTLTG | KTI TLEVESS | DTI DNVKAKI | QDKEGI PPDQ | QRLI FAGKQL | 50 |
| SEQ-ID-NO-34-CLONE-2403-FL | EDGRTLADYN | QKESTLHLV | LRLRGGT MI K | VKTLTGKEI E | DI EPTDTI D | 100 |
| SEQ-ID-NO-35-CLONE-1482731 | EDGRTLADYN | QKESTLHLV | LRLRGGT MI K | VKTLTGKEI E | DI EPTDTI D | 100 |
| SEQ-ID-NO-36-CLONE-522921 | EDGRTLADYN | QKESTLHLV | LRLRGGT MI K | VKTLTGKEI E | DI EPTDTI D | 100 |
| SEQ-ID-NO-37-CLONE-1036726 | EDGRTLADYN | QKESTLHLV | LRLRGGT MI K | VKTLTGKEI E | DI EPTDTI D | 100 |
| SEQ-ID-NO-68-CLONE-1884696 | EDGRTLADYN | QKESTLHLV | LRLGGMQI F | VKTLTGKT T | LEVESSDTI D | 100 |
| SEQ-ID-NO-80-CLONE-2034916 | EDGRTLADYN | QKESTLHLV | LRLRGGMQI F | VKTLTGKT T | LEVESSDTI D | 100 |
| SEQ-ID-NO-34-CLONE-2403-FL | RI KERVEEKE | GI PPVQQRLI | YAGKQLADDK | TAKDYAI EGG | SVLHLVLALR | 150 |
| SEQ-ID-NO-35-CLONE-1482731 | RI KERVEEKE | GI PPVQQRLI | YAGKQLADDK | TAKDYNI EGG | SVLHLVLALR | 150 |
| SEQ-ID-NO-36-CLONE-522921 | RI KERVEEKE | GI PPVQQRLI | YAGKQLADDK | TAKEYNI EGG | SVLHLVLALR | 150 |
| SEQ-ID-NO-37-CLONE-1036726 | RI KERVEEKE | GI PPVQQRLI | YAGKQLADDK | XKDYNI EGG | SVSA— | 144 |
| SEQ-ID-NO-68-CLONE-1884696 | NVKAKI QDKE | GI PPDQRLI | FAGKQLEDGR | LADYNI QKD | STLHLVLRLR | 150 |
| SEQ-ID-NO-80-CLONE-2034916 | NVKVKI QDKE | GI PPDQRLI | FAGKQLEDGR | LADYNI QKE | STLHLVLRLR | 150 |
| SEQ-ID-NO-34-CLONE-2403-FL | GGL— | — | — | — | — | 153 |
| SEQ-ID-NO-35-CLONE-1482731 | GGS— | — | — | — | — | 153 |
| SEQ-ID-NO-36-CLONE-522921 | GGT— | — | — | — | — | 153 |
| SEQ-ID-NO-37-CLONE-1036726 | —SG— | — | — | — | — | 146 |
| SEQ-ID-NO-68-CLONE-1884696 | GG— | — | — | — | — | 152 |
| SEQ-ID-NO-80-CLONE-2034916 | GGMQI FVKTL | TGKTI TLEVE | SSDTI DNVKA | KI QDKEGI PP | DQQRLI FAGK | 200 |
| SEQ-ID-NO-34-CLONE-2403-FL | — | — | —L | | | 154 |
| SEQ-ID-NO-35-CLONE-1482731 | — | — | —D | | | 154 |
| SEQ-ID-NO-36-CLONE-522921 | — | — | —Y | | | 154 |
| SEQ-ID-NO-37-CLONE-1036726 | — | — | —S | | | 147 |
| SEQ-ID-NO-68-CLONE-1884696 | — | — | —F | | | 153 |
| SEQ-ID-NO-80-CLONE-2034916 | QLEDGRTLAD | YNI | | | | 213 |

FIGURE 6

| | | | | | |
|---|---|---|---|---|---|
| SEQ-ID-NO-40-CLONE-2403 | MQI FVKTLTG | KTI TLEVESS | DTI DNVKAKI | QDK | 33 |
| SEQ-ID-NO-205-CLONE-1036726-T | MQI FVKTLTG | KTI TLEVESS | DTI DNVKAKI | QDK | 33 |
| SEQ-ID-NO-211-CLONE-1884696-T | MQI FVKTLTG | KTI TLEVESS | DTI DNVKAKI | QDK | 33 |
| SEQ-ID-NO-213-CLONE-1950105-T | MQI FVKTLTG | KTI TLEVESS | DTI DNVKAKI | QDK | 33 |
| SEQ-ID-NO-218-CLONE-522921-T | MQI FVKTLTG | KTI TLEVESS | DTI DNVKAKI | QDK | 33 |
| SEQ-ID-NO-206-CLONE-1482731-T | MQI FVKTLTG | KTI TLEVESS | DTI DNVKSKI | QDK | 33 |

(Sequence alignment figure showing multiple sequences SEQ-ID-NO-46 through SEQ-ID-NO-84 with conserved regions boxed.)

NUCLEOTIDE SEQUENCES AND POLYPEPTIDES ENCODED THEREBY USEFUL FOR MODIFYING PLANT CHARACTERISTICS IN RESPONSE TO COLD

This application is a divisional of application Ser. No. 16/275,659 filed on Feb. 14, 2019, which application is a divisional of application Ser. No. 15/362,633 filed on Nov. 28, 2016 (now U.S. Pat. No. 10,240,166), which application is a divisional of application Ser. No. 11/779,266 filed on Jul. 17, 2007 (Abandoned), which application is a Continuation-In-Part of application Ser. No. 11/778,060 filed on Jul. 15, 2007 (abandoned), which is a Continuation-In-Part of application Ser. No. 11/248,547 filed on Oct. 12, 2005 (now U.S. Pat. No. 7,244,879), the entire contents of which are hereby incorporated by reference and for which priority is claimed under 35 U.S.C. § 120.

FIELD OF THE INVENTION

The present invention relates to isolated polynucleotides, polypeptides encoded thereby, and the use of those products for making transgenic plants with improved tolerances to environmental stresses such as low or chilling temperatures.

BACKGROUND OF THE INVENTION

Plants are constantly exposed to a variety of biotic (i.e. pathogen infection and insect herbivory) and abiotic (i.e. high or low temperature, drought, flood and salinity) stresses. To survive these challenges to their sessile life, plants have developed elaborate mechanisms to perceive external signals and to manifest adaptive responses with proper physiological and morphological changes (Bohnert et al. 1995). Plants exposed to cold or chilling conditions typically have low yields of biomass, seeds, fruit and other edible products. The term "chilling sensitivity" is used for the description of physiological and developmental damages in the plant caused by low, but above freezing, temperatures. Important agricultural crop plants such as corn, soybean, rice and cotton have tropical ancestors that make them chilling sensitive. In some countries or agricultural regions of the world chilling temperatures are a significant cause of crop losses and a primary factor limiting the geographical range and growing season of many crop species. Another example is that chilling conditions can cause significant concern in early spring planting of corn or canola. Poor germination and reduced growth of chilling sensitive crops in the spring results in less ground coverage, more erosion and increased occurrence of weeds leading to less nutrient supply for the crop.

Typically, chilling damage includes wilting, necrosis or ion leakage from cell membranes, especially calcium leakage, and decreased membrane fluidity, which consequently impacts membrane dependent processes such as: photosynthesis, protein synthesis, ATPase activity, uptake of nitrogen, etc. (see Levitt J (1980) Chilling injury and resistance. In Chilling, Freezing, and High Temperature Stresses: Responses of Plant to Environmental Stresses, Vol 1., T T Kozlowsky, ed, Academic Press, New York, pp 23-64; Graham and Patterson (1982) *Annu Rev Plant Physiol* 33: 347-372; Guy (1990) *Annu Rev Plant Physiol Plant Mol Biol* 41: 187-223; and Nishida and Murata (1996) *Annu Rev Plant Physiol Plant Mol Biol* 47: 541-568.). In addition, cold temperatures are often associated with wet conditions. The combination of cold and wet can result in hypoxic stress on the roots, causing an even more severe reduction of growth rate but, more critically, can be lethal to the plants, especially sensitive plant species such as corn and cotton.

Yet it has been observed that environmental factors, such as low temperature, can serve as triggers to induce cold acclimation processes allowing plants responding thereto to survive and thrive in low temperature environments. It would, therefore, be of great interest and importance to be able to identify genes that regulate or confer improved cold acclimation characteristics to enable one to create transformed plants (such as crop plants) with improved cold tolerance characteristics such as faster germination and/or growth and/or improved nitrogen uptake under cold conditions to improve survival or performance under low or chilling temperatures.

In the fields of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. There is a need for generally applicable processes that improve forest or agricultural plant growth potential. Therefore, the present invention relates to a process for increasing the growth potential in plants under low temperature, chilling or cold conditions, characterized by expression of recombinant DNA molecules stably integrated into the plant genome.

SUMMARY OF THE INVENTION

The present invention, therefore, relates to isolated polynucleotides, polypeptides encoded thereby and the use of those products for making transgenic plants with improved cold tolerance.

The present invention also relates to processes for increasing the growth potential in plants due to cold acclimation, recombinant nucleic acid molecules and polypeptides used for these processes and their uses, as well as to plants with an increased growth potential due to improved cold acclimation. Unless otherwise defined, all scientific and technical terms used herein have the same meaning as commonly understood by one of ordinary skilled in the art to which this invention belongs.

BRIEF DESCRIPTION OF THE FIGURES

FIG. 1 is an alignment of ME01451. In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE (Edgar (2004) Nuc. Acids Res. 32(5):1792-1797).

FIG. 2 is an alignment of ME02779.

FIG. 3 is an alignment of truncated mutant of ME02779.

FIG. 4 is an alignment of ME03944.

FIG. 5 is an alignment of ME05304.

FIG. 6 is an alignment of truncated mutant of ME05304.

FIG. 7 is an alignment of ME03186.

DETAILED DESCRIPTION OF THE INVENTION

1. Definitions

The following terms are utilized throughout this application:

Amino acid: As used herein, "amino acid" refers to one of the twenty biological occurring amino acids and to synthetic amino acids, including D/L optical isomers.

Cell type-preferential promoter or Tissue-preferential promoter: As used herein, these phrases refer to a promoter that drives expression preferentially in a target cell type or tissue, respectively, but may also lead to some transcription in other cell types or tissues as well.

Cold: Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "cold" can be defined as the temperature at which a given plant species will be adversely affected as evidenced by symptoms such as decreased photosynthesis and membrane damage (measured by electrolyte leakage). Since plant species vary in their capacity to tolerate cold, the precise environmental conditions that cause cold stress can not be generalized. However, cold tolerant plants are characterized by their ability to retain their normal appearance or recover quickly from low temperature conditions. Such cold tolerant plants produce higher biomass and yield than plants that are not cold tolerant. Differences in physical appearance, recovery and yield can be quantified and statistically analyzed using well known measurement and analysis methods.

Plant seeds vary considerably in their ability to germinate under cold conditions. Seeds of many plant species will not germinate at temperatures less than 10° C. Once seeds have imbibed water they become very susceptible to disease, water and chemical damage. Seeds that are tolerant to cold stress during germination can survive for relatively long periods under which the temperature is too low to germinate. Since plant species vary in their capacity to tolerate cold during germination, the precise environmental conditions that cause cold stress during germination can not be generalized. However, plants that tolerate cold during germination are characterized by their ability to remain viable or recover quickly from low temperature conditions. Such cold tolerant plants germinate, become established, grow more quickly and ultimately produce more biomass and yield than plants that are not cold tolerant. Differences in germination rate, appearance, recovery and yield can be quantified and statistically analyzed using well known measurement and analysis methods.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region, the 1' or 2' promoter derived from T-DNA of *Agrobacterium tumefaciens* and other transcription initiation regions from various plant genes, such as the maize ubiquitin-1 promoter, known to those of skill.

Control Plant: "Control plant" refers to a plant that does not contain the exogenous nucleic acid present in the transgenic plant of interest, but otherwise has the same of similar genetic background as such a transgenic plant. A suitable control plant can be a non-transgenic segregant from a transformation experiment, or a transgenic plant that contains an exogenous nucleic acid other than the exogenous nucleic acid of interest.

Domain: "Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

Down-regulation: "Down-regulation" refers to regulation that decreases production of expression products (mRNA, polypeptide, or both) relative to basal or native states.

Endogenous: The term "endogenous," within the context of the current invention refers to any polynucleotide, polypeptide or protein sequence which is a natural part of a cell or organism regenerated from said cell.

Exogenous: "Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Expression: As used herein, "expression" refers to the process of converting genetic information of a polynucleotide into RNA through transcription, which is catalyzed by an enzyme, RNA polymerase, and into protein, through translation of mRNA on ribosomes.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical. Within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily the same, degree. Typically, comparable proteins give the same characteristics where the quantitative measurement due to one of the comparables is at least 20% of the other; more typically, between 30 to 40%; even more typically, between 50-60%; even more typically between 70 to 80%; even more typically between 90 to 100% of the other.

Heterologous polypeptide: "Heterologous polypeptide" as used herein refers to a polypeptide that is not a naturally occurring polypeptide in a plant cell, e.g., a transgenic *Panicum* plant transformed with and expressing the coding sequence for a nitrogen transporter from a *Zea* plant.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter which can be utilized with the polynucleotides of the present invention is rd29a, the promoter from an *Arabidopsis* gene and which is induced by cold or dehydration (Baker et al. (1994) *Plant Mol. Biol.* 24:701). Examples of environmental conditions that may affect transcription by inducible promoters include anaerobic conditions, elevated temperature and/or the presence of light.

Isolated nucleic acid: "Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

Masterpool: The "master pools" discussed in these experiments are a pool of seeds from five independent transformation events of the same exogenous nucleotide sequence.

Modulation: As used herein, "Modulation" of the level of a compound or constituent refers to the change in the level of the indicated compound or constituent that is observed as a result of expression of, or transcription from, an exogenous nucleic acid in a plant cell. The change in level is measured relative to the corresponding level in control plants.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Nucleic acid and polynucleotide: "Nucleic acid" and "polynucleotide" are used interchangeably herein, and refer to both RNA and DNA, including cDNA, genomic DNA, synthetic DNA, and DNA or RNA containing nucleic acid analogs.

Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

Operably linked: As used herein, "operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

Percentage of sequence identity: "Percentage of sequence identity," as used herein, is determined by comparing two optimally aligned sequences over a comparison window defined by the length of the longest sequence, where the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981) Add. APL. Math. 2:482, by the homology alignment algorithm of Needleman and Wunsch (1970) *J. Mol. Biol.* 48:443), by the search for similarity method of Pearson and Lipman (1988) *Proc. Natl. Acad. Sci. (USA)* 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens*, such as the T-DNA promoters, can be plant promoters. A typical example of a plant promoter of plant origin is the maize ubiquitin-1 (ubi-1) promoter known to those of skill.

Polypeptide: "Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

Progeny: As used herein, "progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

Regulatory region: As used herein, "regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

Specific Promoter: In the context of the current invention, "specific promoters" refers to promoters that have a high preference for being active in a specific tissue or cell and/or at a specific time during development of an organism. By "high preference" is meant at least a 3-fold, preferably 5-fold, more preferably at least 10-fold still more preferably at least a 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) *Plant Mol Biol.* 30:321-9.); RCc2 and RCc3, promoters that direct root-specific gene transcription in rice (Xu et al. (1995) *Plant Mol. Biol.* 27:237) and TobRB27, a root-specific promoter from tobacco (Yamamoto et al. (1991) *Plant Cell* 3:371).

Stringency: "Stringency" as used herein is a function of probe length, probe composition (G+C content), salt concentration, organic solvent concentration and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$—5° C. to $T_m$—10° C. Medium or moderate stringency conditions are those providing $T_m$—20° C. to $T_m$—29° C. Low stringency conditions are those providing a condition of $T_m$—40° C. to $T_m$—48° C. The relationship of hybridization conditions to $T_m$ (in ° C.) is expressed in the mathematical equation $$T_m = 81.5 - 16.6(\log_{10}[Na^+]) + 0.41(\% \text{ G+C}) - (600/N) \tag{1}$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log\{[Na^+]/(1+0.7[Na^+])\} + 0.41(\% \text{ G+C}) - 500/L \; 0.63(\% \text{ formamide}) \tag{2}$$

where L is the length of the probe in the hybrid (P. Tijessen, "Hybridization with Nucleic Acid Probes" In Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., (1973) *J. Mol. Biol.* 81:123), stringency conditions can be adjusted to favor detection of identical genes or related family members.

Equation (2) is derived assuming equilibrium. Therefore, hybridizations according to the present invention are most preferably performed under conditions of probe excess and for sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Superpool: As used in the context of the current invention, a "superpool" refers to a mixture of seed from 100 different "master pools." The master pools are of 5 different events with the same exogenous nucleotide sequence transformed into them. Thus, while the superpool contains an equal amount of seed from 500 different events, it only represents 100 transgenic plants with a distinct exogenous nucleotide sequence transformed into them.

$T_0$: As used in the current application, the term "T0" refers to the whole plant, explant or callus tissue inoculated with the transformation medium.

$T_1$: As used in the current application, the term $T_1$ refers to either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

Up-regulation: "Up-regulation" refers to regulation that increases the level of an expression product (mRNA, polypeptide, or both) relative to basal or native states.

Vector: "Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

2. Important Characteristics of the Polynuceotides of the Invention

The genes and polynucleotides of the present invention are of interest because when they are misexpressed (i.e. when expressed at a non-natural location or in an increased or decreased amount) they produce plants with improved low temperature, chilling or cold tolerance as discussed below and as evidenced by the results of various experiments. These traits can be used to exploit or maximize plant products. For example, the genes and polynucleotides of the present invention are used to increase the expression of genes that render the plant more tolerant to low temperature, chilling or cold conditions. As a consequence, such transgenic plants do better and grow faster under low temperature, chilling or cold conditions, leading to reduced costs for the farmer and, better yield under low temperatures.

3. The Polynucleotides and Polypeptides of the Invention

The polynucleotides of the invention and the proteins expressed thereby are set forth in the Sequence Listing. Such Sequence Listing consists of functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity. Within this definition homologs, orthologs and analogs are considered to be functionally comparable.

Also, these comparables generally share at least one biochemical and/or phenotypic activity. For example, biochemical activity comparables are proteins that act on the same reactant to give the same product.

Another class of comparables is phenotypic comparables that both give the same physical characteristic, such as increased low temperature, chilling or cold tolerance. Proteins can be considered phenotypic comparables even if the proteins give rise to the same physical characteristic, but to a different degree.

4. Use of the Polynucleotides and Polypeptides to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector and which are suitable for transformation of plant cells. The construct can be made using standard recombinant DNA techniques (see Sambrook et al., Molecular Cloning: A Laboratory Manual, Second Edition, Cold Spring Harbor Laboratory Press, 1989, New York) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by
(a) BAC: Shizuya et al. (1992) *Proc. Natl. Acad. Sci. USA* 89: 8794-8797; Hamilton et al. (1996) *Proc. Natl. Acad. Sci. USA* 93: 9975-9979;
(b) YAC: Burke et al. (1987) *Science* 236:806-812;
(c) PAC: Sternberg N. et al. (1990) *Proc Natl Acad Sci USA*. January; 87:103-7;
(d) Bacteria-Yeast Shuttle Vectors: Bradshaw et al. (1995) *Nucl Acids Res* 23: 4850-4856;
(e) Lambda Phage Vectors: Replacement Vector, e.g., Frischauf et al. (1983) 1 *Mol Biol* 170: 827-842; or Insertion vector, e.g., Huynh et al., In: Glover N M (ed) DNA Cloning: A practical Approach, Vol. 1 Oxford: IRL Press (1985); T-DNA gene fusion vectors: Walden et al. (1990) *Mol Cell Biol* 1: 175-194; and
(g) Plasmid vectors: Sambrook et al., infra.

Typically, the construct comprises a vector containing a sequence of the present invention with any desired transcriptional and/or translational regulatory sequences such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, or hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as the Cauliflower Mosaic Virus 35S. Alternatively, the plant promoter directs transcription of a sequence of the invention in a specific tissue (tissue-specific promoters) or is otherwise under more precise environmental or developmental control (inducible promoters). Typically, preferred promoters to use in the present invention are cold inducible promoters. Many cold-inducible genes, including the cis-elements which confer cold induction, have been identified (Shinozaki et al. (2003) *Curr. Opin. Plant Biol.* 6:410). Examples of such cold-inducible genes include RD29A (Yamaguchi-Shinozaki and Shinozaki (1994) *Plant Cell* 6:251) and CBF/DREB1 (Stockinger et al. (1997) *PNAS* 94:1035. Another preferred embodiment of the present invention is to use seedling specific promoters, endosperm specific promoters and leaf specific promoters. Various plant promoters, including constitutive, tissue-specific and inducible, are known to those skilled in the art and can be utilized in the present invention.

Alternatively, misexpression can be accomplished using a two component system, whereby the first component consists of a transgenic plant comprising a transcriptional activator operatively linked to a promoter and the second component consists of a transgenic plant that comprises sequence of the invention operatively linked to the target-binding sequence/region of the transcriptional activator. The two transgenic plants are crossed and the sequence of the invention is expressed in their progeny. In another alternative, the misexpression can be accomplished by having the sequences of the two component system transformed in one transgenic plant line.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g. Weising et al. (1988) *Ann. Rev. Genet.* 22:421; and Christou (1995) *Euphytica,* v. 85, n.1-3:13-27.

Processes for the transformation of monocotyledonous and dicotyledonous plants are known to the person skilled in the art. A variety of techniques is available for the introduction of DNA into a plant host cell. These techniques include transformation of plant cells by injection, microinjection, electroporation of DNA, PEG, use of biolistics, fusion of cells or protoplasts, and via T-DNA using *Agrobacterium tumefaciens* or *Agrobacterium rhizogenes* or other bacterial hosts, as well as further possibilities.

In addition, a number of non-stable transformation methods that are well known to those skilled in the art may be desirable for the present invention. Such methods include, but are not limited to, transient expression and viral transfection.

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased tolerance to low temperature, chilling or cold conditions without reduction in fertility on essentially any plant, including chilling sensitive crop plants such as corn, soybean, rice and cotton.

The nucleotide sequences according to the invention encode appropriate proteins from any organism, in particular from plants, fungi, bacteria or animals.

The process according to the invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

The process is preferably used with plants that are important or interesting for agriculture, horticulture, biomass for bioconversion and/or forestry. Examples are tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, petunia, guayule, cabbages, spinach, alfalfa, artichokes, corn, wheat, rice, rye, barley, grasses such as switch grass or turf grass, millet, hemp, bananas, poplars, eucalyptus trees and conifers.

Homologs Encompassed by the Invention

It is well known in the art that one or more amino acids in a native sequence can be substituted with other amino acid(s), the charge and polarity of which are similar to that of the native amino acid, i.e. a conservative amino acid substitution, resulting in a silent change. Conservative substitutes for an amino acid within the native polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

In a further aspect of the present invention, nucleic acid molecules of the present invention can comprise sequences that differ from those encoding a protein or fragment thereof selected from the group consisting of SEQ ID NOs: 2-5, 7, 9-18, 20-32, 34-38, 40 and 42-46 due to the fact that the different nucleic acid sequence encodes a protein having one or more conservative amino acid changes.

Polypeptides

Polypeptides described herein include cold tolerance-modulating polypeptides. Cold tolerance-modulating polypeptides can be effective to modulate cold tolerance levels when expressed in a plant or plant cell. Such polypeptides typically contain at least one domain indicative of cold tolerance-modulating polypeptides, as described in more detail herein. Cold tolerance-modulating polypeptides typically have an HMM bit score that is greater than 20, as described in more detail herein. In some embodiments, cold tolerance-modulating polypeptides have greater than 80% identity to SEQ ID NOs: 2, 7, 9, 20, 34, 40, and 42, as described in more detail herein.

In some embodiments, a cold tolerance-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the cold tolerance-modulating activity of a truncated polypeptide. In some embodiments, a truncated polypeptide is a dominant negative polypeptide. SEQ ID NOs 7 and 40 set forth the amino sequences of cold tolerance-modulating polypeptides that are truncated at the 3' end relative to the naturally occurring polypeptides SEQ ID NOs 9 and 34, respectively. Expression in a plant of such a truncated polypeptide confers a difference in the level of cold tolerance in a tissue of the plant as compared to the corresponding level in tissue of a control plant that does not comprise the truncation.

A. Functional Homologs Identified by Reciprocal BLAST

In some embodiments, one or more functional homologs of a reference cold tolerance-modulating polypeptide defined by one or more of the pfam descriptions indicated above are suitable for use as cold tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cold tolerance-modulating polypeptide, or by combining domains from the coding sequences for different naturally-occurring cold tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of cold tolerance-modulating polypeptides. Sequence analysis can involve BLAST, Reciprocal BLAST, or PSI-BLAST analysis of nonredundant databases using a cold tolerance-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a cold tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in cold tolerance-modulating polypeptides, e.g., conserved functional domains.

Conserved regions can be identified by locating a region within the primary amino acid sequence of a cold tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at the Wellcome Trust Sanger Institute and HMMI janelia farm research campus. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1:
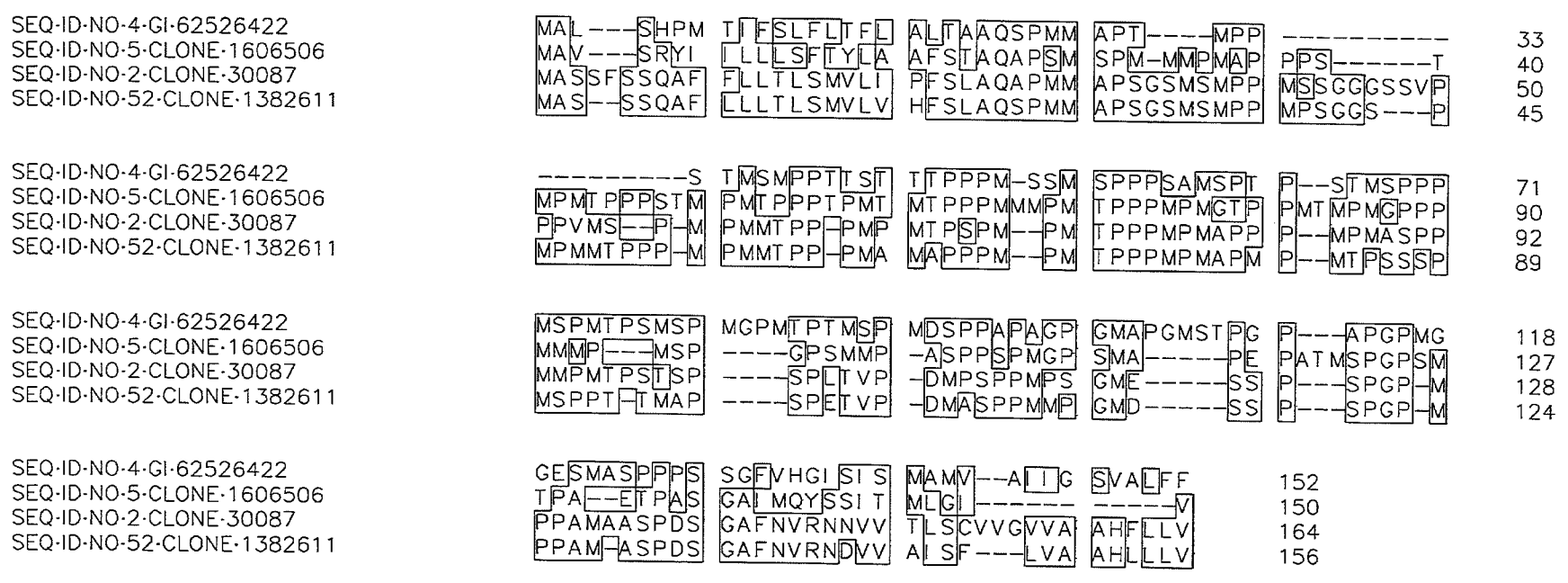
Figure 7:
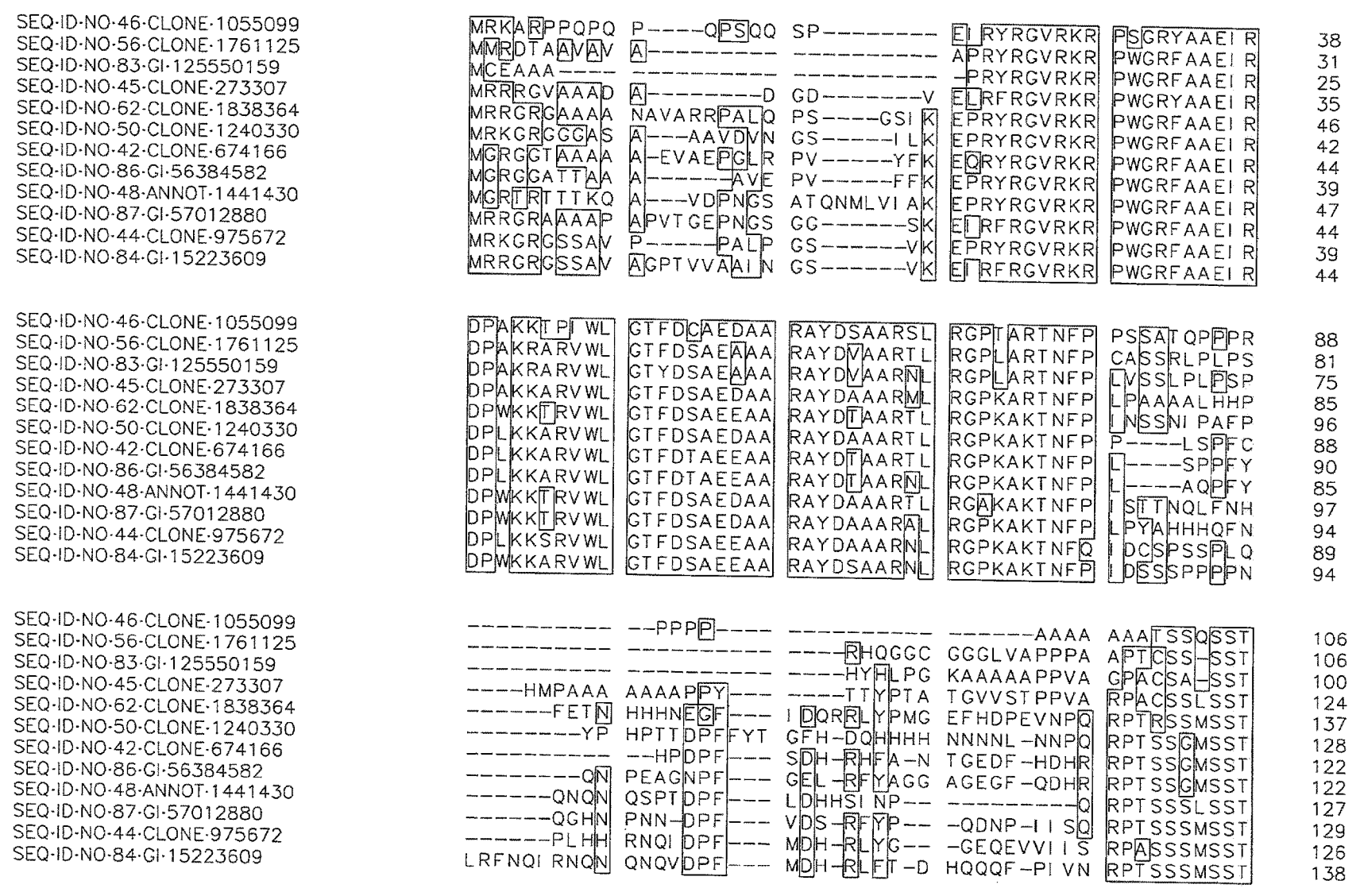

Amino acid sequences of functional homologs of the polypeptide set forth in SEQ ID NOs 2, 7, 9, 20, 34, 40 and 42 are provided in FIGS. 1-7, respectively. In some cases, a functional homolog of SEQ ID NOs 2, 7, 9, 20, 34, 40 and 42 has an amino acid sequence with at least 80% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in the Sequence Listing.

The identification of conserved regions in a cold tolerance-modulating polypeptide facilitates production of variants of cold tolerance-modulating polypeptides. Variants of cold tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in any one of FIGS. 1-7. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

B. Functional Homologs Identified by HMMER

In some embodiments, useful cold tolerance-modulating polypeptides include those that fit a Hidden Markov Model based on the polypeptides set forth in any one of FIGS. 1-7. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An MINI is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, -consistency REPS of 2; -ir, -iterative-refinement REPS of 100; -pre, -pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as the HMMER page on the HHMI janelia farm research campus website; the Eddy Lab Home page on the HHMI janelia farm research campus website; and HMMER 2.3.2 download available on the Fish & Richardson website. Hmmbuild outputs the model as a text file.

The HMM for a group of functional homologs can be used to determine the likelihood that a candidate cold tolerance-modulating polypeptide sequence is a better fit to that particular HMM than to a null HMM generated using a group of sequences that are not structurally or functionally related. The likelihood that a subject polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the subject sequence carries out one or more of the biochemical or physiological function(s) of the polypeptides used to generate the HMM. A high HMM bit score is at least 20, and often is higher.

The cold tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a cold tolerance-modulating polypeptide discussed below is about 50%, 60%, 70%, 80%, 90%, or 95% of the HMM bit score of a functional homolog provided in one of Table 7. In some embodiments, a cold tolerance-modulating polypeptide discussed below fits the indicated HMM with an HMM bit score greater than 20, and has a domain indicative of an cold tolerance-modulating polypeptide. In some embodiments, a cold tolerance-modulating polypeptide discussed below fits the indicated HMM with an HMM bit score greater than 20, and has 80% or greater sequence identity (e.g., 75%, 80%, 85%, 90%, 95%, or 100% sequence identity) to an amino acid sequence shown in any one of FIGS. 1-7.

Polypeptides are shown in Table 7 that have HMM bit scores greater than 20 when fitted to an HMM generated from the amino acid sequences set forth in FIGS. 1-7, respectively.

In another aspect, biologically functional equivalents of the proteins or fragments thereof of the present invention can have about 10 or fewer conservative amino acid changes, more preferably about 7 or fewer conservative amino acid changes and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Inhibition of Expression of a Cold Tolerance-Modulating Polypeptide

Polynucleotides and recombinant constructs described herein can be used to inhibit expression of a cold tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Antisense technology is one well-known method. In this method, a nucleic acid segment from a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, *Methods in Molecular Biology*, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence of a cold tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand of the coding sequence of the cold tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region of an mRNA encoding a cold tolerance-modulating polypeptide, and the other strand of the stem portion of the double stranded RNA comprises a sequence that is similar or identical to the sequence that is complementary to the 3' or 5' untranslated region, respectively, of the mRNA encoding the cold tolerance-modulating polypeptide. In other embodiments, one strand of the stem portion of a double stranded RNA comprises a sequence that is similar or identical to the sequence of an intron in the pre-mRNA encoding a cold tolerance-modulating polypeptide, and the other strand of the stem portion comprises a sequence that is similar or identical to the sequence that is complementary to the sequence of the intron in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence of a cold tolerance-modulating polypeptide. The transcription product can also be unpolyadenylated, lack a 5' cap structure, or contain an unsplicable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a cold tolerance-modulating polypeptide. In some embodiments, the sense or antisense sequence is identical or complementary to a sequence of the regulatory region that drives transcription of the gene encoding a cold tolerance-modulating polypeptide. In each case, the sense sequence is the sequence that is complementary to the antisense sequence.

The sense and antisense sequences can be any length greater than about 12 nucleotides (e.g., 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence encoding a cold tolerance-modulating polypeptide described herein. The sense sequence complementary to the antisense sequence can be a sequence present within the mRNA of the cold tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more anti sense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

In some embodiments, nucleic acid based inhibition of gene expression does not require transcription of the nucleic acid.

Identification of Useful Nucleotide Sequences

The nucleotide sequences of the invention were identified by use of a variety of screens under low temperature, chilling or cold conditions recognized by those skilled in the art to be predictive of nucleotide sequences that provide plants with improved tolerance to low temperature, chilling or cold conditions. One or more of the following screens were, therefore, utilized to identify the nucleotide (and amino acid) sequences of the invention.

1. Cold Germination Superpool Screen 0.5×MS Media is prepared and the pH adjusted to 5.7 using 10N KOH. Seven g/l of Phytagar is added prior to autoclaving.

Individual superpool and control seeds are sterilized in a 30% bleach solution for 5 minutes. Seeds are then rinsed repeatedly with sterile water to eliminate all bleach solution. Seeds are sown on media plates in a monolayer, including wild-type and positive controls. Plates are wrapped in aluminum foil and placed at 4° C. for three days to stratify. At the end of this time, the foil is removed and plates are transferred to an 8° C. Percival with fluorescent bulbs emitting a light intensity of ~100 µEinsteins.

Approximately 10 days after transfer to 8° C., seeds are examined microscopically to identify those that have germinated (defined as cotyledon emergence and expansion). Seedlings with more expanded and greener cotyledons compared to the wild-type population in the same plate are collected. DNA from these candidate seedlings is extracted and the transgene amplified using PCR. The PCR product is sequenced to determine the identity of the transgene and consequently the ME line from which the candidate is derived.

2. Cold Germination Assay

Independent transformation events of the ME lines identified in the Superpool screen are assayed in two generations to validate the cold tolerance phenotype. Media is prepared and seeds sterilized as described above for the Cold Germination Superpool Screen.

Two events with 27 seeds from each event are sown in a latin square layout on square Petri dishes together with 27 wild-type control seeds. Following 3 days of stratification at 4° C., plates are transferred to 8° C. in the light and grown as above. Approximately 10 days after transfer, plates are imaged on a flat-bed scanner. Plate images are analyzed using WinRhizo software to determine the area of each seedling. Subsequently, plates are transferred to 22° C. for several days of growth and then sprayed with Finale™ to identify transgenic seedlings. Seedling area and transgene status data are entered into a database. Events are considered positive for the low temperature, chilling or cold-tolerant phenotype if the seedling area of the transgenic plants within an event is significantly different by a one-tailed student's t-test than the seedling area of the pooled non-transgenic seedlings across all the events for that ME line.

REFERENCES

Levitt (1980) Chilling injury and resistance. In T T Kozlowsky, ed, Chilling, Freezing, and High Temperature Stresses: Responses of Plant to Environmental Stresses, Vol 1. Academic Press, New York, pp 23-64.

Graham and Patterson (1982) *Annu Rev Plant Physiol* 33: 347-372.

Guy (1990) *Annu Rev Plant Physiol Plant Mot Blot* 41: 187-223.

Nishida and Murata (1996) *Annu Rev Plant Physiol Plant Mol Biol* 47: 541-568.

EXAMPLES

Summary

| | |
|---|---|
| Trait area(s) | Cold |
| Sub-trait Area | Cold - germination and vigor |
| Coding sequence/ Species of Origin | 1. Vector Construct Sequence Identifier 14298746 corresponding to Clone 30087 - ME01451; encodes a 164 amino acid protein of unknown function from *Arabidopsis*. <br> 2. Vector Construct Sequence Identifier 14298770 corresponding to Clone 30469 - ME02779 encodes a 78 amino acid protein with identity to the N-terminal half of an *Arabidopsis* class I nonsymbiotic hemoglobin. <br> 3. Vector Construct Sequence Identifier 14301197 corresponding to Clone 271922 - ME03944 encodes a 92 amino acid 60s ribosomal protein L37a protein from *Arabidopsis*. <br> 4. Vector Construct Sequence Identifier 14296769 corresponding to Clone 2403 - ME05304 encodes a truncated ubiquitin-like protein from *Arabidopsis*. <br> 5. Vector Construct Sequence Identifier 14301334 corresponding to Clone 674166 -ME03186 from *Glycine max* encodes a 210 amino acid protein with similarity to the ethylene- responsive element binding protein (ERF) family. |
| Species in which Clone was Tested | *Arabidopsis thaliana* |
| Promoter | 35S, a strong constitutive promoter |
| Insert DNA type | cDNA |

INTRODUCTION

How plants respond to stress in the environment dictates their ability to survive and reproduce. There are probably many mechanisms by which plants regulate the temperatures under which they will germinate (Lu and Hills, 2003). Finding genes that result in stress tolerance when over-expressed has proved difficult because of the large amount of cross-talk and regulation among gene families.

Over-expression of these genes could be useful for increasing low temperature, chilling or cold tolerance in crops. If successfully deployed, low temperature, chilling or cold tolerant genes could enhance crop productivity following intermittent or sustained low temperature, chilling or cold periods that occur early in the growing season when seeds are germinating. Assuming conservation of processes controlling vegetative physiology across species, these genes and proteins are likely to function similarly in other species.

Assays described here focus on low temperature, chilling or cold tolerance in germinating seedlings. The ability to germinate and grow under low temperature, chilling or cold, and wet conditions would allow a longer growing season and mitigate damage caused by unexpected low temperature, chilling or cold periods. If this trait is recapitulated in crops overexpressing these genes, the result could be very valuable in agriculture in many crops and environments and make a significant contribution to sustainable farming. Furthermore, low temperature, chilling or cold tolerance may be modulated by expressing these clones under the control of a low temperature, chilling or cold inducible promoter.

Materials and Methods:

Generation and Phenotypic Evaluation of $T_1$ Events.

Wild-type Arabidopsis Wassilewskija (Ws) plants were transformed with a Ti plasmid containing different Clones in the sense orientation relative to the 35S promoter, by Agrobacterium-Mediated Transformation. The Ti plasmid vector used for this construct, CRS 338, contains the Ceres-constructed, plant selectable marker gene phosphinothricin acetyltransferase (PAT) which confers herbicide resistance to transformed plants. Ten independent transformation events were selected and evaluated for their qualitative phenotype in the $T_1$ generation by selecting Finale™-resistant plants and observing their physical characteristics.

Screening for Low Temperature, Chilling or Cold Germination Candidates.

All superpools (n=91) were screened for cold germination by plating seeds on MS media and germinating them at 8° C. Candidates were chosen based on a comparison to wild-type controls. The candidates were processed as follows.

Process Flow:

Procedure for 1) identifying the candidate from a cold germination superpool screen, 2) confirming the phenotype in the second and third generations and 3) determining the lack of significant negative phenotypes.
  1. Superpools screened for Cold Germination
  2. Cold tolerant candidates identified
  3. Independent events tested for Cold Germination and Finale™ resistance in two generations
  4. For all candidates, at least 2 Events were significantly tolerant to cold in 2 generations
  5. Tested positive events for negative phenotypes Growth Conditions and Planting Schema Under Cold Germination.

Up to five independent $T_2$ transformation events were evaluated for each line under cold conditions. Subsequently, $T_3$ generation seeds for up to five events were evaluated under cold germination conditions. In these assays, the seedling area (a measure of timing of germination and cotyledon expansion) for transgenic plants within an event was compared to the seedling area for non-transgenic segregants pooled across all plates for that line.

Preparation of plates and seed sowing were performed by sowing seeds on 0.5×MS plates and grown at 8° C. Plates were scored on day 10, and analyzed for cotyledon area. After the Cold Germination Assay was complete, plates were transferred to 22° C. and insert-containing plants were identified by spraying the seedlings with Finale™. Transgenic plants are Finale™ resistant.

Screening for Negative Phenotypes.

The events described in this report were analyzed for negative phenotypes. None of the events had (a) reduction in germination of more than 25%, (b) delay in onset of flowering more than 4 days in 50% or more of plants relative to in-flat control, (c) reduction in fertility as evidenced by visual observation of reduction in silique fill or silique number, (d) a reduction in seed dry weight by 25% or more relative to control, or (e) more than 30% reduction in rosette diameter at maturity.

RESULTS

Example 1: ME01451

TABLE 1-1

| Construct | Event/Generation | Plant Stage | Assay | Result |
|---|---|---|---|---|
| 35S::30087 | −01/$T_2$ Finale resistant plants | Seedling | Cold Germination | Significant at p ≤ .05 |
| 35S::30087 | −05/$T_2$ Finale resistant plants | Seedling | Cold Germination | Significant at p ≤ .05 |
| 35S::30087 | −01/$T_3$ Finale resistant plants | Seedling | Cold Germination | Significant at p ≤ .05 |
| 35S::30087 | −05/$T_3$ Finale resistant plants | Seedling | Cold Germination | Significant at p ≤ .05 |

Ectopic expression of Clone 30087 under the control of the 35S promoter induces the following phenotypes:

Early germination at 8° C. resulting in larger seedlings after 10 days of growth in the cold.

Plants from Events −01 and −05 which are heterozygous or homozygous for Clone 30087 do not show any negative phenotypes under long-day conditions.

The gene corresponding to Clone 30087 is up-regulated in developing seedlings, seeds and siliques and down-regulated in drought, heat and ABA.

Two Events of ME01451 Showed Significant Early Germination Under Cold Conditions in Both Generations.

All five events of ME01451 were sown as described in the Cold Germination Assay in both the $T_2$ and the $T_3$ generations. Two events, -01 and -05, were significant in both generations at p=0.05 using a one-tailed t-test assuming unequal variance (Table 1-2). ME01451 transgenic seedlings were significantly larger than the pooled non-transgenic segregants.

TABLE 1-2

T-test comparison of seedling area between transgenic seedlings
and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME01451 | ME01451-01 | 0.0086 | 0.0005 | 25 | 0.0067 | 0.0006 | 54 | 0.00702 |
| ME01451 | ME01451-01-99 | 0.0106 | 0.0006 | 22 | 0.0079 | 0.0010 | 14 | 0.01374 |
| ME01451 | ME01451-05 | 0.0104 | 0.0006 | 18 | 0.0067 | 0.0006 | 54 | 0.00002 |
| ME01451 | ME01451-05-99 | 0.0125 | 0.0007 | 25 | 0.0079 | 0.0010 | 14 | 0.00035 |

Two Events of ME01451 Show 3:1 and 15:1 Segregation for Finale™ Resistance.

Events −01 and −05 segregated 15:1 and 3:1 (R:S), respectively, for Finale™ resistance in the $T_2$ generation (data not shown).

Qualitative Analysis of the $T_1$ Plants:

The physical appearance of all ten $T_1$ plants was identical to the controls.

Qualitative and Quantitative Analysis of the $T_2$ Plants:

Events −01 and −05 of ME01451 exhibited no statistically relevant negative phenotypes.

Germination
  No detectable reduction in germination rate.
General morphology/architecture
  Plants appeared wild-type in all instances.
Days to flowering
  No observable or statistical differences between experimentals and controls.
Rosette area 7 days post-bolting
  No observable or statistical differences between experimentals and controls.
Fertility (silique number and seed fill)
  No observable or statistical differences between experimentals and controls Example 2: ME02779

TABLE 2-1

| Construct | Event/Generation | Plant Stage | Assay | Result |
|---|---|---|---|---|
| 35S::30469 | −01/$T_2$ Finale resistant plants | Seedling | Cold Germination | Significant at p ≤ .05 |
| 35S::30469 | −03/$T_2$ Finale resistant plants | Seedling | Cold Germination | Significant at p ≤ .05 |
| 35S::30469 | −01/$T_3$ Finale resistant plants | Seedling | Cold Germination | Significant at p ≤ .05 |
| 35S::30469 | −03/$T_3$ Finale resistant plants | Seedling | Cold Germination | Significant at p ≤ .05 |

Ectopic expression of Clone 30469 under the control of the 35S promoter induces the following phenotypes:
  Early germination at 8° C. resulting in larger seedlings after 10 days at 8° C.
Plants from Events −01 and −03 which are heterozygous or homozygous for Clone 30469 do not show any negative phenotypes under long-day conditions.
The gene corresponding to Clone 30469 is down-regulated in ABA, heat, and germinating seeds and up-regulated in high nitrogen and most cold and drought treatments.
Clone 30469 encodes a class I nonsymbiotic hemoglobin. These proteins can play a role in acclimation to hypoxic conditions, possibly explaining the cold tolerance phenotype (Hunt et al., 2001). Clone 30469 is a splice variant of a gene that encodes a longer protein.

Two Events of ME02779 Showed Significant Early Germination Under Cold Conditions in Both Generations.

Five events of ME02779 were sown as described in the Cold Germination Assay in both the $T_2$ and the $T_3$ generations. Two events, -01 and −03 were significant in both generations at p=0.05 using a one-tailed t-test assuming unequal variance (Table 2-2). ME02779 transgenic seedlings were significantly larger than the pooled non-transgenic segregants.

TABLE 2-2

T-test comparison of seedling area between transgenic seedlings
and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME02779 | ME02779-01 | 0.0077 | 0.0007 | 12 | 0.0040 | 0.0014 | 3 | 0.01738 |
| ME02779 | ME02779-01-99 | 0.0051 | 0.0005 | 21 | 0.0034 | 0.0002 | 29 | 0.00077 |
| ME02779 | ME02779-03 | 0.0111 | 0.0007 | 19 | 0.0085 | 0.0007 | 40 | 0.00433 |
| ME02779 | ME02779-03-99 | 0.0052 | 0.0006 | 20 | 0.0034 | 0.0002 | 29 | 0.00293 |

Two Events of ME02779 Show 3:1 Segregation for Finale™ Resistance.

Events −01 and −03 segregated 3:1 (R: S) for Finale™ resistance in the $T_2$ generation (data not shown).

Qualitative Analysis of the $T_1$ Plants:

The physical appearance of nine of the ten $T_1$ plants was identical to the controls except for Event −09, which exhibited small rosettes and reduced fertility.

Qualitative and Quantitative Analysis of the $T_2$ Plants:
Events −01 and −03 of ME02779 exhibited no statistically relevant negative phenotypes.
  Germination
    No detectable reduction in germination rate.
  General morphology/architecture
    Plants appeared wild-type in all instances.
  Days to flowering
    No observable or statistical differences between experimentals and controls.
  Rosette area 7 days post-bolting
    No observable or statistical differences between experimentals and controls.
  Fertility (silique number and seed fill)
    No observable or statistical differences between experimentals and controls Example 3: ME03944

TABLE 3-1

| Construct | Event/Generation | Plant Stage | Assay | Result |
| --- | --- | --- | --- | --- |
| 35S::271922 | −02/$T_2$ Finale resistant plants | Seedling | Cold Germination | Significant at p ≤ .05 |
| 35S::271922 | −06/$T_2$ Finale resistant plants | Seedling | Cold Germination | Significant at p ≤ .05 |
| 35S::271922 | −02/$T_3$ Finale resistant plants | Seedling | Cold Germination | Significant at p ≤ .05 |
| 35S::271922 | −06/$T_3$ Finale resistant plants | Seedling | Cold Germination | Significant at p ≤ .05 |

Ectopic expression of Clone 271922 under the control of the 35S promoter induces the following phenotypes:
  Early germination at 8° C. resulting in larger seedlings after 10 days at 8° C.
  Plants from Events −02 and −06 which are heterozygous or homozygous for Clone 271922 do not show any negative phenotypes under long-day conditions.
  The gene corresponding to Clone 271922 shows little differential regulation in transcription profiling experiments on wildtype.
  Clone 271922 encodes a 60s ribosomal protein L37a.

Two events of ME03944 showed significant early germination under cold conditions in both generations.

Four events of ME03944 were sown as described in the Cold Germination Assay in both the $T_2$ and the $T_3$ generations. Two events, −02 and −06, were significant in both generations at p≤0.05 using a one-tailed t-test assuming unequal variance (Table 3-2). The $T_3$ lines are indicated as −99 which indicates that the seeds are the bulked progeny from several $T_2$ plants. ME03944 transgenic seedlings were significantly larger than the pooled non-transgenic segregants.

TABLE 3-2

T-test comparison of seedling area between transgenic seedlings and pooled non-transgenic segregants after 10 days at 8° C.

| | | Transgenic | | | Pooled Non-Transgenics | | | t-test |
| --- | --- | --- | --- | --- | --- | --- | --- | --- |
| Line | Events | Avg | SE | N | Avg | SE | N | p-value |
| ME03944 | ME03944-02 | 0.0115 | 0.0004 | 23 | 0.0069 | 0.0006 | 35 | 3.4023E−08 |
| ME03944 | ME03944-02-99 | 0.0070 | 0.0008 | 15 | 0.0051 | 0.0004 | 29 | 0.0173 |
| ME03944 | ME03944-06 | 0.0106 | 0.0006 | 18 | 0.0069 | 0.0006 | 35 | 2.7850E−05 |
| ME03944 | ME03944-06-99 | 0.0077 | 0.0007 | 21 | 0.0051 | 0.0004 | 29 | 0.0011 |

Two Events of ME03944 Show 3:1 Segregation for Finale™ Resistance.

Events −02 and −06 segregated 3:1 (R: S) for Finale™ resistance in the $T_2$ generation (data not shown).

Qualitative Analysis of the $T_1$ Plants:

The physical appearance of five of the six $T_1$ plants was identical to the controls. Event −03 exhibited a small rosette and curled leaves.

Other Characteristics:

Seedlings from ME03944-06 exhibited elongated hypocotyls. This phenotype co-segregated with Finale™ resistance.

Qualitative and Quantitative Analysis of the $T_2$ Plants:
Events −02 and −06 of ME03944 exhibited no statistically relevant negative phenotypes.
  Germination
    No detectable reduction in germination rate.
  General morphology/architecture
    Plants appeared wild-type in all instances.
  Days to flowering
    No observable or statistical differences between experimentals and controls.
  Rosette area 7 days post-bolting
    No observable or statistical differences between experimentals and controls.
  Fertility (silique number and seed fill)
    No observable or statistical differences between experimentals and controls Example 4: ME05304

TABLE 4-1

| Construct | Event/Generation | Plant Stage | Assay | Result |
| --- | --- | --- | --- | --- |
| 35S::2403 | −01/$T_2$ Finale resistant plants | Seedling | Cold Germination | Significant at p ≤ .05 |
| 35S::2403 | −04/$T_2$ Finale resistant plants | Seedling | Cold Germination | Significant at p ≤ .05 |
| 35S::2403 | −01/$T_3$ Finale resistant plants | Seedling | Cold Germination | Significant at p ≤ .05 |
| 35S::2403 | −04/$T_3$ Finale resistant plants | Seedling | Cold Germination | Significant at p ≤ .05 |

Ectopic expression of Clone 2403 under the control of the 35S promoter induces the following phenotypes:
  Early germination at 8° C. resulting in larger seedlings after 10 days at 8° C.
  Plants from Events −01 and −04 which are heterozygous or homozygous for Clone 2403 do not show any negative phenotypes under long-day conditions.
  The gene corresponding to Clone 2403 shows little differential regulation in transcript profiling experiments on wildtype.

Clone 2403 encodes a truncated ubiquitin-like protein.

Two Events of ME05304 Showed Significant Early Germination Under Cold Conditions in Both Generations.

Four events of ME05304 were sown as described in the Cold Germination Assay in both the $T_2$ and the $T_3$ generations. Two events, -01 and -04 were significant in both generations at p≤0.05 using a one-tailed t-test assuming unequal variance (Table 4-2). The $T_3$ lines are indicated as −99 which indicates that the seeds are the bulked progeny from several $T_2$ plants.

TABLE 4-2

T-test comparison of seedling area between transgenic seedlings and pooled non-transgenic segregants after 10 days at 8° C.

| Line | Events | Transgenic | | | Pooled Non-Transgenics | | | t-test |
|---|---|---|---|---|---|---|---|---|
| | | Avg | SE | N | Avg | SE | N | p-value |
| ME05304 | ME05304-01 | 0.0142 | 0.0009 | 20 | 0.0079 | 0.0006 | 39 | 0.0000 |
| ME05304 | ME05304-01-99 | 0.0061 | 0.0005 | 17 | 0.0049 | 0.0003 | 27 | 0.0213 |
| ME05304 | ME05304-04 | 0.0101 | 0.0007 | 15 | 0.0079 | 0.0006 | 39 | 0.0099 |
| ME05304 | ME05304-04-99 | 0.0067 | 0.0005 | 22 | 0.0049 | 0.0003 | 27 | 0.0014 |

Two Events of ME05304 Show 3:1 Segregation for Finale™ Resistance.

Events −01 and −04 segregated 3:1 (R: S) for Finale™ resistance in the $T_2$ generation (data not shown).

Qualitative Analysis of the $T_1$ Plants:
  The physical appearance of seven of the ten $T_1$ plants was identical to the controls. The other three events exhibited the following phenotypes: late flowering (Events −01, -02 and −08), dark green rosette leaves (Events −01 and −08) and shorter petioles (Events -02 and −08). Event −01 did not reproduce the late-flowering phenotype in the $T_2$ generation.

Qualitative and Quantitative Analysis of the $T_2$ Plants:
Events −01 and −04 of ME05304 exhibited no statistically relevant negative phenotypes.
  Germination
    No detectable reduction in germination rate.
  General morphology/architecture
    Plants appeared wild-type in all instances.
  Days to flowering
    No observable or statistical differences between experimentals and controls.
  Rosette area 7 days post-bolting
    No observable or statistical differences between experimentals and controls.
  Fertility (silique number and seed fill)
    No observable or statistical differences between experimentals and controls.

Example 5: ME03186

TABLE 5-1

| Construct | Event/Generation | Plant Stage | Assay | Result |
|---|---|---|---|---|
| 35S::674166 | −04/$T_3$Finale resistant plants | Seedling | Cold Germination | Significant at p ≤ .05 |
| 35S::674166 | −04/$T_4$ Finale resistant plants | Seedling | Cold Germination | Significant at p ≤ .05 |
| 35S::674166 | −05/$T_2$ Finale resistant plants | Seedling | Cold Germination | Significant at p ≤ .05 |

TABLE 5-1-continued

| Construct | Event/Generation | Plant Stage | Assay | Result |
|---|---|---|---|---|
| 35S::674166 | −05/$T_3$ Finale resistant plants | Seedling | Cold Germination | Significant at p ≤ .05 |

Ectopic expression of Clone 674166 under the control of the 35S promoter results in early germination at 8° C. resulting in larger seedlings after 10 days at 8° C.

Plants from Events −04 and −05 which are hemizygous or homozygous for Clone 674166 do not show any negative phenotypes under long-day conditions.

Two Events of ME03186 Showed Significant Early Germination Under Cold Conditions in Both Generations.

Two events, -04 and −05 were significant in two generations at p≤0.05 using a one-tailed t-test assuming unequal variance (Table 5-2). '−99' signifies that seeds were pooled from several plants.

TABLE 5-2

T-test comparison of seedling area between transgenic seedlings and control non-transgenic segregants after 10 days at 8° C.

| | Event-Gen | Transgenic | | | Control Non-Transgenics[a] | | | t-test |
|---|---|---|---|---|---|---|---|---|
| Events | | Avg | SE | N | Avg | SE | N | p-value |
| ME03186-04-99[b] | 04-T3 | 0.0045 | 0.0003 | 35 | 0.0030 | 0.0002 | 31 | 1.37E−05 |
| ME03186-04-99 | 04-T3 | 0.0092 | 0.0003 | 48 | 0.0051 | 0.0005 | 12 | 3.72E−10 |
| ME03186-04-99-03 | 04-T4 | 0.0107 | 0.0002 | 70 | 0.0083 | 0.0005 | 34 | 2.72E−05 |
| ME03186-04-99-04 | 04-T4 | 0.0120 | 0.0004 | 62 | 0.0083 | 0.0005 | 34 | 3.61E−08 |

TABLE 5-2-continued

T-test comparison of seedling area between transgenic seedlings
and control non-transgenic segregants after 10 days at 8° C.

| Events | Event-Gen | Transgenic Avg | SE | N | Control Non-Transgenics[a] Avg | SE | N | t-test p-value |
|---|---|---|---|---|---|---|---|---|
| ME03186-04-99-07 | 04-T4 | 0.0107 | 0.0003 | 69 | 0.0083 | 0.0005 | 34 | 4.91E−05 |
| ME03186-04-99-08 | 04-T4 | 0.0110 | 0.0003 | 69 | 0.0083 | 0.0005 | 34 | 5.53E−06 |
| ME03186-05[b] | 05-T2 | 0.0051 | 0.0005 | 22 | 0.0038 | 0.0005 | 6 | 0.0332 |
| ME03186-05 | 05-T2 | 0.0067 | 0.0003 | 53 | 0.0054 | 0.0005 | 9 | 0.0106 |
| ME03186-05-04 | 05-T3 | 0.0050 | 0.0003 | 50 | 0.0037 | 0.0003 | 9 | 0.0008 |

[a]Transgenic seedlings were compared to non-transgenic segregants within a seed line except for the $T_4$ generation of Event-04. Since these seed lines were homozygous, they were compared to pooled non-transgenic segregants from another $T_4$ generation event that was grown in the same flat as the $T_4$ generation of Event -04.
[b]These events were sown twice. The first time was to identify ME03186 as a hit. They were repeated the second time with two aenerations to identify ME03186 as a candidate.

Two Events of ME03186 Show 3:1 Segregation for Finale™ Resistance.

Event −05 segregated 3:1 (R: S) for Finale™ resistance in the $T_2$ generation. $T_2$ generation seed was not available for Event −04. However, the $T_3$ generation seeds that were pooled from several $T_2$ plants segregated approximately 2:1 in a manner consistent with a single insert (see Table 5-2).

Qualitative and Quantitative Analysis of the $T_2$ Plants (Screening for Negative Phenotypes):

Events −04 and −05 of ME03186 exhibited no statistically significant negative phenotypes.

Germination
  No detectable reduction in germination rate.
General morphology/architecture
  Plants appeared wild-type in all instances.
Days to flowering
  No observable or statistical differences between experimentals and controls.
Rosette area 7 days post-bolting

REFERENCES

Hunt et ak, (2001) *Plant Mol Biol* 47: 677-692.
Lu and Hills (2002) *Plant Physiol.* 129:1352-8

Example 6: Clone 1055099 (SEQ ID NO: 46)—ME 24967

In the same manner as Example 5, transgenics made with a construct of 35S-Clone 1055099 were screened for cold tolerance. Clone 1055099 (SEQ ID NO: 46) is a wheat functional homolog of clone 674166 (SEQ ID NO: 42), and showed the following results in the seedling cold tolerance assay.

TABLE 6-1

Cold Germination Assay results for ME24967.

| Event | p-values Internal[a] | Pooled[b] | Avg. Seedling Area Transgenic | Internal | Pooled | Sample No. Transgenic | Internal | Pooled |
|---|---|---|---|---|---|---|---|---|
| ME03186-04-99[c] | 0.00224438 | 0.00224438 | 0.0032 | 0.0017 | 0.0017 | 30 | 40 | 40 |
| ME24967-02 | 0.12660455 | 0.45511103 | 0.0053 | 0.0071 | 0.0054 | 29 | 5 | 83 |
| ME24967-03 [d] | 0.01488322 | 0.04610112 | 0.0069 | 0.0031 | 0.0054 | 31 | 3 | 83 |
| ME24967-05 [d] | 0.08783497 | 3.0406E−08 | 0.0115 | 0.0092 | 0.0054 | 23 | 12 | 83 |
| ME24967-10 | 0.40686041 | 0.25206736 | 0.0049 | 0.0053 | 0.0054 | 28 | 6 | 83 |
| ME24967-11 | 0.19290195 | 0.40123421 | 0.0051 | 0.0038 | 0.0054 | 5 | 25 | 83 |
| ME24967-12 | 0.3021565 | 0.00329335 | 0.0032 | 0.0050 | 0.0054 | 27 | 2 | 83 |
| ME24967-13 | 0.24672812 | 0.31347649 | 0.0060 | 0.0077 | 0.0054 | 23 | 7 | 83 |
| ME24967-14 | 0.17548824 | 0.29369895 | 0.0050 | 0.0032 | 0.0054 | 26 | 5 | 83 |
| ME24967-15 | 0.29278326 | 0.38586196 | 0.0057 | 0.0048 | 0.0054 | 22 | 11 | 83 |
| ME24967-16 |  | 0.05451794 | 0.0041 | 0.0018 | 0.0054 | 34 | 1 | 83 |
| ME24967-17 | 0.27484717 | 0.13660585 | 0.0044 | 0.0058 | 0.0054 | 26 | 6 | 83 |

[a]Internal controls are segregating non-transgenic seedlings within an Event.
[b]Pooled controls are all of the segregating non-transgenic seedlings from all of the Events within a line.
[c]ME03186 is a positive control to verify that the experimental conditions were appropriate.
[d] These events show significantly improved seedling area for at least internal or pooled controls.

Example 7—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA*, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e−5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 2, 7, 9, 20, 34, 40 and 42 are shown in FIGS. 1-7, respectively. The BLAST percent identities and E-values of functional homologs to SEQ ID NOs: 2, 7, 9, 20, 34, 40 and 42 are shown in the Sequence Listing. The BLAST sequence identities and E-values given in the Sequence Listing were taken from the forward search round of the Reciprocal BLAST process.

Example 8—Determination of Functional Homologs by Hidden Markov Models

Hidden Markov Models (HMMs) were generated by the program HMMER 2.3.2. To generate each HMM, the default HMMER 2.3.2 program parameters, configured for glocal alignments, were used.

An HMM was generated using the sequences shown in each of FIGS. 1-7 as input. Additional sequences were input into the model, and the HMM bit scores for the additional sequences are shown in the Sequence Listing. The results indicate that these additional sequences are functional homologs of SEQ ID NOs: 2, 7, 9, 20, 34, 40 and 42, respectively. The bit score results are provided in Table 7.

TABLE 7

| Query Identifier | Functional Homolog | Sequence Type | Species | Seq Id No | Length | Pfam |
|---|---|---|---|---|---|---|
| | Ceres CLONE ID no. 30087 | DNA | Arabidopsis thaliana | 1 | 828 | |
| Ceres CLONE ID no. 30087 | Ceres CLONE ID no. 30087 | PRT | Arabidopsis thaliana | 2 | 164 | |
| Ceres Clone ID no. 30087 | Ceres CLONE ID no. 947579 | PRT | Brassica napus | 3 | 155 | |
| Ceres Clone ID no. 30087 | Public GI no. 62526422 | PRT | Brassica napus | 4 | 152 | |
| Ceres Clone ID no. 30087 | Ceres CLONE ID no. 1606506 | PRT | Parthenium argentatum | 5 | 150 | |
| | Ceres CLONE ID no. 30469 | DNA | Artificial Sequence | 6 | 586 | |
| Ceres CLONE ID no. 30469 | Ceres CLONE ID no. 30469 | PRT | Artificial Sequence | 7 | 78 | Globin |
| | Ceres CLONE ID no. 30469_FL | DNA | Arabidopsis thaliana | 8 | 483 | |
| Ceres Clone ID no. 30469 | Ceres CLONE ID no. 30469_FL | PRT | Arabidopsis thaliana | 9 | 160 | Globin |
| Ceres Clone ID no. 30469 | Public GI no. 30909306 | PRT | Raphanus sativus | 10 | 160 | Globin |
| Ceres Clone ID no. 30469 | Public GI no. 37903656 | PRT | Arabidopsis thaliana | 11 | 158 | Globin |
| Ceres Clone ID no. 30469 | Public GI no. 15824736 | PRT | Arabidopsis thaliana | 12 | 163 | Globin |
| Ceres Clone ID no. 30469 | Ceres CLONE ID no. 546001 | PRT | Glycine max | 13 | 161 | Globin |
| Ceres Clone ID no. 30469 | Public GI no. 11095158 | PRT | Glycine max | 14 | 160 | Globin |
| Ceres Clone ID no. 30469 | Public GI no. 12963875 | PRT | Glycine max | 15 | 152 | Globin |
| Ceres Clone ID no. 30469 | Ceres CLONE ID no. 1554560 | PRT | Zea mays | 16 | 165 | Globin |
| Ceres Clone ID no. 30469 | Ceres CLONE ID no. 839727 | PRT | Triticum aestivum | 17 | 162 | Globin |
| Ceres Clone ID no. 30469 | Public GI no. 14701800 | PRT | Triticum aestivum | 18 | 169 | Globin |
| | Ceres CLONE ID no. 271922 | DNA | Arabidopsis thaliana | 19 | 416 | |
| Ceres CLONE ID no. 271922 | Ceres CLONE ID no. 271922 | PRT | Arabidopsis thaliana | 20 | 92 | Ribosomal_L37ae; |
| Ceres Clone ID no. 271922 | Public GI no. 4090257 | PRT | Arabidopsis thaliana | 21 | 92 | Ribosomal_L37ae |
| Ceres Clone ID no. 271922 | Public GI no. 4741896 | PRT | Arabidopsis thaliana | 22 | 92 | Ribosomal_L37ae |
| Ceres Clone ID no. 271922 | Ceres CLONE ID no. 36046 | PRT | Arabidopsis thaliana | 23 | 92 | Ribosomal_L37ae |
| Ceres Clone ID no. 271922 | Public GI no. 6016699 | PRT | Arabidopsis thaliana | 24 | 92 | Ribosomal_L37ae |
| Ceres Clone ID no. 271922 | Ceres CLONE ID no. 664936 | PRT | Glycine max | 25 | 92 | Ribosomal_L37ae |
| Ceres Clone ID no. 271922 | Ceres CLONE ID no. 658438 | PRT | Glycine max | 26 | 92 | Ribosomal_L37ae |
| Ceres Clone ID no. 271922 | Ceres CLONE ID no. 1049262 | PRT | Glycine max | 27 | 92 | Ribosomal_L37ae |
| Ceres Clone ID no. 271922 | Ceres CLONE ID no. 632613 | PRT | Triticum aestivum | 28 | 92 | Ribosomal_L37ae |
| Ceres Clone ID no. 271922 | Ceres CLONE ID no. 1390976 | PRT | Zea mays | 29 | 92 | Ribosomal_L37ae |
| Ceres Clone ID no. 271922 | Ceres CLONE ID no. 1457185 | PRT | Zea mays | 30 | 92 | Ribosomal_L37ae |
| Ceres Clone ID no. 271922 | Public GI no. 56202147 | PRT | Zea mays | 31 | 92 | Ribosomal_L37ae |
| Ceres Clone ID no. 271922 | Public GI no. 58578274 | PRT | Zea mays | 32 | 92 | Ribosomal_L37ae |
| | Ceres CLONE ID no. 2403_FL | DNA | Arabidopsis thaliana | 33 | 632 | |

TABLE 7-continued

| | | | | | | |
|---|---|---|---|---|---|---|
| Ceres CLONE ID no. 2403 | Ceres CLONE ID no. 2403_FL | PRT | Arabidopsis thaliana | 34 | 154 | ubiquitin; |
| Ceres CLONE ID no. 2403 | Ceres CLONE ID no. 2403_FL | PRT | Arabidopsis thaliana | 34 | 154 | ubiquitin; |
| Ceres Clone ID no. 2403 | Ceres CLONE ID no. 1482731 | PRT | Zea mays | 35 | 169 | ubiquitin |
| Ceres Clone ID no. 2403 | Ceres CLONE ID no. 1482731 | PRT | Zea mays | 35 | 169 | ubiquitin |
| Ceres Clone ID no. 2403 | Ceres CLONE ID no. 522921 | PRT | Glycine max | 36 | 154 | ubiquitin |
| Ceres Clone ID no. 2403 | Ceres CLONE ID no. 522921 | PRT | Glycine max | 36 | 154 | ubiquitin |
| Ceres Clone ID no. 2403 | Ceres CLONE ID no. 1036726 | PRT | Brassica napus | 37 | 160 | ubiquitin |
| Ceres Clone ID no. 2403 | Ceres CLONE ID no. 1036726 | PRT | Brassica napus | 37 | 160 | ubiquitin |
| Ceres Clone ID no. 2403 | Ceres CLONE ID no. 513071 | PRT | Glycine max | 38 | 188 | ubiquitin |
| Ceres Clone ID no. 2403 | Ceres CLONE ID no. 513071 | PRT | Glycine max | 38 | 188 | ubiquitin |
| | Ceres CLONE ID no. 2403 | DNA | Artificial Sequence | 39 | 620 | |
| Ceres CLONE ID no. 2403 | Ceres CLONE ID no. 2403 | PRT | Artificial Sequence | 40 | 33 | ubiquitin; |
| | Ceres CLONE ID no. 674166 | DNA | Glycine max | 41 | 1106 | |
| Ceres CLONE ID no. 674166 | Ceres CLONE ID no. 674166 | PRT | Glycine max | 42 | 210 | AP2; |
| Ceres Clone ID no. 674166 | Public GI no. 12322345 | PRT | Glycine max | 43 | 225 | AP2 |
| Ceres Clone ID no. 674166 | Ceres CLONE ID no. 975672 | PRT | Brassica napus | 44 | 215 | AP2 |
| Ceres Clone ID no. 674166 | Ceres CLONE ID no. 273307 | PRT | Zea mays | 45 | 211 | AP2 |
| Ceres Clone ID no. 674166 | Ceres CLONE ID no. 1055099 | PRT | Triticum aestivum | 46 | 194 | AP2 |
| | Ceres ANNOT ID no. 1441430 | DNA | Populus balsamifera subsp. trichocarpa | 47 | 660 | |
| Ceres CLONE ID no. 674166 | Ceres ANNOT ID no. 1441430 | PRT | Populus balsamifera subsp. trichocarpa | 48 | 219 | AP2 |
| | Ceres CLONE ID no. 1240330 | DNA | Glycine max | 49 | 985 | |
| Ceres CLONE ID no. 674166 | Ceres CLONE ID no. 1240330 | PRT | Glycine max | 50 | 222 | AP2 |
| | Ceres CLONE ID no. 1382611 | DNA | Zea mays | 51 | 726 | |
| Ceres CLONE ID no. 30087 | Ceres CLONE ID no. 1382611 | PRT | Zea mays | 52 | 156 | |
| | Ceres CLONE ID no. 1627907 | DNA | Papaver somniferum | 53 | 580 | |
| Ceres CLONE ID no. 271922 | Ceres CLONE ID no. 1627907 | PRT | Papaver somniferum | 54 | 92 | Ribosomal_L37ae |
| | Ceres CLONE ID no. 1761125 | DNA | Panicum virgatum | 55 | 983 | |
| Ceres CLONE ID no. 674166 | Ceres CLONE ID no. 1761125 | PRT | Panicum virgatum | 56 | 192 | AP2 |
| | Ceres CLONE ID no. 1783890 | DNA | Panicum virgatum | 57 | 594 | |
| Ceres CLONE ID no. 271922 | Ceres CLONE ID no. 1783890 | PRT | Panicum virgatum | 58 | 92 | Ribosomal_L37ae |
| | Ceres CLONE ID no. 1802327 | DNA | Panicum virgatum | 59 | 880 | |
| Ceres Clone ID no. 30469 | Ceres CLONE ID no. 1802327 | PRT | Panicum virgatum | 60 | 162 | Globin |
| | Ceres CLONE ID no. 1838364 | DNA | Gossypium hirsutum | 61 | 1017 | |
| Ceres CLONE ID no. 674166 | Ceres CLONE ID no. 1838364 | PRT | Gossypium hirsutum | 62 | 246 | AP2 |
| | Ceres CLONE ID no. 1876458 | DNA | Panicum virgatum | 63 | 708 | |
| Ceres Clone ID no. 30469 | Ceres CLONE ID no. 1876458 | PRT | Panicum virgatum | 64 | 162 | Globin |
| | Ceres CLONE ID no. 1879148 | DNA | Panicum virgatum | 65 | 712 | |
| Ceres Clone ID no. 30469 | Ceres CLONE ID no. 1879148 | PRT | Panicum virgatum | 66 | 164 | Globin |
| | Ceres CLONE ID no. 1884696 | DNA | Gossypium hirsutum | 67 | 1129 | |
| Ceres CLONE ID no. 2403 | Ceres CLONE ID no. 1884696 | PRT | Gossypium hirsutum | 68 | 153 | ubiquitin |
| Ceres CLONE ID no. 2403 | Ceres CLONE ID no. 1884696 | PRT | Gossypium hirsutum | 68 | 153 | ubiquitin |
| | Ceres CLONE ID no. 1916866 | DNA | Gossypium hirsutum | 69 | 679 | |
| Ceres Clone ID no. 30469 | Ceres CLONE ID no. 1916866 | PRT | Gossypium hirsutum | 70 | 163 | Globin |
| | Ceres CLONE ID no. 1950105 | DNA | Panicum virgatum | 71 | 1003 | |
| Ceres CLONE ID no. 2403 | Ceres CLONE ID no. 1950105 | PRT | Panicum virgatum | 72 | 229 | ubiquitin |
| Ceres CLONE ID no. 2403 | Ceres CLONE ID no. 1950105 | PRT | Panicum virgatum | 72 | 229 | ubiquitin |
| Ceres CLONE ID no. 2403 | Ceres CLONE ID no. 1950105 | PRT | Panicum virgatum | 72 | 229 | ubiquitin |
| | Ceres CLONE ID no. 1990746 | DNA | Panicum virgatum | 73 | 724 | |
| Ceres Clone ID no. 30469 | Ceres CLONE ID no. 1990746 | PRT | Panicum virgatum | 74 | 164 | Globin |
| | Ceres CLONE ID no. 2007485 | DNA | Panicum virgatum | 75 | 696 | |
| Ceres CLONE ID no. 674166 | Ceres CLONE ID no. 2007485 | PRT | Panicum virgatum | 76 | 201 | AP2 |
| | Ceres CLONE ID no. 2033803 | DNA | Panicum virgatum | 77 | 698 | |
| Ceres Clone ID no. 30469 | Ceres CLONE ID no. 2033803 | PRT | Panicum virgatum | 78 | 156 | Globin |
| | Ceres CLONE ID no. 2034916 | DNA | Panicum virgatum | 79 | 724 | |
| Ceres CLONE ID no. 2403 | Ceres CLONE ID no. 2034916 | PRT | Panicum virgatum | 80 | 213 | ubiquitin |
| Ceres CLONE ID no. 2403 | Ceres CLONE ID no. 2034916 | PRT | Panicum virgatum | 80 | 213 | ubiquitin |
| Ceres CLONE ID no. 2403 | Ceres CLONE ID no. 2034916 | PRT | Panicum virgatum | 80 | 213 | ubiquitin |
| | Ceres CLONE ID no.651581 | DNA | Glycine max | 81 | 1194 | |
| Ceres CLONE ID no. 674166 | Ceres CLONE ID no. 651581 | PRT | Glycine max | 82 | 224 | AP2 |
| Ceres CLONE ID no. 674166 | Public GI ID no. 125550159 | PRT | Oryza sativa subsp. indica | 83 | 184 | AP2 |
| Ceres CLONE ID no. 674166 | Public GI ID no. 15223609 | PRT | Arabidopsis thaliana | 84 | 225 | AP2 |
| Ceres CLONE ID no. 30087 | Public GI ID no. 30683885 | PRT | Arabidopsis thaliana | 85 | 164 | |
| Ceres CLONE ID no. 674166 | Public GI ID no. 56384582 | PRT | Pisum sativum | 86 | 218 | AP2 |
| Ceres CLONE ID no. 674166 | Public GI ID no. 57012880 | PRT | Nicotiana tabacum | 87 | 225 | AP2 |
| Ceres Clone ID no. 30469 | Public GI ID no. 62548111 | PRT | Gossypium hirsutum | 88 | 163 | Globin |
| Ceres CLONE ID no. 2403 | Ceres CLONE ID no. 100021733 | PRT | Gossypium hirsutum | 89 | 153 | ubiquitin |
| Ceres CLONE ID no. 2403 | Ceres CLONE ID no. 100021733 | PRT | Gossypium hirsutum | 89 | 153 | ubiquitin |
| | Ceres CLONE ID no. 947579 | DNA | Brassica napus | 90 | 775 | |
| | Ceres CLONE ID no. 36046 | DNA | Arabidopsis thaliana | 91 | 1032 | |
| | Ceres CLONE ID no. 1606506 | DNA | Parthenium argentatum | 92 | 492 | |
| | Ceres CLONE ID no. 546001 | DNA | Glycine max | 93 | 970 | |
| | Ceres CLONE ID no. 1554560 | DNA | Zea mays | 94 | 604 | |
| | Ceres CLONE ID no. 839727 | DNA | Triticum aestivum | 95 | 846 | |
| | Ceres CLONE ID no. 664936 | DNA | Glycine max | 96 | 440 | |
| | Ceres CLONE ID no. 658438 | DNA | Glycine max | 97 | 463 | |
| | Ceres CLONE ID no. 1049262 | DNA | Glycine max | 98 | 458 | |

TABLE 7-continued

| | | | | | | |
|---|---|---|---|---|---|---|
| | Ceres CLONE ID no. 632613 | DNA | *Triticum aestivum* | 99 | 600 | |
| | Ceres CLONE ID no. 1390976 | DNA | *Zea mays* | 100 | 546 | |
| | Ceres CLONE ID no. 1457185 | DNA | *Zea mays* | 101 | 550 | |
| | Ceres CLONE ID no. 1482731 | DNA | *Zea mays* | 102 | 668 | |
| | Ceres CLONE ID no. 522921 | DNA | *Glycine max* | 103 | 752 | |
| | Ceres CLONE ID no. 1036726 | DNA | *Brassica napus* | 104 | 484 | |
| | Ceres CLONE ID no. 513071 | DNA | *Glycine max* | 105 | 580 | |
| | Ceres CLONE ID no. 975672 | DNA | *Brassica napus* | 106 | 987 | |
| | Ceres CLONE ID no. 273307 | DNA | *Zea mays* | 107 | 1034 | |
| | Ceres CLONE ID no. 1055099 | DNA | *Triticum aestivum* | 108 | 911 | |
| Ceres Clone ID no. 30469 | Ceres GI ID no. GI_15226675 | PRT | *Arabidopsis thaliana* | 109 | 160 | Globin |
| | Ceres Promoter 21876 | DNA | *Arabidopsis thaliana* | 110 | 1823 | |
| | Ceres Promoter PT0668 | DNA | *Arabidopsis thaliana* | 111 | 1000 | |
| | Ceres Promoter PT0535 | DNA | *Arabidopsis thaliana* | 112 | 1000 | |
| | Ceres Promoter PT0585 | DNA | *Arabidopsis thaliana* | 113 | 999 | |
| | Ceres Promoter PT0613 | DNA | *Arabidopsis thaliana* | 114 | 1000 | |
| | Ceres Promoter PT0625 | DNA | *Arabidopsis thaliana* | 115 | 351 | |
| | Ceres Promoter PT0633 | DNA | *Arabidopsis thaliana* | 116 | 1022 | |
| | Ceres Promoter PT0650 | DNA | *Arabidopsis thaliana* | 117 | 1000 | |
| | Ceres Promoter PT0660 | DNA | *Arabidopsis thaliana* | 118 | 998 | |
| | Ceres Promoter PT0665 | DNA | *Arabidopsis thaliana* | 119 | 1000 | |
| | Ceres Promoter PT0672 | DNA | *Arabidopsis thaliana* | 120 | 999 | |
| | Ceres Promoter PT0676 | DNA | *Arabidopsis thaliana* | 121 | 1000 | |
| | Ceres Promoter PT0678 | DNA | *Arabidopsis thaliana* | 122 | 998 | |
| | Ceres Promoter PT0683 | DNA | *Arabidopsis thaliana* | 123 | 1000 | |
| | Ceres Promoter PT0688 | DNA | *Arabidopsis thaliana* | 124 | 1000 | |
| | Ceres Promoter PT0695 | DNA | *Arabidopsis thaliana* | 125 | 1000 | |
| | Ceres Promoter PT0708 | DNA | *Arabidopsis thaliana* | 126 | 1000 | |
| | Ceres Promoter PT0710 | DNA | *Arabidopsis thaliana* | 127 | 1000 | |
| | Ceres Promoter PT0723 | DNA | *Arabidopsis thaliana* | 128 | 1002 | |
| | Ceres Promoter PT0740 | DNA | *Arabidopsis thaliana* | 129 | 1001 | |
| | Ceres Promoter PT0743 | DNA | *Arabidopsis thaliana* | 130 | 1024 | |
| | Ceres Promoter PT0758 | DNA | *Arabidopsis thaliana* | 131 | 1000 | |
| | Ceres Promoter PT0829 | DNA | *Arabidopsis thaliana* | 132 | 921 | |
| | Ceres Promoter PT0837 | DNA | *Arabidopsis thaliana* | 133 | 763 | |
| | Ceres Promoter PT0838 | DNA | *Arabidopsis thaliana* | 134 | 751 | |
| | Ceres Promoter PT0848 | DNA | *Arabidopsis thaliana* | 135 | 669 | |
| | Ceres Promoter PT0863 | DNA | *Arabidopsis thaliana* | 136 | 702 | |
| | Ceres Promoter PT0879 | DNA | *Arabidopsis thaliana* | 137 | 435 | |
| | Ceres Promoter PT0886 | DNA | *Arabidopsis thaliana* | 138 | 397 | |
| | Ceres Promoter YP0007 | DNA | *Arabidopsis thaliana* | 139 | 1024 | |
| | Ceres Promoter YP0008 | DNA | *Arabidopsis thaliana* | 140 | 1000 | |
| | Ceres Promoter YP0019 | DNA | *Arabidopsis thaliana* | 141 | 999 | |
| | Ceres Promoter YP0028 | DNA | *Arabidopsis thaliana* | 142 | 1024 | |
| | Ceres Promoter YP0039 | DNA | *Arabidopsis thaliana* | 143 | 1024 | |
| | Ceres Promoter YP0050 | DNA | *Arabidopsis thaliana* | 144 | 1024 | |
| | Ceres Promoter YP0086 | DNA | *Arabidopsis thaliana* | 145 | 999 | |
| | Ceres Promoter YP0088 | DNA | *Arabidopsis thaliana* | 146 | 1024 | |
| | Ceres Promoter YP0092 | DNA | *Arabidopsis thaliana* | 147 | 1024 | |
| | Ceres Promoter YP0096 | DNA | *Arabidopsis thaliana* | 148 | 1020 | |
| | Ceres Promoter YP0097 | DNA | *Arabidopsis thaliana* | 149 | 1000 | |
| | Ceres Promoter YP0101 | DNA | *Arabidopsis thaliana* | 150 | 1004 | |
| | Ceres Promoter YP0102 | DNA | *Arabidopsis thaliana* | 151 | 1000 | |
| | Ceres Promoter YP0103 | DNA | *Arabidopsis thaliana* | 152 | 1004 | |
| | Ceres Promoter YP0107 | DNA | *Arabidopsis thaliana* | 153 | 1003 | |
| | Ceres Promoter YP0110 | DNA | *Arabidopsis thaliana* | 154 | 1024 | |
| | Ceres Promoter YP0111 | DNA | *Arabidopsis thaliana* | 155 | 1024 | |
| | Ceres Promoter YP0115 | DNA | *Arabidopsis thaliana* | 156 | 996 | |
| | Ceres Promoter YP0117 | DNA | *Arabidopsis thaliana* | 157 | 1024 | |
| | Ceres Promoter YP0119 | DNA | *Arabidopsis thaliana* | 158 | 1000 | |
| | Ceres Promoter YP0120 | DNA | *Arabidopsis thaliana* | 159 | 999 | |
| | Ceres Promoter YP0121 | DNA | *Arabidopsis thaliana* | 160 | 999 | |
| | Ceres Promoter YP0128 | DNA | *Arabidopsis thaliana* | 161 | 1004 | |
| | Ceres Promoter YP0137 | DNA | *Arabidopsis thaliana* | 162 | 1001 | |
| | Ceres Promoter YP0143 | DNA | *Arabidopsis thaliana* | 163 | 1001 | |
| | Ceres Promoter YP0144 | DNA | *Arabidopsis thaliana* | 164 | 1003 | |
| | Ceres Promoter YP0156 | DNA | *Arabidopsis thaliana* | 165 | 1004 | |
| | Ceres Promoter YP0158 | DNA | *Arabidopsis thaliana* | 166 | 1000 | |
| | Ceres Promoter YP0188 | DNA | *Arabidopsis thaliana* | 167 | 1005 | |
| | Ceres Promoter YP0190 | DNA | *Arabidopsis thaliana* | 168 | 1002 | |
| | Ceres Promoter YP0212 | DNA | *Arabidopsis thaliana* | 169 | 995 | |
| | Ceres Promoter YP0214 | DNA | *Arabidopsis thaliana* | 170 | 1024 | |
| | Ceres Promoter YP0263 | DNA | *Arabidopsis thaliana* | 171 | 911 | |
| | Ceres Promoter YP0275 | DNA | *Arabidopsis thaliana* | 172 | 999 | |
| | Ceres Promoter YP0285 | DNA | *Arabidopsis thaliana* | 173 | 981 | |
| | Ceres Promoter YP0286 | DNA | *Arabidopsis thaliana* | 174 | 996 | |
| | Ceres Promoter YP0337 | DNA | *Arabidopsis thaliana* | 175 | 1000 | |
| | Ceres Promoter YP0356 | DNA | *Arabidopsis thaliana* | 176 | 1000 | |
| | Ceres Promoter YP0374 | DNA | *Arabidopsis thaliana* | 177 | 1000 | |
| | Ceres Promoter YP0377 | DNA | *Arabidopsis thaliana* | 178 | 998 | |

TABLE 7-continued

| | | | | | | |
|---|---|---|---|---|---|---|
| | Ceres Promoter YP0380 | DNA | *Arabidopsis thaliana* | 179 | 999 | |
| | Ceres Promoter YP0381 | DNA | *Arabidopsis thaliana* | 180 | 1000 | |
| | Ceres Promoter YP0384 | DNA | *Arabidopsis thaliana* | 181 | 999 | |
| | Ceres Promoter YP0385 | DNA | *Arabidopsis thaliana* | 182 | 998 | |
| | Ceres Promoter YP0396 | DNA | *Arabidopsis thaliana* | 183 | 1000 | |
| | Ceres Promoter p13879 | DNA | *Arabidopsis thaliana* | 184 | 1514 | |
| | Ceres Promoter p326 | DNA | *Arabidopsis thaliana* | 185 | 1954 | |
| | Ceres Promoter p32449 | DNA | *Arabidopsis thaliana* | 186 | 2016 | |
| | Ceres Promoter PD1367 | DNA | *Arabidopsis thaliana* | 187 | 667 | |
| | Ceres Promoter p530c10 | DNA | *Oryza sativa* | 188 | 1836 | |
| | Ceres Promoter pOsFIE2-2 | DNA | *Oryza sativa* | 189 | 3000 | |
| | Ceres Promoter pOsMEA | DNA | *Oryza sativa* | 190 | 2023 | |
| | Ceres Promoter pOsYp102 | DNA | *Oryza sativa* | 191 | 2034 | |
| | Ceres Promoter pOsYp285 | DNA | *Oryza sativa* | 192 | 1877 | |
| | Ceres Promoter PT0565 | DNA | *Arabidopsis thaliana* | 193 | 1000 | |
| | Ceres Promoter YP0015 | DNA | *Arabidopsis thaliana* | 194 | 999 | |
| | Ceres Promoter YP0087 | DNA | *Arabidopsis thaliana* | 195 | 999 | |
| | Ceres Promoter YP0093 | DNA | *Arabidopsis thaliana* | 196 | 1000 | |
| | Ceres Promoter YP0108 | DNA | *Arabidopsis thaliana* | 197 | 999 | |
| | Ceres Promoter YP0022 | DNA | *Arabidopsis thaliana* | 198 | 999 | |
| | Ceres Promoter YP0080 | DNA | *Arabidopsis thaliana* | 199 | 999 | |
| | Ceres Promoter PR0924 | DNA | *Arabidopsis thaliana* | 200 | 3000 | |
| | Ceres Promoter YP0388 | DNA | *Arabidopsis thaliana* | 201 | 1000 | |
| | Ceres Promoter PD0901 | DNA | *Arabidopsis thaliana* | 202 | 283 | |
| | Ceres Promoter PT0623 | DNA | *Arabidopsis thaliana* | 203 | 1000 | |
| Ceres Clone ID no. 2403 | Truncated version of Ceres CLONE ID no. 100021733 | PRT | Artificial Sequence | 204 | 33 | ubiquitin |
| Ceres Clone ID no. 2403 | Truncated version of Ceres CLONE ID no. 1036726 | PRT | Artificial Sequence | 205 | 33 | ubiquitin |
| Ceres Clone ID no. 2403 | Truncated version of Ceres CLONE ID no. 1482731 | PRT | Artificial Sequence | 206 | 33 | ubiquitin |
| Ceres Clone ID no. 30469 | Truncated Version of Ceres CLONE ID no. 1554560 | PRT | Artificial Sequence | 207 | 80 | Globin |
| Ceres Clone ID no. 30469 | Truncated Version of Ceres CLONE ID no. 1802327 | PRT | Artificial Sequence | 208 | 77 | Globin |
| Ceres Clone ID no. 30469 | Truncated Version of Ceres CLONE ID no. 1876458 | PRT | Artificial Sequence | 209 | 77 | Globin |
| Ceres Clone ID no. 30469 | Truncated Version of Ceres CLONE ID no. 1879148 | PRT | Artificial Sequence | 210 | 79 | Globin |
| Ceres Clone ID no. 2403 | Truncated version of Ceres CLONE ID no. 1884696 | PRT | Artificial Sequence | 211 | 33 | ubiquitin |
| Ceres Clone ID no. 30469 | Truncated Version of Ceres CLONE ID no. 1916866 | PRT | Artificial Sequence | 212 | 76 | Globin |
| Ceres Clone ID no. 2403 | Truncated version of Ceres CLONE ID no. 1950105 | PRT | Artificial Sequence | 213 | 33 | ubiquitin |
| Ceres Clone ID no. 30469 | Truncated Version of Ceres CLONE ID no. 1990746 | PRT | Artificial Sequence | 214 | 79 | Globin |
| Ceres Clone ID no. 30469 | Truncated Version of Ceres CLONE ID no. 2033803 | PRT | Artificial Sequence | 215 | 79 | Globin |
| Ceres Clone ID no. 2403 | Truncated version of Ceres CLONE ID no. 2034916 | PRT | Artificial Sequence | 216 | 33 | ubiquitin |
| Ceres Clone ID no. 2403 | Truncated version of Ceres CLONE ID no. 513071 | PRT | Artificial Sequence | 217 | 33 | ubiquitin |
| Ceres Clone ID no. 2403 | Truncated version of Ceres CLONE ID no. 522921 | PRT | Artificial Sequence | 218 | 33 | ubiquitin |
| Ceres Clone ID no. 30469 | Truncated Version of Ceres CLONE ID no. 546001 | PRT | Artificial Sequence | 219 | 76 | Globin |
| Ceres Clone ID no. 30469 | Truncated Version of Ceres CLONE ID no. 651581 | PRT | Artificial Sequence | 220 | 76 | Globin |
| Ceres Clone ID no. 30469 | Truncated Version of Ceres CLONE ID no. 839727 | PRT | Artificial Sequence | 221 | 77 | Globin |
| Ceres Clone ID no. 30469 | Truncated Version of Public GI ID no. 11095158 | PRT | Artificial Sequence | 222 | 76 | Globin |
| Ceres Clone ID no. 30469 | Truncated Version of Public GI ID no. 12963875 | PRT | Artificial Sequence | 223 | 71 | Globin |
| Ceres Clone ID no. 30469 | Truncated Version of Public GI ID no. 14701800 | PRT | Artificial Sequence | 224 | 84 | Globin |
| Ceres Clone ID no. 30469 | Truncated Version of Public GI ID no. 15226675 | PRT | Artificial Sequence | 225 | 76 | Globin |
| Ceres Clone ID no. 30469 | Truncated Version of Public GI ID no. 15824736 | PRT | Artificial Sequence | 226 | 76 | Globin |
| Ceres Clone ID no. 30469 | Truncated Version of Public GI ID no. 30909306 | PRT | Artificial Sequence | 227 | 76 | Globin |
| Ceres Clone ID no. 30469 | Truncated Version of Public GI ID no. 37903656 | PRT | Artificial Sequence | 228 | 73 | Globin |
| Ceres Clone ID no. 30469 | Truncated Version of Public GI ID no. 62548111 | PRT | Artificial Sequence | 229 | 76 | Globin |

TABLE 7-continued

| Query Identifier | Functional Homolog | Pfam Description | Start | End | Pro-file | HMM Bit Score | FL_Profile | FL_Score |
|---|---|---|---|---|---|---|---|---|
| Ceres CLONE ID no. 30087 | Ceres CLONE ID no. 30087 | | | | Y | | | |
| Ceres Clone ID no. 30087 | Ceres CLONE ID no. 947579 | | | | Y | | | |
| Ceres Clone ID no. 30087 | Public GI no. 62526422 | | | | | | | |
| Ceres Clone ID no. 30087 | Ceres Clone ID no. 1606506 | | | | Y | | | |
| Ceres CLONE ID no. 30469 | Ceres CLONE ID no. 30469 | Globin | 13 | 74 | Y | 184.6 | | 66 |
| Ceres Clone ID no. 30469 | Ceres CLONE ID no. 30469_FL | Globin | 13 | 152 | 184.6 | | Y | 404.9 |
| Ceres Clone ID no. 30469 | Public GI no. 30909306 | Globin | 13 | 152 | | 185.7 | Y | 410.4 |
| Ceres Clone ID no. 30469 | Public GI no. 37903656 | Globin | 10 | 149 | | 172.6 | | 387.2 |
| Ceres Clone ID no. 30469 | Public GI no. 15824736 | Globin | 13 | 152 | | 184.2 | | 405.4 |
| Ceres Clone ID no. 30469 | Ceres CLONE ID no. 546001 | Globin | 13 | 152 | | 182.8 | Y | 402.3 |
| Ceres Clone ID no. 30469 | Public GI no. 11095158 | Globin | 13 | 152 | | 167.8 | | 387.2 |
| Ceres Clone ID no. 30469 | Public GI no. 12963875 | Globin | 8 | 147 | | 145.8 | | 337.1 |
| Ceres Clone ID no. 30469 | Ceres CLONE ID no. 1554560 | Globin | 17 | 157 | | 185.7 | Y | 404.5 |
| Ceres Clone ID no. 30469 | Ceres CLONE ID no. 839727 | Globin | 14 | 154 | | 187.8 | Y | 415.2 |
| Ceres Clone ID no. 30469 | Public GI no. 14701800 | Globin | 21 | 161 | | 170.1 | | 386.9 |
| Ceres CLONE ID no. 271922 | Ceres CLONE ID no. 271922 | Ribosomal L37ae protein family | 2 | 91 | Y | 266.3 | | |
| Ceres Clone ID no. 271922 | Public GI no. 4090257 | Ribosomal L37ae protein family | 2 | 91 | | 265.8 | | |
| Ceres Clone ID no. 271922 | Public GI no. 4741896 | Ribosomal L37ae protein family | 2 | 91 | | 264 | | |
| Ceres Clone ID no. 271922 | Ceres CLONE ID no. 36046 | Ribosomal L37ae protein family | 2 | 91 | | 257.8 | | |
| Ceres Clone ID no. 271922 | Public GI no. 6016699 | Ribosomal L37ae protein family | 2 | 91 | | 257.4 | | |
| Ceres Clone ID no. 271922 | Ceres CLONE ID no. 664936 | Ribosomal L37ae protein family | 2 | 91 | Y | 268.8 | | |
| Ceres Clone ID no. 271922 | Ceres CLONE ID no. 658438 | Ribosomal L37ae protein family | 2 | 91 | | 269 | | |
| Ceres Clone ID no. 271922 | Ceres CLONE ID no. 1049262 | Ribosomal L37ae protein family | 2 | 91 | | 268.9 | | |
| Ceres Clone ID no. 271922 | Ceres CLONE ID no. 632613 | Ribosomal L37ae protein family | 2 | 91 | Y | 269 | | |
| Ceres Clone ID no. 271922 | Ceres CLONE ID no. 1390976 | Ribosomal L37ae protein family | 2 | 91 | Y | 269 | | |
| Ceres Clone ID no. 271922 | Ceres CLONE ID no. 1457185 | Ribosomal L37ae protein family | 2 | 91 | | 269 | | |
| Ceres Clone ID no. 271922 | Public GI no. 56202147 | Ribosomal L37ae protein family | 2 | 91 | | 269 | | |
| Ceres Clone ID no. 271922 | Public GI no. 58578274 | Ribosomal L37ae protein family | 2 | 91 | | 267.2 | | |
| Ceres CLONE ID no. 2403 | Ceres CLONE ID no. 2403_FL | Ubiquitin family | 1 | 74 | | 118.7 | | 416.2 |
| Ceres CLONE ID no. 2403 | Ceres CLONE ID no. 2403_FL | Ubiquitin family | 77 | 150 | | 118.7 | Y | 416.2 |

TABLE 7-continued

| Col1 | Col2 | Family | Start | End | Flag1 | Score | Flag2 | Score2 |
|---|---|---|---|---|---|---|---|---|
| Ceres Clone ID no. 2403 | Ceres CLONE ID no. 1482731 | Ubiquitin family | 1 | 74 | | 118.3 | Y | 417 |
| Ceres Clone ID no. 2403 | Ceres CLONE ID no. 1482731 | Ubiquitin family | 77 | 150 | | 118.3 | Y | 417 |
| Ceres Clone ID no. 2403 | Ceres CLONE ID no. 522921 | Ubiquitin family | 1 | 74 | | 118.7 | Y | 418.4 |
| Ceres Clone ID no. 2403 | Ceres CLONE ID no. 522921 | Ubiquitin family | 77 | 150 | | 118.7 | Y | 418.4 |
| Ceres Clone ID no. 2403 | Ceres CLONE ID no. 1036726 | Ubiquitin family | 1 | 74 | | 118.7 | | 384.4 |
| Ceres Clone ID no. 2403 | Ceres CLONE ID no. 1036726 | Ubiquitin family | 77 | 142 | | 118.7 | Y | 384.4 |
| Ceres Clone ID no. 2403 | Ceres CLONE ID no. 513071 | Ubiquitin family | 1 | 74 | | 114.3 | | 408.6 |
| Ceres Clone ID no. 2403 | Ceres CLONE ID no. 513071 | Ubiquitin family | 77 | 150 | | 114.3 | | 408.6 |
| Ceres CLONE ID no. 2403 | Ceres CLONE ID no. 2403 | Ubiquitin family | 1 | 33 | Y | 87.6 | | -83.1 |
| Ceres CLONE ID no. 674166 | Ceres CLONE ID no. 674166 | AP2 domain | 26 | 89 | Y | 491.8 | | |
| Ceres Clone ID no. 674166 | Public GI no. 12322345 | AP2 domain | 26 | 89 | | 522.4 | | |
| Ceres Clone ID no. 674166 | Ceres CLONE ID no. 975672 | AP2 domain | 21 | 84 | Y | 481.7 | | |
| Ceres Clone ID no. 674166 | Ceres CLONE ID no. 273307 | AP2 domain | 17 | 80 | Y | 419.7 | | |
| Ceres Clone ID no. 674166 | Ceres CLONE ID no. 1055099 | AP2 domain | 20 | 83 | Y | 358.4 | | |
| Ceres CLONE ID no. 674166 | Ceres ANNOT ID no. 1441430 | AP2 domain | 29 | 92 | Y | 504.4 | | |
| Ceres CLONE ID no. 674166 | Ceres CLONE ID no. 1240330 | AP2 domain | 24 | 87 | | 483.3 | | |
| Ceres CLONE ID no. 30087 | Ceres CLONE ID no. 1382611 | | | | Y | | | |
| Ceres CLONE ID no. 271922 | Ceres CLONE ID no. 1627907 | Ribosomal L37ae protein family | 2 | 91 | Y | 268.1 | | |
| Ceres CLONE ID no. 674166 | Ceres CLONE ID no. 1761125 | AP2 domain | 13 | 76 | Y | 363 | | |
| Ceres CLONE ID no. 271922 | Ceres CLONE ID no. 1783890 | Ribosomal L37ae protein family | 2 | 91 | Y | 269 | | |
| Ceres Clone ID no. 30469 | Ceres CLONE ID no. 1802327 | Globin | 14 | 154 | | 191.4 | Y | 417.9 |
| Ceres CLONE ID no. 674166 | Ceres CLONE ID no. 1838364 | AP2 domain | 28 | 91 | Y | 484.1 | | |
| Ceres Clone ID no. 30469 | Ceres CLONE ID no. 1876458 | Globin | 14 | 154 | | 191.9 | | 415.3 |
| Ceres Clone ID no. 30469 | Ceres CLONE ID no. 1879148 | Globin | 16 | 156 | | 185.7 | | 411.2 |
| Ceres CLONE ID no. 2403 | Ceres CLONE ID no. 1884696 | Ubiquitin family | 1 | 74 | | 175.2 | Y | 408 |
| Ceres CLONE ID no. 2403 | Ceres CLONE ID no. 1884696 | Ubiquitin family | 77 | 150 | | 175.2 | Y | 408 |
| Ceres Clone ID no. 30469 | Ceres CLONE ID no. 1916866 | Globin | 13 | 152 | | 188.3 | Y | 409.8 |
| Ceres CLONE ID no. 2403 | Ceres CLONE ID no. 1950105 | Ubiquitin family | 1 | 74 | | 262.8 | | 504.1 |
| Ceres CLONE ID no. 2403 | Ceres CLONE ID no. 1950105 | Ubiquitin family | 77 | 150 | | 262.8 | | 504.1 |
| Ceres CLONE ID no. 2403 | Ceres CLONE ID no. 1950105 | Ubiquitin family | 153 | 226 | | 262.8 | | 504.1 |
| Ceres Clone ID no. 30469 | Ceres CLONE ID no. 1990746 | Globin | 16 | 156 | | 184.9 | | 405.6 |
| Ceres CLONE ID no. 674166 | Ceres CLONE ID no. 2007485 | AP2 domain | 17 | 80 | | 369.2 271.2 | | |
| | Ceres CLONE ID no. 2033803 | | | | | | | |

TABLE 7-continued

| | | | | | | | |
|---|---|---|---|---|---|---|---|
| Ceres Clone ID no. 30469 | Ceres CLONE ID no. 2033803 | Globin | 16 | 148 | 184.9 | | 369.2 |
| Ceres CLONE ID no. 2403 | Ceres CLONE ID no. 2034916 | Ubiquitin family | 1 | 74 | 259.2 | Y | 460.4 |
| Ceres CLONE ID no. 2403 | Ceres CLONE ID no. 2034916 | Ubiquitin family | 77 | 150 | 259.2 | Y | 460.4 |
| Ceres CLONE ID no. 2403 | Ceres CLONE ID no. 2034916 | Ubiquitin family | 153 | 213 | 259.2 | Y | 460.4 |
| Ceres CLONE ID no. 674166 | Ceres CLONE ID no. 651581 | AP2 domain | 24 | 87 | 469.5 | | |
| Ceres CLONE ID no. 674166 | Public GI ID no. 125550159 | AP2 domain | 7 | 70 | | Y | 344 |
| Ceres CLONE ID no. 674166 | Public GI ID no. 15223609 | AP2 domain | 26 | 89 | | Y | 522.4 |
| Ceres CLONE ID no. 30087 | Public GI ID no. 30683885 | | | | | | |
| Ceres CLONE ID no. 674166 | Public GI ID no. 56384582 | AP2 domain | 21 | 84 | | Y | 484.2 |
| Ceres CLONE ID no. 674166 | Public GI ID no. 57012880 | AP2 domain | 26 | 89 | | Y | 521.4 |
| Ceres Clone ID no. 30469 | Public GI ID no. 62548111 | Globin | 13 | 152 | 188.3 | | 409.8 |
| Ceres CLONE ID no. 2403 | Ceres CLONE ID no. 100021733 | Ubiquitin family | 1 | 74 | 175.2 | | 410.3 |
| Ceres CLONE ID no. 2403 | Ceres CLONE ID no. 100021733 | Ubiquitin family | 77 | 150 | 175.2 | | 410.3 |
| Ceres Clone ID no. 30469 | Ceres CLONE ID no. 947579 Ceres CLONE ID no. 36046 Ceres CLONE ID no. 1606506 Ceres CLONE ID no. 546001 Ceres CLONE ID no. 1554560 Ceres CLONE ID no. 839727 Ceres CLONE ID no. 664936 Ceres CLONE ID no. 658438 Ceres CLONE ID no. 1049262 Ceres CLONE ID no. 632613 Ceres CLONE ID no. 1390976 Ceres CLONE ID no. 1457185 Ceres CLONE ID no. 1482731 Ceres CLONE ID no. 522921 Ceres CLONE ID no. 1036726 Ceres CLONE ID no. 513071 Ceres CLONE ID no. 975672 Ceres CLONE ID no. 273307 Ceres CLONE ID no. 1055099 Ceres GI ID no. GI_15226675 Ceres Promoter 21876 Ceres Promoter PT0668 Ceres Promoter PT0535 Ceres Promoter PT0585 Ceres Promoter PT0613 Ceres Promoter PT0625 Ceres Promoter PT0633 Ceres Promoter PT0650 Ceres Promoter PT0660 Ceres Promoter PT0665 Ceres Promoter PT0672 Ceres Promoter PT0676 Ceres Promoter PT0678 Ceres Promoter PT0683 Ceres Promoter PT0688 Ceres Promoter PT0695 Ceres Promoter PT0708 Ceres Promoter PT0710 Ceres Promoter PT0723 Ceres Promoter PT0740 Ceres Promoter PT0743 Ceres Promoter PT0758 Ceres Promoter PT0829 Ceres Promoter PT0837 Ceres Promoter PT0838 Ceres Promoter PT0848 Ceres Promoter PT0863 Ceres Promoter PT0879 Ceres Promoter PT0886 Ceres Promoter YP0007 Ceres Promoter YP0008 Ceres Promoter YP0019 Ceres Promoter YP0028 Ceres Promoter YP0039 Ceres Promoter YP0050 | Globin | 13 | 152 | 184.6 | | 404.9 |

TABLE 7-continued

|  |  |  |  |  |  |  |  |
|---|---|---|---|---|---|---|---|
|  | Ceres Promoter YP0086 |  |  |  |  |  |  |
|  | Ceres Promoter YP0088 |  |  |  |  |  |  |
|  | Ceres Promoter YP0092 |  |  |  |  |  |  |
|  | Ceres Promoter YP0096 |  |  |  |  |  |  |
|  | Ceres Promoter YP0097 |  |  |  |  |  |  |
|  | Ceres Promoter YP0101 |  |  |  |  |  |  |
|  | Ceres Promoter YP0102 |  |  |  |  |  |  |
|  | Ceres Promoter YP0103 |  |  |  |  |  |  |
|  | Ceres Promoter YP0107 |  |  |  |  |  |  |
|  | Ceres Promoter YP0110 |  |  |  |  |  |  |
|  | Ceres Promoter YP0111 |  |  |  |  |  |  |
|  | Ceres Promoter YP0115 |  |  |  |  |  |  |
|  | Ceres Promoter YP0117 |  |  |  |  |  |  |
|  | Ceres Promoter YP0119 |  |  |  |  |  |  |
|  | Ceres Promoter YP0120 |  |  |  |  |  |  |
|  | Ceres Promoter YP0121 |  |  |  |  |  |  |
|  | Ceres Promoter YP0128 |  |  |  |  |  |  |
|  | Ceres Promoter YP0137 |  |  |  |  |  |  |
|  | Ceres Promoter YP0143 |  |  |  |  |  |  |
|  | Ceres Promoter YP0144 |  |  |  |  |  |  |
|  | Ceres Promoter YP0156 |  |  |  |  |  |  |
|  | Ceres Promoter YP0158 |  |  |  |  |  |  |
|  | Ceres Promoter YP0188 |  |  |  |  |  |  |
|  | Ceres Promoter YP0190 |  |  |  |  |  |  |
|  | Ceres Promoter YP0212 |  |  |  |  |  |  |
|  | Ceres Promoter YP0214 |  |  |  |  |  |  |
|  | Ceres Promoter YP0263 |  |  |  |  |  |  |
|  | Ceres Promoter YP0275 |  |  |  |  |  |  |
|  | Ceres Promoter YP0285 |  |  |  |  |  |  |
|  | Ceres Promoter YP0286 |  |  |  |  |  |  |
|  | Ceres Promoter YP0337 |  |  |  |  |  |  |
|  | Ceres Promoter YP0356 |  |  |  |  |  |  |
|  | Ceres Promoter YP0374 |  |  |  |  |  |  |
|  | Ceres Promoter YP0377 |  |  |  |  |  |  |
|  | Ceres Promoter YP0380 |  |  |  |  |  |  |
|  | Ceres Promoter YP0381 |  |  |  |  |  |  |
|  | Ceres Promoter YP0384 |  |  |  |  |  |  |
|  | Ceres Promoter YP0385 |  |  |  |  |  |  |
|  | Ceres Promoter YP0396 |  |  |  |  |  |  |
|  | Ceres Promoter p13879 |  |  |  |  |  |  |
|  | Ceres Promoter p326 |  |  |  |  |  |  |
|  | Ceres Promoter p32449 |  |  |  |  |  |  |
|  | Ceres Promoter PD1367 |  |  |  |  |  |  |
|  | Ceres Promoter p530c10 |  |  |  |  |  |  |
|  | Ceres Promoter pOsFIE2-2 |  |  |  |  |  |  |
|  | Ceres Promoter pOsMEA |  |  |  |  |  |  |
|  | Ceres Promoter pOsYp102 |  |  |  |  |  |  |
|  | Ceres Promoter pOsYp285 |  |  |  |  |  |  |
|  | Ceres Promoter PT0565 |  |  |  |  |  |  |
|  | Ceres Promoter YP0015 |  |  |  |  |  |  |
|  | Ceres Promoter YP0087 |  |  |  |  |  |  |
|  | Ceres Promoter YP0093 |  |  |  |  |  |  |
|  | Ceres Promoter YP0108 |  |  |  |  |  |  |
|  | Ceres Promoter YP0022 |  |  |  |  |  |  |
|  | Ceres Promoter YP0080 |  |  |  |  |  |  |
|  | Ceres Promoter PR0924 |  |  |  |  |  |  |
|  | Ceres Promoter YP0388 |  |  |  |  |  |  |
|  | Ceres Promoter PD0901 |  |  |  |  |  |  |
|  | Ceres Promoter PT0623 |  |  |  |  |  |  |
| Ceres Clone ID no. 2403 | Truncated version of Ceres CLONE ID no. 100021733 | Ubiquitin family | 1 | 33 |  | 87.6 | −83.1 |
| Ceres Clone ID no. 2403 | Truncated version of Ceres CLONE ID no. 1036726 | Ubiquitin family | 1 | 33 | Y | 87.6 | −83.1 |
| Ceres Clone ID no. 2403 | Truncated version of Ceres CLONE ID no. 1482731 | Ubiquitin family | 1 | 33 | Y | 87.1 | −85 |
| Ceres Clone ID no. 30469 | Truncated Version of Ceres CLONE ID no. 1554560 | Globin | 17 | 78 | Y | 185.7 | 61.3 |
| Ceres Clone ID no. 30469 | Truncated Version of Ceres CLONE ID no. 1802327 | Globin | 14 | 75 | Y | 191.4 | 67.2 |
| Ceres Clone ID no. 30469 | Truncated Version of Ceres CLONE ID no. 1876458 | Globin | 14 | 75 |  | 191.9 | 67.7 |
| Ceres Clone ID no. 30469 | Truncated Version of Ceres CLONE ID no. 1879148 | Globin | 16 | 77 |  | 185.7 | 61.3 |
| Ceres Clone ID no. 2403 | Truncated version of Ceres CLONE ID no. 1884696 | Ubiquitin family | 1 | 33 | Y | 87.6 | 65 |
| Ceres Clone ID no. 30469 | Truncated Version of Ceres CLONE ID no. 1916866 | Globin | 13 | 74 | Y | 188.3 | 65 |
| Ceres Clone ID no. 2403 | Truncated version of Ceres CLONE ID no. 1950105 | Ubiquitin family | 1 | 33 | Y | 87.6 | 60.7 |

TABLE 7-continued

| | | | | | | | |
|---|---|---|---|---|---|---|---|
| Ceres Clone ID no. 30469 | Truncated Version of Ceres CLONE ID no. 1990746 | Globin | 16 | 77 | | 184.9 | 60.7 |
| Ceres Clone ID no. 30469 | Truncated Version of Ceres CLONE ID no. 2033803 | Globin | 16 | 77 | | 184.9 | 60.7 |
| Ceres Clone ID no. 2403 | Truncated version of Ceres CLONE ID no. 2034916 | Ubiquitin family | 1 | 33 | | 87.6 | 63.3 |
| Ceres Clone ID no. 2403 | Truncated version of Ceres CLONE ID no. 513071 | Ubiquitin family | 1 | 33 | | 85.9 | 44.7 |
| Ceres Clone ID no. 2403 | Truncated version of Ceres CLONE ID no. 522921 | Ubiquitin family | 1 | 33 | Y | 87.6 | 22.4 |
| Ceres Clone ID no. 30469 | Truncated Version of Ceres CLONE ID no. 546001 | Globin | 13 | 74 | Y | 182.8 | 59.6 |
| Ceres Clone ID no. 30469 | Truncated Version of Ceres CLONE ID no. 651581 | Globin | 13 | 74 | | 185.7 | 63.9 |
| Ceres Clone ID no. 30469 | Truncated Version of Ceres CLONE ID no. 839727 | Globin | 14 | 75 | Y | 187.8 | 63.3 |
| Ceres Clone ID no. 30469 | Truncated Version of Public GI ID no. 11095158 | Globin | 13 | 76 | | 167.8 | 44.7 |
| Ceres Clone ID no. 30469 | Truncated Version of Public GI ID no. 12963875 | Globin | 8 | 69 | | 145.8 | 22.4 |
| Ceres Clone ID no. 30469 | Truncated Version of Public GI ID no. 14701800 | Globin | 21 | 82 | | 170.1 | 45.8 |
| Ceres Clone ID no. 30469 | Truncated Version of Public GI ID no. 15226675 | Globin | 13 | 74 | | 184.6 | 63 |
| Ceres Clone ID no. 30469 | Truncated Version of Public GI ID no. 15824736 | Globin | 13 | 74 | | 184.2 | 60.9 |
| Ceres Clone ID no. 30469 | Truncated Version of Public GI ID no. 30909306 | Globin | 13 | 74 | Y | 185.7 | 63.9 |
| Ceres Clone ID no. 30469 | Truncated Version of Public GI ID no. 37903656 | Globin | 10 | 71 | | 172.6 | 49.6 |
| Ceres Clone ID no. 30469 | Truncated Version of Public GI ID no. 62548111 | Globin | 13 | 74 | | 188.3 | 65 |

The invention claimed is:

1. A plant cell transformed with an exogenous nucleic acid, wherein said exogenous nucleic acid comprises a polynucleotide operably linked to a heterologous promoter, wherein said polynucleotide comprises a nucleotide sequence encoding a polypeptide comprising an amino acid sequence having 95 percent or greater amino acid sequence identity to the amino acid sequence of SEQ ID NO:7, wherein a transgenic plant produced from said transformed plant cell has been selected for having an increased level of cold tolerance as compared to a control plant of the same species that does not comprise said exogenous nucleic acid.

2. A transgenic plant comprising the transformed plant cell of claim 1.

3. The transgenic plant of claim 2, wherein said transgenic plant is a member of a plant species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), and *Pennisetum glaucum* (pearl millet).

4. The transgenic plant of claim 2, wherein said polypeptide comprises the amino acid sequence of SEQ ID NO:7.

5. A vegetative plant product comprising transgenic plant tissue from the transgenic plant according to claim 2.

6. A progeny of the transgenic plant of claim 2, wherein the progeny comprises the exogenous nucleic acid.

7. The transformed plant cell of claim 1, wherein said polypeptide comprises the amino acid sequence of SEQ ID NO:7.

* * * * *

SEQUENCE LISTING

```
<160> NUMBER OF SEQ ID NOS: 229

<210> SEQ ID NO 1
<211> LENGTH: 828
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451
<220> FEATURE:
<221> NAME/KEY: misc_feature
<223> OTHER INFORMATION: Encodes the protein at SEQ ID NO: 2

<400> SEQUENCE: 1
aactttctct tcccactctt tcttttacta ctctcacaca tatctctgtc tatatatcac      60
tttacataaa ccactattcc acacacaaac acacatagcc atggcctctt ctttctcttc     120
acaagccttc ttcttgctca cattgtctat ggttttaatt cctttctctt tagctcaagc     180
tcccatgatg gctccttctg gctcaatgtc catgccgcct atgtctagcg gcggtggaag     240
ctcggttcct cctccagtga tgtctccgat gccaatgatg actccaccac ctatgcctat     300
gactccatca cccatgccca tgactccacc acctatgcct atggctccac caccaatgcc     360
catggcttca ccaccaatga tgccaatgac tccatctaca agcccaagcc cattaacagt     420
tccggatatg ccttcgccgc cgatgccatc cggaatggaa tcttcacctt ctccaggacc     480
catgccaccg gcaatggcgg cttcgccgga ttcgggagct ttcaatgtta gaaacaacgt     540
cgtaacactt tcatgcgttg ttggagttgt tgcagctcat tttctcctcg tttgaaatga     600
ttattgaatt ggtcagcctc gatcgttttc ttgtaattta ctttcatatt ttttttccct     660
```

-continued

```
caaattatta gtggtcatca ttttataata tttgagtttg tgtttgatgt acgattcaga    720
catttgtttg cattatgtgc ttaataagtt tatcgttgac tctacttgaa gagagacttt    780
gtgtgtgatg taaatttctt ctatctatgg aacattgcat tcgtagcc                828
```

<210> SEQ ID NO 2
<211> LENGTH: 164
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451

<400> SEQUENCE: 2

Met Ala Ser Ser Phe Ser Ser Gln Ala Phe Leu Leu Thr Leu Ser
1               5                   10                  15

Met Val Leu Ile Pro Phe Ser Leu Ala Gln Ala Pro Met Met Ala Pro
            20                  25                  30

Ser Gly Ser Met Ser Met Pro Pro Met Ser Ser Gly Gly Gly Ser Ser
        35                  40                  45

Val Pro Pro Val Met Ser Pro Met Pro Met Thr Pro Pro Pro
50                  55                  60

Met Pro Met Thr Pro Ser Pro Met Pro Met Thr Pro Pro Met Pro
65                  70                  75                  80

Met Ala Pro Pro Met Pro Met Ala Ser Pro Pro Met Met Pro Met
                85                  90                  95

Thr Pro Ser Thr Ser Pro Ser Pro Leu Thr Val Pro Asp Met Pro Ser
            100                 105                 110

Pro Pro Met Pro Ser Gly Met Glu Ser Ser Pro Ser Pro Gly Pro Met
        115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val

<210> SEQ ID NO 3
<211> LENGTH: 155
<212> TYPE: PRT
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Functional homolog of Ceres Clone ID no. 30087
    given in SEQ ID NO: 2

<400> SEQUENCE: 3

Met Ala Ala Ser Gln Ala Phe Leu Leu Leu Thr Leu Ser Met Ala Leu
1               5                   10                  15

Val His Phe Ser Leu Ala Gln Ser Pro Met Met Ala Pro Ser Gly Ser
            20                  25                  30

Met Ser Met Pro Pro Met Pro Ser Gly Gly Ser Pro Met Pro Met Met
        35                  40                  45

Thr Pro Pro Pro Met Pro Met Thr Pro Pro Met Ala Met Ala
50                  55                  60

Pro Pro Pro Met Pro Met Thr Pro Pro Met Pro Met Ala Pro Met
65                  70                  75                  80

Pro Met Thr Pro Ser Ser Ser Pro Met Ser Pro Thr Thr Met Ala
            85                  90                  95

Pro Ser Pro Glu Thr Val Pro Asp Met Ala Ser Pro Pro Met Met Pro
            100                 105                 110

Gly Met Glu Ser Ser Pro Ser Pro Gly Pro Met Pro Pro Ala Met Ala
            115                 120                 125

Ser Pro Asp Ser Gly Ala Phe Asn Val Arg Asn Asp Val Val Ala Ile
    130                 135                 140

Ser Phe Leu Val Ala Ala His Leu Leu Leu Val
145                 150                 155

<210> SEQ ID NO 4
<211> LENGTH: 152
<212> TYPE: PRT
<213> ORGANISM: Brassica napus
<220> FEATURE:
<221> NAME/KEY: misc_feature
<223> OTHER INFORMATION: Public GI no. 62526422
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 4

Met Ala Leu Ser His Pro Met Thr Ile Phe Ser Leu Phe Leu Thr Phe
1               5                   10                  15

Leu Ala Leu Thr Ala Ala Gln Ser Pro Met Met Ala Pro Thr Met Pro
            20                  25                  30

Pro Ser Thr Met Ser Met Pro Pro Thr Thr Ser Thr Thr Thr Pro Pro
        35                  40                  45

Pro Met Ser Ser Met Ser Pro Pro Ser Ala Met Ser Pro Thr Pro
    50                  55                  60

Ser Thr Met Ser Pro Pro Pro Met Ser Pro Met Thr Pro Ser Met Ser
65                  70                  75                  80

Pro Met Gly Pro Met Thr Pro Thr Met Ser Pro Met Asp Ser Pro Pro
            85                  90                  95

Ala Pro Ala Gly Pro Gly Met Ala Pro Gly Met Ser Thr Pro Gly Pro
            100                 105                 110

Ala Pro Gly Pro Met Gly Gly Glu Ser Met Ala Ser Pro Pro Pro Ser
        115                 120                 125

Ser Gly Phe Val His Gly Ile Ser Ile Ser Met Ala Met Val Ala Ile
    130                 135                 140

Ile Gly Ser Val Ala Leu Phe Phe
145                 150

<210> SEQ ID NO 5
<211> LENGTH: 150
<212> TYPE: PRT
<213> ORGANISM: Parthenium argentatum
<220> FEATURE:
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 5

Met Ala Val Ser Arg Tyr Ile Ile Leu Leu Leu Ser Phe Thr Tyr Leu

```
            1               5                  10                 15
          Ala Ala Phe Ser Thr Ala Gln Ala Pro Ser Met Ser Pro Met Met Met
                          20                 25                 30

Pro Met Ala Pro Pro Ser Thr Met Pro Met Thr Pro Pro Pro Ser
                      35                 40                 45

Thr Met Pro Met Thr Pro Pro Pro Thr Pro Met Thr Met Thr Pro Pro
                      50                 55                 60

Pro Met Met Met Pro Met Thr Pro Pro Met Pro Met Gly Thr Pro
           65                 70                 75                 80

Pro Met Thr Met Pro Met Gly Pro Pro Met Met Met Pro Met Ser
                          85                 90                 95

Pro Gly Pro Ser Met Met Pro Ala Ser Pro Pro Ser Pro Met Gly Pro
                         100                105                110

Ser Met Ala Pro Glu Pro Ala Thr Met Ser Pro Gly Pro Ser Met Thr
                         115                120                125

Pro Ala Glu Thr Pro Ala Ser Gly Ala Ile Met Gln Tyr Ser Ser Ile
                         130                135                140

Thr Met Leu Gly Ile Val
          145                 150
```

<210> SEQ ID NO 6
<211> LENGTH: 586
<212> TYPE: DNA
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779
<220> FEATURE:
<221> NAME/KEY: misc_feature
<223> OTHER INFORMATION: Encodes the protein at SEQ ID NO: 7

<400> SEQUENCE: 6

```
aaaagatcta caaaacagag agttgtatac tttaaatcat ttagaggttg tgaaatatta      60
tggagagtga aggaaagatt gtgttcacag aagagcaaga ggctcttgta gtgaagtctt     120
ggagtgtcat gaagaaaaac tcagctgaat taggtctcaa actcttcatc aagatctttg     180
agattgcacc aacaacgaag aagatgttct ctttcttgag agactcacca attcctgctg     240
agcaaaatcc aaagctcaag cctcacgcaa tgtctgtttt tgtcatgtac aactgaggaa     300
aacagggaaa gttacggtga gggagactac tttgaagaga cttggagcca gccattctaa     360
atacggtgtc gttgacgaac actttgaggt ggccaagtat gcattgttgg agacgataaa     420
ggaggcagtg ccggagatgt ggtcaccgga gatgaaggtg gcttggggtc aggcttatga     480
tcaccttgtt gctgccatta agctgaaat gaatctttcc aactaaaaaa tcatatacta     540
ttatatagtt gtaaacttgt aataaatatt tcattttgaa ttgttc                   586
```

<210> SEQ ID NO 7
<211> LENGTH: 78
<212> TYPE: PRT
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779
<220> FEATURE:
<221> NAME/KEY: misc_feature
<222> LOCATION: (13)..(74)
<223> OTHER INFORMATION: Pfam Name: Globin Pfam Description: Globin

<400> SEQUENCE: 7

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Tyr Asn
65                  70                  75

<210> SEQ ID NO 8
<211> LENGTH: 483
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<223> OTHER INFORMATION: Encodes the protein at SEQ ID NO: 9

<400> SEQUENCE: 8
atggagagtg aaggaaagat tgtgttcaca gaagagcaag aggctcttgt agtgaagtct     60
tggagtgtca tgaagaaaaa ctcagctgaa ttaggtctca aactcttcat caagatcttt    120
gagattgcac caacaacgaa gaagatgttc tctttcttga gagactcacc aattcctgct    180
gagcaaaatc caaagctcaa gcctcacgca atgtctgttt ttgtcatgtg ttgtgaatca    240
gcagtacaac tgaggaaaac agggaaagtt acggtgaggg agactacttt gaagagactt    300
ggagccagcc attctaaata cggtgtcgtt gacgaacact ttgaggtggc caagtatgca    360
ttgttggaga cgataaagga ggcagtgccg gagatgtggt caccggagat gaaggtggct    420
tggggtcagg cttatgatca ccttgttgct gccattaaag ctgaaatgaa tctttccaac    480
taa                                                                  483

<210> SEQ ID NO 9
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<222> LOCATION: (13)..(152)
<223> OTHER INFORMATION: Pfam Name: Globin
    Pfam Description: Globin
<220> FEATURE:
<221> NAME/KEY: misc_feature
<223> OTHER INFORMATION: Functional homolog of Ceres Clone ID no. 30469
    given in SEQ ID NO: 7

<400> SEQUENCE: 9

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

```
Met Phe Ser Phe Leu Arg Asp Ser Pro Ile Pro Ala Glu Gln Asn Pro
 50                  55                  60

Lys Leu Lys Pro His Ala Met Ser Val Phe Val Met Cys Cys Glu Ser
 65                  70                  75                  80

Ala Val Gln Leu Arg Lys Thr Gly Lys Val Thr Val Arg Glu Thr Thr
                 85                  90                  95

Leu Lys Arg Leu Gly Ala Ser His Ser Lys Tyr Gly Val Val Asp Glu
                100                 105                 110

His Phe Glu Val Ala Lys Tyr Ala Leu Leu Glu Thr Ile Lys Glu Ala
            115                 120                 125

Val Pro Glu Met Trp Ser Pro Glu Met Lys Val Ala Trp Gly Gln Ala
        130                 135                 140

Tyr Asp His Leu Val Ala Ala Ile Lys Ala Glu Met Asn Leu Ser Asn
145                 150                 155                 160

<210> SEQ ID NO 10
<211> LENGTH: 160
<212> TYPE: PRT
<213> ORGANISM: Raphanus sativus
<220> FEATURE:
<221> NAME/KEY: misc_feature
<223> OTHER INFORMATION: Public GI no. 30909306
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 10

Met Glu Ser Glu Gly Lys Ile Val Phe Thr Glu Glu Gln Glu Ala Leu
 1               5                  10                  15

Val Val Lys Ser Trp Ser Val Met Lys Lys Asn Ser Ala Asp Leu Gly
                 20                  25                  30

Leu Lys Leu Phe Ile Lys Ile Phe Glu Ile Ala Pro Thr Ala Lys Lys
             35                  40                  45

Leu Phe Ser Phe Leu Arg Asp Ser Pro Ile Pro Ala Glu Gln Asn Pro
 50                  55                  60

Lys Leu Lys Pro His Ala Met Ser Val Phe Val Met Cys Cys Glu Ser
 65                  70                  75                  80

Ala Ala Gln Leu Arg Lys Thr Gly Lys Val Thr Val Lys Glu Thr Thr
                 85                  90                  95

Leu Lys Arg Leu Gly Ala Asn His Ser Lys Tyr Gly Val Val Asp Glu
                100                 105                 110

His Phe Glu Val Thr Lys Tyr Ala Leu Leu Glu Thr Ile Lys Glu Ala
            115                 120                 125

Val Pro Glu Met Trp Ser Pro Glu Met Lys Ser Ala Trp Gly Gln Ala
        130                 135                 140

Tyr Asp His Leu Val Ala Ala Ile Lys Ala Glu Met Lys Pro Ser His
145                 150                 155                 160

<210> SEQ ID NO 11
<211> LENGTH: 158
<212> TYPE: PRT
<213> ORGANISM: Arabidopsis thaliana
<220> FEATURE:
<221> NAME/KEY: misc_feature
```

```
<223> OTHER INFORMATION: Public GI no. 37903656
<220> FEATURE:
<221> NAME/KEY: misc_feature
<222> LOCATION: (10)..(149)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 11

Met Glu Gly Lys Val Phe Thr Glu Glu Gln Glu Thr Leu Val Val Lys
1               5                   10                  15

Ser Trp Gly Val Met Lys Lys Asn Ala Ala Glu Leu Gly Leu Lys Phe
            20                  25                  30

Phe Leu Lys Ile Phe Glu Ile Ala Pro Ser Ala Gln Lys Leu Phe Ser
        35                  40                  45

Phe Leu Arg Asp Ser Asp Ile Pro Leu Glu Lys Asn Pro Lys Leu Lys
    50                  55                  60

Pro His Ala Met Ser Val Phe Val Met Thr Cys Glu Ser Ala Val Gln
65                  70                  75                  80

Leu Arg Lys Ala Gly Lys Val Thr Val Arg Glu Ser Thr Leu Lys Arg
                85                  90                  95

Leu Gly Gly Val His Phe Lys Ser Gly Val Val Asp Glu His Tyr Glu
            100                 105                 110

Val Thr Lys Phe Ala Leu Leu Glu Thr Ile Lys Glu Ala Leu Pro Glu
        115                 120                 125

Met Trp Ser Pro Glu Met Lys Asn Ala Trp Gly Glu Ala Tyr Asp Gln
    130                 135                 140

Leu Val Ala Ala Ile Lys Ser Glu Met Lys Pro Pro Leu Asn
145                 150                 155

<210> SEQ ID NO 12
<211> LENGTH: 163
<212> TYPE: PRT
<213> ORGANISM: Arabidopsis thaliana
<220> FEATURE:
<221> NAME/KEY: misc_feature
<223> OTHER INFORMATION: Public GI no. 15824736
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 12

Met Ala Thr Tyr Glu Gly Lys Val Phe Thr Glu Glu Gln Glu Ala Leu
1               5                   10                  15

Val Val Lys Ser Trp Thr Val Met Lys Lys Thr Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
```

```
                         85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
            115                 120                 125

Val Pro Asp Met Trp Ser Asp Glu Met Lys Asn Ala Trp Gly Glu Ala
            130                 135                 140

Tyr Asp Arg Leu Val Ala Ala Ile Lys Ile Glu Met Lys Ala Cys Ser
145                 150                 155                 160

Gln Ala Ala

<210> SEQ ID NO 13
<211> LENGTH: 161
<212> TYPE: PRT
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 13

Met Thr Thr Thr Leu Glu Arg Gly Phe Ser Glu Glu Gln Glu Ala Leu
1               5                   10                  15

Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
        35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met Thr Cys Asp Ser
65                  70                  75                  80

Ala Val Gln Leu Arg Lys Ala Gly Lys Val Thr Val Arg Glu Ser Asn
            85                  90                  95

Leu Lys Lys Leu Gly Ala Thr His Phe Arg Thr Gly Val Ala Asn Glu
            100                 105                 110

His Phe Glu Val Thr Lys Phe Ala Leu Leu Glu Thr Ile Lys Glu Ala
            115                 120                 125

Val Pro Glu Met Trp Ser Pro Ala Met Lys Asn Ala Trp Gly Glu Ala
            130                 135                 140

Tyr Asp Gln Leu Val Asp Ala Ile Lys Ser Glu Met Lys Pro Pro Ser
145                 150                 155                 160

Ser

<210> SEQ ID NO 14
<211> LENGTH: 160
<212> TYPE: PRT
<213> ORGANISM: Glycine max
<220> FEATURE:
<221> NAME/KEY: misc_feature
<223> OTHER INFORMATION: Public GI no. 11095158
<220> FEATURE:
<221> NAME/KEY: misc_feature
<222> LOCATION: (13)..(152)
```

```
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 14

Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
            20                  25                  30

Leu Lys Leu Phe Leu Lys Ile Phe Glu Ile Ala Pro Ser Ala Gln Lys
        35                  40                  45

Leu Phe Ser Phe Leu Lys Asp Ser Lys Val Pro Leu Glu Gln Asn Thr
    50                  55                  60

Lys Leu Lys Pro His Ala Met Ser Val Phe Leu Met Thr Cys Glu Ser
65                  70                  75                  80

Ala Val Gln Leu Arg Lys Ser Gly Lys Val Thr Val Arg Glu Ser Ser
                85                  90                  95

Leu Lys Lys Leu Gly Ala Asn His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Glu Met Trp Ser Pro Ala Met Lys Asn Ala Trp Gly Glu Ala
    130                 135                 140

Tyr Asp Gln Leu Val Asn Ala Ile Lys Ser Glu Met Lys Pro Ser Ser
145                 150                 155                 160

<210> SEQ ID NO 15
<211> LENGTH: 152
<212> TYPE: PRT
<213> ORGANISM: Glycine max
<220> FEATURE:
<221> NAME/KEY: misc_feature
<223> OTHER INFORMATION: Public GI no. 12963875
<220> FEATURE:
<221> NAME/KEY: misc_feature
<222> LOCATION: (8)..(147)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 15

Met Ser Ser Phe Ser Glu Glu Gln Glu Ala Leu Val Val Lys Ser Trp
1               5                   10                  15

Gly Ser Met Lys Lys Asp Ala Gly Glu Trp Gly Leu Lys Phe Phe Leu
            20                  25                  30

Lys Ile Phe Glu Ile Ala Pro Ser Ala Lys Lys Met Phe Ser Phe Leu
        35                  40                  45

Lys Asp Ser Asn Val Pro Leu Asp Gln Asn Pro Lys Leu Lys Ile His
    50                  55                  60

Ala Lys Ser Val Leu Val Met Thr Cys Glu Ala Ala Val Gln Leu Arg
65                  70                  75                  80

Lys Ala Gly Lys Val Val Val Arg Asp Ser Thr Leu Lys Lys Ile Gly
                85                  90                  95

Ala Thr His Phe Lys Tyr Gly Val Val Asp Glu His Phe Glu Val Thr
            100                 105                 110
```

```
Lys Tyr Ala Leu Leu Glu Thr Ile Lys Glu Ala Ser Gln Glu Met Trp
            115                 120                 125

Ser Val Glu Met Lys Asn Ala Trp Gly Glu Ala Tyr Asp Gln Leu Val
        130                 135                 140

Ser Ala Ile Lys Thr Glu Met Lys
145                 150

<210> SEQ ID NO 16
<211> LENGTH: 165
<212> TYPE: PRT
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<222> LOCATION: (17)..(157)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 16

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

Thr Cys Glu Ala Ala Ala Gln Leu Arg Lys Ala Gly Lys Val Thr Val
                85                  90                  95

Arg Glu Thr Thr Leu Lys Arg Leu Gly Ala Thr His Leu Arg Tyr Gly
            100                 105                 110

Val Ala Asp Gly His Phe Glu Val Thr Gly Phe Ala Leu Leu Glu Thr
        115                 120                 125

Ile Lys Glu Ala Leu Pro Ala Asp Met Trp Ser Leu Glu Met Lys Lys
    130                 135                 140

Ala Trp Ala Glu Ala Tyr Ser Gln Leu Val Ala Ala Ile Lys Arg Glu
145                 150                 155                 160

Met Lys Pro Asp Ala
                165

<210> SEQ ID NO 17
<211> LENGTH: 162
<212> TYPE: PRT
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
``` given in SEQ ID NO: 7

<400> SEQUENCE: 17

Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
            20                  25                  30

Gly Leu Arg Phe Phe Leu Lys Ile Phe Glu Ile Ala Pro Ser Ala Arg
        35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met Thr Cys Glu
65                  70                  75                  80

Ala Ala Ala Gln Leu Arg Lys Ala Gly Lys Ile Thr Val Arg Glu Thr
                85                  90                  95

Thr Leu Lys Arg Leu Gly Gly Thr His Leu Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Gly Pro Glu Met Arg Asn Ala Trp Gly
    130                 135                 140

Glu Ala Tyr Asp Gln Leu Val Ala Ala Ile Lys Gln Glu Met Lys Pro
145                 150                 155                 160

Ser Glu

<210> SEQ ID NO 18
<211> LENGTH: 169
<212> TYPE: PRT
<213> ORGANISM: Triticum aestivum
<220> FEATURE:
<221> NAME/KEY: misc_feature
<223> OTHER INFORMATION: Public GI no. 14701800
<220> FEATURE:
<221> NAME/KEY: misc_feature
<222> LOCATION: (21)..(161)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 18

Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met
            20                  25                  30

Lys Lys Asp Ser Ala Asn Ile Gly Leu Arg Phe Phe Leu Lys Ile Phe
        35                  40                  45

Glu Val Ala Pro Ser Ala Ser Gln Met Phe Ser Phe Leu Arg Asn Ser
    50                  55                  60

Asp Val Pro Leu Glu Lys Asn Pro Lys Leu Lys Thr His Ala Met Ser
65                  70                  75                  80

Val Phe Val Met Thr Cys Glu Ala Ala Ala Gln Leu Arg Lys Ala Gly
                85                  90                  95

Lys Val Thr Val Arg Asp Thr Thr Leu Lys Arg Leu Gly Ala Thr His
            100                 105                 110

Phe Lys Tyr Gly Val Gly Asp Ala His Phe Glu Val Thr Arg Phe Ala
        115                 120                 125

Leu Leu Glu Thr Ile Lys Glu Ala Val Pro Val Asp Met Trp Ser Pro
            130                 135                 140

Ala Met Lys Ser Ala Trp Ser Glu Ala Tyr Asn Gln Leu Val Ala Ala
145                 150                 155                 160

Ile Lys Gln Glu Met Lys Pro Ala Glu
                165

<210> SEQ ID NO 19
<211> LENGTH: 416
<212> TYPE: DNA
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<223> OTHER INFORMATION: Encodes the protein at SEQ ID NO: 20

<400> SEQUENCE: 19
gctcattagg gtttctcatc tacgacggcg tggtgttcct ccttcctgct ctgaaaaatg     60
gcgaagagaa cgaagaaggt tggaatcgtc ggcaaatacg gaacacgtta tggtgcgagt    120
atcaggaagc agattaagaa gatggaggtc agccagcaca gcaagtactt ctgtgagttc    180
tgtggcaagt acggagtgaa gcgaaaggct gttggtatct ggggttgcaa ggattgtggc    240
aaggtcaagg caggtggtgc ttacacaatg aacaccgcca gtgcggtcac tgttagaagc    300
acgatcagaa ggttgaggga gcagatcgag ggttaaaagt ctgctggctt tttatatttg    360
gtttccttgt tttgacaatt taagttttgc atcaacagtg agaacatgtt ttgatt        416

<210> SEQ ID NO 20
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<222> LOCATION: (2)..(91)
<223> OTHER INFORMATION: Pfam Name: Ribosomal_L37ae;
      Pfam Description: Ribosomal L37ae protein family

<400> SEQUENCE: 20

Met Ala Lys Arg Thr Lys Lys Val Gly Ile Val Gly Lys Tyr Gly Thr
1               5                   10                  15

Arg Tyr Gly Ala Ser Ile Arg Lys Gln Ile Lys Lys Met Glu Val Ser
            20                  25                  30

Gln His Ser Lys Tyr Phe Cys Glu Phe Cys Gly Lys Tyr Gly Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Ile Glu Gly
            85                  90

```
<210> SEQ ID NO 21
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 4090257
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 21

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Pro Ser Ala Val Thr Val Arg
65                  70                  75                  80

Ser Thr Ile Arg Arg Leu Arg Glu Gln Thr Glu Gly
                85                  90

<210> SEQ ID NO 22
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 4741896
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 22

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Tyr Ala Val Lys
        35                  40                  45

Arg Lys Ala Val Gly Ile Trp Gly Cys Lys Ala Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 23
<211> LENGTH: 92
<212> TYPE: PRT
```

-continued

```
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<222> LOCATION: (45)..(45)
<223> OTHER INFORMATION: Xaa is any aa, unknown, or other
<220> FEATURE:
<221> NAME/KEY: misc_feature
<222> LOCATION: (49)..(49)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 23

Met Ala Lys Arg Thr Lys Lys Val Gly Ile Val Gly Lys Tyr Gly Thr
1               5                   10                  15

Arg Tyr Gly Ala Ser Ile Arg Lys Gln Ile Lys Lys Met Glu Val Ser
                20                  25                  30

Gln His Ser Lys Tyr Phe Cys Glu Phe Cys Gly Lys Xaa Gly Val Lys
            35                  40                  45

Xaa Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Ile Glu Gly
                85                  90

<210> SEQ ID NO 24
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 6016699
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 24

Met Thr Lys Arg Thr Lys Lys Ala Arg Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Asn Lys Tyr Phe Cys Glu Phe Cys Gly Lys Tyr Ser Val Lys
            35                  40                  45

Arg Lys Val Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ser
                85                  90
```

<210> SEQ ID NO 25
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<222> LOCATION: (2)..(91)
<223> OTHER INFORMATION: Pfam Name: Ribosomal_L37ae
    Pfam Description: Ribosomal L37ae protein family
<220> FEATURE:
<221> NAME/KEY: misc_feature
<223> OTHER INFORMATION: Functional homolog of Ceres Clone ID no. 271922
    given in SEQ ID NO: 20

<400> SEQUENCE: 25

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Gly
                85                  90

<210> SEQ ID NO 26
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<222> LOCATION: (2)..(91)
<223> OTHER INFORMATION: Pfam Name: Ribosomal_L37ae
    Pfam Description: Ribosomal L37ae protein family
<220> FEATURE:
<221> NAME/KEY: misc_feature
<223> OTHER INFORMATION: Functional homolog of Ceres Clone ID no. 271922
    given in SEQ ID NO: 20

<400> SEQUENCE: 26

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 27

```
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 27

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 28
<211> LENGTH: 92
<212> TYPE: PRT
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 28

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 29
<211> LENGTH: 92
<212> TYPE: PRT
<213> ORGANISM: Zea mays
```

```
<220> FEATURE:
<221> NAME/KEY: misc_feature
<223> OTHER INFORMATION: Ceres CLONE ID no. 1390976
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 29

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 30
<211> LENGTH: 92
<212> TYPE: PRT
<213> ORGANISM: Zea mays
<220> FEATURE:
<221> NAME/KEY: misc_feature
<223> OTHER INFORMATION: Ceres CLONE ID no. 1457185
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 30

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 31
<211> LENGTH: 92
<212> TYPE: PRT
<213> ORGANISM: Zea mays
<220> FEATURE:
<221> NAME/KEY: misc_feature
<223> OTHER INFORMATION: Public GI no. 56202147
```

```
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 31

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 32
<211> LENGTH: 92
<212> TYPE: PRT
<213> ORGANISM: Zea mays
<220> FEATURE:
<221> NAME/KEY: misc_feature
<223> OTHER INFORMATION: Public GI no. 58578274
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 32

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Glu Tyr Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 33
<211> LENGTH: 632
<212> TYPE: DNA
<213> ORGANISM: Arabidopsis thaliana
<220> FEATURE:
<221> NAME/KEY: misc_feature
<223> OTHER INFORMATION: Ceres CLONE ID no. 2403_FL
<220> FEATURE:
<221> NAME/KEY: misc_feature
<223> OTHER INFORMATION: Encodes the protein at SEQ ID NO: 34
```

<400> SEQUENCE: 33

```
attccccatc gcacagaccc gcctaagaat ccgagagaga agaagagata atgcagatct    60
tcgtcaaaac cctcaccggc aaaactataa ccctagaggt tgagagcagc gacaccatcg   120
acaatgttaa agccaaaatc caggacaaat agggcatacc acctgatcaa cagaggctga   180
tttttgctgg taagcaattg gaagatggcc ggaccttagc tgactacaac atccagaaag   240
agtctactct tcatcttgtc ctcaggctca gaggtggaac catgatcaag gtgaagacac   300
tcactggaaa agaaatcgag attgatatcg aaccaaccga cactattgat cggatcaaag   360
aacgtgttga agaaaagaa ggcatccctc ctgttcaaca aaggctcatc tatgccggaa    420
aacagcttgc tgatgacaaa acggccaaag attatgcgat agagggaggc tctgttcttc   480
atttggttct tgctcttagg ggtggtcttc tctgatctga ataaataagc ttttcaacaa   540
acatctttcc cctcactatt gtcctccttt tgtggaattc atgacacaca aaaattgcta   600
tgggaaattg aatattatg atgttttttc tc                                  632
```

<210> SEQ ID NO 34
<211> LENGTH: 154
<212> TYPE: PRT
<213> ORGANISM: Arabidopsis thaliana
    220>
<221> NAME/KEY: misc_feature
<223> OTHER INFORMATION: Ceres CLONE ID no. 2403_FL
<220> FEATURE:
<221> NAME/KEY: misc_feature
<222> LOCATION: (1)..(74)
<223> OTHER INFORMATION: Pfam Name: ubiquitin
    Pfam Description: Ubiquitin family
<220> FEATURE:
<221> NAME/KEY: misc_feature
<222> LOCATION: (77)..(150)
<223> OTHER INFORMATION: Pfam Name: ubiquitin
    Pfam Description: Ubiquitin family
<220> FEATURE:
<221> NAME/KEY: misc_feature
<223> OTHER INFORMATION: Functional homolog of Ceres Clone ID no. 2403
    given in SEQ ID NO: 40

<400> SEQUENCE: 34

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Ala Ile Glu Gly Gly Ser Val Leu His
    130                 135                 140

Leu Val Leu Ala Leu Arg Gly Gly Leu Leu
145                 150
```

```
<210> SEQ ID NO 35
<211> LENGTH: 154
<212> TYPE: PRT
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 35

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Asn Ile Glu Gly Gly Ser Val Leu His
    130                 135                 140

Leu Val Leu Ala Leu Arg Gly Gly Ser Asp
145                 150

<210> SEQ ID NO 36
<211> LENGTH: 154
<212> TYPE: PRT
<213> ORGANISM: Glycine max
<220> FEATURE:
<221> NAME/KEY: misc_feature
<223> OTHER INFORMATION: Ceres CLONE ID no. 522921
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40
```

-continued

<400> SEQUENCE: 36

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Glu Tyr Asn Ile Glu Gly Gly Ser Val Leu His
    130                 135                 140

Leu Val Leu Ala Leu Arg Gly Gly Thr Tyr
145                 150

<210> SEQ ID NO 37
<211> LENGTH: 147
<212> TYPE: PRT
<213> ORGANISM: Brassica napus
<220> FEATURE:
<221> NAME/KEY: misc_feature
<223> OTHER INFORMATION: Ceres CLONE ID no. 1036726
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(142)
<223> OTHER INFORMATION: Pfam Name: ubiquitin
      Pfam Description: Ubiquitin family
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 37

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

```
Asp Thr Ile Asp Arg Ile Lys Glu Arg Val Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Xaa Lys Asp Tyr Asn Ile Glu Gly Gly Ser Val Ser Ala
    130                 135                 140

Ser Gly Ser
145

<210> SEQ ID NO 38
<211> LENGTH: 153
<212> TYPE: PRT
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 38

Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Ser Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Asn Ile Glu Gly Gly Ser Val Leu His
    130                 135                 140

Leu Xaa Leu Ala Leu Arg Gly Gly Tyr
145                 150

<210> SEQ ID NO 39
<211> LENGTH: 620
<212> TYPE: DNA
<213> ORGANISM: Artificial Sequence
<220> FEATURE:
<223> OTHER INFORMATION: Ceres CLONE ID no. 2403
<220> FEATURE:
```

```
<221> NAME/KEY: misc_feature
<223> OTHER INFORMATION: Ceres SEED LINE ID no. ME05304
<220> FEATURE:
<221> NAME/KEY: misc_feature
<223> OTHER INFORMATION: Encodes the protein at SEQ ID NO: 40

<400> SEQUENCE: 39
attccccatc gcacagaccc ccctaagaat ccgagagaga agaagagata atgcagatct      60
tcgtcaaaac cctcaccggc aaaactataa ccctagaagt tgagagcagc gacaccatcg     120
acaatgttaa agccaaaatc caggacaaag agggcatacc acctgatcaa cagaggctga     180
tttttgctgg taagcaattg gaagatggcc ggaccttagc tgattacaac atccagaaag     240
agtctactct tcatcttgtc ctcaggctca gaggtggaac catgatcaag gtgaagacac     300
tcactggaaa agaaatcgag attgatatcg aaccaaccga cactattgat cggatcaaag     360
aacgtgttga agagaaagaa ggcatccctc ctgttcaaca aaggctcata tatgccggaa     420
aacagcttgc tgatgacaaa acggccaaag attatgcgat agaggaggc tctgttcttc      480 atttggttct tgctcttagg ggtggtcttc tctgatctta ataaataagc ttttcaacaa     540
acatcttttc cctcactatt gtcctcctta tgtggaattc atgacacacc aaaattgcta     600
tgggaaattg gaatattatg                                                 620

<210> SEQ ID NO 40
<211> LENGTH: 33
<212> TYPE: PRT
<213> ORGANISM: Artificial Sequence
<220> FEATURE:
<223> OTHER INFORMATION: Ceres CLONE ID no. 2403
<220> FEATURE:
<221> NAME/KEY: misc_feature
<223> OTHER INFORMATION: Ceres SEED LINE ID no. ME05304
<220> FEATURE:
<221> NAME/KEY: misc_feature
<222> LOCATION: (1)..(33)
<223> OTHER INFORMATION: Pfam Name: ubiquitin
      Pfam Description: Ubiquitin family

<400> SEQUENCE: 40

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 41
<211> LENGTH: 1106
<212> TYPE: DNA
<213> ORGANISM: Glycine max
<220> FEATURE:
<221> NAME/KEY: misc_feature
<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<223> OTHER INFORMATION: Encodes the protein at SEQ ID NO: 42

<400> SEQUENCE: 41
atatttttgt gtagatgaag atcaacaaga gaaggtgttg ttgtgagttg tgttgttatg      60
gtaccttcct tcaaccacaa aacctctctc cctctaccac ccattctctt ctctctctct     120
ctctcccgtc ctccatctct caccttctca atctcttcac caccaccatc atcatcatta     180
```

-continued

```
tcttctccaa tctctataac ctcgaaatcc ctcaaaacct ctccctcaaa ccaaatgaaa      240
tgaccctttt gtgagaacat ttttccccc ttaagaaaag gtcaaaggct gcaacttttt       300
cttaaccaat ctcacatttt tttattttc aacgtatttt ggccaggttt ggttttctgg       360
gttgtcttgg aattcaaaaa agattccaac tttgaagatg ggtaggggtg gaaccgccgc      420
ggcggcggcg gaggtcgccg aacccggttt aaggccggtt tatttcaaag aacagcgata      480
taggggcgtc agaaaaagac cgtggggccg gttcgctgcc gaaatcagag acccctttgaa    540 gaaagccagg gtttggctcg aacctttga caccgccgag gaggcggcgc gtgcctacga       600
cacggcggcg agaaccctcc ggggaccaaa ggcgaagacc aatttccctc tttctccgcc      660
gttctaccat cccgatccat tttccgatca ccggcacttc gccaacaccg gcgaagattt      720
ccacgatcac cggcgaccaa catccagtgg catgagcagc accgtagagt ccttcagcgg      780 ccccgtgct gccgtgccgg cgacagcgcc ggtggccacc ggccggagat atccccggac       840 gccaccgtt atccccgagg actgccgcag cgactgcgat tcgtcgtcct ccgtcgttga      900
cgacggcgaa ggcgacaacg tggcgtcgtc gttcccgcga gaaccgttgc cgtttgatct     960
aaacgcgttg ccgttagacg atgctgacgt ggcaaccgat gatctgttct gcaccgttct    1020
ttgcctctga tgagaaaaaa tgaaaaaacg gaacgaaatg atgtatttgg ttcgttgacg    1080
gaattattat tattttttc tttctt                                          1106
```

<210> SEQ ID NO 42
<211> LENGTH: 210
<212> TYPE: PRT
<213> ORGANISM: Glycine max
<220> FEATURE:
<221> NAME/KEY: misc_feature
<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<222> LOCATION: (26)..(89)
<223> OTHER INFORMATION: Pfam Name: AP2
    Pfam Description: AP2 domain
<220> FEATURE:
<221> NAME/KEY: misc_feature
<222> LOCATION: (26)..(89)
<223> OTHER INFORMATION: Pfam Name: AP2;
    Pfam Description: AP2 domain

<400> SEQUENCE: 42

```
Met Gly Arg Gly Gly Thr Ala Ala Ala Ala Glu Val Ala Glu Pro
1               5                   10                  15

Gly Leu Arg Pro Val Tyr Phe Lys Glu Gln Arg Tyr Arg Gly Val Arg
            20                  25                  30

Lys Arg Pro Trp Gly Arg Phe Ala Ala Glu Ile Arg Asp Pro Leu Lys
        35                  40                  45

Lys Ala Arg Val Trp Leu Gly Thr Phe Asp Thr Ala Glu Glu Ala Ala
    50                  55                  60

Arg Ala Tyr Asp Thr Ala Ala Arg Thr Leu Arg Gly Pro Lys Ala Lys
65                  70                  75                  80

Thr Asn Phe Pro Leu Ser Pro Pro Phe Tyr His Pro Asp Pro Phe Ser
                85                  90                  95

Asp His Arg His Phe Ala Asn Thr Gly Glu Asp Phe His Asp His Arg
            100                 105                 110

Arg Pro Thr Ser Ser Gly Met Ser Ser Thr Val Glu Ser Phe Ser Gly
        115                 120                 125
```

```
Pro Arg Ala Ala Val Pro Ala Thr Ala Pro Val Ala Thr Gly Arg Arg
    130                 135                 140

Tyr Pro Arg Thr Pro Pro Val Ile Pro Glu Asp Cys Arg Ser Asp Cys
145                 150                 155                 160

Asp Ser Ser Ser Val Val Asp Asp Gly Glu Gly Asp Asn Val Ala
                165                 170                 175

Ser Ser Phe Pro Arg Glu Pro Leu Pro Phe Asp Leu Asn Ala Leu Pro
                180                 185                 190

Leu Asp Asp Ala Asp Val Ala Thr Asp Asp Leu Phe Cys Thr Val Leu
                195                 200                 205

Cys Leu
    210

<210> SEQ ID NO 43
<211> LENGTH: 225
<212> TYPE: PRT
<213> ORGANISM: Glycine max
<220> FEATURE:
<221> NAME/KEY: misc_feature
<223> OTHER INFORMATION: Public GI no. 12322345
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 43

Met Arg Arg Gly Arg Gly Ser Ser Ala Val Ala Gly Pro Thr Val Val
1               5                   10                  15

Ala Ala Ile Asn Gly Ser Val Lys Glu Ile Arg Phe Arg Gly Val Arg
                20                  25                  30

Lys Arg Pro Trp Gly Arg Phe Ala Ala Glu Ile Arg Asp Pro Trp Lys
            35                  40                  45

Lys Ala Arg Val Trp Leu Gly Thr Phe Asp Ser Ala Glu Glu Ala Ala
50                  55                  60

Arg Ala Tyr Asp Ser Ala Ala Arg Asn Leu Arg Gly Pro Lys Ala Lys
65                  70                  75                  80

Thr Asn Phe Pro Ile Asp Ser Ser Pro Pro Pro Asn Leu Arg
                85                  90                  95

Phe Asn Gln Ile Arg Asn Gln Asn Gln Asn Gln Val Asp Pro Phe Met
                100                 105                 110

Asp His Arg Leu Phe Thr Asp His Gln Gln Gln Phe Pro Ile Val Asn
                115                 120                 125

Arg Pro Thr Ser Ser Ser Met Ser Ser Thr Val Glu Ser Phe Ser Gly
                130                 135                 140

Pro Arg Pro Thr Thr Met Lys Pro Ala Thr Thr Lys Tyr Pro Arg
145                 150                 155                 160

Thr Pro Pro Val Val Pro Glu Asp Cys His Ser Asp Cys Asp Ser Ser
                165                 170                 175

Ser Ser Val Ile Asp Asp Asp Ile Ala Ser Ser Arg Arg
                180                 185                 190

Arg Asn Pro Pro Phe Gln Phe Asp Leu Asn Phe Pro Pro Leu Asp Cys
                195                 200                 205

Val Asp Leu Phe Asn Gly Ala Asp Asp Leu His Cys Thr Asp Leu Arg
```

210                 215                 220

Leu
225

<210> SEQ ID NO 44
<211> LENGTH: 215
<212> TYPE: PRT
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<222> LOCATION: (21)..(84)
<223> OTHER INFORMATION: Pfam Name: AP2
      Pfam Description: AP2 domain
<220> FEATURE:
<221> NAME/KEY: misc_feature
<222> LOCATION: (174)..(174)
<223> OTHER INFORMATION: Xaa is any aa, unknown, or other
<220> FEATURE:
<221> NAME/KEY: misc_feature
<222> LOCATION: (194)..(194)
<223> OTHER INFORMATION: Xaa is any aa, unknown, or other
<220> FEATURE:
<221> NAME/KEY: misc_feature
<222> LOCATION: (208)..(208)
<223> OTHER INFORMATION: Xaa is any aa, unknown, or other
<220> FEATURE:
<221> NAME/KEY: misc_feature
<222> LOCATION: (209)..(209)
<223> OTHER INFORMATION: Xaa is any aa, unknown, or other
<220> FEATURE:
<221> NAME/KEY: misc_feature
<222> LOCATION: (214)..(214)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 44

Met Arg Lys Gly Arg Gly Ser Ser Ala Val Pro Pro Ala Leu Pro Gly
1               5                   10                  15

Ser Val Lys Glu Pro Arg Tyr Arg Gly Val Arg Lys Arg Pro Trp Gly
            20                  25                  30

Arg Phe Ala Ala Glu Ile Arg Asp Pro Leu Lys Lys Ser Arg Val Trp
        35                  40                  45

Leu Gly Thr Phe Asp Ser Ala Glu Glu Ala Ala Arg Ala Tyr Asp Ala
    50                  55                  60

Ala Ala Arg Asn Leu Arg Gly Pro Lys Ala Lys Thr Asn Phe Gln Ile
65                  70                  75                  80

Asp Cys Ser Pro Ser Ser Pro Leu Gln Pro Leu His His Arg Asn Gln
                85                  90                  95

Ile Asp Pro Phe Met Asp His Arg Leu Tyr Gly Gly Glu Gln Glu Val
            100                 105                 110

Val Ile Ile Ser Arg Pro Ala Ser Ser Met Ser Ser Thr Val Lys
        115                 120                 125

Ser Cys Ser Gly Val Arg Pro Ala Ser Ser Val Ala Lys Ala Ala
    130                 135                 140

Thr Lys Arg Tyr Pro Arg Thr Pro Val Ala Pro Glu Asp Cys Arg
145                 150                 155                 160

Ser Asp Cys Asp Ser Ser Ser Val Val Glu Asp Gly Xaa Asp Ile
                165                 170                 175

Ala Ser Ser Ser Ser Arg Arg Lys Pro Pro Phe Glu Phe Asp Leu Asn 180              185              190
Phe Xaa Pro Leu Asp Gly Val Asp Leu Phe Val Gly Ala Asp Asp Xaa
        195              200              205

Xaa Cys Thr Asp Leu Xaa Leu
        210              215

<210> SEQ ID NO 45
<211> LENGTH: 211
<212> TYPE: PRT
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<222> LOCATION: (17)..(80)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 45

Met Arg Arg Arg Gly Val Ala Ala Ala Asp Ala Asp Gly Asp Val Glu
1               5                   10                  15

Leu Arg Phe Arg Gly Val Arg Lys Arg Pro Trp Gly Arg Tyr Ala Ala
            20                  25                  30

Glu Ile Arg Asp Pro Ala Lys Lys Ala Arg Val Trp Leu Gly Thr Phe
        35                  40                  45

Asp Ser Ala Glu Asp Ala Ala Arg Ala Tyr Asp Ala Ala Ala Arg Met
50                  55                  60

Leu Arg Gly Pro Lys Ala Arg Thr Asn Phe Pro Leu Pro Ala Ala Ala
65                  70                  75                  80

Ala Leu His His Pro His Met Pro Ala Ala Ala Ala Ala Ala Ala Pro
            85                  90                  95

Pro Tyr Thr Thr Tyr Pro Thr Ala Thr Gly Val Val Ser Thr Pro Pro
        100                 105                 110

Val Ala Arg Pro Ala Cys Ser Ser Leu Ser Ser Thr Val Glu Ser Phe
        115                 120                 125

Ser Gly Ala Arg Pro Arg Pro Val Leu Pro Pro Arg Phe Pro Pro Pro
130                 135                 140

Ser Ile Pro Asp Gly Asp Cys Arg Ser Asp Cys Gly Ser Ser Ala Ser
145                 150                 155                 160

Val Val Asp Asp Asp Cys Thr Asp Ala Ala Ala Ser Ala Ser Cys Pro
                165                 170                 175

Phe Pro Leu Pro Phe Asp Leu Asn Leu Pro Pro Gly Gly Gly Gly Ala
            180                 185                 190

Gly Val Gly Phe Tyr Ala Asp Glu Gly Asp Glu Leu Arg Leu Thr Ala
        195                 200                 205

Leu Arg Leu
    210

<210> SEQ ID NO 46
<211> LENGTH: 194
<212> TYPE: PRT
<213> ORGANISM: Triticum aestivum
<220> FEATURE:
<221> NAME/KEY: misc_feature
<223> OTHER INFORMATION: Ceres CLONE ID no. 1055099
<220> FEATURE:

```
<221> NAME/KEY: misc_feature
<222> LOCATION: (20)..(83)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 46
```

Met Arg Lys Ala Arg Pro Pro Gln Pro Gln Pro Gln Pro Ser Gln Gln
1               5                   10                  15

Ser Pro Glu Ile Arg Tyr Arg Gly Val Arg Lys Arg Pro Ser Gly Arg
            20                  25                  30

Tyr Ala Ala Glu Ile Arg Asp Pro Ala Lys Lys Thr Pro Ile Trp Leu
        35                  40                  45

Gly Thr Phe Asp Cys Ala Glu Asp Ala Ala Arg Ala Tyr Asp Ser Ala
    50                  55                  60

Ala Arg Ser Leu Arg Gly Pro Thr Ala Arg Thr Asn Phe Pro Pro Ser
65              70                  75                  80

Ser Ala Thr Gln Pro Pro Pro Arg Pro Pro Pro Ala Ala Ala Ala
                85                  90                  95

Ala Ala Ala Thr Ser Ser Gln Ser Ser Thr Val Glu Ser Trp Ser Gly
            100                 105                 110

Gly Gly Pro Arg Ala Pro Ala Arg Ala Arg Ser Ala Ala Arg Ala Gly
            115                 120                 125

Thr Ala Lys Glu Gly Glu Glu Asp Cys Arg Ser Tyr Cys Gly Ser Ser
    130                 135                 140

Ser Ser Val Leu Leu Glu Glu Gly Ala Asp Ala Ala Ala Ser Arg
145                 150                 155                 160

Ser Pro Leu Pro Phe Asp Leu Asn Met Pro Pro Gln Glu Gly Ala
                165                 170                 175

Leu Asp Ala Glu Ala Asp Gln Met Thr Cys Arg Tyr Asp Thr Leu Leu
            180                 185                 190

Arg Leu

```
<210> SEQ ID NO 47
<211> LENGTH: 660
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1441430
<220> FEATURE:
<221> NAME/KEY: misc_feature
<223> OTHER INFORMATION: Encodes the protein at SEQ ID NO: 48

<400> SEQUENCE: 47
atggggagaa caagaacaac aacaaaacag gctgttgacc caaatggatc tgcaacccaa      60
aatatgttag taattgcaaa agagcccaga tacagaggag tacgaaagag accatgggga     120
agattcgctg cggagattag agatccctgg aaaaagacca gagtttggct gggcaccttc     180
gactctgcag aggatgcagc gcgtgcctac gatgcggctg ctcgcaccct ccgcggagca     240
aaggccaaga caaactttcc tatctccaca acgaaccagt tattcaatca tcaaaatcaa     300
aaccaaagcc caaccgatcc cttcttggat caccacagta taaatcccca agacccaca     360 tctagcagtt tgagcagtac agtggagtct ttcagcggtc ctaggcctcc gcagccaaca     420
acaacaacaa aatcgggaaa tgggccgagg agatctcatc cacggatccc accggttgtt     480
```

```
ccagaagatt gtcatagcga ttgcgattca tcttcttcgg tggttgatga cagagatgtc        540
gcatccgctg cttcttcttt gtgccgcaag cctttgcctt tcgatctaaa tttcccaccg        600
ttggaccagg ttgacttggg ctctggtgat gatctccact gcactgcttt atgcctttga        660
```

```
<210> SEQ ID NO 48
<211> LENGTH: 219
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no. 1441430
<220> FEATURE:
<221> NAME/KEY: misc_feature
<222> LOCATION: (29)..(92)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 48

Met Gly Arg Thr Arg Thr Thr Thr Lys Gln Ala Val Asp Pro Asn Gly
1               5                   10                  15

Ser Ala Thr Gln Asn Met Leu Val Ile Ala Lys Glu Pro Arg Tyr Arg
            20                  25                  30

Gly Val Arg Lys Arg Pro Trp Gly Arg Phe Ala Ala Glu Ile Arg Asp
        35                  40                  45

Pro Trp Lys Lys Thr Arg Val Trp Leu Gly Thr Phe Asp Ser Ala Glu
    50                  55                  60

Asp Ala Ala Arg Ala Tyr Asp Ala Ala Ala Arg Thr Leu Arg Gly Ala
65                  70                  75                  80

Lys Ala Lys Thr Asn Phe Pro Ile Ser Thr Thr Asn Gln Leu Phe Asn
                85                  90                  95

His Gln Asn Gln Asn Gln Ser Pro Thr Asp Pro Phe Leu Asp His His
            100                 105                 110

Ser Ile Asn Pro Gln Arg Pro Thr Ser Ser Ser Leu Ser Ser Thr Val
        115                 120                 125

Glu Ser Phe Ser Gly Pro Arg Pro Gln Pro Thr Thr Thr Thr Lys
    130                 135                 140

Ser Gly Asn Gly Pro Arg Arg Ser His Pro Arg Ile Pro Pro Val Val
145                 150                 155                 160

Pro Glu Asp Cys His Ser Asp Cys Asp Ser Ser Ser Val Val Asp
                165                 170                 175

Asp Arg Asp Val Ala Ser Ala Ala Ser Ser Leu Cys Arg Lys Pro Leu
            180                 185                 190

Pro Phe Asp Leu Asn Phe Pro Pro Leu Asp Gln Val Asp Leu Gly Ser
        195                 200                 205

Gly Asp Asp Leu His Cys Thr Ala Leu Cys Leu
    210                 215

<210> SEQ ID NO 49
<211> LENGTH: 985
<212> TYPE: DNA
<213> ORGANISM: Glycine max
<220> FEATURE:
<221> NAME/KEY: misc_feature
<223> OTHER INFORMATION: Ceres CLONE ID no.1240330
<220> FEATURE:
<221> NAME/KEY: misc_feature
<223> OTHER INFORMATION: Encodes the protein at SEQ ID NO: 50
```

<400> SEQUENCE: 49

```
attattcctc ttccatctct attctccata acacccacca caccacttgt gaaaaacctc    60
attaatatca cacactgaca tgtatctctg agctccaatc caatacaaga ccacaccttg   120
tcgtgtcgga cgaaccttgg tgtctgtttt tttttttttt tcattatttt ctccgaagag   180
atgaggaagg gcagaggtgg aggcgcctcg gcggcggcgg tggatgtgaa cggatccatt   240
ttaaaggagc ctcggtaccg gggcgtgagg aagagaccgt gggggagatt cgccgcggag   300
atcagagacc cgttgaagaa agccagggtt tggttgggaa ccttcgattc tgccgaggat   360
gctgctcgtg cctacgacgc cgccgctcgg actctccgag gtcccaaggc caaaacaaat   420
ttcccccctc tctcaccttt ttgctatcca cacccccacca ccgatccttt cttctacact   480
ggtttccacg atcaacacca ccaccacaac aacaacaacc ttaacaaccc tcaaagaccc   540
acttcaagtg gcatgagtag caccgttgag tccttcagtg ggccccgccc tcccaccacc   600
accactacca ccacaaccac aactgcgacg ccgttttttga ctgctacgcg agatacccg   660
cgcactcccc ctcttgtccc tgaagactgc cacagtgact gcgactcttc ctcctccgtc   720
gttgacgacg gcgacgacaa catcgtttcg tcgtcgtttc gacctcccctt gccgtttgat   780
ctcaacgcgc tgccgtttga tgatgctgcc gcggatgatg atctacgccg caccgcgctt   840
tgtctctgat gatgattatc gtgcgatgat gattttaat ttctcatttt tttacttgat   900
ttttttgtta ttgctatgca gaagaaatat atatttaaaa tgatgatcag atgtaagatt   960
atggtaatat gatcttaatt ctgtg                                         985
```

```
<210> SEQ ID NO 50
<211> LENGTH: 222
<212> TYPE: PRT
<213> ORGANISM: Glycine max
<220> FEATURE:
<221> NAME/KEY: misc_feature
<223> OTHER INFORMATION: Ceres CLONE ID no. 1240330
<220> FEATURE:
<221> NAME/KEY: misc_feature
<222> LOCATION: (24)..(87)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42
```

<400> SEQUENCE: 50

```
Met Arg Lys Gly Arg Gly Gly Gly Ala Ser Ala Ala Val Asp Val
1               5                   10                  15

Asn Gly Ser Ile Leu Lys Glu Pro Arg Tyr Arg Gly Val Arg Lys Arg
                20                  25                  30

Pro Trp Gly Arg Phe Ala Ala Glu Ile Arg Asp Pro Leu Lys Lys Ala
            35                  40                  45

Arg Val Trp Leu Gly Thr Phe Asp Ser Ala Glu Asp Ala Ala Arg Ala
        50                  55                  60

Tyr Asp Ala Ala Ala Arg Thr Leu Arg Gly Pro Lys Ala Lys Thr Asn
65                  70                  75                  80

Phe Pro Pro Leu Ser Pro Phe Cys Tyr Pro His Pro Thr Thr Asp Pro
                85                  90                  95

Phe Phe Tyr Thr Gly Phe His Asp Gln His His His Asn Asn Asn
            100                 105                 110

Asn Leu Asn Asn Pro Gln Arg Pro Thr Ser Ser Gly Met Ser Ser Thr
```

Val Glu Ser Phe Ser Gly Pro Arg Pro Thr Thr Thr Thr Thr
      115                 120                 125
130                 135                 140

Thr Thr Thr Thr Ala Thr Pro Phe Leu Thr Ala Thr Arg Arg Tyr Pro
145                 150                 155                 160

Arg Thr Pro Pro Leu Val Pro Glu Asp Cys His Ser Asp Cys Asp Ser
                    165                 170                 175

Ser Ser Ser Val Val Asp Asp Gly Asp Asp Asn Ile Val Ser Ser Ser
                180                 185                 190

Phe Arg Pro Pro Leu Pro Phe Asp Leu Asn Ala Leu Pro Phe Asp Asp
                195                 200                 205

Ala Ala Ala Asp Asp Asp Leu Arg Arg Thr Ala Leu Cys Leu
210                 215                 220

<210> SEQ ID NO 51
<211> LENGTH: 726
<212> TYPE: DNA
<213> ORGANISM: Zea mays
<220> FEATURE:
<221> NAME/KEY: misc_feature
<223> OTHER INFORMATION: Ceres CLONE ID no.1382611
<220> FEATURE:
<221> NAME/KEY: misc_feature
<223> OTHER INFORMATION: Encodes the protein at SEQ ID NO: 52

<400> SEQUENCE: 51
acttttctct cccattcttt tacaactcac gttgcacagc cttttctct atatattact      60 tgacataaac tactattcac aacacaaaca cacacataac catggcctct tcttcacaag    120
ctttcctttt gctcacattg tctatggttt tagttcattt ctctttagct caatctccca    180
tgatggctcc ttctggctcc atgtccatgc cgccaatgcc tagcggcggc tctccaatgc    240
caatgatgac tccaccacct atgccaatga tgactccacc acctatggct atggctccac    300
cacctatgcc tatgactcca ccaccaatgc ccatggctcc gatgccaatg actccatctt    360
caagtccaat gagcccacca actactatgg ccccaagtcc agaaacagtc cctgatatgg    420
cttcgccacc gatgatgcca ggaatggatt cttctccttc tccgggaccc atgccaccgg    480
caatggcctc tccagattcc ggagcattca atgtaagaaa cgacgtcgta gcaatttcgt    540
tccttgttgc agtcatttg ctcctagttt gagattatta ttaaattggc cagcgtcgtg    600
tttgtgtaat ttactttcat ttttttctcg agccattaat tttcatgttt tatcatatat    660
ttgggtttgt gtttgatatg gtacgattca gacatttgtt tgcttaataa gttatcgtt    720 gactct                                                              726

<210> SEQ ID NO 52
<211> LENGTH: 156
<212> TYPE: PRT
<213> ORGANISM: Zea mays
<220> FEATURE:
<221> NAME/KEY: misc_feature
<223> OTHER INFORMATION: Ceres CLONE ID no. 1382611
<220> FEATURE:
<221> NAME/KEY: misc_feature
<223> OTHER INFORMATION: Functional Homolog of Ceres CLONE ID no. 30087
      Given in SEQ ID NO: 2

<400> SEQUENCE: 52

Met Ala Ser Ser Ser Gln Ala Phe Leu Leu Leu Thr Leu Ser Met Val
1               5                   10                  15

Leu Val His Phe Ser Leu Ala Gln Ser Pro Met Met Ala Pro Ser Gly

```
                20                  25                  30
Ser Met Ser Met Pro Pro Met Pro Gly Gly Ser Pro Met Pro Met
            35                  40                  45

Met Thr Pro Pro Pro Met Pro Met Met Thr Pro Pro Pro Met Ala Met
 50                  55                  60

Ala Pro Pro Pro Met Pro Met Thr Pro Pro Pro Met Pro Met Ala Pro
 65                  70                  75                  80

Met Pro Met Thr Pro Ser Ser Ser Pro Met Ser Pro Pro Thr Thr Met
            85                  90                  95

Ala Pro Ser Pro Glu Thr Val Pro Asp Met Ala Ser Pro Pro Met Met
            100                 105                 110

Pro Gly Met Asp Ser Ser Pro Ser Pro Gly Pro Met Pro Pro Ala Met
            115                 120                 125

Ala Ser Pro Asp Ser Gly Ala Phe Asn Val Arg Asn Asp Val Val Ala
            130                 135                 140

Ile Ser Phe Leu Val Ala Ala His Leu Leu Leu Val
145                 150                 155
```

<210> SEQ ID NO 53
<211> LENGTH: 580
<212> TYPE: DNA
<213> ORGANISM: Papaver somniferum
<220> FEATURE:
<221> NAME/KEY: misc_feature
<223> OTHER INFORMATION: Ceres CLONE ID no.1627907
<220> FEATURE:
<221> NAME/KEY: misc_feature
<223> OTHER INFORMATION: Encodes the protein at SEQ ID NO: 54

<400> SEQUENCE: 53

```
gcagaagcac aaggtaagat tgaaggagga gaccggaact cttcttcgcc aaaaccctag    60
ttcgagctca ccaacaacaa tctttcgcaa tgactaagcg taccaagaag gccggaattg   120
tgggtaaata tggtaccaga tatggagctt cattaaggaa acagattaag aagatggaag   180
tgagtcagca tgcaaagtac ttctgtgagt tctgcggaaa gtacgctgtg aagagacagg   240
ctgttggaat ctggggatgc aaggattgtg gcaaagttaa agctggtggt gcttacactt   300
tgaacaccgc cagtgccgtg acagttagaa gcaccattag aaggttgagg gagcaaactg   360
aatcttagat tgatctcgtt atctatattt tgtattttgg tactgggtga gaggtaccat   420
cagagctaat ttagtgttta tcaccttttc tggtcttcaa gaactagtta gtcatttttgt   480
tattcagaga ttttttgataa tgtctagtat cttacatttg tgagcagact atttctttgt   540
ttcaaattat ggagttctga tgaatcttat atttattctc                          580
```

<210> SEQ ID NO 54
<211> LENGTH: 92
<212> TYPE: PRT
<213> ORGANISM: Papaver somniferum
<220> FEATURE:
<221> NAME/KEY: misc_feature
<223> OTHER INFORMATION: Ceres CLONE ID no. 1627907
<220> FEATURE:
<221> NAME/KEY: misc_feature
<222> LOCATION: (2)..(91)
<223> OTHER INFORMATION: Pfam Name: Ribosomal_L37ae
     Pfam Description: Ribosomal L37ae protein family
<220> FEATURE:
<221> NAME/KEY: misc_feature
<223> OTHER INFORMATION: Functional Homolog of Ceres CLONE ID no. 271922
     Given in SEQ ID NO: 20

<400> SEQUENCE: 54

```
Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ala Lys Tyr Phe Cys Glu Phe Cys Gly Lys Tyr Ala Val Lys
        35                  40                  45

Arg Gln Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90
```

<210> SEQ ID NO 55
<211> LENGTH: 983
<212> TYPE: DNA
<213> ORGANISM: Panicum virgatum
<220> FEATURE:
<221> NAME/KEY: misc_feature
<223> OTHER INFORMATION: Ceres CLONE ID no.1761125
<220> FEATURE:
<221> NAME/KEY: misc_feature
<223> OTHER INFORMATION: Encodes the protein at SEQ ID NO: 56

<400> SEQUENCE: 55

```
accagaccac accacaccac accgcgtcca catcctcccg cgcttctccg ctcagcccgc      60
gcgtttccgc tgaggaggga tagccgcgcg gcgcgtcgag gggtttgtct ttgatcgggt     120
agctgaggct gagcgggcgg ggcaggatga tgcgcgacac ggcggccgtg gccgtggcgg     180
cgccgcggta caggggcgtg cggaagcggc cgtggggccg gttcgcggcg gagatccgcg     240
acccggcgaa gcgcgcgcgc gtctggctcg gcaccttcga ctccgccgag gccgcggcgc     300
gcgcctacga cgtcgccgcg cggacccgc gcggcccgct cgccaggacc aacttcccct     360
gcgcctcctc ccgcctcccg ctgccctccc gccaccaagg cggctgtggc ggcggcctcg     420
tcgcgccgcc gcccgccgcg ccgacgtgca gctccagctc caccgtcgag tcctccagcg     480
gaccccgagg ggcgcccagg gctgctgcgg cggcggcgcc tcgaattcgg aggcggtcgg     540
tgaaaaagcc gcggccggca gcgcccgaca tcgactgcca cagcgactgc gcctcgtcgg     600
cctccgtcgt ggacgacggc gacgacgcct ccacggtccg gtcgcgcgcg ccgttcgacc     660
tcaacgtccc ggctccggtg gacggtgacc acgccctcga cctctgcacg gagctgcggc     720
tctgagcaat atgatcctcg aacaacaaca acagcaaaac attgaaggcg attttccc     780
ggtcttcttt tcctgactaa attctgatat gatcaatatg ctcgagagtt ctcgttttct     840
ttaacgcctc ttgtatttgg atctgctacc atcttctctg cccattctat ttgtacacca     900
gataacatgt aagatgttca cgaattaaca catatctttt cttaaaaaaa tgaattaaca     960
cggaaaaaaa aaaaaaaaa aaa                                              983
```

<210> SEQ ID NO 56
<211> LENGTH: 192
<212> TYPE: PRT
<213> ORGANISM: Panicum virgatum
<220> FEATURE:
<221> NAME/KEY: misc_feature
<223> OTHER INFORMATION: Ceres CLONE ID no. 1761125
<220> FEATURE:
<221> NAME/KEY: misc_feature
<222> LOCATION: (13)..(76)
<223> OTHER INFORMATION: Pfam Name: AP2

```
                Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 56

Met Met Arg Asp Thr Ala Ala Val Ala Val Ala Ala Pro Arg Tyr Arg
1               5                   10                  15

Gly Val Arg Lys Arg Pro Trp Gly Arg Phe Ala Ala Glu Ile Arg Asp
            20                  25                  30

Pro Ala Lys Arg Ala Arg Val Trp Leu Gly Thr Phe Asp Ser Ala Glu
        35                  40                  45

Ala Ala Ala Arg Ala Tyr Asp Val Ala Ala Arg Thr Leu Arg Gly Pro
    50                  55                  60

Leu Ala Arg Thr Asn Phe Pro Cys Ala Ser Ser Arg Leu Pro Leu Pro
65                  70                  75                  80

Ser Arg His Gln Gly Gly Cys Gly Gly Gly Leu Val Ala Pro Pro
                85                  90                  95

Ala Ala Pro Thr Cys Ser Ser Ser Thr Val Glu Ser Ser Ser Gly
            100                 105                 110

Pro Arg Gly Ala Pro Arg Ala Ala Ala Ala Ala Pro Arg Ile Arg
        115                 120                 125

Arg Arg Ser Val Lys Lys Pro Arg Pro Ala Ala Pro Asp Ile Asp Cys
130                 135                 140

His Ser Asp Cys Ala Ser Ser Ala Ser Val Val Asp Asp Gly Asp Asp
145                 150                 155                 160

Ala Ser Thr Val Arg Ser Arg Ala Pro Phe Asp Leu Asn Val Pro Ala
                165                 170                 175

Pro Val Asp Gly Asp His Ala Leu Asp Leu Cys Thr Glu Leu Arg Leu
            180                 185                 190

<210> SEQ ID NO 57
<211> LENGTH: 594
<212> TYPE: DNA
<213> ORGANISM: Panicum virgatum
<220> FEATURE:
<221> NAME/KEY: misc_feature
<223> OTHER INFORMATION: Ceres CLONE ID no.1783890
<220> FEATURE:
<221> NAME/KEY: misc_feature
<223> OTHER INFORMATION: Encodes the protein at SEQ ID NO: 58

<400> SEQUENCE: 57
gagccctacc cgcacccgcg ccgccgccgc cccgcgcccc gtcgccgcag acgactccgc      60
cccgtcgccg cgatgacgaa gcgcaccaag aaggccggaa tcgtcggcaa atatggaact     120
aggtatggtg ctagcttgcg taagcaaatc aagaagatgg aggtgtctca gcactccaag     180
tacttctgcg agttctgtgg aaagtttgct gtgaaaagga aagcagttgg aatctgggga     240
tgcaaggact gcgggaaggt taaggctggt ggtgcttaca ccatgaacac tgctagtgca     300
gtcaccgtca ggagcacaat ccgtcgcttg agggagcaga ctgaagcata atcggagctc     360
ttctctgcag tagtcctgtg cttttttgtac cgtctaagac atatggctgt ttggcctaag     420
aacattcatg aatattctgg ttatgcttaa ggatatcaaa aattatggtg ctaaaatttg     480
tacttcgttg ctgttgcaaa gttgacctgt cttgatccat tcataatgta gaatttcctc     540
atggttctta tctccagttt gctactcttt ggccaaaaaa aaaaaaaaaa aaaa           594
```

```
<210> SEQ ID NO 58
<211> LENGTH: 92
<212> TYPE: PRT
<213> ORGANISM: Panicum virgatum
<220> FEATURE:
<221> NAME/KEY: misc_feature
<223> OTHER INFORMATION: Ceres CLONE ID no. 1783890
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional Homolog of Ceres CLONE ID no. 271922
      Given in SEQ ID NO: 20

<400> SEQUENCE: 58

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 59
<211> LENGTH: 880
<212> TYPE: DNA
<213> ORGANISM: Panicum virgatum
<220> FEATURE:
<221> NAME/KEY: misc_feature
<223> OTHER INFORMATION: Ceres CLONE ID no.1802327
<220> FEATURE:
<221> NAME/KEY: misc_feature
<223> OTHER INFORMATION: Encodes the protein at SEQ ID NO: 60

<400> SEQUENCE: 59
acacagatac attcgtcgat ccaccactgt ccagtgcttg gcggttacgc acgcacgcac      60
acagatagga ttatctttta ctacaccaac tcaccaagat actagcaagc cgaatcgaca     120
aacaagcagc aggaagagga ggcatggcgc tcgcggaggg gaacgtcatc ttcggcgagg     180
agcaggaggc gctggtgctc aagtcgtggg ccctcatgaa gaaggactcg gccgacctcg     240
gcctccgctt cttcctcaag atcttcgaga tcgcgccgtc ggcgaagcag atgttctcgt     300
tcctgcgcga ctccgacgtg ccgctcgaga agaaccccaa gctcaagaac acgccatgt     360 ccgtcttcgt catgacctgc gaggcggcgg cgcagctacg gaaggccggg aaggtcaccg     420
tcagggagac gacgctcaag cggctgggcg ccacgcactt caagtacggc gtcgccgacg     480
gccacttcga ggtgacgagg ttcgcgctgc tggagacgat aaaggaggcg cttcccgccg     540
acatgtggag cctggagatg aagaacgcct ggagcgaggc ttacaaccag ctggtggcgg     600
ccatcaagca ggagatgaag cctgccgcat gatgctgctg ctgctactga gatgaagcct     660
gcccgcatga tgctgctgct gctactcggc ctccgcgctg agttcccccct acgatgcacc     720 accatctcca aattcttcat cgctgttttt tttttttttgc tgttttgact tgtattgtgc     780
attttccaaa tctctcgatg gagacaagtg tgatgactaa ttttgagag catgtatata      840
```
tgttgtgatg agcattgaat aaaaaaaaaa aaaaaaaaa          880

<210> SEQ ID NO 60
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1802327
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 60

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Asn His Ala Met Ser Val Phe Val Met Thr Cys Glu
65                  70                  75                  80

Ala Ala Ala Gln Leu Arg Lys Ala Gly Lys Val Thr Val Arg Glu Thr
                85                  90                  95

Thr Leu Lys Arg Leu Gly Ala Thr His Phe Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Ser Leu Glu Met Lys Asn Ala Trp Ser
    130                 135                 140

Glu Ala Tyr Asn Gln Leu Val Ala Ala Ile Lys Gln Glu Met Lys Pro
145                 150                 155                 160

Ala Ala

<210> SEQ ID NO 61
<211> LENGTH: 1017
<212> TYPE: DNA
<213> ORGANISM: Gossypium hirsutum
<220> FEATURE:
<221> NAME/KEY: misc_feature
<223> OTHER INFORMATION: Ceres CLONE ID no.1838364
<220> FEATURE:
<221> NAME/KEY: misc_feature
<223> OTHER INFORMATION: Encodes the protein at SEQ ID NO: 62

<400> SEQUENCE: 61
cctgcccatt tccatcttcc ttctttcctt cctctttcct tgtcttctt gctttatctt          60 cccttatct tcaatctttt ctgttctgtt tttttcttag attcataggt aagttcgttt         120
tggttggctt gattatttcc tcacttccct tcttttttgg ttcatcgtga tcttttcatc         180 aaccccttt gattgttata tagattgtta ctattctttt aatctttaa atatttttt           240 tccatgagga gagggagagg tgccgcagct gcaaacgccg tagctaggag accggcactg         300
caacccagcg gatctattaa agagccgaga tacagaggtg ttagaaaaag gccatggggc         360

-continued

```
agattcgcgg ccgagattcg agacccttgg aagaagacca gggtctggtt agggacgttc      420
gactcggccg aagaagccgc tcgagcctac gatacggcgg cgaggacgct ccgtggaccc      480
aaagctaaaa caaatttccc cataaattct tcaaatatcc cggcttttcc tttcgaaacc      540
aatcatcacc acaacgaagg gttcatcgac caacgccggt tatatccgat gggcgaattt      600
catgaccccg aagtgaatcc acagagaccc acgaggagta gcatgagtag cacggtggag      660
tcgtttagtg gacccagacc ggcccaacca ccgcaaaagt cggcggactt cgcggtggtt      720
tcgactagga agtactatcc gaggccgccg ccagtagagc cagaggattg tcatagtgac      780
tgtgattcat catcgtcggt ggttgatgat ggggatatcg cgttgtcttc ttgtcggaaa      840
actttgcctt tcgatctcaa ttttccaccc ttggatgaag atggaagatc tccagtgtac      900
tgctttatgt ctttgatcgc gatgccggtg atgaatgatg atgatcgatt attggatctc      960
tttttctttt ttaaaaaatg ttagctttt taagcggaaa aaaaaaaaaa aaaaaa         1017
```

<210> SEQ ID NO 62
<211> LENGTH: 246
<212> TYPE: PRT
<213> ORGANISM: Gossypium hirsutum
<220> FEATURE:
<221> NAME/KEY: misc_feature
<223> OTHER INFORMATION: Ceres CLONE ID no. 1838364
<220> FEATURE:
<221> NAME/KEY: misc_feature
<222> LOCATION: (28)..(91)
<223> OTHER INFORMATION: Pfam Name: AP2
    Pfam Description: AP2 domain
<220> FEATURE:
<221> NAME/KEY: misc_feature
<223> OTHER INFORMATION: Functional Homolog of Ceres CLONE ID no. 674166
    Given in SEQ ID NO: 42

<400> SEQUENCE: 62

Met Arg Arg Gly Arg Gly Ala Ala Ala Ala Asn Ala Val Ala Arg Arg
1               5                   10                  15

Pro Ala Leu Gln Pro Ser Gly Ser Ile Lys Glu Pro Arg Tyr Arg Gly
                20                  25                  30

Val Arg Lys Arg Pro Trp Gly Arg Phe Ala Ala Glu Ile Arg Asp Pro
            35                  40                  45

Trp Lys Lys Thr Arg Val Trp Leu Gly Thr Phe Asp Ser Ala Glu Glu
        50                  55                  60

Ala Ala Arg Ala Tyr Asp Thr Ala Ala Arg Thr Leu Arg Gly Pro Lys
65                  70                  75                  80

Ala Lys Thr Asn Phe Pro Ile Asn Ser Ser Asn Ile Pro Ala Phe Pro
                85                  90                  95

Phe Glu Thr Asn His His His Asn Glu Gly Phe Ile Asp Gln Arg Arg
                100                 105                 110

Leu Tyr Pro Met Gly Glu Phe His Asp Pro Glu Val Asn Pro Gln Arg
            115                 120                 125

Pro Thr Arg Ser Ser Met Ser Ser Thr Val Glu Ser Phe Ser Gly Pro
        130                 135                 140

Arg Pro Ala Gln Pro Gln Lys Ser Ala Asp Phe Ala Val Val Ser
145                 150                 155                 160

Thr Arg Lys Tyr Tyr Pro Arg Pro Pro Val Glu Pro Glu Asp Cys
                165                 170                 175

His Ser Asp Cys Asp Ser Ser Ser Val Val Asp Asp Gly Asp Ile
            180                 185                 190

```
Ala Leu Ser Ser Cys Arg Lys Thr Leu Pro Phe Asp Leu Asn Phe Pro
            195                 200                 205

Pro Leu Asp Glu Asp Gly Arg Ser Pro Val Tyr Cys Phe Met Ser Leu
    210                 215                 220

Ile Ala Met Pro Val Met Asn Asp Asp Asp Arg Leu Leu Asp Leu Phe
225                 230                 235                 240

Phe Phe Phe Lys Lys Cys
                245
```

<210> SEQ ID NO 63
<211> LENGTH: 708
<212> TYPE: DNA
<213> ORGANISM: Panicum virgatum
<220> FEATURE:
<221> NAME/KEY: misc_feature
<223> OTHER INFORMATION: Ceres CLONE ID no.1876458
<220> FEATURE:
<221> NAME/KEY: misc_feature
<223> OTHER INFORMATION: Encodes the protein at SEQ ID NO: 64

<400> SEQUENCE: 63

```
acacagatac attcgtcgat ccaccactgt ccagtgcttg gcggttacgc acgcacgcac      60
acagatagga ttatctttta ctacaccaac tcaccaagat actagcaagc cgaatcgaca     120
aacaagcagc aggaagagga ggcatggcgc tcgcggaggg gaacgtcatc ttcggcgagg     180
agcaggaggc gctggtgctc aagtcgtggg ccctcatgaa gaaggactcg gccgacctcg     240
gcctccgctt cttcctcaag atcttcgaga tcgcgccgtc ggcgaagcag atgttctcgt     300
tcctgcgcga ctccgacgtg ccgctcgaga agaaccccaa gctcaagacc cacgccatgt     360
ccgtcttcgt catgacctgc gaggcggcgg cgcagctacg gaaggccggg aaggtcaccg     420
tcagggagac gacgctcaag cggctgggcg ccacgcactt caagtacggc gtcgccgacg     480
gccacttcga ggtgacgagg ttcgcgctgc tggagacgat aaaggaggcg cttcccgccg     540
acatgtggag cctggagatg aagtacgcct ggagcgaggc ttacaaccag cttgtggcgg     600
ccatcaagca ggagatgaag cctgccgcat gatgctgctg ctgctactcg gcctccgcgc     660
tgagttcccc ctacgatgca ccaccatctc caaattcttc atcgctgt                708
```

<210> SEQ ID NO 64
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1876458
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 64

```
Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
            35                  40                  45
```

Gln Met Phe Ser Phe Leu Arg Asp Ser Asp Val Pro Leu Glu Lys Asn
    50                  55                  60

Pro Lys Leu Lys Thr His Ala Met Ser Val Phe Val Met Thr Cys Glu
65                  70                  75                  80

Ala Ala Ala Gln Leu Arg Lys Ala Gly Lys Val Thr Val Arg Glu Thr
                85                  90                  95

Thr Leu Lys Arg Leu Gly Ala Thr His Phe Lys Tyr Gly Val Ala Asp
                100                 105                 110

Gly His Phe Glu Val Thr Arg Phe Ala Leu Leu Glu Thr Ile Lys Glu
            115                 120                 125

Ala Leu Pro Ala Asp Met Trp Ser Leu Glu Met Lys Tyr Ala Trp Ser
    130                 135                 140

Glu Ala Tyr Asn Gln Leu Val Ala Ala Ile Lys Gln Glu Met Lys Pro
145                 150                 155                 160

Ala Ala

<210> SEQ ID NO 65
<211> LENGTH: 712
<212> TYPE: DNA
<213> ORGANISM: Panicum virgatum
<220> FEATURE:
<221> NAME/KEY: misc_feature
<223> OTHER INFORMATION: Ceres CLONE ID no.1879148
<220> FEATURE:
<221> NAME/KEY: misc_feature
<223> OTHER INFORMATION: Encodes the protein at SEQ ID NO: 66

<400> SEQUENCE: 65
acacagatac attcgtcgat ccaccactgt ccagtgctcg gctcggttac gcacgcacgc      60
acacaaattg tagtacctgt gttttacacc accaaagata ctagcaagcc gagtcgacaa     120
acaaagcagc aggaagaggc atggcgctcg ctgacgggaa cggcgcggcc atcttcggcg     180
aggagcagga ggcgctggtg ctcaagtcgt gggccctcat gaagaaggac tcggccgacc     240
tcggcctccg cttcttcctc aagatcttcg agatcgcgcc gtcggcgaag cagatgttct     300
cgttcctgcg cgactccgac gtgccgctgg agaagaaccc caagctcaag acccacgcca     360
tgtccgtctt cgtcatgacc tgcgaggcgg cagcgcagct acggaaggcc gggaaggtca     420
ccgtcaggga cgacgcgctc aagcggctgg gcgcaacgca cttcaagtac ggcgtcgccg     480
acggccactt cgaggtgaca aggttcgcgc tgctggagac gataaaggag gcgcttcccg     540
ccgacatgtg gagcctggag atgaagaacg cctggagcga ggcttacaac cagctcgtgg     600
cggccatcaa gcaggagatg aagcctgctg catgatgctg catgctgcta catactcggc     660
ctccgagttc ccctacgat gcaccaccat ctccaagttc ttcatcgcta tt              712

<210> SEQ ID NO 66
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1879148
<220> FEATURE:
<221> NAME/KEY: misc_feature
<222> LOCATION: (16)..(156)
<223> OTHER INFORMATION: Pfam Name: Globin
        Pfam Description: Globin
<220> FEATURE:
<221> NAME/KEY: misc_feature
<223> OTHER INFORMATION: Functional homolog of Ceres Clone ID no. 30469
        given in SEQ ID NO: 7

<400> SEQUENCE: 66

```
Met Ala Leu Ala Asp Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Ala Gln Leu Arg Lys Ala Gly Lys Val Thr Val Arg
                85                  90                  95

Glu Thr Thr Leu Lys Arg Leu Gly Ala Thr His Phe Lys Tyr Gly Val
            100                 105                 110

Ala Asp Gly His Phe Glu Val Thr Arg Phe Ala Leu Leu Glu Thr Ile
        115                 120                 125

Lys Glu Ala Leu Pro Ala Asp Met Trp Ser Leu Glu Met Lys Asn Ala
    130                 135                 140

Trp Ser Glu Ala Tyr Asn Gln Leu Val Ala Ala Ile Lys Gln Glu Met
145                 150                 155                 160

Lys Pro Ala Ala
```

<210> SEQ ID NO 67
<211> LENGTH: 1129
<212> TYPE: DNA
<213> ORGANISM: Gossypium hirsutum
<220> FEATURE:
<221> NAME/KEY: misc_feature
<223> OTHER INFORMATION: Ceres CLONE ID no.1884696
<220> FEATURE:
<221> NAME/KEY: misc_feature
<223> OTHER INFORMATION: Encodes the protein at SEQ ID NO: 68

<400> SEQUENCE: 67

```
atccgccccc atttgttcgc tctgtatatt gaacttttct ttctcgattt tctctttgaa      60
caaaaatgat gaagatcttc aaccagactc tcaccggcaa gactatcacg ctcgaggtcg     120
agagctccga caccatcgaa ggcgccaaca ccattctcca agatggaggg agcctccctc     180
cttaccgaac ccgactgatc ttcgccggac aacagcttga ggacggactg accttgtgcg     240
attacaacat cttaaaggag gtcaactctc cacctcttcc tccggttgcg cggtgggatg     300
cttaccttcc ggaggacctt gaccggcaat accatcactc tccaggtcta aagcgccgac     360
tcgatcaagt tcgttcacgc taacatccaa gactaggaag gcgtccccccc ataccaacta     420
cgactctgct tcgaccgaaa acaacttgaa gacggccgta ccttggccga ctacaacatc     480
cagaaggagt caacgctcca tcttgtcctt cgtttgcgtg gcgggatgca aatcttcgtt     540
aagacgctta cgggaaagac gatcactctc gaggtcgaga gctctgacac gatcgacaac     600
gtgaaagcca aaatccaaga caaggaaggc atcccgccag accagcaacg tctcatcttc     660
gccggaaagc aactcgagga cgggcggact ttagccgatt acaatatcca gaaggaatcg     720
actcttcatc tggtcctgcg tcttggaggt gggatgcaga tcttcgtcaa gactttgacc     780
ggtaagacga ttactttaga agtggagagc tcggatacga ttgataacgt gaaagcgaag     840
attcaggaca agaaggaat tccaccagat cagcaaggt tgattttgc tgggaacaa        900
ctggaagacg gaaggacttt ggctgattac aatattcaaa aggattccac tcttcacctt     960
```

-continued

```
gttcttcgtc ttcgtggtgg gttctaagcc ttaaggtctc ccttaatgtg ggttttctgg    1020
ttttacgtga aggactgtgc cctgtaatgg cctttttaaaa aatttctagt ctttgtttac    1080
cggttgcatc tatgtatggt ttctcttaga atggaattag catatttac               1129
```

<210> SEQ ID NO 68
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 1884696
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 68

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Asp Ser Thr Leu His
    130                 135                 140

Leu Val Leu Arg Leu Arg Gly Gly Phe
145                 150

<210> SEQ ID NO 69
<211> LENGTH: 679
<212> TYPE: DNA
<213> ORGANISM: Gossypium hirsutum
<220> FEATURE:
<221> NAME/KEY: misc_feature
<223> OTHER INFORMATION: Ceres CLONE ID no.1916866
<220> FEATURE:
<221> NAME/KEY: misc_feature
<223> OTHER INFORMATION: Encodes the protein at SEQ ID NO: 70

<400> SEQUENCE: 69

```
aaatcaaata cctactgcaa ttaaaatccc ggaattactt aaacaacaat ggctacctat    60
gaaggtaaag ttttcactga agaacaagaa gctttggtgg tcaagtcatg gactgtaatg   120
```

```
aagaagaacg cagctgaatt gggtcttaaa ttcttcttga agatatttga gattgcacca    180
tcagccaaga aactattctc attcttgaga gactccaatg ttccattgga gcaaaacaca    240
aagctgaagc cccatgccat gtctgtcttt gtcatgacat gtgaatctgc agtgcaactg    300
cgtaaagcag gcaaagttac agtgagggaa tcaaatttga agaaattagg agctacccat    360
tttaagtatg gggtagttga tgaacatttt gaggtaacaa aatttgctct tttggagacc    420
ataaaagaag cagtaccaga tatgtggtca gatgagatga agaatgcatg gggtgaagcc    480
tatgatcgtt tggtcgcagc cattaaaata gaaatgaagg catgctcaca agctgcatga    540
tttcacaagt tccctacatt attgcttgtt aattttgggt ccaataagat tgaaagtttt    600
caatcattta aacatgtaat gtaacatagc tattgctcat cactactgtt ttttttccct    660
agtttgtttg ctcctgttc                                                 679
```

<210> SEQ ID NO 70
<211> LENGTH: 163
<212> TYPE: PRT
<213> ORGANISM: Gossypium hirsutum
<220> FEATURE:
<221> NAME/KEY: misc_feature
<223> OTHER INFORMATION: Ceres CLONE ID no. 1916866
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 70

Met Ala Thr Tyr Glu Gly Lys Val Phe Thr Glu Glu Gln Glu Ala Leu
 1               5                  10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Gln Ala Ala

<210> SEQ ID NO 71
<211> LENGTH: 1003
<212> TYPE: DNA
<213> ORGANISM: Panicum virgatum
<220> FEATURE:

<221> NAME/KEY: misc_feature
<223> OTHER INFORMATION: Ceres CLONE ID no.1950105
<220> FEATURE:
<221> NAME/KEY: misc_feature
<223> OTHER INFORMATION: Encodes the protein at SEQ ID NO: 72

<400> SEQUENCE: 71

```
atcgccacaa gttcgcgatc tctcgatttc acaaatcgcc gagaagaccc gagcagagaa      60
gttccctccg atcgccttgc caagatgcag atctttgtga agacactcac tggcaagact     120
atcacccttg aggtggagtc ttctgacaca attgacaatg tcaaggcaaa gatccaggac     180
aaggaaggga ttcctccaga ccagcagcgc cttatcttcg ctggcaagca gcttgaggat     240
ggccgtacac ttgcagatta acacattcag aaggagtcca cactgcacct tgtcctcagg     300
ctgcgtggag gcatgcagat tttcgtgaag accctcactg caagacgat caccctggag      360
gtggagtcat ctgacaccat cgacaatgtg aaggcaaaga tccaggacaa ggagggcatc     420
ccccctgacc agcagcgcct catctttgca ggcaagcagt tggaggatgg gcgaactctg     480
gctgactaya atatccagaa agaatcmacc ctgcacctsg tsctccgcct gcgtggtgga     540
atgcagatct tgtgaagac gcttaccggc aagaccatca ccttggaggt ggagtcttcg      600
gacaccatcg acaatgtgaa ggcgaagatt caggacaagg agggcattcc tccggaccag     660
crgcgcctca tctttgctgg caagcagcta gaggacgggc gtaccctggc ggattacaac     720
atccagaagg agtccaccct ccaccttgtc ctgcgcctcc gtggtggttt ctgagcctag     780
tgctcctgag ttgcctttg tcgttatggt caacctctgg tttaagtcgt gtgaactctc      840
tgcattgcgt tgctagtgtc tggttgtggt tgtaataaga acatgaagaa catgttgctg     900
tggatcacat gactttttt ttttgaaccg gaagatcaca tgactttcat ggctttaagt      960
tcctgaactc tgaaatctgg accccctttt aagctctgaa ctc                      1003
```

<210> SEQ ID NO 72
<211> LENGTH: 229
<212> TYPE: PRT
<213> ORGANISM: Panicum virgatum
<220> FEATURE:
<221> NAME/KEY: misc_feature
<223> OTHER INFORMATION: Ceres CLONE ID no. 1950105
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (153)..(226)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40
<220> FEATURE:
<221> NAME/KEY: misc_feature
<222> LOCATION: (135)..(135)
<223> OTHER INFORMATION: Xaa is any aa, unknown, or other
<220> FEATURE:
<221> NAME/KEY: misc_feature
<222> LOCATION: (141)..(141)
<223> OTHER INFORMATION: Xaa is any aa, unknown, or other
<220> FEATURE:
<221> NAME/KEY: misc_feature -continued

```
<222> LOCATION: (145)..(145)
<223> OTHER INFORMATION: Xaa is any aa, unknown, or other
<220> FEATURE:
<221> NAME/KEY: misc_feature
<222> LOCATION: (146)..(146)
<223> OTHER INFORMATION: Xaa is any aa, unknown, or other
<220> FEATURE:
<221> NAME/KEY: misc_feature
<222> LOCATION: (193)..(193)
<223> OTHER INFORMATION: Xaa is any aa, unknown, or other

<400> SEQUENCE: 72

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Xaa Asn Ile Gln Lys Glu Xaa Thr Leu His
    130                 135                 140

Xaa Xaa Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Xaa Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Phe
225

<210> SEQ ID NO 73
<211> LENGTH: 724
<212> TYPE: DNA
<213> ORGANISM: Panicum virgatum
<220> FEATURE:
<221> NAME/KEY: misc_feature
<223> OTHER INFORMATION: Ceres CLONE ID no.1990746
<220> FEATURE:
<221> NAME/KEY: misc_feature
<222> LOCATION: (623)..(623)
<223> OTHER INFORMATION: n is a, c, t, g, unknown, or other
<220> FEATURE:
<221> NAME/KEY: misc_feature
<222> LOCATION: (624)..(624)
<223> OTHER INFORMATION: n is a, c, t, g, unknown, or other
<220> FEATURE:
<221> NAME/KEY: misc_feature
<222> LOCATION: (625)..(625)
<223> OTHER INFORMATION: n is a, c, t, g, unknown, or other
<220> FEATURE:
```

```
<221> NAME/KEY: misc_feature
<223> OTHER INFORMATION: Encodes the protein at SEQ ID NO: 74

<400> SEQUENCE: 73
acacagatac actcgtcgat ccaccagacc accactgtcc agtgctcggc tcggttacgc      60
acgcacgcac acaaatagga gtacctgttt tacaccacca agatactagc aagcccaagc     120
cgagtcgaca aacaagcagc aggaagaggc atggcgctcg cggaggggaa cggcgcggcc     180
atcttcggcg aggaacagga ggcgctggtg ctcaagtcgt gggcccctca tgaagaaggac    240
tcggccgacc tcggcctccg cttcttcctc aagatcttcg agatcgcgcc gtcggcgaag     300
cagatgttct cgttcctgcg cgactccgac gtgccgctgg agaagaaccc caagctcaag     360
acccacgcca tgtccgtctt cgtcatgacc tgcgaggcgg cagtgcagct acggaaggcc     420
gggaaggtca ccgtcaggga cgacgctc aagcggctgg cgcaacgca cttcaagtac        480
ggcgtcgccg acggccactt cgaggtgaca aggttcgcgc tgctggagac gataaaggag     540
gcgcttcccg ccgacatgtg gagcctggag atgaagaacg cctggagcga ggcttacaac     600
cagctcgtgg cggccatcaa gcnnnagatg aagcctgccg catgatgctg catgctgcta     660
catactcggc ctccgagtcc cccctacgat gcaccaccat ctcccagttc ttcatcgcta     720
tttt                                                                  724

<210> SEQ ID NO 74
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1990746
<220> FEATURE:
<221> NAME/KEY: misc_feature
<222> LOCATION: (16)..(156)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
<220> FEATURE:
<221> NAME/KEY: misc_feature
<222> LOCATION: (158)..(158)
<223> OTHER INFORMATION: Xaa is any aa, unknown, or other
<220> FEATURE:
<221> NAME/KEY: misc_feature
<222> LOCATION: (159)..(159)
<223> OTHER INFORMATION: Xaa is any aa, unknown, or other

<400> SEQUENCE: 74

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Val Gln Leu Arg Lys Ala Gly Lys Val Thr Val Arg
                85                  90                  95

Glu Thr Thr Leu Lys Arg Leu Gly Ala Thr His Phe Lys Tyr Gly Val
            100                 105                 110
```

Ala Asp Gly His Phe Glu Val Thr Arg Phe Ala Leu Leu Glu Thr Ile
        115                 120                 125

Lys Glu Ala Leu Pro Ala Asp Met Trp Ser Leu Glu Met Lys Asn Ala
    130                 135                 140

Trp Ser Glu Ala Tyr Asn Gln Leu Val Ala Ala Ile Lys Xaa Xaa Met
145                 150                 155                 160

Lys Pro Ala Ala

<210> SEQ ID NO 75
<211> LENGTH: 696
<212> TYPE: DNA
<213> ORGANISM: Panicum virgatum
<220> FEATURE:
<221> NAME/KEY: misc_feature
<223> OTHER INFORMATION: Ceres CLONE ID no.2007485
<220> FEATURE:
<221> NAME/KEY: misc_feature
<223> OTHER INFORMATION: Encodes the protein at SEQ ID NO: 76

<400> SEQUENCE: 75
agagcagggg gatggaagaa aataaactac tggccaaacc ctagccgagc cccgggtccg     60
ctcaccgcct tcccaccccc ccacccaccc acctgccccc cccccccccc cgccctcgcc    120
gtccgcgatg cgccgggcga agccgccgca gccgcagccg tcgccgtcgc cggagatccg    180
gtaccgcggc gtgcggaggc ggccatcggg gcgctacgcc gccgagatcc gggacccggc    240
caagaagacc ccgatctggc tcggcacctt cgactccgcc gaggccgccg cgcgcgccta    300
cgacgccgcc gcccgatccc tccgcgggcc caccgcccgc accaacttcc ccagcgccgc    360
ggcccccgcg ccgcggcaca gcaggccccc cgcccctcc gccgccgcgc aggcggctgc    420
cgcggcggca gcgccacgt ccagccacag cagcaccata gagtcgtgga gcgacggcgc    480
gacccgcgcc gcgctggcgc gtagcgctgc ctccgtcctg gcgcgcagcg ccgctccgac    540
ggaggaggaa gacgaggact gccgcagcta ctgcggatcc tcgtcgtccg tcctctgcga    600
agacactggg ggcgacgatg cggccgcctc ccgcgcgccc ctgccgttcg atctgaacct    660
gccgccgcct catgacgcgg cctccgagac cgatca                             696

<210> SEQ ID NO 76
<211> LENGTH: 201
<212> TYPE: PRT
<213> ORGANISM: Panicum virgatum
<220> FEATURE:
<221> NAME/KEY: misc_feature
<223> OTHER INFORMATION: Ceres CLONE ID no. 2007485
<220> FEATURE:
<221> NAME/KEY: misc_feature
<222> LOCATION: (17)..(80)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 76

Met Arg Arg Ala Lys Pro Pro Gln Pro Gln Pro Ser Pro Ser Pro Glu
1               5                   10                  15

Ile Arg Tyr Arg Gly Val Arg Arg Arg Pro Ser Gly Arg Tyr Ala Ala
            20                  25                  30

Glu Ile Arg Asp Pro Ala Lys Lys Thr Pro Ile Trp Leu Gly Thr Phe
        35                  40                  45

```
Asp Ser Ala Glu Ala Ala Arg Ala Tyr Asp Ala Ala Arg Ser
    50                  55                  60

Leu Arg Gly Pro Thr Ala Arg Thr Asn Phe Pro Ser Ala Ala Pro
65                  70                  75                  80

Ala Pro Arg His Ser Arg Pro Ala Pro Ser Ala Ala Gln Ala
                85                  90                  95

Ala Ala Ala Ala Ala Ala Thr Ser Ser His Ser Ser Thr Ile Glu
            100                 105                 110

Ser Trp Ser Asp Gly Ala Thr Arg Ala Ala Leu Ala Arg Ser Ala Ala
            115                 120                 125

Ser Val Leu Ala Arg Ser Ala Ala Pro Thr Glu Glu Glu Asp Glu Asp
    130                 135                 140

Cys Arg Ser Tyr Cys Gly Ser Ser Ser Val Leu Cys Glu Asp Thr
145                 150                 155                 160

Gly Gly Asp Asp Ala Ala Ala Ser Arg Ala Pro Leu Pro Phe Asp Leu
                165                 170                 175

Asn Leu Pro Pro Pro His Asp Ala Ala Ser Glu Thr Asp Gln Met Gly
                180                 185                 190

Ala Arg Tyr Asp Thr Leu Leu Arg Leu
            195                 200

<210> SEQ ID NO 77
<211> LENGTH: 698
<212> TYPE: DNA
<213> ORGANISM: Panicum virgatum
<220> FEATURE:
<221> NAME/KEY: misc_feature
<223> OTHER INFORMATION: Ceres CLONE ID no.2033803
<220> FEATURE:
<221> NAME/KEY: misc_feature
<223> OTHER INFORMATION: Encodes the protein at SEQ ID NO: 78

<400> SEQUENCE: 77
acacagatac attcgtcgat ccaccagacc accactgtcc agtgctcggc tcggttacgc      60
acgcacgcac acaaatagga gtacctgttt tacaccaaga tactagcaag cccaagccga     120
gtcgacaaac aagcagcagg aagaggcatg gcgctcgcgg aggggaacgg cgcggccatc     180
ttcggcgagg agcaggaggc gctggtgctc aagtcgtggg ccctcatgaa gaaggactcg     240
gccgacctcg gcctccgctt cttcctcaag atcttcgaga tcgcgccgtc ggcgaagcag     300
atgttctcgt tcctgcgcga ctccgacgtg ccgctggaga agaaccccaa gctcaagacc     360
cacgccatgt ccgtcttcgt catgacctgc gaggcggcag cgcagctacg gaaggccggg     420
aaggtcaccg tcagggagac gacgctcaag cggctgggcg caacgcactt caagtacggc     480
gtcgccgacg gccacttcga ggtgacaagg ttcgcgcttc ccgccgactt gtggagcctg     540
gagatgaaga acgcctggag cgaggcttac aaccagctcg tggcggccat caagcaggag     600
atgaagcctg ccgcatgatg ctgcatgctg ctacatactc ggcctccgag ttccccctac     660
gatgcaccac catctccaag ttctttcatt gtcttgtg                              698

<210> SEQ ID NO 78
<211> LENGTH: 156
<212> TYPE: PRT
<213> ORGANISM: Panicum virgatum
<220> FEATURE:
<221> NAME/KEY: misc_feature
<223> OTHER INFORMATION: Ceres CLONE ID no. 2033803
<220> FEATURE:
<221> NAME/KEY: misc_feature
<222> LOCATION: (16)..(148)
```

<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 78

```
Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Gln Leu Arg Lys Ala Gly Lys Val Thr Val Arg
                85                  90                  95

Glu Thr Thr Leu Lys Arg Leu Gly Ala Thr His Phe Lys Tyr Gly Val
                100                 105                 110

Ala Asp Gly His Phe Glu Val Thr Arg Phe Ala Leu Pro Ala Asp Leu
            115                 120                 125

Trp Ser Leu Glu Met Lys Asn Ala Trp Ser Glu Ala Tyr Asn Gln Leu
        130                 135                 140

Val Ala Ala Ile Lys Gln Glu Met Lys Pro Ala Ala
145                 150                 155
```

<210> SEQ ID NO 79
<211> LENGTH: 724
<212> TYPE: DNA
<213> ORGANISM: Panicum virgatum
<220> FEATURE:
<221> NAME/KEY: misc_feature
<223> OTHER INFORMATION: Ceres CLONE ID no.2034916
<220> FEATURE:
<221> NAME/KEY: misc_feature
<223> OTHER INFORMATION: Encodes the protein at SEQ ID NO: 80

<400> SEQUENCE: 79

| aatccaatct | cccccgatcc | ccaatcgcga | attcccctct | ccggcaggcg | aagcaatcga | 60 |
| ggggcaccct | ttcatctcgt | caagatgcag | atctttgtga | agaccctcac | tggtaagacc | 120 |
| atcaccctcg | aggttgagtc | ctcggatacc | attgacaacg | tcaaggctaa | atccaggac | 180 |
| aaggagggga | tccctccgga | ccagcagcgc | ctcatctttg | ccggcaagca | gctcgaagat | 240 |
| gggaggacgc | ttgctgacta | caacatccag | aaggagtcca | ccctccacct | cgtgctcagg | 300 |
| ctcagggggtg | gtatgcagat | ctttgtcaag | actctcaccg | gcaagacgat | tactcttgag | 360 |
| gttgagtcct | cggacacgat | cgacaatgta | aaggtgaaga | tccaagacaa | ggaggggatc | 420 |
| ccaccggacc | agcagcgcct | catctttgcc | ggcaagcagc | tcgaggatgg | ccgcactctg | 480 |
| gctgactaca | acattcagaa | agagtcgacc | cttcaccttg | tgctcaggct | gagggggaggc | 540 |
| atgcaaatat | ttgtcaagac | tctgactggc | aagaccatca | cgcttgaggt | ggagtcgtct | 600 |
| gacaccattg | ataatgtgaa | ggcgaagatc | caagacaagg | agggcatccc | gccggaccag | 660 |
| cagcgcctga | tctttgccgg | taagcagctg | gaggatggtc | gtaccctggc | agactataat | 720 |
| attc | | | | | | 724 |

```
<210> SEQ ID NO 80
<211> LENGTH: 213
<212> TYPE: PRT
<213> ORGANISM: Panicum virgatum
<220> FEATURE:
<221> NAME/KEY: misc_feature
<223> OTHER INFORMATION: Ceres CLONE ID no. 2034916
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (153)..(213)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 80

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Val Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile
    210

<210> SEQ ID NO 81
<211> LENGTH: 1194
<212> TYPE: DNA
<213> ORGANISM: Glycine max
<220> FEATURE:
<221> NAME/KEY: misc_feature
```

<223> OTHER INFORMATION: Ceres CLONE ID no.651581
<220> FEATURE:
<221> NAME/KEY: misc_feature
<222> LOCATION: (678)..(678)
<223> OTHER INFORMATION: n is a, c, t, g, unknown, or other
<220> FEATURE:
<221> NAME/KEY: misc_feature
<222> LOCATION: (679)..(679)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 82

<400> SEQUENCE: 81

| | | | | | |
|---|---|---|---|---|---|
| gtgtagttga | aggagcagaa | gaagaagaag | agaaggtggt | accgccttca | attctctttt | 60 |
| tctctctcca | tttctcatcc | tcatcatctt | attattcctc | ttccatctct | attctccata | 120 |
| acacccacca | caccacttgt | gaaaaacctc | attaatatca | cacactgaca | tgtatctctg | 180 |
| agctccaatc | caatacaaga | ccacaccttg | tcgtgtcgga | cgaaccttgg | tgtctgtttt | 240 |
| ttttttttt | tttcattatt | ttctccgaag | agatgaggaa | gggcaraggt | ggaggcgcct | 300 |
| cggcggcggc | ggtggatgtg | aacggatcca | ttttaaagga | gcctcggtac | cggggcgtga | 360 |
| ggaagagacc | gtgggggaga | ttcgccgcgg | agatcagaga | cccgttgaag | aaagccaggg | 420 |
| tttggttggg | aaccttcaat | tctgccgagg | atgctgctcg | tgcctacrac | gccgccgctc | 480 |
| ggactctccg | aggtcccaag | gccaaaacaa | atttcccccc | tctctcacct | ttttgctatc | 540 |
| cacacccac | caccgatcct | ttcttstaca | ctggtttcca | cgatcaacac | caccaccaca | 600 |
| acaacaacaa | ccttaacaac | cctcaaagac | ccacttcaag | tggcatgagt | agcmccgttg | 660 |
| agtccttcag | tgggccnnc | ccttttccc | ccaccaccac | cmctaccacc | acaaccacaa | 720 |
| ctgcgacgcc | gtttttgact | gctacgcgga | gatacccgcg | cactcccct | cttgtccctg | 780 |
| aagactgcca | cagtgactgc | gactcttcct | cctccgtcgt | tgacgacggc | gacgacaaca | 840 |
| tcgtttcgtc | gtcgtttcga | cctcccttgc | cgtttgatct | caacgcgctg | ccgtttgatg | 900 |
| atgctgccgc | ggatgatgat | ctacgccgca | ccgcgctttg | tctctgatga | tgattatcgt | 960 |
| gcgatgatga | tttttaattt | ctcattttt | tacttgattt | ttttgttatt | gctatgcaga | 1020 |
| agaaatatat | atttaaaatg | atgatcagat | gtaagattat | ggtaatatga | tcttaattct | 1080 |
| gtgagaggaa | gattccgtgt | tggttatatt | ttcttctttt | tattatttt | ttaaacattt | 1140 |
| ttatttagaa | ggaaatattg | aatgaaaaga | aaaagagaa | agtaattatg | atcg | 1194 |

<210> SEQ ID NO 82
<211> LENGTH: 224
<212> TYPE: PRT
<213> ORGANISM: Glycine max
<220> FEATURE:
<221> NAME/KEY: misc_feature
<223> OTHER INFORMATION: Ceres CLONE ID no. 651581
<220> FEATURE:
<221> NAME/KEY: misc_feature
<222> LOCATION: (24)..(87)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42
<220> FEATURE:
<221> NAME/KEY: misc_feature
<222> LOCATION: (137)..(137)
<223> OTHER INFORMATION: Xaa is any aa, unknown, or other

<400> SEQUENCE: 82

-continued

```
Met Arg Lys Gly Arg Gly Gly Ala Ser Ala Ala Val Asp Val
1               5                   10                  15

Asn Gly Ser Ile Leu Lys Glu Pro Arg Tyr Arg Gly Val Arg Lys Arg
            20                  25                  30

Pro Trp Gly Arg Phe Ala Ala Glu Ile Arg Asp Pro Leu Lys Lys Ala
        35                  40                  45

Arg Val Trp Leu Gly Thr Phe Asn Ser Ala Glu Asp Ala Ala Arg Ala
50                  55                  60

Tyr Asp Ala Ala Ala Arg Thr Leu Arg Gly Pro Lys Ala Lys Thr Asn
65                  70                  75                  80

Phe Pro Pro Leu Ser Pro Phe Cys Tyr Pro His Pro Thr Thr Asp Pro
                85                  90                  95

Phe Phe Tyr Thr Gly Phe His Asp Gln His His His Asn Asn Asn
            100                 105                 110

Asn Leu Asn Asn Pro Gln Arg Pro Thr Ser Ser Gly Met Ser Ser Thr
        115                 120                 125

Val Glu Ser Phe Ser Gly Pro Arg Xaa Phe Ser Pro Thr Thr Thr Thr
130                 135                 140

Thr Thr Thr Thr Thr Thr Ala Thr Pro Phe Leu Thr Ala Thr Arg Arg
145                 150                 155                 160

Tyr Pro Arg Thr Pro Pro Leu Val Pro Glu Asp Cys His Ser Asp Cys
                165                 170                 175

Asp Ser Ser Ser Ser Val Val Asp Asp Gly Asp Asp Asn Ile Val Ser
            180                 185                 190

Ser Ser Phe Arg Pro Pro Leu Pro Phe Asp Leu Asn Ala Leu Pro Phe
        195                 200                 205

Asp Asp Ala Ala Ala Asp Asp Asp Leu Arg Arg Thr Ala Leu Cys Leu
210                 215                 220
```

<210> SEQ ID NO 83
<211> LENGTH: 184
<212> TYPE: PRT
<213> ORGANISM: Oryza sativa subsp. indica
<220> FEATURE:
<221> NAME/KEY: misc_feature
<223> OTHER INFORMATION: Public GI ID no. 125550159
<220> FEATURE:
<221> NAME/KEY: misc_feature
<222> LOCATION: (7)..(70)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 83

```
Met Cys Glu Ala Ala Ala Pro Arg Tyr Arg Gly Val Arg Lys Arg Pro
1               5                   10                  15

Trp Gly Arg Phe Ala Ala Glu Ile Arg Asp Pro Ala Lys Arg Ala Arg
            20                  25                  30

Val Trp Leu Gly Thr Tyr Asp Ser Ala Glu Ala Ala Ala Arg Ala Tyr
        35                  40                  45

Asp Val Ala Ala Arg Asn Leu Arg Gly Pro Leu Ala Arg Thr Asn Phe
50                  55                  60

Pro Leu Val Ser Ser Leu Pro Leu Pro Ser His Tyr His Leu Pro
65                  70                  75                  80

Gly Lys Ala Ala Ala Ala Ala Pro Pro Val Ala Gly Pro Ala Cys Ser
                85                  90                  95
```

```
Ala Ser Ser Thr Val Glu Ser Ser Gly Pro Arg Gly Pro Arg Pro
            100                 105                 110

Ala Ala Thr Ala Ala Ala Val Pro Arg Arg Arg Val Pro Arg Pro Ala
        115                 120                 125

Pro Pro Ala Pro Asp Ala Gly Cys His Ser Asp Cys Ala Ser Ser Ala
130                 135                 140

Ser Val Val Asp Asp Ala Asp Asp Ala Ser Thr Val Arg Ser Arg Val
145                 150                 155                 160

Ala Ala Phe Asp Leu Asn Leu Pro Pro Leu Asp Arg Asp His Val
                165                 170                 175

Asp Leu Cys Thr Asp Leu Arg Leu
            180

<210> SEQ ID NO 84
<211> LENGTH: 225
<212> TYPE: PRT
<213> ORGANISM: Arabidopsis thaliana
<220> FEATURE:
<221> NAME/KEY: misc_feature
<223> OTHER INFORMATION: Public GI ID no. 15223609
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 84

Met Arg Arg Gly Arg Gly Ser Ser Ala Val Ala Gly Pro Thr Val Val
1               5                   10                  15

Ala Ala Ile Asn Gly Ser Val Lys Glu Ile Arg Phe Arg Gly Val Arg
            20                  25                  30

Lys Arg Pro Trp Gly Arg Phe Ala Ala Glu Ile Arg Asp Pro Trp Lys
        35                  40                  45

Lys Ala Arg Val Trp Leu Gly Thr Phe Asp Ser Ala Glu Glu Ala Ala
50                  55                  60

Arg Ala Tyr Asp Ser Ala Ala Arg Asn Leu Arg Gly Pro Lys Ala Lys
65                  70                  75                  80

Thr Asn Phe Pro Ile Asp Ser Ser Pro Pro Pro Asn Leu Arg
                85                  90                  95

Phe Asn Gln Ile Arg Asn Gln Asn Gln Asn Val Asp Pro Phe Met
            100                 105                 110

Asp His Arg Leu Phe Thr Asp His Gln Gln Gln Phe Pro Ile Val Asn
            115                 120                 125

Arg Pro Thr Ser Ser Ser Met Ser Ser Thr Val Glu Ser Phe Ser Gly
        130                 135                 140

Pro Arg Pro Thr Thr Met Lys Pro Ala Thr Thr Lys Arg Tyr Pro Arg
145                 150                 155                 160

Thr Pro Pro Val Val Pro Glu Asp Cys His Ser Asp Cys Asp Ser Ser
                165                 170                 175

Ser Ser Val Ile Asp Asp Asp Asp Ile Ala Ser Ser Arg Arg
            180                 185                 190

Arg Asn Pro Pro Phe Gln Phe Asp Leu Asn Phe Pro Pro Leu Asp Cys
        195                 200                 205

Val Asp Leu Phe Asn Gly Ala Asp Asp Leu His Cys Thr Asp Leu Arg
```

Leu
225

<210> SEQ ID NO 85
<211> LENGTH: 164
<212> TYPE: PRT
<213> ORGANISM: Arabidopsis thaliana
<220> FEATURE:
<221> NAME/KEY: misc_feature
<223> OTHER INFORMATION: Public GI ID no. 30683885
<220> FEATURE:
<221> NAME/KEY: misc_feature
<223> OTHER INFORMATION: Functional Homolog of Ceres CLONE ID no. 30087
      Given in SEQ ID NO: 2

<400> SEQUENCE: 85

Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
                20                  25                  30

Ser Gly Ser Met Ser Met Pro Pro Met Ser Ser Gly Gly Gly Ser Ser
            35                  40                  45

Val Pro Pro Val Met Ser Pro Met Pro Met Met Thr Pro Pro Pro
50                  55                  60

Met Pro Met Thr Pro Pro Pro Met Pro Met Thr Pro Pro Pro Met Pro
65                  70                  75                  80

Met Ala Pro Pro Pro Met Pro Met Ala Ser Pro Pro Met Met Pro Met
                85                  90                  95

Thr Pro Ser Thr Ser Pro Ser Pro Leu Thr Val Pro Asp Met Pro Ser
            100                 105                 110

Pro Pro Met Pro Ser Gly Met Glu Ser Ser Pro Ser Pro Gly Pro Met
        115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val

<210> SEQ ID NO 86
<211> LENGTH: 218
<212> TYPE: PRT
<213> ORGANISM: Pisum sativum
<220> FEATURE:
<221> NAME/KEY: misc_feature
<223> OTHER INFORMATION: Public GI ID no. 56384582
<220> FEATURE:
<221> NAME/KEY: misc_feature
<222> LOCATION: (21)..(84)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 86

Met Gly Arg Gly Gly Ala Thr Thr Ala Ala Ala Ala Val Glu Pro Val
1               5                   10                  15

Phe Phe Lys Glu Pro Arg Tyr Arg Gly Val Arg Lys Arg Pro Trp Gly
                20                  25                  30

Arg Phe Ala Ala Glu Ile Arg Asp Pro Leu Lys Lys Ala Arg Val Trp

```
              35                  40                  45
Leu Gly Thr Phe Asp Thr Ala Glu Glu Ala Ala Arg Ala Tyr Asp Thr
 50                  55                  60

Ala Ala Arg Asn Leu Arg Gly Pro Lys Ala Lys Thr Asn Phe Pro Leu
 65                  70                  75                  80

Ala Gln Pro Phe Tyr Gln Asn Pro Glu Ala Gly Asn Pro Phe Gly Glu
                     85                  90                  95

Leu Arg Phe Tyr Ala Gly Gly Ala Gly Glu Gly Phe Gln Asp His Arg
                100                 105                 110

Arg Pro Thr Ser Ser Gly Met Ser Ser Thr Val Glu Ser Phe Gly Gly
                115                 120                 125

Pro Arg Pro Val Arg Pro Pro Met Pro Pro Ser Ala Val Thr Gly Arg
                130                 135                 140

Arg Tyr Pro Arg Thr Pro Pro Val Ala Pro Gly Asp Cys Arg Ser Asp
145                 150                 155                 160

Cys Asp Ser Ser Ser Val Val Asp Asp Ala Asp Asn Asp Asn Ala
                    165                 170                 175

Ala Ser Ser Thr Met Leu Ser Phe Lys Arg Gln Pro Leu Pro Phe Asp
                180                 185                 190

Leu Asn Ala Pro Pro Leu Glu Glu Gly Asp Val Ala Asn Gly Leu Gly
                195                 200                 205

Glu Asp Leu His Cys Thr Leu Leu Cys Leu
                210                 215

<210> SEQ ID NO 87
<211> LENGTH: 225
<212> TYPE: PRT
<213> ORGANISM: Nicotiana tabacum
<220> FEATURE:
<221> NAME/KEY: misc_feature
<223> OTHER INFORMATION: Public GI ID no. 57012880
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 87

Met Arg Arg Gly Arg Ala Ala Ala Pro Ala Pro Val Thr Gly Glu
 1               5                  10                  15

Pro Asn Gly Ser Gly Gly Ser Lys Glu Ile Arg Phe Arg Gly Val Arg
                 20                  25                  30

Lys Arg Pro Trp Gly Arg Phe Ala Ala Glu Ile Arg Asp Pro Trp Lys
                 35                  40                  45

Lys Thr Arg Val Trp Leu Gly Thr Phe Asp Ser Ala Glu Asp Ala Ala
 50                  55                  60

Arg Ala Tyr Asp Ala Ala Ala Arg Ala Leu Arg Gly Pro Lys Ala Lys
 65                  70                  75                  80

Thr Asn Phe Pro Leu Pro Tyr Ala His His Gln Phe Asn Gln Gly
                     85                  90                  95

His Asn Pro Asn Asn Asp Pro Phe Val Asp Ser Arg Phe Tyr Pro Gln
                100                 105                 110

Asp Asn Pro Ile Ile Ser Gln Arg Pro Thr Ser Ser Ser Met Ser Ser
                115                 120                 125
```

```
Thr Val Glu Ser Phe Ser Gly Pro Arg Pro Pro Ala Pro Arg Gln
    130                 135                 140

Gln Thr Thr Ala Ser Ser Arg Lys Tyr Thr Arg Ser Pro Pro Val Val
145                 150                 155                 160

Pro Asp Asp Cys His Ser Asp Cys Asp Ser Ser Ser Val Val Asp
                    165                 170                 175

His Gly Asp Cys Glu Lys Glu Asn Asp Asn Asp Asn Asp Asn Ile Ala
                180                 185                 190

Ser Ser Ser Phe Arg Lys Pro Leu Leu Phe Asp Leu Asn Leu Pro Pro
                195                 200                 205

Pro Met Asp Asp Ala Gly Ala Asp Asp Leu His Cys Thr Ala Leu Cys
    210                 215                 220

Leu
225

<210> SEQ ID NO 88
<211> LENGTH: 163
<212> TYPE: PRT
<213> ORGANISM: Gossypium hirsutum
<220> FEATURE:
<221> NAME/KEY: misc_feature
<223> OTHER INFORMATION: Public GI ID no. 62548111
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 88

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
                20                  25                  30

Leu Lys Phe Phe Leu Lys Ile Phe Glu Ile Ala Pro Ser Ala Lys Lys
            35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Leu Ala Ala

<210> SEQ ID NO 89
<211> LENGTH: 153
<212> TYPE: PRT
<213> ORGANISM: Gossypium hirsutum
<220> FEATURE:
```

```
<221> NAME/KEY: misc_feature
<223> OTHER INFORMATION: Ceres CLONE ID no. 100021733
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 89

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Phe
145                 150

<210> SEQ ID NO 90
<211> LENGTH: 775
<212> TYPE: DNA
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Encodes the protein at SEQ ID NO: 3

<400> SEQUENCE: 90
ctctctagat cttggatcac tcggacgaca tgtgttggat cccagtgcac tggccctgcc      60
agcctactca aaaaaacswt samttttckc tcccattstt tkacractca tcgttggcac     120
wtcctwcttt ctstatatat tacttgacat wawcyrctmt ycacmwcaca wacacacacw     180
taaccatggc cagcttcaca wgctttcctt ttgctcacat tgyctatggc tttagytcat     240
ytctctttag ctcwatctcc catgatggct ccttctggct ccatgtccat gscgckchat     300
gccatagcgg cggctctcca atgccaatga tgactccacc acctatgcca atgatgactc     360
cmccgcctat ggctatggct ccaccaccta tgcctatgac tccaccacca atgcccatgg     420
ctccgatgcc aatgactcca tcttcaagtc caatgagccc accaactact atggccccaa     480
```

```
gtccagaaac agtccctgat atggcttcgc caccgatgat gccgggaatg gagtcttctc      540
cttctccggg acccatgcca ccggcaatgg cctctccaga ttccggagca ttcaatgtaa      600
gaaacgacgt cgtagcaatt tcgttccttg ttgcagctca tttgctccta gtttgagatt      660
attattaaat tggccagcgt cgtgttgtgt aatttacttt cattttttct cgagccatta      720
gttttcatgt tttatcatat atttgggttt gtgtttgata tggtacgatt cagmc           775
```

<210> SEQ ID NO 91
<211> LENGTH: 1032
<212> TYPE: DNA
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<223> OTHER INFORMATION: Encodes the protein at SEQ ID NO: 23

<400> SEQUENCE: 91

```
gctcattagg gtttctcatc tacggcgtgg tgttcctcct tcctgctctg aaaaatggcg       60
aagagaacga agaaggttgg aatcgtcggc aaatacggaa cacgttatgg tgcgagtatc      120
aggaagcaga ttaagaagat ggaggtcagc cagcacagca agtacttctg tgagttctgt      180
ggcaagtacg gagtgaagcg aaaggctgtt ggtatctggg gttgcaagga ttgtggcaag      240
gtcaaggcag gtggtgctta cacaatgaac accgccagtg cggtcactgt tagaagcacg      300
atcagaaggt tgagggagca gatcgagggt taaaagtctg ctgaggaaga tgctgagaca      360
gtatacgctt gtatcgactt ggtatcaacg ataatacaga ggaagctgag gaagatcaag      420
gagaaggact cagaccatgg aaggcacatg aaaggtttca acagattgaa ggtaagggaa      480
ccagtgattg agccggttgt ggaggatgtt gaggacagta ctgactcgag cgtaggagaa      540
gaagaagaag aggatgattt gatcaaggag attgtccgta ccaagacttt cgagatgcca      600
ccattgactg tcgctgaggc agtcgagcag ctggaactag tcagtcacga cttctatggc      660
ttccaaaatg aaaactggtg agataaacat agtgtacaag agaaaagaag gaggttacgg      720
tctgataatc ccaaagaaag acgggaaggc cgagaaggtt gagccgcttc caaccgagca      780
attgaatgaa cactctttcg ccgagtagac tgcctctgca cacaccaaaa ccgataagct      840
catctctcct tacagtttac ctgtgtagga gttagggttc ttgaataaac aatgcaacaa      900
agattgtaga agtcagtgta cataaaaaaa tggccaacca ctctttgtta cttttgtggt      960
gaaaaggaag atcttaattc tctttccatc agatgatagc aatacatttt ttcataaaca     1020
agaatgttac at                                                         1032
```

<210> SEQ ID NO 92
<211> LENGTH: 492
<212> TYPE: DNA
<213> ORGANISM: Parthenium argentatum
<220> FEATURE:
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Encodes the protein at SEQ ID NO: 5

<400> SEQUENCE: 92

```
atctagcttc aaccttttt tcctctcact actcaattca atatggctgt ctcacgttac        60
attatcctac tcttatcctt cacctacttg gctgccttct ccaccgctca agctccatca      120
atgtcaccaa tgatgatgcc catggcacca ccaccatcga cgatgcccat gacaccacca      180
```

```
ccatcgacga tgcccatgac accaccacca acgcccatga ccatgacacc accaccaatg      240
atgatgccca tgacaccacc accaatgccc atggggacac accaatgac aatgcccatg       300 ggaccgccac caatgatgat gcccatgagc ccaggaccat ccatgatgcc agcctccccg      360
ccatcaccca tgggaccgtc catggcacct gaaccagcta ccatgtcgcc tggaccctcc      420
atgacgcctg ctgagacacc agccagtggc gctatcatgc agtattctag catcactatg     480
ttgggcattg tg                                                         492

<210> SEQ ID NO 93
<211> LENGTH: 970
<212> TYPE: DNA
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<223> OTHER INFORMATION: Encodes the protein at SEQ ID NO: 13

<400> SEQUENCE: 93
agatataatc gaaaaaaatt actgtttgga tatattccac tatttagaaa gcaaaatgga      60
ctacgaaaac ttgagtaaca aggtaagcca cacaaatggg aatgactccc cattacaatg    120
aagggccaac ttcattttca atgaatccca ctataaaaac tttagcaatg caaaagctaa    180
aacatcaacc atttcctcat ccactttcac tggaatcaca atcctgaaac aaaaacatct    240
tagcatttaa catactacta gacaacatga ccaccacatt ggaaagaggt ttctcggaag    300
agcaagaagc tctggtggtg aagtcatgga atgtcatgaa gaagaattct ggagagttgg    360
gtctcaagtt tttcttgaaa atatttgaga ttgctccatc agctcagaaa ttgttctcat    420
tcttgagaga ttcaacggtt cctttggagc aaaatcccaa gctcaagccc catgccgtgt    480
ctgtctttgt aatgacctgt gattcagcag ttcagctgcg gaaggccggg aaagtcactg    540
tcagagaatc aaacttgaaa aaattaggtg ctacccattt tagaaccggc gtagcaaacg    600
agcatttcga ggtgacaaag tttgcactgt tggagaccat aaaagaagct gtaccagaaa    660
tgtggtcacc ggctatgaag aatgcatggg agaagcttaa tgatcagctg gtcgatgcca    720
ttaaatctga aatgaaacca ccctcctctt agactccagt ttaagcagtt cctttccttc    780
cctctcaatt ctcaaattgt tatattaata aaagtgagaa agtttaggct tgtgcttttta    840 ttttgtgtga atgtaatata ctttgtgtac gtagacttgg ctattgggag ttgctaggtt    900
gggaagtgtt tcgcattcaa caattctgta gttgaaggtg attaaatgaa ttatagctat    960
ttgtttcttc                                                            970

<210> SEQ ID NO 94
<211> LENGTH: 604
<212> TYPE: DNA
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<223> OTHER INFORMATION: Encodes the protein at SEQ ID NO: 16

<400> SEQUENCE: 94
tcgtatccac ccaacctccc actgtaaaaa agagcagcgg aacgtgcgtg catccatcca      60
attccaatcc cagtcccaat cccaccagtg tccagtgctc ggggaaccga cacagctcct    120
```

| | |
|---|---|
| cagcagagaa gccagcccga tcagcagaca gcaggcatgg cgctcgcgga ggccgacgac | 180 |
| ggcgcggtgg tcttcggcga ggagcaggag gcgctggtgc tcaagtcgtg ggccgtcatg | 240 |
| aagaaggacg ccgccaacct gggcctccgc ttcttcctca aggtcttcga gatcgcgccg | 300 |
| tcggcgaagc agatgttctc gttcctgcgc gactccgacg tgccgctaga gaagaacccc | 360 |
| aagctcaaga cgcacgccat gtccgtcttc gtcatgacct gcgaggcggc ggcgcagctc | 420 |
| cgcaaggccg ggaaggtcac cgtgagggag accacgctca gaggctgggc gccacgcac | 480 |
| ttgaggtacg gcgtcgcaga tggacacttc gaggtgacgg ggttcgcgct gcttgagacg | 540 |
| atcaaggagg cgctccccgc tgacatgtgg agcctcgaga tgaagaaagc ctgggccgag | 600 |
| gcct | 604 |

<210> SEQ ID NO 95
<211> LENGTH: 846
<212> TYPE: DNA
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<223> OTHER INFORMATION: Encodes the protein at SEQ ID NO: 17

<400> SEQUENCE: 95

| | |
|---|---|
| acgccgtccg tttctggctc atcaggaggt ccaaaggccg cgcaagtcga cctatataag | 60 |
| cgcctccgct ccagcttggg atcaaatcac gaccaacacg taccggatct tgaccgaccg | 120 |
| aaccattcag tgctcgcgct cactcacgca tcatagccaa gttaagcggg aaggaaggaa | 180 |
| ggaaggaagc catgtctgcc gcggagggag ccgtcgtgtt cagcgaggag aaggaggcgc | 240 |
| tggtgctcaa gtcatgggcc atcatgaaga aggattccgc caaccttggg ctccgcttct | 300 |
| tcctcaagat cttcgagatc gcgccgtcgg cgaggcagat gttcccgttc ctgcgcgact | 360 |
| ccgacgtgcc gctggagacc aaccccaagc tcaagaccca cgccgtgtcc gtcttcgtca | 420 |
| tgacgtgcga ggctgctgcg cagctgcgga agccgggaa gatcaccgtc agggagacca | 480 |
| ccctgaagag gctgggcggc acgcacttga aatacggcgt ggcagatggc cactttgagg | 540 |
| tgacgcggtt cgctctgctc gagacgatca aggaggcgct tccggcggac atgtggggc | 600 |
| cggagatgag gaacgcgtgg ggcgaggcct acgaccaact ggtcgcggcc atcaagcaag | 660 |
| agatgaagcc ctctgagtag ctcatccatt gtactcatat catatgccac gcaacttccg | 720 |
| tccatatccg tccaactttc gttgcttgac cggttcactc atgtcaccat attgtgtttg | 780 |
| tattgtgtgt ttacgtgtac taacgcatat tgtaaaatgg cattcaata aaggaacaaa | 840 |
| ttgtgc | 846 |

<210> SEQ ID NO 96
<211> LENGTH: 440
<212> TYPE: DNA
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<223> OTHER INFORMATION: Encodes the protein at SEQ ID NO: 25

<400> SEQUENCE: 96

| | |
|---|---|
| ctcttgtctt agtctaataa acaacacgga cgcagagcct tcgatccaga aaccatgact | 60 |
| aagagaacga agaaggcagg cattgtcgga aaatatggta cccgatatgg tgctagtttg | 120 |

```
cggaagcaga ttaagaagat ggaagttagt cagcatagca aattcttttg tgaattttgt      180
gggaagtatg ctgtgaagag gaaggctgtg ggaatatggg gatgcaagga ttgtggtaaa      240
gtgaaagctg gcggtgccta cactttgaat actgcaagtg ctgtcactgt gcgcagcacc      300
atccggaggt tgagggaaca aaccgagggt tgagctttt ggttgatgtt agattttgag       360
caaattaact ggagaaatga ttcgtttttg tttaggaagc tgtattgttt caacttacaa      420
tgcagtgtga attgctttcg                                                  440
```

<210> SEQ ID NO 97
<211> LENGTH: 463
<212> TYPE: DNA
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<223> OTHER INFORMATION: Encodes the protein at SEQ ID NO: 26

<400> SEQUENCE: 97

```
atatawcttg actctccgca attccctgtc tcckccgccg cagcttccgt ctcccggatt       60
tcgccgcctg ccgcakccgc agcagctcgc cgsccacgcs tcctayccgt cgacgagatg      120
acgaascgca ccaagaaggc tggaattgtc ggcaaatatg gtacccgtta tggtgccagt      180
ttgcgtaagc agatcargaa gatggaggtg tctcagcact ccaagtactt ckgtgagttc      240
tgtgggaagt ttgctgtgaa gaggaaagsa gttggaattt ggggatgcaa tggactgtgg      300
gaaggwsaag gaaaccttcg ccwkaaaccg tgagctcgaa gtgmggtcca ctccaggwgg      360
gccatgctcg gggccttggg swgcagtctt ccccgaagct attgtyccgc aacggggtca      420
agtttggaga agctgtgtgg ttcaaggccg ggtcccagat ctt                        463
```

<210> SEQ ID NO 98
<211> LENGTH: 458
<212> TYPE: DNA
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<223> OTHER INFORMATION: Encodes the protein at SEQ ID NO: 27
<220> FEATURE:
<221> NAME/KEY: misc_feature
<222> LOCATION: (224)..(224)
<223> OTHER INFORMATION: n is a, c, t, g, unknown, or other

<400> SEQUENCE: 98

```
aacaaaccct cgttcacggt tcaacttcag cagccgcgcc tctaacttgt agcagcgata       60
cctcttctct tatcactaaa aaatgaccaa gagaaccaag aaggccggta ttgttggaaa      120
atacggcacc cgatatggtg ctagtttaag gaagcaaatc aagaagatgg aagttagtca      180
gcacagtaaa ttcttttgtg agttctgtgg aaagtacgct gttnagagga aggccgtggg      240 tatttgggc tgcaaagatt gtggaaaagt gaaggctgga ggtgcttaca cattgaatac       300
tgcgagtgct gtcactgtcc ggagcaccat tcggaggctg agagagcaga ctgagagttg      360
aaagcagttt acacttttca tttgtttcca aagcttattt taaaattatc atacaatttt      420
ggcaggtcta tgttaggaat attagtaatg tgctactt                              458
```

<210> SEQ ID NO 99

```
<211> LENGTH: 600
<212> TYPE: DNA
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<223> OTHER INFORMATION: Encodes the protein at SEQ ID NO: 28

<400> SEQUENCE: 99
ctcaaaaccc taggcttcca tatataactt gactctccac aattccctgt ctccgccgcc      60
gcagctttcg tctcccggat ttcgccgccg cagccgctca ccgccacgc ctcctacccg      120
tcgacgagat gacgaagcgc accaagaagg ctggtattgt cggcaaatat ggtacccgtt    180
atggtgccag tttgcgtaag cagatcaaga agatggaggt gtctcagcac tccaagtact    240
tctgtgagtt ctgtgggaag tttgctgtga agaggaaagc agttggaatt tggggatgca    300
aggactgtgg gaaggtgaag gctggcggtg cttacactat gaacactgcc agtgcggtca    360
ctgtcaggag cactatccgt cgtttgaggg agcagactga agcataagtt gctactagtg    420
ttttgtccta gtgaatcatc tgggatttcg cagtttagac gatactttgg attcagttcc    480
attggctgtt tagtcaagga ttatctttgt acttggtgcg atgatgttct gttatgttat    540
tctcccaccc ttttgttgcc tgattccact ctgatttact gtggattctg atttgccttc    600

<210> SEQ ID NO 100
<211> LENGTH: 546
<212> TYPE: DNA
<213> ORGANISM: Zea mays
<220> FEATURE:
<221> NAME/KEY: misc_feature
<223> OTHER INFORMATION: Ceres CLONE ID no. 1390976
<220> FEATURE:
<221> NAME/KEY: misc_feature
<223> OTHER INFORMATION: Encodes the protein at SEQ ID NO: 29

<400> SEQUENCE: 100
aagcatccac aattccacat aacctcgccc gcgccgcctc ccccacgaga cgccttcttg     60
ctctcgcttc cggtgacgcc cgccacttcc tccccgacga gatgacgaaa cgcaccaaga   120
aggcaggaat cgttggcaaa tatggtacca ggtatggtgc cagtttacgt aaacagatca   180
agaagatgga ggtctcgcag cactccaaat acttctgtga gttctgtggc aagtttgccg   240
tgaagaggaa agcagttggt atctggggat gcaaggactg tgggaaggtt aaggccggtg   300
gcgcctacac aatgaacact gctagtgcgg tcactgtgag aagcacaatc cggcgcctgc   360
gggagcagac cgaagcatga ttgcgggcag cttgaaaagg agtacctgga ttttttgtagt   420
tcagccaaga gccgtgaacc attttgcctt tttagctaaa tgaacaagaa atgttttatct   480
atctgtagtg accactttgt actcatggtt tgtcatgcta aattgatggt atgcactatg    540
caatgc                                                                                  546

<210> SEQ ID NO 101
<211> LENGTH: 550
<212> TYPE: DNA
<213> ORGANISM: Zea mays
<220> FEATURE:
<221> NAME/KEY: misc_feature
<223> OTHER INFORMATION: Ceres CLONE ID no. 1457185
<220> FEATURE:
<221> NAME/KEY: misc_feature
<223> OTHER INFORMATION: Encodes the protein at SEQ ID NO: 30

<400> SEQUENCE: 101
```

-continued

```
atatataact tgactctccg caattccctg tctccgccgc cgcagcttcc gtctcccgga      60
tttcgccgcc gccgcagccg cagcagctcg ccgcccacgc ctcctacccg tcgacgagat     120
gacgaagcgc accaagaagg ctggaattgt cggcaaatat ggtacccgtt atggtgccag     180
tttgcgtaag cagatcaaga agatggaggt gtctcagcac tccaagtact tctgtgagtt     240
ctgtgggaag tttgctgtga agaggaaagc agttggaatt tggggatgca aggactgtgg     300
gaaggtgaag gctggcggtg cttacaccat gaacactgcc agtgcggtca ctgtcaggag     360
cactatccgt cgcttgaggg agcagactga agcataagtt gctactagtg ttttgtccta     420
gtgaatcatc tgggattttg cagtttagac gatactttgg attcagttct gttggctgtt     480
tagtcaagga ttatctttgt acttggtgcg atgatgttct gttatgttat tctctcaccc     540
tttttttgcc                                                            550
```

<210> SEQ ID NO 102
<211> LENGTH: 668
<212> TYPE: DNA
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<223> OTHER INFORMATION: Encodes the protein at SEQ ID NO: 35

<400> SEQUENCE: 102

```
aaaaattcat tgatcgaaaa aaagaaaaaa gaaagaaaag aaaagatgca gatcttcgtg      60
aaaaccttga ccggcaaaac cataacccta gaggttgaaa gcagcgacac catcgacaat    120
gtcaaatcca aaatccagga caaagagggg ataccacctg atcaacagag gctcatcttt    180
gctgggaaac aacttgagga tggtcgaacg ctagctgact acaacattca gaaagagtcc    240
actcttcact tggttctgag gcttaggggg gggaccatga tcaaggtcaa gactctcact    300
ggtaaagaaa tcgaaattga tatcgaacct accgatacta ttgaccggat caaggaacgt    360
gttgaggaga aagaaggcat ccctcctgtt caacaaaggc tcatctatgc tgggaaacag    420
ctagctgatg acaaaacggc aaaggactac aacatagagg gaggctctgt tcttcatctg    480
gtccttgctc tcagggggtgg ttctgactaa ataactattt gctctagagt tcctttcaat    540
ggctttggtt ggttgaatcc atgagacaaa gtgaatacaa tttggatttc gtgctttggt    600
tactatgatg ctatttcagc tggtttggat caatttacca aaaaaaaaa aaaaaaaaa    660 aaaaaaag                                                              668
```

<210> SEQ ID NO 103
<211> LENGTH: 752
<212> TYPE: DNA
<213> ORGANISM: Glycine max
<220> FEATURE:
<221> NAME/KEY: misc_feature
<223> OTHER INFORMATION: Ceres CLONE ID no. 522921
<220> FEATURE:
<221> NAME/KEY: misc_feature
<223> OTHER INFORMATION: Encodes the protein at SEQ ID NO: 36
<220> FEATURE:
<221> NAME/KEY: misc_feature
<222> LOCATION: (639)..(639)
<223> OTHER INFORMATION: n is a, c, t, g, unknown, or other
<220> FEATURE:
<221> NAME/KEY: misc_feature
<222> LOCATION: (674)..(674)
<223> OTHER INFORMATION: n is a, c, t, g, unknown, or other
<220> FEATURE:

```
<221> NAME/KEY: misc_feature
<222> LOCATION: (690)..(690)
<223> OTHER INFORMATION: n is a, c, t, g, unknown, or other
<220> FEATURE:
<221> NAME/KEY: misc_feature
<222> LOCATION: (697)..(697)
<223> OTHER INFORMATION: n is a, c, t, g, unknown, or other
<220> FEATURE:
<221> NAME/KEY: misc_feature
<222> LOCATION: (700)..(700)
<223> OTHER INFORMATION: n is a, c, t, g, unknown, or other
<220> FEATURE:
<221> NAME/KEY: misc_feature
<222> LOCATION: (714)..(714)
<223> OTHER INFORMATION: n is a, c, t, g, unknown, or other

<400> SEQUENCE: 103
aattacaaat acaaatacga ataccctttct ctctcacaca aaacactagt ccctcccttc    60
ttccttgtct cttttctcttc tcaacaacat gcagatcttc gtcaagactt tgactggcaa   120
gaccatcacc ctcgaggtcg agagtagcga caccatcgac aacgtcaagg ccaagatcca   180
ggacaaggaa ggtatccctc ctgaccagca gagtttgatt tttgctggta agcagctgga   240
agatggtcgc actcttgctg attataacat acaaaaggaa tcaacacttc acttggtctt   300
gaggctcagg ggaggaacca tgattaaagt gaagactcta actggaaaag aaattgaaat   360
tgacattgag ccaactgata caatcgaccg gatcaaggaa cgcgttgaag aaaaagaggg   420
aattccacct gtgcagcaga gactcatata tgcaggtaaa cagcttgctg atgacaaaac   480
agctaaagag tacaacattg agggtggttc tgtacttcac ttggtgcttg cattgagggg   540
tggtacttat tagtgtagat gccatatcag aacccaaaga catgaaagga agctctattc   600
ctgccccgtc tctctgaaga catcattgtt cttttatgng cttggttttt gtaattgtgg   660
ctactattgg tggncagtaa ctcagtatcn ttttagntgn atgctattta aaancccttaa  720 ggtgggcctt tatatgaata tctgaaccaa tg                                 752

<210> SEQ ID NO 104
<211> LENGTH: 484
<212> TYPE: DNA
<213> ORGANISM: Brassica napus
<220> FEATURE:
<221> NAME/KEY: misc_feature
<223> OTHER INFORMATION: Ceres CLONE ID no. 1036726
<220> FEATURE:
<221> NAME/KEY: misc_feature
<223> OTHER INFORMATION: Encodes the protein at SEQ ID NO: 37

<400> SEQUENCE: 104
gaaatcaaat aaaaaaatct ttaagcaaga aaagaaagaa aatgcagatc ttcgtcaaaa    60
ccctgacggg gaaaaccata accctggagg ttgaaagcag cgacaccatc gacaatgtca   120
aagccaaaat ccaggacaaa gaaggaatac cgccggatca gcagaggctg atcttcgctg   180
ggaagcaact agaagacggt agaaccctttg cggactacaa catccagaaa gagtccactc   240
ttcacttggt cttgaggctt aggggtggca ccatgatcaa ggtcaagact ctcactggca   300
aagaaatcga gattgacatc gaacctaccg acaccattga tcgcatcaag gagcgtgttg   360
aggagaaaga aggcatccct cctgttcaac agaggctcat ctacgctgga aaacagctag   420
ctgatgacaa gacggcmaaa gactacaaca tcgagggagg ctctgtttct gcatctggtt   480
cttg                                                               484

<210> SEQ ID NO 105
<211> LENGTH: 580
```

```
<212> TYPE: DNA
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<223> OTHER INFORMATION: Encodes the protein at SEQ ID NO: 38
<220> FEATURE:
<221> NAME/KEY: misc_feature
<222> LOCATION: (543)..(543)
<223> OTHER INFORMATION: n is a, c, t, g, unknown, or other

<400> SEQUENCE: 105
aagaaaaagg aaattttctt gggcgttctt cggcttcgtt gtcacaaggt tcgagttcgt      60
caccgtctag tacgactgtg cgagggagga agaggcgagg agaagatgca gatcttcgtg     120
aagaccctga cggggaagac catcaccctc gaggtggaga gcagcgacac cgtcgacaac     180
gtcaaagcca aaatccagga caaggaaggg attcccccag atcaacagcg actgatattc     240
gctggcaagc agctggagga tggacgcacg ctggctgact acaacatcca aaaggagtca     300
actcttcatt tggtcctcag gcttaggggt ggaaccatga tcaaggtcaa aactctcact     360
gggaaagaga tcgagatcga cattgaaccc actgactcga ttgacaggat caaggagcgt     420
gttgaagaga aagaaggcat tcctcccgtg cagcaaaggc tcatctatgc tggtaagcag     480
cttgctgatg acaagaccgc aaaggactac aacatcgagg gtggatctgt cctccatctt     540
gtncttgctc tgaggggtgg ttactagtct aaacctgatg                           580

<210> SEQ ID NO 106
<211> LENGTH: 987
<212> TYPE: DNA
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<223> OTHER INFORMATION: Encodes the protein at SEQ ID NO: 44

<400> SEQUENCE: 106
attccatcaa cttcagacac acagatctct tctcaatcac attacttctg gttctcccac      60
catgaggaaa gggagaggct cttccgccgt tccacccgcc cttcccggat ctgtgaagga     120
gccgaggtac agaggcgtta ggaagagacc ttggggccgt ttcgccgccg agatccgtga     180 cccccttgaaa aaatcccgag tctggctcgg cacgttcgac tccgcggagg aagccgcacg     240
cgcctacgac gcagccgctc gtaacctccg cggtccaaag gccaagacca acttccaaat     300
cgactgttct ccttcctctc ctctccaacc actccatcat cggaaccaga tcgatccctt     360
tatggaccac cggttatacg gcggagagca ggaggttgtt atcatcagcc ggccggcgag     420
tagcagcatg agcagcaccg ttaagtcgtg cagcggagtg agaccagcgt cttcttccgt     480
ggcgaaggcg gcgacgaaga gatatccacg gactccgccg gtggcgccgg aggattgccg     540
cagcgactgc gattcgtcgt cgtcggtggt tgaagacgga sacgacatag cttcgtcgtc     600
ttcgcggcgg aaaccgccgt ttgagtttga tcttaatttt ccsccgttgg atggcgttga     660
cttattcgta ggcgcggacg atctccactg caccgatctg cgtctttgat ctttgagcac     720
aatgacaaca aagatgatga agaagtgata gggagagaga gtttgtgtta agatctgttg     780
ttgtaagaac cagatctgtg tttcattcac ttgtctgttt cttataaaga tcaaaccttt     840
gttacatgta acacttatat agctgctgat gattcttaat tattcaaaat ccaaagtctg     900
```

| | |
|---|---|
| tagaatttat acagtatcta tcactgatgt gcttatggat ggtttggagt atgaggctac | 960 |
| attttcataa atacattcaa tgtgtgt | 987 |

<210> SEQ ID NO 107
<211> LENGTH: 1034
<212> TYPE: DNA
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<223> OTHER INFORMATION: Encodes the protein at SEQ ID NO: 45

<400> SEQUENCE: 107

| | |
|---|---|
| ctctccttcc ttcacggatt cccaaatact cgcttccaat accaattctc cgatccacgt | 60 |
| tcgttcccgc accctcgcgc tccgctgatc cggcggcatg cggcgccgcg gcgtggcggc | 120 |
| ggctgatgcg gacggtgacg tggagttgcg gttccgcggg gtgcggaaga ggccgtgggg | 180 |
| ccggtacgca gcggagatcc gggacccggc gaagaaggcg cgcgtctggc tcggcacatt | 240 |
| cgactccgcc gaggacgccc ccgcgcccta cgacgccgca gcgcggatgc tgcgcgggcc | 300 |
| caaggccagg accaacttcc cgctccccgc cgcagccgcc ctccaccacc ccacatgcc | 360 |
| cgctgctgcc gccgcagcag ctccaccata cacaacatat cccaccgcca cgggcgtcgt | 420 |
| ctcgacgccg ccggtcgcca gaccggcttg cagcagcctc agctccaccg tggagtcctt | 480 |
| cagcggcgcg cggccgcggc ctgtgctccc gccgcggttc cctccgccgt cgattcctga | 540 |
| tggcgactgc cgcagcgact gtggttcctc ggcctcggtc gtggacgacg actgcacgga | 600 |
| cgcggccgcc tctgcgtcgt gccccttccc gctcccgttc gacctcaacc tgcccccagg | 660 |
| cggcggcgga gccggcgtcg ggttttacgc cgatgaggag gatgagctca ggctcacggc | 720 |
| gctgcggctg tgacgtcgag ctcaatcgag ccgctgctta gaaagaggaa aaggagaaaa | 780 |
| atatttggtt cttcccttct cttgtagccg acacgaactc tccatccact acgatgttgt | 840 |
| tgtttacttg atctgattat gatatttgcc tgaatcctag tcaacttacc tgcatgcatg | 900 |
| cctgcttgtt ttctggcgat tgaggattat cgccaaacgc caaatcttgc agcagctgtt | 960 |
| gtactgtaat atatcaacat tttacttcct tcctcttatg aggaaagaga cagataaagt | 1020 |
| aacttatttc aatc | 1034 |

<210> SEQ ID NO 108
<211> LENGTH: 911
<212> TYPE: DNA
<213> ORGANISM: Triticum aestivum
<220> FEATURE:
<221> NAME/KEY: misc_feature
<223> OTHER INFORMATION: Ceres CLONE ID no. 1055099
<220> FEATURE:
<221> NAME/KEY: misc_feature
<223> OTHER INFORMATION: Encodes the protein at SEQ ID NO: 46

<400> SEQUENCE: 108

| | |
|---|---|
| aaacaaaaaa ccaccagggg aagaagggaa agacacacgc cactgtgacc aaaccctagg | 60 |
| ccggccgcga tgcgcaaggc gaggccgccg cagccccagc cgcagccgtc gcagcagtcg | 120 |
| ccggagatcc ggtaccgcgg cgtgcggaag cgcccctcgg gccgctacgc cgccgagatc | 180 |
| cgggaccccg ccaagaagac gccgatctgg ctcggcacct tcgactgcgc cgaggacgcc | 240 |
| gcccgcgcct acgactccgc cgcccgatcc ctccgcgggc ccaccgcccg caccaacttc | 300 |
| ccgccctcct ccgccacgca gccgccgccg aggccccctc ccccgcggc cgcggccgcg | 360 |

```
gccgccacgt ccagccagag cagcaccgtc gagtcctgga gcggcggcgg gccccgcgcc    420
cccgccaggg cccgcagcgc cgcccgagcg ggcacggcca aggaggggga ggaggactgc    480
cgcagctact gcggctcctc gtcctccgtc ctcctcgagg agggcgcgga cgacgcggcc    540
gcctcccgct ccccgctgcc cttcgatctg aacatgccgc cccgcagga gggggcgctt     600 gacgccgagg ccgatcagat gacctgccgg tacgacacgc tgctccgcct ctagctccac    660
gacgacgaga gcaaggattc gtgggagggg aactgggaaa aggaacgaga aaagcgcttg    720
cccccgctcc gctccggtcc gtcttccgat gatctcgtgg tgttctctct ttgttagaaa    780
tggataattc ttgccatttt tttttcttac tttctttcct tcttcttttt ttttcttct    840 taccactttg attcgatatg tgaataattg agtcatgtaa gctgcgagca aggaaatctg    900
agcttttcct t                                                         911
```

<210> SEQ ID NO 109
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres GI ID no. GI_15226675
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 109

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
        115                 120                 125

Val Pro Glu Met Trp Ser Pro Glu Met Lys Val Ala Trp Gly Gln Ala
    130                 135                 140

Tyr Asp His Leu Val Ala Ala Ile Lys Ala Glu Met Asn Leu Ser Asn
145                 150                 155                 160

<210> SEQ ID NO 110
<211> LENGTH: 1823
<212> TYPE: DNA
<213> ORGANISM: Arabidopsis thaliana
<220> FEATURE:
<221> NAME/KEY: misc_feature
<223> OTHER INFORMATION: Ceres Promoter 28176

<400> SEQUENCE: 110

```
gtctcttaaa aaggatgaac aaacacgaaa ctggtggatt atacaaatgt cgccttatac    60
atatatcggt tattggccaa aagagctatt ttaccttatg gataatggtg ctactatggt   120
tggagttgga ggtgtagttc aggcttcacc ttctggttta agccctccaa tgggtaatgg   180
taaatttccg gcaaaaggtc ctttgagatc agccatgttt tccaatgttg aggtcttata   240
ttccaagtat gagaaaggta aaataaatgc gtttcctata gtggagttgc tagatagtag   300
tagatgttat gggctacgaa ttggtaagag agttcgattt tggactagtc cactcggata   360
ctttttcaat tatggtggtc ctggaggaat ctcttgtgga gtttgatatt tgcgagtata   420
atctttgaac ttgtgtagat tgtacccaaa accgaaaaca tatcctatat aaatttcatt   480
atgagagtaa aattgtttgt tttatgtatc atttctcaac tgtgattgag ttgactattg   540
aaaacatatc ttagataagt ttcgttatga gagttaatga tgattgatga catacacact   600
cctttatgat ggtgattcaa cgttttggag aaaatttatt tataatctct cataaattct   660
ccgttattag ttgaataaaa tcttaaatgt ctcctttaac catagcaaac caacttaaaa   720
atttagattt taaagttaag atggatattg tgattcaacg attaattatc gtaatgcata   780
ttgattatgt aaaataaaat ctaactaccg gaatttattc ataactcca ttgtgtgact    840
gcatttaaat atatgtttta tgtcccatta attaggctgt aatttcgatt tatcaattta   900
tatactagta ttaatttaat tccatagatt tatcaaagcc aactcatgac ggctagggtt   960
ttccgtcacc ttttcgatca tcaagagagt tttttttataa aaaatttat acaattatac  1020
aatttcttaa ccaaacaaca cataattata agctatttaa catttcaaat tgaaaaaaaa  1080
aatgtatgag aattttgtgg atccattttt gtaattcttt gttgggtaaa ttcacaacca  1140
aaaaaataga aaggcccaaa acgcgtaagg gcaaattagt aaaagtagaa ccacaaagag  1200
aaagcgaaaa ccctagacac ctcgtagcta taagtaccct cgagtcgacc aggattaggg  1260
tgcgctctca tatttctcac attttcgtag ccgcaagact cctttcagat tcttacttgc  1320
aggttagata ttttctctct ttagtgtctc cgatcttcat cttcttatga ttattgtagc  1380
tgtttagggt ttagattctt agttttagct ctatattgac tgtgattatc gcttattctt  1440
tgctgttgtt atactgcttt tgattctcta gctttagatc cgtttactcg tcgatcaata  1500
ttgttcctat tgagtctgat gtataatcct ctgattaatt gatagcgttt agttttgata  1560
tcgtcttcgc atgttttttta tcatgtcgat ctgtatctgc tctggttata gttgattctg  1620
atgtatttgg ttggtgatgt tccttagatt tgatatacct gttgtctcgt ggtttgatat  1680
gatagctcaa ctggtgatat gtggttttgt ttcagtggat ctgtgtttga ttatattgtt  1740
gacgttttgg ttgttgtatg gttgatggtt gatgtatttt tgttgattct gatgtttcga  1800
tttttgttttt tgttttgaca gct                                         1823
```

<210> SEQ ID NO 111
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0668

<400> SEQUENCE: 111

```
atagagtttt actatgcttt tggaatcttt cttctaatgt gccaactaca gagaaataca    60
tgtattacca ctaggaatcg gaccatatca tagatatcag gattagataa ctagttctcg   120
```

-continued

| | |
|---|---|
| tcgctatcac ttcgcattaa gttctagtaa ttgttaaaga ttctaatttt ttactaaaca | 180 |
| aaaactaaat caacatcaaa tatgcaaagt gtgtgttgtc cacacaagtg actcaaagta | 240 |
| tacgcaggtg ggattggacc atattattgc aaatcgtttc cgaaccactc atatttcttt | 300 |
| ttttctctcc tttttttatc cggagaatta tggaaccact tcatttcaac ttcaaaacta | 360 |
| attttttggt tcagtgatca aatacaaaaa aaaaaaaaa gttatagata ttaaatagaa | 420 |
| aactattcca atcttaaaaa tacaaatgaa accataattt taatttatac aaaactattt | 480 |
| aattagctaa gggttgtctt aacgtttaga aaataaaaaa ttatgattgt ctgtttaaaa | 540 |
| ttacaatgaa tgaataaaaa aaatatgcaa tgaatgaaag aataaatttt gtacatccga | 600 |
| tagaatgaga aaatgaattt tgtacaaacc actcaagaat tcaaaacaat tgtcaaagtt | 660 |
| ttcttctcag ccgtgtgtcc tcctctccta gccgccacat ctcacacact aatgctaacc | 720 |
| acgcgatgta accgtaagcg ctgagttttt gcatttcaga tttcacttcc accaaacaaa | 780 |
| actcgccacg tcatcaatac gaatcattcc gtataaacgt ctagattctt tacagcctac | 840 |
| aatgttctct tctttggtcg gccattattt aacgctttga acctaaatct agcccagcca | 900 |
| acgaagaaga cgaagcaaat ccaaaccaaa gttctccatt ttcgtagctt ctttaagctt | 960 |
| tttcagtatc atagagacac ttttttttt ttgattagaa | 1000 |

<210> SEQ ID NO 112
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0535

<400> SEQUENCE: 112

| | |
|---|---|
| ttagtgaaat tatgacatta agtaaggttt tcttagttag ctaatgtatg gctattcaat | 60 |
| tgttatgtta ggctatttta gttagtatat gaatttaggc agtctatgca aatgatttcg | 120 |
| ttttcatttt ttcatatgta aacatcaaga tcaagtaacg ccattcgagt tgatattttt | 180 |
| tttttaaatt agtgtgtgta aattttggac cgcttatttg agtttgctaa tgaagttgca | 240 |
| tatatattac gttaaaccat aggcaaacta atttgaaaca tccgattcga tttcctgtaa | 300 |
| tttttcttgg ttaattgacc aaaatcaaga tcttcagaaa taaaataaaa gacgaaagaa | 360 |
| agctgtcgca aagcagattg tgttaaaaaa aagtggattg ggctcaaacg caacttgtcc | 420 |
| agcccgtgac aattacccta tacgcaagta agagtaacgt atcactggca aaagttggta | 480 |
| ttagttacga tatctttgtc atgggggcat gcatgggcat ggcttaagag ttaagcctta | 540 |
| agaagagtcc cacactcgtg actctcatga tcacttgttg tttcttacgg gcaaatacat | 600 |
| ttaactttat tcttcattta ttcacctata ttcttttgga taataacttt tctctatata | 660 |
| aaataacaaa catcgtacgt ttcatttatt tacaacaagc gatgagaatt aaaaggagac | 720 |
| cttaattgat gatactcttc ttttctctcg gttacaacgg gattattaca gataatgata | 780 |
| atctatatgg atgctgacgt ggaaaaacaa aatttggtga aacacgtcaa ttaagcacga | 840 |
| cttttccatg gctagtggct aagatcgttt catcacatgg ctatatcata taatacttgg | 900 |
| atgaattcaa aataaacgac tgagaaaatg tccacgtcac ggcgcaccgc tttggactta | 960 |
| agtctcctat aataaataca acaccaaaca ttgcattcca | 1000 |

<210> SEQ ID NO 113
<211> LENGTH: 999

```
<212> TYPE: DNA
<213> ORGANISM: Arabidopsis thaliana
<220> FEATURE:
<221> NAME/KEY: misc_feature
<223> OTHER INFORMATION: Ceres Promoter PT0585

<400> SEQUENCE: 113
tgaagtcatt taatatgagt ttgacattag gtaaacctaa tctatgagat tatagaatgt      60
agcaaaacta tcaatgtttc ttttccaaaa tattttgtgg ttttctttt tggttcatta     120 tgttttgtta tttgtgaatt attttaatat gaagtaatta tattgatttt atatgatata    180
catattattt tgatataaaa tttaacactt atccattaaa atagcatggg cataatcaaa    240
atcgggacta ttacgatgaa aagatagtt aaattgtatg ataaaataaa atgtgtaaga    300
ttaaaatttt gggttttaga aaattactaa acaaaatata gacaaagtat gttgactatt    360
atttaaaatt taaatatcat caataagata tagttaaagt cattaagtgt atagcaaaat    420
gaaaattcta agattaaaat tcgattaaaa ttttttttac taaattaaat atttaaaaat    480
agggattatc atttactatt tacaattcta atatcatggg taaaaattga taactttttt    540
taaacccgcc tatctaggtg ggcctaacct agtttactaa ttactatatg attaacttat    600
taccactttt acttcttctt ttttggtcaa attacttat tgttttttat aaagtcaaat    660
tactctttgc attgtaaata atagtagtaa ctaaaatctt aaaacaaaat attcaacctt    720
tcccattatt ggaatggtaa tgtcttcaac accattgacc aacgttaagg aatgtctttt    780 aatattttg gaacctaaat gctaatactg tataccacaa tcacttatga gtattgaagt    840
tgagatagag gaggtacaag gagaccttat ctgcagaaga caaaaagcca tttttagcaa    900
aactaaagaa agaaaaaaga ttgaaacaca aatatgcgcc actcgtagtc caccccctatc   960 tctttggcaa aagccacttc actctttttc ccttttat                            999

<210> SEQ ID NO 114
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0613

<400> SEQUENCE: 114
ttaatactaa cattgtagaa agccacaaaa aagaaattga aatgtgagta gatgctgagt     60
cagaggtttg gtcaatacac aacagctaat tgagataata ttatacacgt cacgatgact   120
tgttttttct cctcccaact tgttaatttc tttattctta aaattaaacc atcgcaaaaa   180
cagaagaaca cagctgtttt tctcgactcc caatttctat tttgctgcta aggacatttc   240
atttcattat ttcccaattc aggactcctt agattttcct aaatttgttt tcctaacttg   300
ctctctctca ttctaacatt ttctcatttt tttagattat cttgtactt ttagtagatt   360 attttatcag gttttacaaa catacattga cattctaaaa agggcttcta aaaattcagt   420
gtggaatgct gatatactaa aaaaaggtca tgcaaaatta tctacgattt atctaaaatt   480 agataaatttg ccatatataa ctattaacta ataatcgatc ctttgatttt ttgtttagat   540
aaaacgaaac agctatatct ttttttttg ttatcggatt ttaatcgaat aaaagctgaa   600 aataacagt tatatcttct tctttttaa ctaatgaaac agttatatct taaacaaaca   660
acagaaacag taaatatta atgcaaatcc gcgtcaagag ataaattta acaaactaat   720 aacaattgag ataagattag cgcaaaagaa actctaattt tagagcgtgt aaacacaaac   780
```

```
acgtcttgaa agtaaacgtg aattacacgc ttctaaaacg agcgtgagtt ttggttataa      840
cgaagatacg gtgaagtgtg acacctttct acgttaattt cagtttgagg acacaactca      900
agttatgttt gatatctaag gacttgcact gtctccaaat ctgcaggaag gactttttga      960
ttggatcaat ataaatacca tctccattct cgtctccttc                           1000

<210> SEQ ID NO 115
<211> LENGTH: 351
<212> TYPE: DNA
<213> ORGANISM: Arabidopsis thaliana
<220> FEATURE:
<221> NAME/KEY: misc_feature
<223> OTHER INFORMATION: Ceres Promoter PT0625

<400> SEQUENCE: 115
gatcatgatc agtttcaact cgctgtgccc acgtgtcgag agatcggcac gtgcctgagc       60
tctcagccgc tcataaatac acttgtttag tagcaacagt atactatagt agtcctctcc      120
tgtttggctt ttagcttgca tcgatggatg gatggatgga tcgcatgaga gggcttcgcg      180
aaggtacgga accttacaca acgcgtgtcc tttctacgtg gccatcgtgt aggcgtctcg      240
ccatgctacg tgtcccggag gatgtctcga tgccaaccct tataaatact gttccattcc      300
aatcccatcg ccacagccag tgcaaatctg atcgatcaag ataatcgagc a              351

<210> SEQ ID NO 116
<211> LENGTH: 1022
<212> TYPE: DNA
<213> ORGANISM: Arabidopsis thaliana
<220> FEATURE:
<221> NAME/KEY: misc_feature
<223> OTHER INFORMATION: Ceres Promoter PT0633

<400> SEQUENCE: 116
cccgatcggc cttaatctga gtcctaaaaa ctgttatact taacagttaa cgcatgattt       60
gatggaggag ccatagatgc aattcaatca aactgaaatt tctgcaagaa tctcaaacac      120
ggagatctca aagtttgaaa gaaaatttat ttcttcgact caaaacaaac ttacgaaatt      180
taggtagaac ttatatacat tatattgtaa ttttttgtaa caaaatgttt ttattattat      240
tatagaattt tactggttaa attaaaaatg aatagaaaag gtgaattaag aggagagagg      300
aggtaaacat tttcttctat tttttcatat tttcaggata aattattgta aaagtttaca      360
agatttccat ttgactagtg taaatgagga atattctcta gtaagatcat tatttcatct      420
acttctttta tcttctacca gtagaggaat aaacaatatt tagctccttt gtaaatacaa      480
attaattttc gttcttgaca tcattcaatt ttaattttac gtataaaata aaagatcata      540
cctattagaa cgattaagga gaaatacaat tcgaatgaga aggatgtgcc gtttgttata      600
ataaacagcc acacgacgta aacgtaaaat gaccacatga tgggccaata gacatggacc      660
gactactaat aatagtaagt tacattttag gatggaataa atatcatacc gacatcagtt      720
tgaaagaaaa gggaaaaaaa gaaaaaataa ataaaagata tactaccgac atgagttcca      780
aaaagcaaaa aaaagatca agccgacaca gacacgcgta gagagcaaaa tgactttgac      840
gtcacaccac gaaaacagac gcttcatacg tgtcccttta tctctctcag tctctctata      900
aacttagtga gaccctcctc tgttttactc acaaatatgc aaactagaaa acaatcatca      960
ggaataaagg gtttgattac ttctattgga aagaaaaaaa tctttggaaa aggcctgcag     1020
gg                                                                    1022
```

```
<210> SEQ ID NO 117
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0650

<400> SEQUENCE: 117
catacttaat tctaaaaaaa caacacttat agtttataag cagctcttat gataaaaatc      60
tttctgagtt atagctctgt taaacttgta ttcaccccaa aaacggatgt ttcatttctt     120 atttttact tggagtattt tattgtaatt tgtaaaaaaa aatgtaaagt gggggatatc      180
atgaaaaaca acgtcacttt gtttggtcac aatatacatt tgataaaata atggtcgtcg     240
cgtgatttag ttgattttg ttttatcaac cacgtgtttc acttgatgag tagtttatat      300
agttaacatg attcggccac ttcagatttg ggtttgccca catgacat accgacatag       360 aaggttaaat ccacgtggga atgccaata ttcaatgttt ggttttcaaa agagaatcat      420
ttctttatat gatctcaaaa gtatggaatt gaaatgacta atgagcacat gcaattggtg    480
ctatcttaaa aaccgaacgt ctttgaattt aatttgtttt tcaccaaagg tacctaatga    540 aacccttca ttaaaaaata aaggtaacaa acaaattttt gtattggaaa aaacatttttt    600 tggaatatat aatttggtaa tagaattatg agcaaaaaag aaaaagaaaa gaaagaataa    660
tgagcataat aaagcctttta cagtattact aattgggccg agcagttttg ggctcttgat    720
catgtctagt aatcttaaac agacgataaa gttaactgca atttagttgg ttcaggtgag    780
ctaccaaatc caaaaatacg cagattaggt tcaccgtacc ggaacaaacc ggatttatca    840
aaatccttaa gttatacgaa atcacgctttt tccttcgatt tctccgctct tctccactct   900
tcttctctgt tctatcgcag acattttgt ttatatgcat acataataat aatacactct     960
tgtcaggatt tttgattctc tctttggttt tctcggaaaa                         1000

<210> SEQ ID NO 118
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0660

<400> SEQUENCE: 118
caagtcaagt tccaatattc taaggagaaa taatagtata ctaaacatac attagagagg     60
ttaaacttct ttttggatttt aagtgtgtat gcataggcta tttattctta agtataacta   120
ttaactgtag ctagatttat acaagaaata cataaaactt tatgcatgtg aggtagccat    180
gaatatacgt acatgttgca atcgattata catgttgtat ttggatttct ctatacatgt    240
tttaacttgt cattctctaa gtatatacat accattaata ctgtgggcat gagtttatga    300
taagactttt cttttggaga ccagttttgt tttccttttcc acctatattt gtctataggc    360
ttcacggtac actagtttac aagtgttttt atatgttcta aataaaattg agattttccg    420
gaacggtatg atctgtttgc aaataaggac gtatatataa cagtatcaaa tatatttgtt    480
gttataaggc aataatatat tttctgagat attgcgtgtt acaaaaaaga aatatttgtt    540
aagaaaaaaa aagatggtcg aaaaagggga gtaggtgggg gcggtcggct tttgattagt    600
aataaaagaa accacacgag tgacctaccg attcgactca acgagtctac cgagctaaca    660
cagattcaac tcgctcgagc ttcgttttat gacaagttgg tttttttttt tttttttaat    720
```

```
tttttcatct tcttgggttt ggttgggtca ctcttcaggt caggtgtgta aaaaagaaag    780
aaagaaaaga gagattgttg tgttgtaacc cctttgacta aaatctaatg aacttttta    840 acacaacaaa actccttcag atctgaaagg gttcttcttc tcttagtc tcttcgtcct    900 tttattctcc gtcgtcgttt catgatctga ctctctggtc ttctcttctt cttcttcttc    960
ttctattttt tcttacttcg tcactgttgt gtctgaac                            998
```

```
<210> SEQ ID NO 119
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0665

<400> SEQUENCE: 119
aaaaaggatg ggtaatggga cctatttcc ccaacatccc acatgcacac ttccctctcc     60
attctctcac attatttct ttcattctaa tttatccatt ccgtgtgtaa catattcact    120
aataatctca tctcactaac tcattcattg attgtgatat gtttatctag aattagtgtt    180
ttaacactgt gtctacatat gatttccttt tcattgtatg tgaacatgtt aactcactaa    240
tcattttgta ttttcgagtt aacatgagtc tccacttcgg tagactaaag taaagatagg    300
tttgagtata ataagtttta aaatttgctt taaaatcaat atttataaat aagttttat    360 cataagtgat ttttgtatgt tatattggac cttgtataaa cagactacag aagaaaatta    420
tttatgagaa cttgtaatgt tagagtggac ctcgtataaa ctaattatgt gggcttttac    480
cataaactat ttatgaaaat tattatggcc cacaccacta taactaaagc ccacatattt    540
agcagcccag tttcattgta agagacatgt tcgctctgga actagaattt tctggttttt    600
gggtatttgt tttcttatgt gtagagaaat gatggtaacg attaaatgtt gtgtattaca    660
atttacaatg gtaagacgat taatatattt acacacaatt ttgttgttgc tgtaacacgt    720
tagtgtgtgt gatgatagaa tttcataaag ctttaactac gaggggcaaa atgttaattc    780
taaatagttg acagcagaaa aagatatgta tacataatat aaggattaaa acgtaaataa    840
taataaataa ggcgagttaa attaaaaccc tgttaaaacc ctagcttgaa acacatgtat    900
aaaaacactt gcgagcgcag cttcatcgcc atcgccattc tctctctcat caaaagcttt    960
tctccttgat tttcgcattc tttagagtct aacgcaaag                          1000
```

```
<210> SEQ ID NO 120
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0672

<400> SEQUENCE: 120
cagccgtaaa tcctccataa atttattttg caagttttgc tcattatata atgagcggaa     60
tttatgatat aatcgtttgt aataatgtta tgttttgatc aaaatttgaa attaaaagta    120
ggtgagaact tgttatacag tgtagataag gtggatcttg aatataaaaa taaaatttat    180
aagatgtatt taaagcagaa aagcataaaa ctttagataa aataatgtaa aaatgtgtta    240
gcatcaatgt tgggatattg gccgacccga acttaatcaa tgtcggaagc cattacttct    300
ctcccaaaag acctttttcc ttcggagaac taggaacttc ctcactacct ttcgcttaac    360
gtgaaagcca taaatttcat atattcataa aaatcagaaa atctaaaact gtttagtatc    420
```

```
acctgttttt ggtatagact attggttttg tgttacttcc taaactatat gatttcgtac      480
ttcattggat cttatagaga tgaatattcg taaaaagata agttatctgg tgaaacgtta      540
cttcagtcat gttgggtcta gatttacata ctactatgaa acatttttaag ataataatta    600 tcctagccaa ctatatgttc tatattatgg gccaagaaga tatagaacta aaagttcaga     660
atttaacgat ataaattact agtatattct aatacttgaa tgattactgt tttagttgtt     720
tagaataaat agtagcgtgt tggttaagat accatctatc cacatctata tttgtgtggg     780
ttacataaaa tgtacataat attatataca tatatatgta tattttgat aaagccatat      840 attactcctt gacctctgcc cccatttcct tttactataa ataggaatac tcatgatcct     900
ctaattcagc aatcaacacc aacgaacaca accttttcca aagccaataa taaaagaaca    960
aaagctttta gtttcatcaa agacgaagct gccttagaa                            999
```

<210> SEQ ID NO 121
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0676

<400> SEQUENCE: 121

```
aagatagtac agtttcagtg ttttgagaaa aaaagctgaa ctaaaactaa aatgtttaag      60
gacacaatat ttagtttcaa ttagataatt caacagtttg aacaattttt tttttttttt     120
tttgaagtca tttattata caatgtttta aaacgcatta agcatttagg cagccgacaa      180
acgcctattg tctaactgta aataggcgct tccacttagg ttcatattgc atatttacta     240
tatgtgtata gtgacaaaaa ccaatatttc tcttattttg gatgaaggta tagtagttgt     300
taaatgttca atataattaa gcattaatga caaataaaat aaaattaatt tagttgataa     360
aaagataatc ttataaaaag atcgatgaat agatataatg gtttactgaa ttctatagct     420
cttaccttgc acgactatgt cccaaggaga ggaagtacct taactataat tctgaacata    480
attttgtcta tcttggtgag tattatatga cctaaaccct ttaataagaa aaagtataat     540
actggcgtaa cgtaataaat taacacaatc ataagttgtt gacaagcaaa aaaacataca     600
taatttgttt aatgagatat attagttata gttcttatgt caaagtacaa ttatgcctac     660
caaaattaat taatgatttc aacaggaagt ctgagatgat gggccgacgt gtagttacgt     720
ttcttgaatt gtgagagatg gtatttatta tactgaagaa acattatttt actaaataaa     780
ttttcatttc acatcttctg taatcaatgc gggtagatga agaagttgtt aatacgatgg     840
ccaaccatat ggatctcttt tttggcgttt ctatatatag taacctcgac tccaaaggca    900
ttacgtgact caataaaatc aagtcttttg tttccttta tccaaaaaaa aaaaaaagtc     960
ttgtgtttct cttaggttgg ttgagaatca tttcatttca                          1000
```

<210> SEQ ID NO 122
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0678

<400> SEQUENCE: 122

```
aattaaatga aaccgcccct aaattaggag ggatttgggt aagtggtaac acattcactg      60
```

```
gaaacatgtg aagaaaggag gatgtcaagt agctgaaaac tcagtatagt aaccaacggc    120
ttctcaccaa cctttcatta ataatttggt catccctata tttttattca acattttgtt    180
tttcaatagc ttagagcacc ttaataccct tcagtgtttt tttataaaaa aaacaaaaat    240
tgggattaat catcaatccc caaatgtaac gttacttag attatgttca tttttctata    300
cacacaaatc atattctttt gttttaatct tcgaaaaacg agaggacatt aaataccct     360 aaaaaaggag gggacattac taccaacgta cattaacatg tttgatagca aacgatttat    420
tttgttcgtt ttgaaaaggg gaaagtaatg tgtaaattat gtaaagatta ataaactttt    480
atggtatagt aacattttcg aataataaga gagggaaaac actcgccatt gtcggcaatt    540
tagaaccaat attagaaggg ttttttttaga gaaaaaggac ttaaaagttt agagacctta    600
acaacaactt atttagaaat agacatgctt aagttgacaa cagcgagttt attttctata    660
tcgaagaaaa atacgaactt tttcttaatt agatttcgaa tgcatgcact atcgagaatc    720
gaccgtcaca agaaaaaact aatatacata ctgtacatat ctatattcaa tattggtggg    780
gatgggttta atgtgtattt ataattcatg gataaattca cacaataagg tccatgaaac    840
tagaaggtac caaaaataag cattaatgac tctttgccac ttatatatat gattctctca    900
tagtaccatt ttattctccc aaacctatct tcttcttcct ctcttgtctc tctcgctctc    960
tctcttctac attgtttctt gaggtcaatc tattaaaa                           998
```

```
<210> SEQ ID NO 123
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0683

<400> SEQUENCE: 123
```

```
gattgaatga tgagtgtgca cccttgtatt actaataaaa aatttagcaa cagttataag     60
ctaacgtcat ccatgagtca ttcattagat tcactatttg cgttctcaaa aatcgaattg    120
ttaaaatttg agaagctcta atatacgagt caatgagatg tggcaaaagc atgtccttga    180
ccataaaatt tcgaggggtc aactcattag ataaggacaa gaatcaacca attgaaggcg    240
tcttctataa caagtttctt tattactaat attaaagtcc aatggggtga gggggagaag    300
aacttaaata aaaggaaata attggtaagt gaataaaatc taaatacgat actagatgat    360
tgatttgtgc tagtgcatgg tattagatca gatatgtgtt actattcgaa ttcaaattgg    420
catattccat gttgttgata agaaaattgt agaagtgtaa aagctgagtt actatattca    480
aactagtggt ttacataaag tgagacaaca actgtttcac aaaaatgact ataaaatagt    540
aagtagtatt aggtcaattg attttaaaat tttaatcaaa ttcaaatttg tgatataatc    600
aaatttgttt atagaaaatg ttaagaaatc aattttggca gaactaattc agtgagaaac    660
aatcatttac aaaaacaatt ttaacattat ttaacagtaa gatttgacat ttaacccgtt    720
cgtgtgaacc catcatatct aacatggctc tacccatgac gcctccatgc catggacaat    780
tttgacagat cagaagttct gaacgtggac gaggtaagaa caccatgatg atacgattgg    840
agttagttat gtcgccaccg acatcactgc caatctcatt aataaaagtg gtactaaatc    900
tctaatctct attaactata aatataacaa agaaccaaaa gaaagtttct tatctctctt    960
atctttcata atttccaaga aacacaaacc ttttctacta                         1000
```

```
<210> SEQ ID NO 124
```

<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0688

<400> SEQUENCE: 124

| | | | | | |
|---|---|---|---|---|---|
| acgttcagag | gcatcgcttt | tgtacaaatt | gaagcgggtt | tgttcaatat | ttaaaataac | 60 |
| acaggaaaca | ttcaaatgta | ttattgatgt | tgcttaggtt | tgtgaaatga | tatgaaccat | 120 |
| atcgtatata | ttactagatt | tttcttatat | gttttaaggg | tagtggggct | gacctatcat | 180 |
| tctgtttggc | attaccaatc | agactatcag | agtattcacc | attcaggatt | ccataactag | 240 |
| aaaaagaagg | ggtttacatt | ttctcatact | gtataatttt | ctactatcag | agattttatc | 300 |
| gattacatta | atctcatagt | gattattctg | atttataaaa | aagttgacaa | aataattaaa | 360 |
| accagtattt | tataacaaga | ttgtctctct | cccatggcca | ttattttgac | ctctgactta | 420 |
| tttaaatctt | aattaacagc | ataatactgt | attaagcgta | tttaaatgaa | acaaaataaa | 480 |
| agaaaaaaag | aacaaaacga | aagagtggac | cacatgcgtg | tcaagaaagg | ccggtcgtta | 540 |
| ccgttaaggt | gtgtcgaact | gtgattgggc | cacgttaacg | gcgtatccaa | aagaaagaaa | 600 |
| gggcacgtgt | atagatctag | gaaaaaagaa | agaatggacg | gtttagattg | tatctaggta | 660 |
| ccaggaaatg | gaacgtcaca | ccaaacggta | cgtgtcggat | cctgcccgtt | gatgctgacg | 720 |
| gtcagcaact | tccccttatt | catgcccccc | tgcccgttaa | ttacgtgtaa | cccttccatg | 780 |
| cgaaaatcaa | acccttttttt | tttttttgcgt | tcttcttcaa | cttttctttt | taaatcaaac | 840 |
| ctttttctttt | taaatcaca | ttgcatttcc | taacgctcaa | caaaatctct | ctctactaat | 900 |
| atctctctct | ctctctctct | attgttgaag | aagactcata | atcggagatt | gtttgttttt | 960 |
| ggtttgctct | gtaaattgga | gaagttttgt | tagagatcaa | | | 1000 |

<210> SEQ ID NO 125
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0695

<400> SEQUENCE: 125

| | | | | | |
|---|---|---|---|---|---|
| aacattttct | ttaacttact | cttaaatttt | aatagtaagt | tgatgcatgt | tatgttgatc | 60 |
| cgtcttgatc | acaaatattg | ttttatggac | gaattctttg | acagtaaatg | gctatagtga | 120 |
| ctcagcttgg | agcatcccga | tatgaaaaca | aagtgcagta | ttgtgtcgtg | gtcatcacta | 180 |
| acgcactttc | ctagaactat | cgcgcgtgtt | tgacctatgc | aacacaccag | atgtcatgaa | 240 |
| cgtatactta | aatagaaaca | atgatataga | caattggcta | tattctgtca | tggaacgcaa | 300 |
| accggataac | atgtctatta | gattcatcgg | acttgatcat | ggttatgtct | taatagacga | 360 |
| attctttgtt | aacgattggt | taaaacggct | cacgttagag | catcctacta | tgacttcaaa | 420 |
| attgataaat | attacatgga | aatcacttta | attttagtta | gaaggtagtt | aatttagata | 480 |
| ttcttattta | ataaattaaa | aaatagaaga | aaaaagatg | agaagagttt | ttgtttataa | 540 |
| aataagaaat | atcttttatt | gtaattttaa | aattaaacaa | atttaattta | tattaaaatt | 600 |
| atctttgttt | tattgttaag | gcaataatta | ttttttttggt | gggaattgtt | aaaacaataa | 660 |
| ttagtatact | gttaagtggt | cctttaataa | taagataacg | tgatttaaaa | aagaacgaga | 720 |
| caggctaata | tagtagagag | gaaaaaatac | aatttaggcc | caataaagcc | caatatagag | 780 |

```
ttgtgctcaa acacaggtct tcgccagatt tcctatgacg ccgtgtgtca atcatgacgc      840
caagtgtcat tcaagaccgt cacgtggcgt tgtttctaca cataggcgat ccatacaaat      900
cagtaacaaa cacgaaaaga gcattcatat gtacgaaagt agaaagaag agactctttg       960 tgataaaact aagtaagaaa tagcataaaa gtaaaaggga                           1000
```

<210> SEQ ID NO 126
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0708

<400> SEQUENCE: 126

```
gtttccaaaa ctagtattct ttatttgctc tattcattat attttatat ttgtaacgtc        60 ccgaccgtct ttattaggtt tcgacaatca cttctcggaa ggtcgtccat cctgaaatta      120
ctctatccta aacatgttta actataaaat tctctcgaaa cttttgtaac gtatataacc      180
acataaattc tcttaaactt atttgcatac accattatat ttctgaaatc gatatgttac      240
aatattattt aatatttaga ttacttttac tgaatcgaat taaatatcaa atcgaaacaa      300
atctaatcta ccaaaaataa ttttgttata acatttctt gcctagttct acctcatata       360
cattttagtt aaagaaagaa atcacaacaa ttcccataat tcaataatta aatccacaaa      420
atcttggagt aagtaagaga ataaaaaga tagtatctta acataaacaa ttcaaagatg       480
ctctctcaca caattcacac acacttacaa aacaaaagac agaaacaatg ttttcattca      540
aatcaaaaga agttataaca ctagtacaaa aaaagctcaa attctaatag taactctttt      600
tatttcccaa ttacccaaag attctctctc acttcacaaa actagctttg agagtcgtgt      660
tccacaaaat ccattaaagc tgaaacggtt ttgctcacca ttcaaacaaa tacaaaattg      720 caaaaccca attataaca aaataatata aaattaaac cgctaaaaag agtgaaccaa         780
caaaaatcgc cgaatgtgtg tgtaatgaga aaaccgaccc atcatcccaa tcatctcttc      840
ccgtgtcact ctcttcctct cccacgtttc ttctctcttc cctttatggg ttttaacttc      900
tccttcttct tcttcttcaa tcttcagttt tcaaattcaa caacaattca cattttgatt      960
tcttcatcat ctctctctct ctcgcttctc tctcaaatcg                           1000
```

<210> SEQ ID NO 127
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0710

<400> SEQUENCE: 127

```
tagtgcgcgt ggggagaggg aatggtgaaa ccttagtggt taagttatga ggaaaatgat        60
aaaaggataa aacaatcaaa tgcagcttga aacggccata acataaagta ccttatggtg      120
gtgcgaatat ttttgtgttt ctttcactct tttattgctg aaagctacga cacttgtctt      180
aatatattgt ttccgcaagt cacatgatct acttttatt taacgtctag aaacgccgag      240
atatatgatg attagtatat cacgtctatg caaattgtta gttcgtgttt ggccaaaaga      300
tatcgagaca tgtctgaaga accgagtctg gttttgagat atttcttcaa gcattactat      360
acaatagaaa aaggagacac gcgaatatga taatagcaaa aggcataaaa aggcgaaaat      420
```

-continued

| | | |
|---|---|---|
| taaagaaaaa cgtaaagtga tttggcctca atcaacggga acgtatctta attttagagg | 480 | |
| ttcttcttt actttttgaga cgagagagtt tgcgtctttg cgagctgctt tggttgacta | 540 | |
| aacattatca tattgaaaac caaaatacaa cggaggaata tttgtcacag tttcactttc | 600 | |
| acattgtttc cttaacgttt aatcaacctt gttcaaaatt tctatagttg taatcatcat | 660 | |
| tgtttacaaa attttcgttc aaagatgatt ttaaataaaa ttgtgaaaga aaacctttc | 720 | |
| tgaaataagg attggatgat agtgttaaaa gaaaaatatg aactgaggca aaagaggag | 780 | |
| tggtccccgg aagattgtga atgtgtcat ctaaaccagc cagacgtagt cacgtgttct | 840 | |
| ctctagcttt atgaacttcc ttagccagca ccatcattgt gattgtagta tatatgtaac | 900 | |
| cctaccttca tctctcccat tttccattct ccatatagac tcctttacaa tatacaaaac | 960 | |
| ctatccaaaa gcgaagaagc caagcaaaca tattataaaa | 1000 | |

<210> SEQ ID NO 128
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter PT0723

<400> SEQUENCE: 128

| | | |
|---|---|---|
| gtcatatctt atcaacacgt caacgatcaa aacctttagc ctattaaatt caacggctta | 60 | |
| gatcaaaacg aaactaggtg ggtcccactt ttaatatcgt ggctgcataa catttcctcg | 120 | |
| ataactgaag ccgttgtggt ctttctcaga atctggtgct taaacactct ggtgagttct | 180 | |
| agtacttctg ctatgatcga tctcattacc atttcttaaa tttctctccc taaatattcc | 240 | |
| gagttcttga ttttttgataa cttcaggttt tctcttttg ataaatctgg tctttccatt | 300 | |
| ttttttttt tgtggttaat ttagtttcct atgttcttcg attgtattat gcatgatctg | 360 | |
| tgtttggatt ctgttagatt atgttattgg tgaatatgta tgtgtttttg catgtctggt | 420 | |
| tttggtctta aaaatgttca aatctgatga tttgattgaa gcttttttag tgttggtttg | 480 | |
| attcttctca aaactactgt taatttacta tcatgttttc caactttgat tcatgatgac | 540 | |
| acttttgttc tgctttgtta taaaattttg gttggttga ttttgtaatt atagtgtaat | 600 | |
| tttgttagga atgaacatgt tttaatactc tgttttrcga tttgtcacac attcgaatta | 660 | |
| ttaatcgata atttaactga aaattcatgg ttctagatct tgttgtcatc agattatttg | 720 | |
| tttcgataat tcatcaaata tgtagtcctt ttgctgattt gcgactgttt catttttttct | 780 | |
| caaaattgtt ttttgttaag tttatctaac agttatcgtt gtcaaaagtc tctttcattt | 840 | |
| tgcaaaatct tctttttttt tttgtttgta actttgtttt ttaagctaca catttagtct | 900 | |
| gtaaaatagc atcgaggaac agttgtctta gtagacttgc atgttcttgt aacttctatt | 960 | |
| tgtttcagtt tgttgatgac tgctttgatt ttgtaggtca aa | 1002 | |

<210> SEQ ID NO 129
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter PT0740

<400> SEQUENCE: 129

| | | |
|---|---|---|
| tgtggccact aaagatttac ccttaaccgg gcccatataa gcccacgtca agtggcgctt | 60 | |
| atacgctctc cgtaagagag ccaacatttg gtatgtaatg ttgcaaatta ttcttcaaga | 120 | |

```
caataaattc aaatataatt caatattgtc caaatatagt gatgtacttc agttgtgcac        180
atagaaactc cactaaacca acttttagat agatgcattc acaaattttc aacaatgtcg        240
cgaaagtcta atccatcacc agattctaac attttaatta ttatatttaa ctatacatac        300
tctaatcagc atgagtcaaa cgtgtacaat agcccaagca tataataaga ccaaagtcaa        360
actcaaataa atgtctccaa actcaaaact tgaaaaagac ctaattatta catggtagat        420
atgactttgt cgacaagtaa accaactaat cctcgaagct accttctctt cccagttatt        480
atgtgtgatc gatttataaa tctcttcttc taataacacc tatattttc ttatgatgtg         540 aataaatata aaacttttaa ctttaaaaca tatttatccg aaatattgca cttagatttc        600
aaatagataa ataatagtac tatctaactg atattgaaaa gacctaacac ggaaaacagt        660
tttataaaaa atcccaaatg tgggtaatta tcttgatttc ttgggggaaa cagaaaatgg        720
attaagatta atcggagtcg tgtcaagcag ctcgttaata actgtagcaa gttgactgag        780
taagcatcaa cgtgtcatct ccgtaaagcc cattatttct agtctcgccg cgtcttctct        840
tccacgtagc acttcacttt ttctctcctt ttgtttcctt tggaacacaa acgtttctat        900
ttataggaat aattacgtcg tccgtatctg tgtcggaaca tagatccaaa ttaaaagcga        960
cttacttaat tacatatcgt tcgtgttttt ttcttcaaaa a                           1001

<210> SEQ ID NO 130
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter PT0743

<400> SEQUENCE: 130
tcgattggcc cgatcggccc caaaatcaag ctgagccgct tcaaacttca gcttttgaaa         60 tcaccccccaa actcatgtcc tcttatcatt ataactaaag gatctttcat tttatttaac      120
tcatcgtctt gcactaccca acccaaaggt tccaactata cccgaagctt tctaaaggtc       180
caaagacttt ttttttcgag ccagactatt caagccaaga aaagccaaac cccacaagcc      240
agtacttttc aattccatat tataaactta tctgtcttgt tttagtccca ctaaaaacaa      300
cagaatttaa tttaggttga gctaaaaccc ttgacaaaag tgtatagtcg tcgattcagt      360
agcacactca tcactcatca gatttgatag ttgacctaaa gtatgactac tccatttcaa     420
ctaacaaatg aaaataaaag agacctaagg gttagaggat tgaaactata ctctcaagtc    480
ttttatcact aggctactac cagctagtta acttgatgga tttaagcaag aaaacgtaga   540
atttatattc gagcagattg tttagctaaa aaagcttggg tttgaaattg ccttttctcc   600
catataagca cgtcggttcc taaataactc tttctagcgg agagtgtctt tccaataatt   660
taataaaaat ggtgtttgta tatcaaaaaa aaagaaaaa agaaactgat cgagatagaa    720
cgtttgcagt tttataaaca atttaaaaaa caaaaaaaat taaactcaat gtatttttta   780
ttaattcaca aacaataata aatcatagga tcgaatattt acacggtatc aaaacctact    840
cgccgctact atataaaaat tgaagtcaaa tatcaaccgc aattattaaa ccagcaagac    900
aataattcat aaacttaata taaacataaa taaattaatg ttacacaacg atatatggtg   960
agggttatta ctatcttctt cctctcaaaa cacatctcct aaccttaagc tttagacggc     1020
ctgc                                                                    1024
```

<210> SEQ ID NO 131
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0758

<400> SEQUENCE: 131

```
agctagccac atcagtgacc aaaaaagata attaacaaac caaataaaat aacaaatttt       60
gatcatttgg aataaaattt ataaaaggaa cgaaagcgcc ttctcacggg tcccatccat      120
tgaaatatat tctctctttt tgctctatat aataataacg cgtactaatt tgtagtatat      180
attattacaa agtcgatatt tgattgtttt gtgaacgttg atatattaat tttcttggat      240
gatgacaaaa aaagtcatag aaagtaacgt gtgaacatag cattaacaaa atacaaacat      300
aatatataac caaatatatg aaaataggat aaaatctcat tgaatagatc ttcttctatt      360
caaatatata aatatttgtt tgtctataaa attaacagag cattcacatt atctaaaata      420
atagtaaaat caaaataaaa ctaaataaaa ataactctgg ttttataacg attgatttta      480
aatattagtt tttgttgtaa agagatcatt atatatgtct gtaatatttt tatactgagt      540
tacatgatat ttagttatta tagcgtaatt aactaagata agaaattaac taaagtgata      600
ttctgattat tattattttt gttaggacac gtacgtggaa aaactaaaca ctataggtta      660
caaaacggta taataaactc accattactg gaaaatgttt gcatttgact caataagtaa      720
cttattataa gttactgata taatgcatag ttttgaaatt cttaaataaa ttattttggt      780
ttcgcatgaa aatatgaaag gagagaaatt tattattgtc acttatatat atatacatcg      840
taatcatttt ttcgtgaata attctctctc ccattccatt atttctcagt atctctcttt      900
cttccccttta ctttattgtt gcttttaaac cttcaatttg ctcataaacc aaatatataa      960
tatcaaaaca aacaaacaaa aaatcagaat tcccctaata                           1000
```

<210> SEQ ID NO 132
<211> LENGTH: 921
<212> TYPE: DNA
<213> ORGANISM: Arabidopsis thaliana
<220> FEATURE:
<221> NAME/KEY: misc_feature
<223> OTHER INFORMATION: Ceres Promoter PT0829

<400> SEQUENCE: 132

```
aaagttttga attattggga atcaatttcg aagttttgta attctttggg ggctaatagg       60
atattttatt ttcttggttt cgtctattgt tgttttttcta tttatggttg ggcttttaga      120
actctggaca ggcccatgtc atatgttttc ccttctcctt atattttttca tttttcatttt     180
tgttaaatta atgcataata tccaaaaaca atttaaattt ttgaaggaac cctttagtta      240
cggctccgaa gctttcacaa gtgagaatgt gagatcaaag aaggcaaatg gaggatttta      300
aaagttaaaa tcatctttta tctgcaaaag ttgacaattt ttttgtatca aatctaaatc      360
atcaaactct cttaaactac aagagcataa caacctctat gtaatccatg aaataatctg      420
cttgaaggac ataacataaa tcattatggc tagagtgact aacttcaatc aaatcctctt      480
aactctagct cccttacaat ggtatcgtaa aacattatgc attagggatt gttgtcctag      540
gaaaataaaa taaaaatccc cacagaccaa ctaccatttt aacttaaaaa taagcttcgt      600
ccgcgacgaa ttgttttcca tcctaaaaat agaatggtgt aatctgctaa tggtttagtt      660
ccattaactt gcaagttcta ttgaaagcct aaatgtcaat aaagatatta aaattcggag      720
```

| | |
|---|---|
| tcaaaagaca aatgaatcaa aagcaacaag acaagtcagc tccattcttc actacccatc | 780 |
| ttttacaata atcatctct cttttcacaa atttcaaact actctcattg ccctttagct | 840 |
| ttgttataga gccaacacta cagagagact cacacacttg tttcaataat taaatctgaa | 900 |
| tttggctctt cttataaact a | 921 |

```
<210> SEQ ID NO 133
<211> LENGTH: 763
<212> TYPE: DNA
<213> ORGANISM: Arabidopsis thaliana
<220> FEATURE:
<221> NAME/KEY: misc_feature
<223> OTHER INFORMATION: Ceres Promoter PT0837

<400> SEQUENCE: 133
```

| | |
|---|---|
| aactacaagg gagacataat atcaccatct ggttcctgtt atcatctgaa gatttcttgt | 60 |
| tttaccttcc agtgataaaa tgatccttat aatacatata gatatattaa attgctgtat | 120 |
| tttaagatta tagatatata aggtacatga gagtgtttat ttaaaaaaat tcacttggaa | 180 |
| ttcatgtttt gtgatacgtt agattggaat ccatttggga aaagaagaat catctgttct | 240 |
| tatgtctcaa attttgactt cattcacttt tcttcttgtc ttttaagaaa gcttccacaa | 300 |
| tctaactgtt cgatgtgaaa actgagattc gagtaagaaa atgtgaactg tgttatactg | 360 |
| tttttttaatt agataattta gattgcactc agataaatta ataacattcc tcgaatactt | 420 |
| ttatgtgatt ggatatatta ggtatatctg ccaaccaacc aataaactgc tatgtttaaa | 480 |
| caaattaaat aaaattagtat atgtttactc aagaataaag aagatagaaa agaaaattct | 540 |
| atatgagcta aatttgctgg aggaggcatc ggacgtgggt accagaccctt ccaagcaca | 600 |
| cgagtagtgc ttagccatgt catgctaaca tacaccatttt ggttcataca aaatccaaat | 660 |
| caaaatctat ttttaaaatc ttttgcacac gtctttgaaa aacacctctc atactatagc | 720 |
| tacggaagct tcaatttcaa ggtttgtcta aaagctaacg att | 763 |

```
<210> SEQ ID NO 134
<211> LENGTH: 751
<212> TYPE: DNA
<213> ORGANISM: Arabidopsis thaliana
<220> FEATURE:
<221> NAME/KEY: misc_feature
<223> OTHER INFORMATION: Ceres Promoter PT0838

<400> SEQUENCE: 134
```

| | |
|---|---|
| atactggtat gcttaaggtt gaagccaaga tctctgtctt acccaagtaa ccactttcta | 60 |
| ttagaaggga tcaacactaa gaatatggag atttaagcct aagggctaag gcggttctca | 120 |
| acaatacatg atgtgaatac aatcacagac gatttactga ggtttgttga taagatcttg | 180 |
| atcagtctct gcatcatctg ttcaacaatc tcaatctttg actgtttgct ttcggagcca | 240 |
| taaacagagg aatcccttat tccctgttat aggagcaata caccaagtat tatttccatg | 300 |
| gctgaaattc tcttatggaa acctaattgt tccattgaag ctgtaaaatc gaatctggtg | 360 |
| aatattctcg agcaaagccg catgctaatt atgtcaattc agaagagttt gattaggaga | 420 |
| ctcgaagcga gtttgatgat ctttcttgat gttcaactcc gattgtaagg gtataattga | 480 |
| cttttcatgt attacggctc caccacctga cactaaggca ctctttgtcc atctcgttgg | 540 |
| tatcatcgga ttcggatggt aaaaataaaa agagcagagg aaacttgtta ctcatgcaag | 600 |
| cttctcaggt gccacgtcac tccattacgt gtcatcttca cacaccatct cgctcaaaac | 660 |
| cgatctcatt tttcaaacct taaaggcaga agcaactgat taagttaaca ctcttgagaa | 720 |

```
gctctcgatt aagcttgaac ttggaggatc a                              751
```

<210> SEQ ID NO 135
<211> LENGTH: 669
<212> TYPE: DNA
<213> ORGANISM: Arabidopsis thaliana
<220> FEATURE:
<221> NAME/KEY: misc_feature
<223> OTHER INFORMATION: Ceres Promoter PT0848

<400> SEQUENCE: 135

```
tctctttaaa tcagttaact aaccgtttat atatttacga taaggtttga agagattatt   60
gataaaataa tacatttcat aatcccgcgt tcaaccgttt aaagtaacat ttaagttgac  120
tatatctaat ttttttttcca ttaaatatgg agctggtaaa ctttatcaac ttctaaaaag  180
tgtaacaaca aaaattaggt caatcacaat tctgtttttt ttattatttt ggattgactt  240
ccaattgcaa atagtcttag tgatcaccat tatcatacat atacatcca gtaggtttc   300 atcatgatat accacaaagt atttgacaag ccatatggtt ttggatcaaa aagtcggtcc  360
aaaattaatg ttttatgtgc aagaaccgac ccattgtaca cacgtgttaa catcttcaag  420
actttcatct ctatttttct tttggtcatt aagatatccca ttgatccgaa tctgttacat  480
tcccacctac ttttttaatt tttactatcc actccaaatt aaacacaacc gatgatttta  540
ataattggaa gcttttaaaa atatttcaaa acaagcctct ttgtgtttgt ctatatatat  600
acacgtaata agaaggtgaa tgaatctcac agcttacttg ttctaaggct tccaataacg  660
aaaacagta                                                          669
```

<210> SEQ ID NO 136
<211> LENGTH: 702
<212> TYPE: DNA
<213> ORGANISM: Arabidopsis thaliana
<220> FEATURE:
<221> NAME/KEY: misc_feature
<223> OTHER INFORMATION: Ceres Promoter PT0863

<400> SEQUENCE: 136

```
cgggaaacga caatctgatc tctagtccag tcgattggcc cgatcggccg attataaact   60
tacatgagac aagtataaat aattattata aacttattaa gtttaagatc aaggcttttg  120
tgcaatgtat caatgaatgt tagatgtgat atgatgaaag caatgttta aacacataca   180 tagtcattga tcggaatgtg tgttattaga aatgcatgcc taagccgata gggttatcta  240
tgtttggtct tggacattat agccaaattt cgaatctaat tcttccaata tatatttttt  300 ttttttttgct tagggccact actagtattg cttatcaatt ttaagagctc atgaaaatgc  360
aacaatatag tagttgcaaa tccttgtttc aagagaaatc aaagggccac ttgtgaattg  420
aataataata atatttgcaa ataacctttc actaaaccat accaacaaaa ccacacagat  480
ttggcaaaga cataaccttt gggagacgtg aaaaggctca aaatttgaca attgtcctta  540
caaattcgct cattagtgca attgtgagat tgtttgcat ccaaatccaa ttcataactc  600
acactcgtct caaattcgaa aaggcctgca gggccagtgc actgggatcc aacaatgtcc  660
tccgactcgt ccaagatcaa gaggaagcgg aaccgcaccg cg                     702
```

<210> SEQ ID NO 137
<211> LENGTH: 435
<212> TYPE: DNA
<213> ORGANISM: Arabidopsis thaliana
<220> FEATURE:

<221> NAME/KEY: misc_feature
<223> OTHER INFORMATION: Ceres Promoter PT0879

<400> SEQUENCE: 137

| | | | | | |
|---|---|---|---|---|---|
| ttctaggaag | actggtcaag | ctaagctgtt | tctgtttttt | gttttttgtac | tttacttttt | 60 |
| gtttgctagt | gggaactggg | tttattgggc | cttgaagttg | ataaaagatg | aataaaagac | 120 |
| atatcgccta | aagcccatat | gagaagcaga | agacaaaaac | ctccaacttt | gggcataaat | 180 |
| tttgattata | gttaaaagtc | cagacccaat | ttggcacctg | gcttagttac | gattctaagg | 240 |
| catgacacct | gcctaatatg | tttattacag | aaaataaaga | gaatcagcta | ggtgtccctt | 300 |
| attgaacaca | ttaacaaact | ccaacgacac | tacgtgtctt | cgtgactctt | actatatcca | 360 |
| aaaacctata | gctaaagctg | aattttccat | gattagtata | gtcccaacca | aaaaaatact | 420 |
| gaagaaggca | taagc | | | | | 435 |

<210> SEQ ID NO 138
<211> LENGTH: 397
<212> TYPE: DNA
<213> ORGANISM: Arabidopsis thaliana
<220> FEATURE:
<221> NAME/KEY: misc_feature
<223> OTHER INFORMATION: Ceres Promoter PT0886

<400> SEQUENCE: 138

| | | | | | |
|---|---|---|---|---|---|
| agtgtatttg | aaaacgacat | tgaagaatta | atatattttt | ttttaatttt | agtttttat | 60 |
| agtacaaata | ttaaaacaaa | caatcctacc | atatcataac | atttgtaaat | aacatttaa | 120 |
| gttttgtttt | gagttttaat | taattttcta | tgacaaaaaa | atgaagtcaa | tagactaagt | 180 |
| gaatcatata | gtataaataa | acacaattta | aatagtttca | aataaattta | gaaagaataa | 240 |
| aacaaataga | aatcagaagg | tgtctgtttc | ctcctcgcaa | catacgatca | aagagaaaca | 300 |
| acttgacccct | ttacattgct | caagagctca | tctcttccct | ctacaaaaat | ggccgcacgt | 360 |
| ctccaacctt | ctcccaactc | cttcttccgc | catcatc | | | 397 |

<210> SEQ ID NO 139
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0007

<400> SEQUENCE: 139

| | | | | | |
|---|---|---|---|---|---|
| agcagaacaa | ctatatttat | tgtgtcacat | aaatctgaga | tcatttataa | ccaccaaaga | 60 |
| acctatacac | agtaaatgac | aaatgtatct | ccctctatct | ctattgccca | tatgtagatg | 120 |
| ctaaagtaag | atttctcttt | tttttaatgt | acttttttt | gtataaagta | tattccataa | 180 |
| gaaaaaggaa | aagcttgttt | atggatcaat | tgaccccaaa | aaagtttttt | agatcaaagc | 240 |
| ccaatataaa | aaaaaacac | agtagtgaca | caaaggaact | taaataaacc | atgaattgat | 300 |
| ctataaacag | tagagatcga | taaggcgaac | attttccatg | tgaagtgtct | tctttcatct | 360 |
| ataatatttt | tgacatccaa | taatttcctc | tataatatca | ttcacataat | tgatagaaac | 420 |
| attatgttag | aattgtccac | atcatttgag | ctgtaatata | ttctgtttta | acaaattata | 480 |
| tggtagttgc | ttaatcttat | gtccatcttc | ttctatgcat | cgttttcgcg | cctagttgtc | 540 |
| cagtccattt | caactaccta | cctctaattc | ttatcttaaa | acaacatttt | ttaatttaag | 600 |
| tattatgctc | aaagactaac | tagatagaaa | accgttatta | aacattaaac | gaattaaaag | 660 |

```
tcttacatgg aaaatgtagg tttataaacc acgagttatg attgacaata aaaaaaatgc    720
aaatcatcaa tcaaaagaga cttgagtgcg actctatatc aaccattgca attaaaatta    780
tctatcacaa aaattttaga cagattaagt taatttagtc taaattcact aatttatttt    840
ctataattag taattaacta tatttattta tttacacatt ttctgataat ttagaaattt    900
gcatgaataa caaatataag attttggaaa ttagtagcaa atttaattaa taattatttt    960
tgcctaaatg aaccaaacta taaaacctcc acatacacca gtcatcaaat ttacagagac   1020
aaca                                                                1024
```

<210> SEQ ID NO 140
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0008

<400> SEQUENCE: 140

```
ctcgagagat gaagtcttag taatgtttga acaaacaata atcacgtttt ccatcaaatt     60
cgagcattta agtttatat  tactacatgc cccaagatga taccgtccat ctcatccgaa    120
aatatttctg aaattgcgct aagacaacaa tgtttgctca aattcgatca tttaaagttt    180
acaaatctct catcaatctt acaaacttct cacactaaac agaggtacat attttcttat    240
aaagacaaaa ggttcgaaca gctggcttct caactcgagt tgtttgtcag ggcctctctt    300
cactaactac aagttggtac ttcaaatatt ggtggctagc ttcacgtgat attgtctaca    360
aattaaaccc atgaaaaagc tgcattaatt gttccaagtg aaccctgagg agtgtcaata    420
gtctttgctt tagtgtgatc attaaaccaa atctctaaat tcctaatttg tactaacatt    480
tggaacgtat ttcctactct tctccctgct ccaactccca aaaataagat tagttagatt    540
tctataacta atatacatgt atactcccaa aaacagtaaa accatattaa taaagctaat    600
tttgcataga tttatttcgg taaaccggcg gttcaagttg ggaaaaaaa  agacaaacgg    660 tctaaagtca tccaaagaca aaaaaccaaa gacaagttga gagagacgag accaatcaca    720
acattgcttc gtagattgcg tgacatcatc cttgacggct actttcattt gtgtcttatt    780
tggataaaac gcacgtgttt aattcacgaa ccttcatagc aataagaaat ttccattact    840
ttcatatttt caacttttttt tattacccat tacatgctta aaatattaat tcacaagtct    900
ttgtcaaaat tcaatatttt ccaggttcat gaacccttttt tatctcaatc tactctataa    960
tatctcccta taaattacaa caaaacctct ttattttttca                         1000
```

<210> SEQ ID NO 141
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0019

<400> SEQUENCE: 141

```
gatataagta gaatcatttt ttgccgccgt ttctcgctaa cacaccgaaa actgaatcaa     60
atctcctagc tcttctacgc aaaatcgagt gcatcgacaa tggcggaacg tggtgtcgaa    120
cgtggtggag atcgcggcga tttcggacgt ggattcggtg gtcgcggcgg tggaagaggt    180
ggtccgagag gtcgtggtcg ccgtgcaggt cgtgctccag aggaggagaa atgggtgcca    240
gtgactaagc ttggtcgtct cgtaaaggaa ggtaagatca caaagattga gcagatctac    300
```

```
ctccattctc tcccagtcaa ggagtaccag atcatagatt tactcgtcgg tccttcattg      360
aaagacgaag tgatgaaaat catgccggtt caaaaacaaa ccagagccgg tcagagaacg      420
agattcaagg ccttcatcgt cgtcggagat agtaacggtc acgtcggatt aggagtcaaa      480
tgctccaagg aagttgcgac ggcgatcaga ggcgcgatca ttctcgcgaa attgtctgtg      540
gttccgatac gaagaggtta ttggggtaac aagattggaa aaccacatac ggttccgtgt      600
aaggtaaccg ggaaatgtgg atctgttact gtacgtatgg ttccagctcc gagaggttct      660
ggtattgtgg cggctagagt tcctaagaag gttcttcaat tcgctggaat tgatgatgtc      720
tttacttctt ctagaggatc caccaaaact cttggaaact tcgtcaaggt atgtactttc      780
acaatggctg ttttggtttg atgaactctg aattaggcag tgaaaagta atcattacca       840 gttaagtgaa tttatattga agattaggat ttagctgatt gtattggttt gagcatgtga      900
gtttgtgttt aagattgctt gaattgaaat gctttaggtt gtttgattac gctaaattct      960
gactaatgta attcaaattg ttgttgtttt ttttggtc                              999

<210> SEQ ID NO 142
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0028

<400> SEQUENCE: 142
gtcagtgaag tcgattggta gtacttgaaa cacttggttg gtttcatgta tttggcctat       60
atataaacaa acatcgtaat tatatacgga ttttttttcgg aattttacgc catatctgta    120
agtatatata acatgcatgt cgttttcaaa ttcatatgat gaacgatcca cgtaagtgct     180
actactccta caatattgca tgagagagat atgtatttat aaattttatt ttgaagaaga    240
aataagaggg aaggttactt gggtggatcg atgtgaaaac aaaagaagaa aaagcgaaac    300
ccactaagcc attacatgat atcgaccttc ttatcttttt cctctttatt ttatttttct    360
catcttcttt ttgtcaggac ttttttctac ttaatgaaac ctccaaacta tctaactaat    420
acactcccat gtagaataaa gaaaattata taagatattg ttgatatttt gtaactagaa    480
aatatatttg ctctgtaatt tttcgtaagt taaatcaaca ttttaaagta gaaacaaata    540
ttactgcaaa aagtaggatc attatttttg tccaaaatct cagttagcta tagggttgta    600
gtaaaaacaa aacacattct tgatttgccc caaaaaataa agagagagaa gaatattgtt    660
caaaagtggt ctcttctctc tctaattatg ttttcactaa acccaattag attcaaacag    720
tctacaaagt ccaaaagata aacatgggac aacaattcga tgcaaaaaat cctctttca    780 tgctcttttt ttattctcta gtcttttaaa ttactaataa aaactcacaa atccaccaaa    840
cccattctct acaactcacc ttcatctaga tttacccact cccaccgaga aacacaagaa    900
aaaaaatata catatataaa tatacaagac aacacatgat gctgatgcaa tatacacaac   960
aaagtattaa atcttagata ttgtgggtct cccttcttc tattcatttt cttattcatt    1020
aaaa                                                                1024

<210> SEQ ID NO 143
<211> LENGTH: 1024
<212> TYPE: DNA
<213> ORGANISM: Arabidopsis thaliana
<220> FEATURE:
<221> NAME/KEY: misc_feature
```

<223> OTHER INFORMATION: Ceres Promoter YP0039

<400> SEQUENCE: 143

| | | | | | |
|---|---|---|---|---|---|
| ccgttcgagt | atttgaaaat | ttcgggtaca | cccgcctaaa | taggcggacc | ttatctagta | 60 |
| tatatataca | tttgaactat | attgtttact | ttttagttga | tttaggctat | gtcatgacat | 120 |
| tgacataaat | ctacctgtta | tttatcacgt | gtaattcgtg | taaagtgtaa | actagaaagt | 180 |
| tcaaatacgt | atttgttttt | gttctgttat | ataggattgt | catagttgta | aatctacaat | 240 |
| ttattacaac | atgaataagt | acacaagcaa | tgtaattgga | tttaattgct | aaactcttta | 300 |
| catggtcaat | ctaaatttga | taagaaatac | gtcacatatt | actaagactg | atagttttt | 360 |
| tgttgtcacc | aattatttt | gttaaattga | cgaaaacaat | tccaaaaact | caaatgtaca | 420 |
| aaatcataca | gtctcacaaa | catctcatag | agaaagatat | aaatctccca | tatgggaacg | 480 |
| ataacacgag | gtcgaaatac | tattcgtaaa | actaaaacgc | cttagttata | aatcgttagt | 540 |
| tgtaaccgcg | gtcgagaata | catacagatc | cacgaaacta | ctactacaca | tgctgctgaa | 600 |
| ttggaatttg | gaaaagacca | tcttctttag | gaagagctca | cccaatgagt | gacaaaggtg | 660 |
| tcggtggctt | gttttctacc | catatgtata | catcaaatgg | tagtttcatt | aacgtttggt | 720 |
| tttgagaaaa | gtaagacttt | ggctagtagc | taggttcgta | tataataaac | tcttttgaga | 780 |
| aagttcatca | ctggtggaaa | atgttaaacc | ggttttttct | catttttcc | gccatgttaa | 840 |
| ccaccggttt | aaaaagaccg | taacacattg | aaagattaat | aagggtatat | ttgtaattac | 900 |
| ggtttgctgg | caattttttaa | ttattatttt | aattagagaa | aatagagaag | ccctatcaat | 960 |
| gtacatggta | tatatataaa | aggcaaaaacc | ctagaaaacg | atactattcg | actcagccgt | 1020 |
| cctt | | | | | | 1024 |

<210> SEQ ID NO 144
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0050

<400> SEQUENCE: 144

| | | | | | |
|---|---|---|---|---|---|
| aatctgatct | ctagtccagt | cgattggtac | ttgagggaaa | catcatattt | ttaaaccttg | 60 |
| tctcagtaag | ctaacacaca | cccccttgtga | ttacttatcc | atgtttatcc | acaagaatgc | 120 |
| agttggattg | agatatttc | ttcttgttg | aaatcaggcc | tcaaggtgtt | catgtggtct | 180 |
| gcaaaaaaat | tcccaaaaat | aaagatagtg | acatctgaaa | tcgataatgg | attagacgaa | 240 |
| gagtttcgtg | ttattccttg | gtatgggcgg | gtttggggac | agatattttg | gcacagacga | 300 |
| ggactaggcc | actgtggtcc | tgcagcatta | ggtgtcccctt | ccatgtcctg | cattacatttt | 360 |
| tattgatgga | ttcatcaccc | tatctactac | aacggctaca | caaactatga | agagttttgt | 420 |
| ttactaataa | atgcccaagt | gagggtcga | tcgaacccgg | gacacgtttt | tcagtttacc | 480 |
| atatagaatt | atccttggaa | cccttgatac | tccatagaac | atcaccacct | ctgttgtcat | 540 |
| ctcaggaatc | caggttcaaa | cctagtctct | ctctccctag | tgggaggtat | atggccactg | 600 |
| ggccaatgat | gacaaaatgc | aaaaaaaata | aaatacattt | gggttcatta | tctaaaatat | 660 |
| ctcttgtgtt | tgtaagtttt | ggttgcacac | tcgtgtggtt | gaagtgtgtg | tgagaggtac | 720 |
| tatacaatac | actctgcttt | tgttttgtac | ctatctcttt | ctcttctcca | catatccaag | 780 |
| actttgggga | taaagctgag | atcattggtt | gccatttggt | tgtgtagaag | caatcaccca | 840 |

| | |
|---|---|
| tttgctttat ccgaggttga taaatttcct cgggttctcc ttctgacacg tatgacaaat | 900 |
| tctaatagta tattcctcgt agatattacc tatatattct caatagttgc aggtacttaa | 960 |
| ggctttgtct tggcatcctc gtcctcttca gcaaaactcg tctctcttgc actccaaaaa | 1020 |
| gcaa | 1024 |

<210> SEQ ID NO 145
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0086

<400> SEQUENCE: 145

| | |
|---|---|
| cttatccttt aacaatgaac aggtttttag aggtagcttg atgattcctg cacatgtgat | 60 |
| cttggcttca ggcttaattt tccaggtaaa gcattatgag atactcttat atctcttaca | 120 |
| tacttttgag ataatgcaca agaacttcat aactatatgc tttagtttct gcatttgaca | 180 |
| ctgccaaatt cattaatctc taatatcttt gttgttgatc tttggtagac atgggtacta | 240 |
| gaaaaagcaa actacaccaa ggtaaaatac ttttgtacaa acataaactc gttatcacgg | 300 |
| aacatcaatg gagtgtatat ctaacggagt gtagaaacat ttgattattg caggaagcta | 360 |
| tctcaggata ttatcggttt atatggaatc tcttctacgc agagtatctg ttattcccct | 420 |
| tcctctagct ttcaatttca tggtgaggat atgcagtttt ctttgtatat cattcttctt | 480 |
| cttctttgta gcttggagtc aaaatcggtt ccttcatgta catacatcaa ggatatgtcc | 540 |
| ttctgaattt ttatatcttg caataaaaat gcttgtacca attgaaacac cagcttttg | 600 |
| agttctatga tcactgactt ggttctaacc aaaaaaaaaa aaatgtttaa tttacatatc | 660 |
| taaaagtagg tttagggaaa cctaaacagt aaaatatttg tatattattc gaatttcact | 720 |
| catcataaaa acttaaattg caccataaaa ttttgtttta ctattaatga tgtaatttgt | 780 |
| gtaacttaag ataaaaataa tattccgtaa gttaaccggc taaaaccacg tataaaccag | 840 |
| ggaacctgtt aaaccggttc tttactggat aaagaaatga aagcccatgt agacagctcc | 900 |
| attagagccc aaaccctaaa tttctcatct atataaaagg agtgacatta gggttttgt | 960 |
| tcgtcctctt aaagcttctc gttttctctg ccgtctctc | 999 |

<210> SEQ ID NO 146
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0088

<400> SEQUENCE: 146

| | |
|---|---|
| tcgattggga ttactacttc atctagtaag gttctgaaaa cgtttgttgt tgataaggaa | 60 |
| gattcgtctc aggttattac tgttgatctt caaggtttgt gattgtgacg cttatacatg | 120 |
| tgctgaaact gtggtgttta tttattgaaa acaaaaaaaa agtctctctt gtagtttcat | 180 |
| tgtactaaat agaaaacaag aaacgttttt ttctttaatc ttctacattg ataatattgg | 240 |
| atcaaaggat tgtttctgca agacacaaca caaacatact tatactagtt tacttctact | 300 |
| aagtactaac tacataccca tacacacact tgcacctaga ctttacttct agacatcatt | 360 |
| accctaaggt agaccaagc ttacaagcaa gttttaccga caactcttac attacaactc | 420 |
| tagtctgtag tctttaacgt agacttacta actagtcatt agtggtttaa ttttttaaat | 480 |

| | | |
|---|---|---|
| tttcatccat atgtttttgt tgtagatata aactaaagtc ggtcacattt aataattgtc | 540 | |
| attatgtccg cgtaaaagtc aattcagcta ttggacattt atgaaatgta agattttctc | 600 | |
| tctcatttcc ccgtgcgtga agacatgcat tggttttttct gtaataatca acaaatccaa | 660 | |
| accccttttc gatctttatt tggacattgt tagagacaaa atttctctat agtcttttc | 720 | |
| ctaatttgat accatgtttt tgtttctgca caaatttact cactggttta actaactatc | 780 | |
| cacttattta tgattttacc attaggcgtc agctagccct agtcaaattt gtaaacaagc | 840 | |
| caagctatct acataaatcg agatgtcatt aacgttaatc gtcgttaatt cgaatttgaa | 900 | |
| aacatagata gctttagcag tacaatgggc aatggtaaga agaatagcaa aaggcccaat | 960 | |
| atttggtttg cagaaattaa agccttaaaa aaaagcccac agatatttgt caaagaaccc | 1020 | |
| taat | 1024 | |

<210> SEQ ID NO 147
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0092

<400> SEQUENCE: 147

| | | |
|---|---|---|
| aaagattgag ttgagagaga tggtggagac gcagaacaga caaagggagt ttaccatata | 60 | |
| gtgctctaaa gggcaatgag attgcagtga tgtggctatc cggggaatca tcgcaggtta | 120 | |
| ttccttccca tgagcaacaa tcaatggatg ggttccaatt cagaggagaa acagaagaag | 180 | |
| aaacgttttcc agagaaccac agtagggatt ctcgatcttg cgagttgcag agagcctctg | 240 | |
| aaactgcaat agaaaggaca ctgatgaaaa gaacacactg aaggagtatg ccaatcatgt | 300 | |
| gaaaactcag agcttgtatt ggtcttgtgg ttgatgaagt tctcacaaaa cctttggctt | 360 | |
| tgaatctccc ctcattagtc atggtgagaa caagaacaag acgagaaaca gacaaagaag | 420 | |
| atgaaaaaac ttgttggcca gtgttgacta agggggaata gccccagaca taacaaaatt | 480 | |
| agacttgtcg tacatcttta atatttttt atctgtttct ttgtcctgac gctttcatta | 540 | |
| ttcctgtgat caattttctc ataccattgg tccatcgtta atcctttctt aatttcattt | 600 | |
| tctacgtaac atgagaggag accaagtcct atgagaacag ttgacgtaac agtggttgtt | 660 | |
| aagttaagtt aaaaagagga agctagtgag agtgaccgtt aggtagagaa gtgagatctt | 720 | |
| taaccactct tctttctctc tctctctgct ttttcgtcg tctttcacat ctactgttcg | 780 | |
| caaactctct tatgcttcca ataatggtga taccaattga gacttgcagg agaatctcct | 840 | |
| cttctccaca ctctatcaac tggtcagcca tggaatggtc gtttcagttt caatattcct | 900 | |
| ggattctttt taaggattcc tgtttctctt ctgttcctgg tatattctta acgacgaaat | 960 | |
| tagtatcgga tcctggtaat acattttgaa gcttttaagt accattgcac tgggatccaa | 1020 | |
| caat | 1024 | |

<210> SEQ ID NO 148
<211> LENGTH: 1020
<212> TYPE: DNA
<213> ORGANISM: Arabidopsis thaliana
<220> FEATURE:
<221> NAME/KEY: misc_feature
<223> OTHER INFORMATION: Ceres Promoter YP0096

<400> SEQUENCE: 148

```
gaggtcagtg agtcgattgg tgcaaaattg aaaaattgaa gggtgaaaca aatttaaaga      60
taatatctat taaatcctct aattttaaaa atttagcaaa aattgtattt tcttatggat     120
ctgttagttc acacgtatct taattagtac caaatcatat ctaatgatta gtgataaaac     180
tagttagata tctatatgtg tctttaccat ttaacttgaa tccttcttct ttttttacg      240 taaacaactt gaatccttcg ttaatacata aatttaaagc attttttctt taattctatt     300
gatcggtata tatttactat aagttttagc tcatatgcaa tttcaaatga tatgctttta     360
aattttgtct aggtgtgata gttgtatctt taacataaat cttatagcaa aattatactt     420
gatattctaa atttatctat ttgctcttgt gaacctcata ttagtctaga gaaactttga     480
aatcctttca attagttgta tgtccaatac atttttacta acatttatta gtctttttaa     540
ttaagattat tgttagaaaa aaaaagattt tttaaaaata aataatatgt tttagataca     600
atgtgagtta ggcttcttat atttttaaaaa ataaatttat ttcatactta aaaatagttt    660
ggaatttcaa tttatttggc tgaataccat aaaaatatgtc aatttgaacc ttatacccat    720
tgactatttg gtgttagaaa ccctttaaca aaaaaaaact atttggtgtt agatatcaaa     780
ataaaaaaag tttaaccatt ggtttcttat attgaattgg atattgttac atgtattaaa     840 gttttttttgg tttaattttg aaacgttgat agaaactatt aagtttaagt ttggtagtat    900
atttatttgt ggaaaattta attgccatta aatataacgt caacttttt tggttttttt      960 tgagaagtta cgttgtgatt ttgatttcct atataaaagt tagattacgt catttttttaa   1020

<210> SEQ ID NO 149
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0097

<400> SEQUENCE: 149
ttcatcttta tatttaagag tttaaaaact gcaactttttg tttttctttc actaagtctt    60
atggccacag ttaattaaaa gcagatgaaa ggtggtccaa tggaaaagga gaatgtgatt    120
gggctagttg ggagagttct gatgtctagt gttgggtaca cgtgtccgtc agttacacat    180
agcattaaat cagacggcat gtcattattc aaatctagtt cacatagtac gactaatagc    240
tgataaatta atgattatac agcatatgaa ttatgaattc aaaaaaaaaa aaaaattgaa    300
aatgttaagg agatgctata ttttacaaaa ttcatcgcaa tgctttctac taatttgcta    360
agtggtcttc tccagttagt cttgtcgatt ccaagcgata ttattaaatc ttgaagcatc    420
gctcaaagca ttatagctta agataaccaa attgttatta aaaacaccta gtgaaatttt    480
taaattaaaa caatttgat atctttgtaa tatctaatac tactcttttct gtgtctaaaa    540 ggattaattt tcaaaaattt cacacatatt aaaaaaaaaa aaaaattact agctaaacaa    600
ttttcaataa tcataaaaca atagtaactt aataattttt ttttatttc aaaatagtcc    660 ttcaagttta caattcattt tagtattata atcaacaaaa tttgtattaa aaagttggaa   720
aattaatctt tgtggaacaa aaaaatctag aaatcatttt ttagaattag agagaggttt   780 gataaaaaaaa aataaaaaaa aatagagaga ggtagtacat actaaacgat gtgatactac    840
tattgacaaa atcttaattc tcagttttagt agaataaact agaaggaatg aatgaagtaa   900
atgcgaatcc aactactaac aaaccctact tagtcatcat atttttcccat atgaaatccc    960 tatataaacc catcatcatc tcccactttt ttcatatcca                         1000
```

```
<210> SEQ ID NO 150
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0101

<400> SEQUENCE: 150
ttctcgttct ctagaatatt gctggaccgg attaggtcaa tattattggg ccagattaga      60
tattgaattg tcgacgttgc ttacgttacg ttatatcttg tttaagaatt aaacctatcg     120
acttagtctt aattaagaaa acattgcctt aaattctctg gtctgcgacc gttttttga     180 ccgttaaccc ctaattaaag aaacaaaata attatagaaa gagcactgaa atgtgattat     240
tttaacagta ctcttatgag aaaattcgta cttttttagtt ttttttttgt acaaatctct     300
aagaaaaaca ctactactaa ttaagaaacg tttcaaacaa ttttattttc gttggctcat     360
aatctttctt tctcggtccg ggactaaccg ttggcaaaaa aaaaaaaaaa gttgacaata     420
attattaaag cgtaaatcat acctctcaaa taaaaacttg aatttggaaa caaagacaac     480
taaaaaactc gaatttaaga gaattcctaa aatcaagtga agtatcatca cttggtaaaa     540
tttcataacc gttggcttct atttctatgt gtgccttggt ttgcaggaga taatatttca     600
tttccaacca atgatattcg tacacatagt caaacaaatg tttgtctttg ttattatatt     660
gagaaagaaa caagaaagag agagagagat agataagacg aaggaagtga agcttccaag     720
cgcccaccgt taaaaatctc gtgtgcaagt ttcaaataca agtggccggt ggtctccata     780
atttgatcgt catccaatta aaaaggaaga aaaagcgtgt tttatacaag aaaactcatt     840
aaaatagcaa gtctagaaat atctcaacac taatctacca cgtctattac acacacacac     900
acacacactt gatcttaatt tattttcaag attcaagaaa atacccattc cattaccaca     960
acttgaccac acgcctatat ataaaacata aagcccttt cccc                    1004

<210> SEQ ID NO 151
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0102

<400> SEQUENCE: 151
atttggttga taacgttttc actcgactaa ttatatactt cagaaggata gtaatagaat      60
accaaaataa ttaaatgatt ggttagtgcc ttagtggaga ctttttaacc gattctaata     120
gactaatgat gtagctaagc atttatttgg gatcatcact gtttgaaaac gtgaaatgtg     180
ataaaagtta tgaaacgatt aaaatataaa ataaccgtac aaaacattat gtaccgtttt     240
tttctctgtt cttttggcga tttggtttag ttcgttacac tctaaatgtt attgcagata     300
tatatataat gatgcatttg catctgagga acatataatt ccggttaaca cttccaaatc     360
ttatatccgt ctaggtaggg attttataaa tcatttgtgt catcatgcgt tatgcttgtc     420
ggctttgacc ataacgcaga gatatagaac tagcttttac ttaacttta gatttattat     480 ttgatctaga gttaagtgga gatatatagt gttttgtta gattattggt ggatgtgaga     540
gtttgtcttt agtttcaagt tgagaatata aggcaagagg agactctgag gcaatcagag     600
gttttgattg gcaaaatatc caaaaggccc aaaccaagtc gaagcccatc tcgtacaaaa     660 aagaaagag atctgtaaga aaaatattc tttgatattc ttacaaaaat aagtgtaaaa     720
```

```
cttttattag tcaaaatctt caatctttaa aaactctcat cactcctacg aaagcgcgtg      780
agagttatga gacattcctt aatagcatta ctcacaagtc acaagttcaa aacgtctgac      840
tgaaacagaa acaagccttt gttgaagtct tgaagaagag acattagtac tcgtcgtata      900
gccataaaag gtaatatacg aaatttcttc gctaatctct tcaccttcct ctacgcgttt      960
cactttcact ttataaatcc aaatctccct tcgaaaacat                           1000

<210> SEQ ID NO 152
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0103

<400> SEQUENCE: 152
gttttgaaga acaatctgga tcgaaatcta acataaggtc atcgtattca agttacgcag       60
tcaaggactt gacatcatcc tactctggtc tgaggttacc acttccaaag atgggatttt      120
tcgactcggt atgcttccta agaaattcgt tttattgaac ctagcaaata tcttgtaatg      180
taagattcct gagatgatga agaaaaaaca aacttttgtt acagcaggag aacggagaga      240
aagaaaacag agaaccaaat gctcttgaag caaacagaag aagaagacac aaatccaaac      300
ttgagacttc ttctacacca gaaaaccgca gcattctggg acaacgcaaa acacgaaagt      360
gaaacgggca atgatatata tgtcttgggt gcgttacaag gcatcgtttg caactgttga      420
gttggataag tcaactgtct tcttttcctt tggttgtagt agctgccttt ttttttccttt      480 gttgctttaa gaaatagccc gaaaaaaaga atgttctaca tttcggagca gaaaactaac      540
cgaatgagtt tttggtcgga tcatcggatc gatcagatat attttgagtt acgaactgtt      600
ataaaaaaag ccataatttt gtgttgagtt tgcaaaatac cttataactt gttatttgag      660
attgcacctc catatatatt aattcgtaag agtatttatt aagtaagctt tagtatataa      720 cctttttttcc tttaaagtaa gttaatgttc tactaaataa tagtaaagtt gaagaaccgc      780
tccgttttta caccatgcac gtgttatcta acaaagaaaa tatggtacac ctaatggcta      840
atgcaaagga caacacaatg aaactaactt gactctgtgt tatagaaacc catagacatc      900
tgcatacatc ctagtatttg tataaattgg actcaaattc ctgaggacaa tcatagcaaa      960
caatcacatc atcgcaatat acataaacaa aagaggaaga aaaa                     1004

<210> SEQ ID NO 153
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0107

<400> SEQUENCE: 153
taacaatcct tgggaacatt gcatccatag atatccggtt aagatcgatc tttgaactca       60
taaaaactag tagattggtt ggttggtttc catgtaccag aaggcttacc ctattagttg      120
aaagttgaaa ctttgttccc tactcaattc ctagttgtgt aaatgtatgt atatgtaatg      180
tgtataaaac gtagtactta aatgactagg agtggttctt gagaccgatg agagatggga      240
gcagaactaa agatgatgac ataattaaga acgaatttga aaggctctta ggtttgaatc      300
ctattcgaga atgttttttgt caaagatagt ggcgattttg aaccaaagaa aacatttaaa      360
```

```
aaatcagtat ccggttacgt tcatgcaaat agaaagtggt ctaggatctg attgtaatttt      420 tagacttaaa gagtctctta agattcaatc ctggctgtgt acaaaactac aaataatcta      480
ttttagacta tttgggcctt aactaaactt ccactccatt atttactgag gttagagaat      540
agacttgcga ataaacacat tccccgagaa atactcatga tcccataatt agtcggaggg      600
tatgccaatc agatctaaga acacacattc cctcaaattt taatgcacat gtaatcatag      660
tttagcacaa ttcaaaaata atgtagtatt aaagacagaa atttgtagac ttttttttgg      720
cgttaaaaga agactaagtt tatacgtaca ttttatttta agtggaaaac cgaaatttc      780 catcgaaata tatgaattta gtatatatat ttctgcaatg tactattttg ctattttggc      840
aactttcagt ggactactac tttattacaa tgtgtatgga tgcatgagtt tgagtataca      900
catgtctaaa tgcatgcttt gtaaaacgta acggaccaca aaagaggatc catacaaata      960
catctcatag cttcctccat tattttccga cacaaacaga gca                        1003
```

<210> SEQ ID NO 154
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0110

<400> SEQUENCE: 154

```
gggatgcggt tccgcttcct cttgatcttg gacgagtcgg aggacattgt tggatcccag       60
tgcaatggta atataaaaca agaaaacaag agattttata ggacaatcac taaatgacat      120
ttaattgatt aaacatttat tcattaataa ttgtatgtta ctaacttcaa catttaataa      180
ttttgtttaa gatacgttta catcagagac tattaatatt tttacaggtt gtaacttaa       240 actttgtctt gaatcgaaca tgactataga ttttgggcaa acttaaagat aacaacattt      300
ccgttttttt tcaaattatt acaaatcaaa ctgatatatt agacacaaca cgattacacg      360
taatgaaaaa agaaaaagat aaaaagataa aagaagggat cgattctgtt tggtctggtt      420
tagtgagatt caaagttaag ctcttccttt caagacatgc cttcttaaac cgggaatgtg      480
aacgtttgta atgtagtccg tccagttaat gcttccaaca tcaaatccaa attctctctt      540
ctcgtcctct gacatattct ccattaatct ctggggtatt gctgttatca aatctgtaaa      600
agaaaccaaa aaaaaagat gaaaactttg cgggtaccgg ttttgtctgc tctaagaatt      660
agaatgttaa tgagttctgt cttaccttcc accatagaaa gtgtatggct cataaatagt      720
agcaaggtgt ttggcttgtt caacagattt cttgcatata aactttagct tctgcatcat      780
cttactatcc actgaactca taccactcat caacccactc cgttcttgag catctctcca      840
caaatgatcc gagaaatcat caacggaatt gaaaagtttc atcaaacgca ccataatagg      900 atcacctta gagtccatgc atggagatgt tttgtagtgg ttataaagaa gctccgctaa       960
gtcttcgaaa accagcgggt ttatcgccga agaagcgatc tgatacacgt ttatttcagg     1020
ttcc                                                                  1024
```

<210> SEQ ID NO 155
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0111

<400> SEQUENCE: 155

```
cgattggatt tagtctatac attatagggc gcaagtttgt ggatttaaga attatataaa      60
aacttgaaat atatagtttt tatgcattct cctcttgtgt aatacataaa ccaaatatga     120
gataggttaa tctgtatttc agataatatt aaattccaaa caatattttt acttgttata     180
agaaggcaat aatatctctc tgttaatgg caagtggtac caagtagtat taaactatta     240
atgcaatgga agagtactgt tggaaattat aatcctctat cacacattca aacagatctc     300
ctgaaatctt ctcttccaaa cttgtacttc tctgatccaa atgtaggctc caaaatatag     360
acatttacca tttactaagt ccacaactcc tttcttgtct ccttcaaaaa tgactcttgt     420
gtaaccacca tatgactccg acagttcggc attgccatga tgagagctta aaaattcacc     480
ttcctgagca tttcaagtct tcactccctt agcttgacct gaaccaagat aaaatgcctt     540
tgtcgtcccg taatatccat cctgctttgg acggcatcat agttacattc gatccatcct     600
atttacaatg ttattttagt attaaaaaca tgacaataaa tttgttgtta aacatattca     660
aatacaatat gattggattt ataagtaatt gtaatatgaa atgtccttag taatatgtta     720
aaaaatacat agatacacac acgtactaaa agaggcaacg cgggagatgt cattagagga     780
agaactagga agcagagcgt tcatgcaaaa tgctaccaaa aacgttaatg caatatctca     840
actaatcagc acagtccatt tcatactgag aatgtaaaaa ccaatcagca tcgtccattt     900
tttcatctaa ttatttgtta actcttaatt ggccacaact tccaaccaca tgacgctctt     960
tctattccct ttatatattc ccatctcaaa tgttcttgga gacacaaaat atcataaaca    1020
tata                                                                 1024
```

<210> SEQ ID NO 156
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0115

<400> SEQUENCE: 156

```
gtcgattgga tgatgaacat tctacatata taattattat gtttaagcac ttagacagca      60
taaattcttt ctaattatat aaatctaacc ttgttacatt gtacatctat aaattacttg     120
aagaaataac gagttctatt tcttttttaaa aattaaaaat actataccat atctcagtga     180
ttaagttgaa ccaaaaggta cggaggagaa acaagcattt gattcttcct tattttattt     240
tattcatctc tcactaatga tggtggagaa aaaagaaaa tacctaacaa acaaatatat     300
attgtcatac aaaaatattt ctatatttttt agttaattag tttatattcc tcacttttca     360
gggcttatat aagaaagtga gcaaacacaa atcaaaatgc agcagcaaat actatcatca     420
cccatctcct tagttctatt ttataattcc tcttcttttt gttcatagct ttgtaattat     480
agtcttattt ctctttaagg ctcaataaga ggaggtacta ttactacact tctctctact     540
tttacttgta ttttagcatt aaaatcctaa atccgtttt aaattcaaaa ataaacttag     600
agatgtttaa tctcgattcg ttttttcggc tttaggagaa taattatatg aaattagtat     660
ggatatcttt actagtttcc attcaaatga ttctgatttc aatctaatac tctcactctt     720
taattaaact atatgtagtg taatttcaca ctgttaaatt tctaccatgt catgtatatt     780
agagttgcat agaaaattgt aaaacatcca tttgaattcg aatgaaacaa aatgttttaa     840
aataaaattt tggtttttaa aagaaaaatc taaaactgaa ttatatcgtt taaccaagtt     900
gtaaaagtca taaaacgtag tatcttgtaa atcgctcttc cacggtccaa atagacttct     960
```

```
agtaataaac aagtaaaact aattttggtt tcttac                              996
```

<210> SEQ ID NO 157
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0117

<400> SEQUENCE: 157

```
gtcagtgagt cgattggatc acagtccttt atgataaaac aaactcataa ttattccacc     60
gacaacatgc gttttaaatt attttttctt aaattatatt atattatatt gatatcaacc    120
tagctaaaat aattcggatg gcgaaatcgg acaattttta atagaaaaaa tgggtatgaa    180
gatagtctat gattccgttc ttagcgacta gagggacctg ctcaaatctc ccgggtgata    240
cgcgatgtca agctcaatag aaccccacaa ccgacgagac cgagaaatcc ttgatttggg    300
ctagaagatt ttgaaataaa tttaatatat tctaagtaac ttgcttaaat ttttttttcaa   360
actctaaaga cataactaac ataaagtaaa aaaaaaaaag ttaatacatg ggaagaaaaa    420
aattaaacta atgattagct ctctaacgtg tttaatctcg tatcaagttt ttttttaaaa    480
attatattgc tattaaaaca ttgtactatt gtttctattt tgtttagcta ttattcttgt    540
gaaatgaaaa gttgtgttta ttcaattact aaatggcaat atttatcttg gaaaactata    600
cctctaattg gattaggccc tagacatcct ctttagctta ttgacgttaa aattattccc    660
aaaactatta agtttagta gtttgaaaga tgcatcaaga cctactcaga taggtaaaag    720
tagaaaacta cagttagtgt gattatattt taaaatatat aaaacaatct tattaaacta    780
aatattcaag atatatactc aaatggaaga taaaaacatt tagtctgtta ccactaccag    840
cctagctagt cactaatagt cactttggaa ctgagtagat atttgcatct tgagttacca    900
tggactcaaa agtccaaaaa gagaccccga gtgaaaatgc taccaactta ataacaaaga    960
agcatttaca gcggtcaaaa agtatctata aatgtttaca caacagtagt cataagcacc   1020
attg                                                                1024
```

<210> SEQ ID NO 158
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0119

<400> SEQUENCE: 158

```
taccaaaaat aaggagtttc caaaagatgg ttctgatgag aaacagagcc catccctctc     60
cttttcccct tcccatgaaa gaaatcggat ggtcctcctt caatgtcctc cacctactct    120
tctcttcttt ctttttttct ttcttattat taaccattta attaatttcc ccttcaattt    180
cagtttctag ttctgtaaaa agaaaataca catctcactt atagatatcc atatctattt    240
atatgcatgt atagagaata aaaagtgtg agtttctagg tatgttgagt atgtgctgtt    300
tggacaattg ttagatgatc tgtccatttt tttctttttt cttctgtgta taaatatatt    360
tgagcacaaa gaaaaactaa taaccttctg ttttcagcaa gtagggtctt ataaccttca    420
aagaaatatt ccttcaattg aaaacccata aaccaaaata gatattacaa aaggaaagag    480
agatattttc aagaacaaca taattagaaa agcagaagca gcagttaagt ggtactgaga    540
```

```
taaatgatat agtttctctt caagaacagt ttctcattac ccaccttctc ctttttgctg    600
atctatcgta atcttgagaa ctcaggtaag gttgtgaata ttatgcacca ttcattaacc    660
ctaaaaataa gagatttaaa ataaatgttt cttctttctc tgattcttgt gtaaccaatt    720
catgggtttg atatgttcct tggttattgc ttatcaacaa agagatttga tcattataaa    780
gtagattaat aactcttaaa cacacaaagt ttctttatttt tttagttaca tccctaattc   840
tagaccagaa catggatttg atctatttct tggttatgta ttcttgatca ggaaaaggga    900
tttgatcatc aagattagcc ttctctctct ctctctagat atctttcttg aatttagaaa    960
tctttattta attatttggt gatgtcatat ataggatcaa                          1000
```

<210> SEQ ID NO 159
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0120

<400> SEQUENCE: 159

```
tagttttga tttaatctac gttttctta atcataaatg ggtaattatt agttttgca       60 aaatcaaaat ccaaaaattg ttctaaacac tgcaaccatt taaggcctat atcactcaga    120
aaatttctgg tgggagaact aatcgtttgt cctttctaaa tctcacatat tagaatttag    180
aattagtgtg ctacataaga atattagttc agctcggaac aactattttt tggtaaaaca    240
gagaacttaa acaaatgcat tattttatca acatgcattt tgaattgaat ataaaatttc    300
ataattgtaa agacataaat tacataaaat tttacatgaa aaaatagata tagaaagaaa    360
atgaaactaa ctgatgatat gctctctaaa ttttttaatc tcataacaag aattcaaatt    420
aattagttca tattttggt taatataaca tttacctgtc taagttggaa ctttcattt     480 tttctgttt gtttagtcag tattcttaat gtgaaacgga aagttgaatt tattcaaact    540
taaattcaat agcattaatt aaaggcgaaa gctattatct ctacatgtgg ttcaaactag    600
acatccaatt taattagctt attgacgttg aaatgttttc caaaactact atagtttggc    660
aatttgaaag atgcatcaga actactcaga caggtaaaag tagaacctct agctgtgtga    720
attgtatgtt agtccataaa gaacatcttg taaacttcat acttaagata tatattacaa    780
tatatacttg aatggtagat aaaaacgatt agtctgattg ctagcatact cacaactatt    840
tggaaatgag taagatattg gcattctaga gttactacta tggagacaaa agtcgaataa    900
aagagacctc acgtgaaaat gttacgagct agtaaaaaaa gcatttacac taacggtaaa    960
aaaagtatct ataaatgttt acacaaggta gtagtcatt                           999
```

<210> SEQ ID NO 160
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0121

<400> SEQUENCE: 160

```
ttggattttt tttttgttga gtcagcagac catctaatct ctcttttcc accacagcct     60 gctttctatg aagcatttgg gcttacggtt gtggaatcaa tgacttgtgc actcccaacg    120
tttgctacct gtcatggtgg acccgcagag attatcgaaa acggagtttc tgggttccac    180
attgacccat atcatccaga ccaggttgca gctaccttgg tcagcttctt tgagacctgt    240
```

```
aacaccaatc caaatcattg ggttaaaatc tctgaaggag ggctcaagcg aatctatgaa    300
aggttggccc attctccttg acaggcttaa caatacaact tgtatcgctt caacaagatg    360
atggcttaat aaggatttt tgcatgtatag gtacacatgg aagaagtact cagagagact    420
gcttaccctg gctggagtct atgcattctg gaaacatgtg tctaagctcg aaggagaga    480 aacacgacgt tacctagaga tgttttactc attgaaattt cgtgatttgg ttagtgtaac    540
ccactgttat tcttttgatg tctacatcta ctttacttac attattcttt tcttcggttt    600
gcaggccaat tcaatcccgc tggcaacaga tgagaactga tcatgacagg gtaggatttt    660
atttcctgca ctttctttag atcttttgtt tgtgttatct tgaataaaaa ttgttgggtt    720
ttgtttcctt cagtggtttg attttggact tatttgtgtt aatgttgttt tggctgttct    780
cttaatatca ataacaaata aatttactgg ttggtatcta agatctaaca atagttacta    840
tttttagagg taaagacacc aaccttgtta tattggtcag agagctaaaa ccttgacttg    900
ttgggaaaac aaaactctaa tgacagaaaa tctgacatga tgccttataa ttcacagcct    960
catgttctac ataaatccta acaatagcac tttgtttct                          999

<210> SEQ ID NO 161
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0128

<400> SEQUENCE: 161
gataaactga taatggaaaa gaacaaagaa accagttttt aactatttgc atatgtaatt    60
tatttgttgc aaattatatt tagttaaaat gtttcctcta tttatatata tatatatcag   120
tcaagcacta tgtataagaa atgtcaattt ataaattttt acatgtcctt taacagaaag   180
aaaatgaatt tttacatgtc attcatagag agtcactcgt ttatttctta tatagagaat   240
aacacactca catgcatatg catgcaatat gatacatttt atgacaaaga taatcaacgg   300
aaacggtcaa gacataattt gataaacaac ttgcacgatg cacagatctg atcaaatata   360
taactcttta acatatccaa aatattcaaa aagaaaaact cgatccaaac tagcaacatc   420
acgctcacgc ggtaggctaa aaatttatta atctccaaaa gtctttctta tgaacactgc   480
aaacacaaca acttgaaaag tcatataggt ttagatgatg acgcgtattg gctatcgctt   540
accggagtgg ctcataaata caataaacaa tacgtaaaag tcaaagtcaa atatatttag   600
tcaactataa ccattaatcg ggcaaaacct ttagctgtca aaacaacgtg aaaacgatat   660
ttgtatatat catcaagaat cagtagataa gagaatgatt taatccctg actattacaa    720 ttttggtgta ataaacagtc tctattggtt tttattcttt gttttaattt ctcatgacct   780
atagagagaa ttaggtagtt tcgaaaattg gctaatcaac ttttgaaaac tactgtctac   840
tttgcttaaa ttctctacac ttagtttcgg ataagataat tgtcggacta atagttaatc   900
ccttgacaat ctttgatatt ataaaaggtt tagttaatct cttctctata taaatattca   960
tacaccagct ttcaaaaata tataatccaa acaccaaaaa caaa                   1004

<210> SEQ ID NO 162
<211> LENGTH: 1001
<212> TYPE: DNA
<213> ORGANISM: Arabidopsis thaliana
<220> FEATURE:
<221> NAME/KEY: misc_feature
```

<223> OTHER INFORMATION: Ceres Promoter YP0137

<400> SEQUENCE: 162

```
gtggcacatg ctgaaacccc gagcatctct ccggaagaca cgcgtcgttc gctccaaaga      60
aaacagtcac agctgccgga gaatctccgc cgtcttcttc tgccaccgga aaaactctct     120
ccaccacttt cagtgcccac ctcgtgttat atccactgta tcctcgtagc accatatcag     180
cctaataaaa ttttatgtat caaattttaa gacatagccg aaactacact atactagaca     240
ataataatat gatttgtttc ctgaaaaatt atggtttcat gagaaacatt aatcatctat     300
aaaacaaatt agctatggca tcgaagagtt atcaatcaaa actgatgaat ctttacttaa     360
tatatacaac atatctttac cttgcggcgg agaagatcgg cgagagaagc accccagcca     420
ccgtcactaa aggattcttc agtgatggaa tcaccaaaga gaaaaaccct ccgtctcatc     480
atcttccaca caatcttctt gagaaaatct gagagataag aaaggtgtag tggttttgct     540
gaagtgatcg tgtttgattt agtaaagaaa tgctttattt attgttgggg gaaacataaa     600
taaataaagt aaaagtggat gcactaaatg ctttcaccca ctaatcaccg acctttcatg     660
gtttattgtg aaatacactc atagatagac atacaatacc ttatgtacgt aaataacatt     720
ttatttgtcg acacttatgt aagtaacgca tagattattt tctatgtgat tgccactctc     780
agactctcag tttcaaccaa taataacaat aactacaaca acattaatca taaacatatg     840
ctctggttta caattaaagc ttagattaag aaactgtaac aacgttacag aaaaaaaatg     900
ttatttacgt tttgtaagat tagtctctag aatcatcacc gttttttata tattaatgat     960
tctttcttat atataaaacc tttctcgaaa tacccatgaa a                        1001
```

<210> SEQ ID NO 163
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0143

<400> SEQUENCE: 163

```
atacaacaga tggcagatat cgagttaaat acgtgaatca gccgttacga tattttaaaa      60
ctagaaaatt atttaaaaat attgcaaaat accatttaat ttcattgttc ataaaaaaaa     120
gaaattcaaa aacttaaaaa ctgattcaaa aatttggatt aattctcatt aacagtcttc     180
aacactacaa caacatgttt ctaatttatt ttatatttta ataattaaac aatatatacg     240
tctgcacatt gttgctccga cataatctag tataaaaata gttgcagcat atgtgaaaag     300
caagcagcat ttatcactca atactttaa ttttatctgt tgtatgtatt aaggttttgt     360
agctttaaga aaacgcttat aatataaaat aacttctaaa agatatttca tgcgtataca     420
ataaatattt gtgaaaaaac atttcgaaaa cgtgtacaat atataaacta ttgtgttatc     480
ttttgacatt caaacaaatg ttgacaatgt aatttttatcc atgatatgat tggccaatta     540
gctgcgaggt aaaaatccgt atacgagtaa aagtaagata aaatttcgca agaagatttt     600
tagcaggaaa tctaagacaa gtgtcatgaa cgtgtcaatc aacaaacgaa aaggagaatt     660
atagaatcca gattcgacgt accacattaa taaatatcaa aacatttat gttattttat     720
ttttgctctg gcagttacac tcttttttcat tgctccaata aaaaaatcac tcgcatgcat     780
gcatatatat acaccatagt aaactccgcc tcttcttcat tttaaaagta tcagtttaca     840
ctgacacaat ccttaactat tttcctttgt tcttcttcat ctttattaca catttttttc     900
```

| | |
|---|---|
| aaggtaacaa ataatctttt taagtcactt ttatactctt taaatcttag attgatatat | 960 |
| gaatgcatgt taatatttca agatttatag gtctaccaaa c | 1001 |

<210> SEQ ID NO 164
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0144

<400> SEQUENCE: 164

| | |
|---|---|
| aaacgttgca agattattga ttgtgagaaa gagtgctcaa ggtagtactg atttctgtaa | 60 |
| agctcacggt ggtgggaaac gatgttcttg gggagatggg aaatgtgaga aaatttgcta | 120 |
| gaggaaagaa gcggtttatg cgctgcgcat aacactatta tgtctcggga gaacaaagat | 180 |
| ggaagcaaga gcggtttgat tggaccggga ctctttagtg gccttgtttt tggctctact | 240 |
| tctgatcatt ctcagtctgg agctagcgct gtctctgatt gtactgattc tgttgaacga | 300 |
| atacagtttg agaataggca gaagaacaag aagatgatga taccgatgca ggttctagta | 360 |
| ccttcatcaa tgaaatctcc aagtaattca catgaaggag aaacaaacat ctatgacttc | 420 |
| atggttccgg aggagagagt tcacggcggt gggctagtaa tgtctttact tggtggctcc | 480 |
| attgatcgaa actgaaagcc atttatggta aaagtgtcac attctcagca aaaacctgtg | 540 |
| taaagctgta aaatgtgtgg gaatctccga atctgtttgt agccggttac gttatgctgg | 600 |
| atcaaaaact caagatttgt tggatattgt tatgctggat cggtggtgaa accacttccc | 660 |
| ggttgctaaa taaataaacg ttttttgtttt ataatctttt tcactaaacg gcagtatggg | 720 |
| cctttagtgg gcttccttta agcgaccaat acaatcgtcg caccggaatc tactaccatt | 780 |
| tataggttta ttcatgtaaa acctcggaaa atttgagagc cacaacggtc aagagacaaa | 840 |
| aacaacttga agataaaggg ataaggaagg cttcctacat gatggacaac atttctttcc | 900 |
| acacaaattc tcataataaa aatcttataa tacaaatact tacgtcataa tcattcaatc | 960 |
| tagtccccat gttttaaggt cctgtttctt gtctgataca aat | 1003 |

<210> SEQ ID NO 165
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0156

<400> SEQUENCE: 165

| | |
|---|---|
| ttggtttgca ttgtgaagat ttgtattaac tatagaacat tgaattgatg gtgttaagtt | 60 |
| cttacacaag cgtgcttctc ggtttgaact gttttctttg tatgttgaat cagagcttag | 120 |
| tttataggaa ccagagtatc tacttagtca ttctctgatg ctaagtgcta aggttctacc | 180 |
| tagttgccct ctaggccctt atgttattga taacttatga agctatttga acacttgatt | 240 |
| cttaggagac ctaagttggt acagccagat agagtgtatg ttcttgttct ctatgtgaca | 300 |
| ggatcaagct gccacacata gttcaagggt atgctctgtg tgggtttgct cagattgagg | 360 |
| acaaatctat acaaggaagt agagtctttg acattttgat gttgtatgat aagaagaaga | 420 |
| aggagagta ataagaaag agaaaaggga aacagaaaca cgtgggagaa catcccaaag | 480 |
| aggaagcaca cgcggatctt catgcaaagc tccccgattc tcccatgtgg tccctttctc | 540 |
| cctttgtccc cctcctcttt cttctttct catttactc ctttttttac cattatacaa | 600 |

```
cgaatctttt ttatcataat tttttggttt tggtttattt tccaataaca ctttcttggt      660
tacttcccat tctcactttt tcatataaga aactcacttg gggaaactta tgtttgagaa      720
tgacaagtct ttttagagaa agtgatgtaa caaatctaaa gtgattatat aataaccttg      780
cacaatgttt ttgattttt gtaagattcg aatattaggt ttattattcg tagggaataa      840
acttactttc aaaagcgttc ataagttaat actttcatat atgatcataa gtacggacac      900
tattgttttt tgtttgtttg tgtttattct aaaagaaagt agcttttaat tgaaatgtcc      960
tcggaggcac agtttaaagt tcgagtgtaa cagtttctaa ggca                      1004
```

<210> SEQ ID NO 166
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0158

<400> SEQUENCE: 166

```
ttattagatt aatagattgc attgcattgc ttgtgctttc aatttacaaa ttgtctccca       60
actccatcga cacatctctt tttgtgtata taagattcag acttgttata ttttttttat      120
aaatatgtta ttagcatctt aagttaaatt gattttttat atctgcatta aggattacac      180
gactatattt gcgattgtgt gttggttaaa atataattta ggattgtctt taactacatt      240
taggattata tgactatatt tggttaaata taaaatctag ctgtgattat tagtattcaa      300
aaataagtag cctaaccaat taaaacaacg gctattgggg caaattagaa cattttagtg      360
tgtccaaaat ataatggtca ttaggtcata ttcctcctag cttcatcgca gcataattga      420
atgattgcct tatttagaag agcttttcca ctttcccaaa atctaggtgg gatcttttg      480 ttttgacctt cattttctt gtttaccatt tttagctaaa ttatttacga ttacaaaaga      540
tatcaaaagt tggatcataa tacaatttat agacttactg tagaaaattc gtatgtacaa      600
gtacaacaaa ttcttcataa taaattttga aaattctatt acaaatgttg taagaaatag      660
aatttgaaat atatataaac taaggagaaa aaaaaagaga acatgcattg ctctagtcag      720
agtggaccaa catcaacgag ataagataac ataaaaacca actcaccata actaaaaaca      780
tcccaagaga tccaacgatt catatcaaac acaaaaacat cgaacgatca gatttaaacc      840
atctctggta tctccaaaac acaaacactt ttttttttct tttgtctgaa tggaacaaaa      900
gcatgcgaca tctctgtgtc tttatcttct ctctcctctt cttgaaaaac tgaacctta      960 attctttctt cacatctcct ttagctttct gaagctgcta                           1000
```

<210> SEQ ID NO 167
<211> LENGTH: 1005
<212> TYPE: DNA
<213> ORGANISM: Arabidopsis thaliana
<220> FEATURE:
<221> NAME/KEY: misc_feature
<223> OTHER INFORMATION: Ceres Promoter YP0188

<400> SEQUENCE: 167

```
gattggtatg aaatttcgga gaccaacaaa aaaaacttta ttgagcttgg agtgaagcta       60
tatatatggg gcaagatcat aatatgtttta tatcggcctt ttcgttaact gaaaataata      120
gttttgagaa atatatcaaa tggtaaacag acatcatctt tgaaaaatac catcaatgaa      180
gttaatattg ttattggcat atggtttacc catcttaatt ttaatgcaac caaacaaaca      240
```

| agaaacaaaa actgtataag atacaagtg ttttacgatt ttccgtctta aaaccgaaat | 300 |
| atttttgttc ctacgacttt aaacggactt tgcttaagtt gtgtgcatgt aagctcgtcg | 360 |
| tccctcgatt gtcatcaaca ttcaccaata tcagcctcta tcacacgagt gaaggtggtg | 420 |
| attcggctta atgaaaacag agaaatattt caatatgatt cctattaaat tttaaatctt | 480 |
| ttttctcaat ctctagattt tcattaaaag catcatgatt tttttccact atgttcatat | 540 |
| atctctatca cagttttagg tacattgtag aaattggata agatacgtca tacgtctaac | 600 |
| atgaatttgg tctagcaagg aaggtttgag ataataagtg aaaagaaaac acaagataat | 660 |
| aaattataat ttataaatgc tttatagtat tgaaaaataa gatgattttt ttttttttta | 720 |
| ataccggatt ggctgatcca cttatgatga ctcaaatgtt attaagtttc aagacaattt | 780 |
| atgatgacac aaatcacaat gagtcaatag tagccacgaa gccagaaaaa aaaaatgtac | 840 |
| tacaaaaaga taatgatagt acaaaatgat acgtcgtact gccacatgta cgacacaact | 900 |
| cgattaccaa aaagcagagc catccaacca taaaactcaa aacacacaga ttccactggc | 960 |
| gtgtgctctc ctcacttcac tcgtccttga aacttgaggt actga | 1005 |

<210> SEQ ID NO 168
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter YP0190

<400> SEQUENCE: 168

| taaatagtga cattggtaag aagaaaaaaa acactattaa atagtgaaaa aatggtttat | 60 |
| aactctctta attaacatta cttattattg ctagcaccta aaatctccca caaaatattt | 120 |
| gttgtaaaac acaaatttac aaaatgattt tgttttttaaa ttagtaacac atgttcatat | 180 |
| atacgttaat aagaacatac cctatatgat tttatataaa aaaatttctt tgagacgtct | 240 |
| tattctttt tctttaataa tatgcaattg tgagagtttg gatttgaatg gtagcattag | 300 |
| aagcaaactt gaaccaaaca tatttcatga agtcaaactt gaaccaatgt gatcactaat | 360 |
| cacagtgttc gcagtgtaag gcatcagaaa atagaagaag ggacatagct atgaatcata | 420 |
| taatcttgac acatgtttta taggttttag gtgtgtatgc taacaaaaaa tgagacagct | 480 |
| ttcttctaat agacttaata tttgggctaa atgtaccaca gttgtgaatt tcttacaaaa | 540 |
| atgggccgag ctacaaaaaa ctacaggccc actctcaact cttatcaaac gacagcgttt | 600 |
| tacttttta aaagcacaca cttttttgttt ggtgtcggtg acggtgagtt tcgtccgctc | 660 |
| ttcctttaaa ttgaagcaac ggttttgatc cgatcaaatc caacggtgct gattacacaa | 720 |
| agcccgagac gaaaacgttg actattaagt taggttttaa tctcagccgt taatctacaa | 780 |
| atcaacggtt ccctgtaaaa cgaatcttcc ttccttcttc acttccgcgt cttctctctc | 840 |
| aatcacctca aaaaaatcga tttcatcaaa atattcaccc gcccgaattt gactctccga | 900 |
| tcatcgtctc cgaatctaga tcgacgagat caaaacccta gaaatctaaa tcggaatgag | 960 |
| aaattgattt tgatacgaat tagggatctg tgtgttgagg ac | 1002 |

<210> SEQ ID NO 169
<211> LENGTH: 995
<212> TYPE: DNA
<213> ORGANISM: Arabidopsis thaliana
<220> FEATURE:
<221> NAME/KEY: misc_feature
<223> OTHER INFORMATION: Ceres Promoter YP0212

<400> SEQUENCE: 169

```
agtcgattgg tacactctta atttaattag agtaagagat caacaaaaat atagaatttt      60
ctttatatcg aagtgctacg accttatata tatagaaaaa aaagcatagg tgaatctcta     120
aattgagatt gtgctgtagt aaacatatta agttttagt tttttaaga atgaatctt        180
tttgttgatt aattcaaact agtagtcatt aagattccgg agattccaat ttagaaaagt    240
caaagattca aagaacaagt ccaggtccac atgttgaatc cgattcatca tccactcatc    300
cttcatatct tcctccaccg tctccgccca aaaatcaat aacataaaa atcctaaaa       360
aaacatattt gattttgaaa aaactttatc atatattata ttaattaaat agttatccga    420
tgactcatcc tatggtcagg gccttgctgt ctctgacgtc cttaattatc attatttta     480
aatttgtctc tctcagaaaa ttacgccaca atcttcctct ttccttttc cgaaaacagc     540
taatatttgt ggacctaaac taaataacgt agcctctaga ttttatataa ttactaatac    600
tatatgctac tacttgttat tatttactcc aatcatatat gataccaatc aagaatcact    660
acataagtag aaaactttgc aatgagtcca ttaattaaaa ttaagaataa acttaaaatt    720
ttatggtatt ttaagattcc ctttggattg taatgacaag aaatcagcaa attagtcgta    780
actcgtaaga ataaacaaga tcaattttta ctttctttac aaagattccg ttgtaatttt    840
agaaattttt ttttgtcact gtttttttat agattaattt atctgcatca atccgattaa    900
gaagtgtaca catgggcatc tatatatatc taacaggtaa aacgtgtatg tacatgcata    960
aggttttacg tgcttctata aatatatgtg gcagt                               995
```

<210> SEQ ID NO 170
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0214

<400> SEQUENCE: 170

```
ccagtcgatt ggcgcctcgc atgcctatca tatttaaccg tcaataatgg atttggcggt     60
tttggtaggc cgggtcaacc ggattaaaag aaaacggttt ggagtccttc cttgcaattg   120
aattttcaca cattcggggtt ttgtgatttc tctgtcataa tgggcccggc acatatggtt   180
cataacccat gtgggcctat ggtataattt ttccaattaa aactattgtt aggtcgataa   240
aacaaaaaac aataaaaacg agtggaatac acataccaaa aagaatgtga tgaacattag   300
taattttatt ttgatggtta atgaaaaaca aaataaatgc atcttggcat cttccgttgg   360
aaagcgcaaa tagggcagat tttcagacag atatcactat gatgggggt gagagaaaga   420
aaacgaggcg tacctaatgt aacactactt aattagtcgt tagttatagg acttttttt   480
tgtttgggcc tagttatagg atcataaggt aaaaatgaag aatgaatatt agattagtag   540
gagctaatga tggagttaag tatgcacgtg taagaactgg gaagtgaaac ctcctgtatg   600
gtgaagaaac tatacaacaa agcccttgt tggtgtatac gtattaatt ttattcttt      660
atcacaagcg atacgtatct aagacataa taaatatata tcttactcat aataaatatc    720
ttaagatata tatacagtat acacctgtat atatataata aataggcata tagtagaaat   780
taatatgagt tgttgttgtt gcaaatatat aaatcaatca aaagatttaa aacccaccat   840
tcaatcttgg taagtaacga aaaaaaggg aagcaagaag aaccacagaa aaggggggcta  900
acaactagac acgtagatct tcatctgccc gtccatctaa cctaccacac tctcatcttc    960
```

```
tttttcccgt gtcagtttgt tatataagct ctcactctcc ggtatatttc cccattgcac   1020
tgga                                                                1024

<210> SEQ ID NO 171
<211> LENGTH: 911
<212> TYPE: DNA
<213> ORGANISM: Arabidopsis thaliana
<220> FEATURE:
<221> NAME/KEY: misc_feature
<223> OTHER INFORMATION: Ceres Promoter YP0263

<400> SEQUENCE: 171
atctagctgt ggattccacc aaaattctgg cagggccatg atctaaaaac tgagactgcg     60
cgtgttgttt tgcagtgatt tgtatttcat atttgcacca tcctacacag tccacttggt    120
atcgtaacca acataagga gaacctaatt acattattgt tttaatttcg tcaaactggt    180
ttttaccttt tagttacata gttgattctt catttgtttt agtagttatg gagcacaata    240
atgtgcaaca aagaaagatc atagtggatt aatatgttga gaggtcagaa attcttggtt    300
aacaaaaaaa agttacaagg actgagattt tgggtgggag aaagccatag cttttaaaac    360
atgattgaac ttaaaagtga tgttatggtt tgaggggaaa aaggttgatg tcaactaaga    420
tagttgaagt aatgtcttaa actaaagtaa accaccggtc caaccgtggt ccggaagcat    480
ctctggtatg atttatccta aaaatcaaaa tagtagaaac atactttaaa tatatacatt    540
gatcggacga aaattgtaaa ctagtatagt ttcaaaaact agttgaacag gttatgtacc    600
ttaaacattt atttcaaact taaacactaa agaaacatata tgaatagaag tttatataaa    660
ttactatata tctaccataa atctcttata attatgatgt cacgatgagg aagtgttgaa    720
acgttaaaat gccaaaatat aagcatgcga cggaattttg gcagaagatt gtagagttgt    780
aatctgtcgc aatcattact cgtgctagca ttttcatttt tcccttcatt tgtggataac    840
gcacgatata acattctaca caccaacaag attctataaa aacgcaaagg ttgtctccat    900
agaatatcgt c                                                         911

<210> SEQ ID NO 172
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0275

<400> SEQUENCE: 172
aaacattaat atgtagtaac tatgggcgta tgctttactt tttaaaatgg gcctatgcta     60
taattgaatg acaaggatta aacaactaat aaaattgtag atgggttaag atgacttatt    120
tttttactta ccaatttata aatgggcttc gatgtactga aatatatcgc gcctattaac    180
gaggccattc aacgaatgtt ttaagggccc tatttcgaca ttttaaagaa cacctaggtc    240
atcattccag aaatggatat tataggattt agataaattic ccacgtttgg tttatttatc    300 tatttttga cgttgaccaa cataatcgtg cccaaccgtt tcacgcaacg aatttatata    360
cgaaatatat atattttca aattaagata ccacaatcaa aacagctgtt gattaacaaa    420 gagattttt ttttttggtt ttgagttaca ataacgttag aggataaggt ttcttgcaac    480
gattaggaaa tcgtataaaa taaaatatgt tataattaag tgttttattt tataatgagt    540
attaatataa ataaaacctg caaaggata gggatattga ataataaaga gaaacgaaag    600
```

| | |
|---|---|
| agcaatttta cttctttata attgaaatta tgtgaatgtt atgtttacaa tgaatgattc | 660 |
| atcgttctat atattgaagt aaagaatgag tttattgtgc ttgcataatg acgttaactt | 720 |
| cacatataca cttattacat aacatttatc acatgtgcgt cttttttttt ttttactttg | 780 |
| taaaatttcc tcacttttaa gacttttata acaattacta gtaaaataaa gttgcttggg | 840 |
| gctacaccct ttctccctcc aacaactcta tttatagata acattatatc aaaatcaaaa | 900 |
| catagtccct ttcttctata aaggtttttt cacaaccaaa tttccattat aaatcaaaaa | 960 |
| ataaaaactt aattagtttt tacagaagaa aagaaaaca | 999 |

<210> SEQ ID NO 173
<211> LENGTH: 981
<212> TYPE: DNA
<213> ORGANISM: Arabidopsis thaliana
<220> FEATURE:
<221> NAME/KEY: misc_feature
<223> OTHER INFORMATION: Ceres Promoter YP0285

<400> SEQUENCE: 173

| | |
|---|---|
| gggattatat atgatagacg attgtatttg cgggacattg agatgtttcc gaaaatagtc | 60 |
| atcaaatatc aaaccagaat ttgatgtgaa aacactaatt aaaacatata attgacaact | 120 |
| agactatatc atttgttaag ttgagcgttg aaagaaaatg aaagagtgta gactgtagta | 180 |
| cgtatgagtt tcccaaaaga tggtgcttga atattattgg gaagagactt tggttggttc | 240 |
| ggttgaatga agattttttac ctgccatgtt gatagagaaa ggcaaataaa tgtaggggtc | 300 |
| gatgtctaac gtaaagactg gatcaaccaa gagtcctcct cctcgtcttc accaaaaaaa | 360 |
| aagagtcctc ctcgtggaaa cttatttctt ctccagccaa gatctcatct catctcttca | 420 |
| ctctatgaaa tataaaggaa tcttatggtt tttctaaaaa ctatagtacg tctatatacc | 480 |
| aaaggaaaca atataaaatc agttaatctg ataaattttg agtaaataat aaagttaact | 540 |
| ttgtacttac ctatatcaaa ctaattcaca aaataaagta ataataacaa agaattttta | 600 |
| gtagatccac aatatacaca cacactatga gaaatcataa tagagaattt taatgatttt | 660 |
| gtctaactca tagcaacaag tcgctttggc cgagtggtta aggcgtgtgc ctgctaagta | 720 |
| catgggctct gcccgcgaga gttcgaatct ctcaggcgac gtttcttttg ttttcggcca | 780 |
| taaaggaaaa agcccaatta acacgtctcg cttataagcc cataaagcaa acaatgggct | 840 |
| gtctctgtct cactcacaca cgcgttttcc tacttttga ctatttttat aaccggcggg | 900 |
| tctgacttaa ttagggtttt ctttaataat cagacactct ctcactcgtt tcgtcaacat | 960 |
| tgaacacaga caaaaccgcg t | 981 |

<210> SEQ ID NO 174
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0286

<400> SEQUENCE: 174

| | |
|---|---|
| gaaaacaatc ataggttacg ctattatcat cgaaaggtat gtgatgcata ttcccattga | 60 |
| accagatttc catatatttt atttgtaaag tgataatgaa tcacaagatg attcaatatt | 120 |
| aaaaatgggt aactcacttt gacgtgtagt acgtggaaga atagttagct atcacgcata | 180 |
| catatatcta tgaataagtg tgtatgacat aagaaactaa aatatttacc taaagtccag | 240 |
| ttactcatac tgatttcatg catatatgta ttatttattt attttttaata aagaagcgat | 300 |

```
tggtgttttc atagaaatca tgatagattg ataggtattt cagttccaca aatctagatc      360
tgtgtgctat acatgcatgt attaattttt tccccttaaa tcatttcagt tgataatatt      420
gctctttgtt ccaactttag aaaaggtatg aaccaacctg acgattaaca agtaaacatt      480
aattaatctt tatatgagat aaaaccgagg atatatatga ttgtgttgct gtctattgat      540
gatgtgtcga tattatgctt gttgtaccaa tgctcgagcc gagcgtgatc gatgccttga      600
caaactatat atgtttcccg aattaattaa gttttgtatc ttaattagaa taacattttt      660
atacaatgta atttctcaag cagacaagat atgtatccta tattaattac tatatatgaa      720
ttgccgggca cctaccagga tgtttcaaat acgagagccc attagtttcc acgtaaatca      780
caatgacgcg acaaaatcta gaatcgtgtc aaaactctat caatacaata atatatattt      840
caagggcaat ttcgacttct cctcaactca atgattcaac gccatgaatc tctatataaa      900
ggctacaaca ccacaaagga tcatcagtca tcacaaccac attaactctt caccactatc      960
tctcaatctc tcgtttcatt tcttgacgcg tgaaaa                                996

<210> SEQ ID NO 175
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0337

<400> SEQUENCE: 175 taatttttt attttggaa ctaacactta ttagtttagg tttccatcac ctatttaatt         60
cgtaattctt atacatgcat ataatagaga tacatatata caaatttatg atcattttg       120 cacaacatgt gatctcattc attagtatgc attatgcgaa aacctcgacg cgcaaaagac      180
acgtaatagc taataatgtt actcatttat aatgattgaa gcaagacgaa aacaacaaca      240
tatatatcaa attgtaaact agatatttct taaaagtgaa aaaaaacaaa gaaatataaa      300 ggacaattt gagtcagtct cttaatatta aaacatatat acataaataa gcacaaacgt       360
ggttacctgt cttcatgcaa tgtggacttt agtttatcta atcaaaatca aaataaaagg      420
tgtaatagtt ctcgtcattt ttcaaatttt aaaaatcaga accaagtgat ttttgtttga      480
gtattgatcc attgtttaaa caatttaaca cagtatatac gtctcttgag atgttgacat      540
gatgataaaa tacgagatcg tctcttggtt ttcgaatttt gaactttaat agttttcttt      600
tttagggaaa ctttaatagt tgtttatcat aagattagtc acctaatggt tacgttgcag      660
taccgaacca atttttttacc cttttttcta aatgtggtcg tggcataatt tccaaaagag      720
atccaaaacc cggtttgctc aactgataag ccggtcggtt ctggtttgaa aaacaagaaa      780
taatctgaaa gtgtgaaaca gcaacgtgtc tcggtgtttc atgagccacc tgccacctca      840
ttcacgtcgg tcattttgtc gtttcacggt tcacgctcta gacacgtgct ctgtccccac      900
catgactttc gctgccgact cgcttcgctt tgcaaactca aacatgtgtg tatatgtaag      960
tttcatccta ataagcatct cttaccacat taattaaaaa                           1000

<210> SEQ ID NO 176
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0356
```

<400> SEQUENCE: 176

```
ttagttcatt gaaacgtcaa cttttactt gcaaccactt tgtaggacca ttaactgcaa     60
aataagaatt ctctaagctt cacaaggggt tcgtttggtg ctataaaaac attgttttaa   120
gaactggttt actggttcta taaatctata aatccaaata tgaagtatgg caataataat   180
aacatgttag cacaaaaaat actcattaaa ttcctaccca aaaaaatct ttatatgaaa    240
ctaaaactta tatacacaat aatagtgata caaagtaggt cttgatattc aactattcgg   300
gattttctgg tttcgagtaa ttcgtataaa aggtttaaga tctattatgt tcactgaaat   360
cttaactttg ttttgtttcc agttttaact agtagaaatt gaaattttta aaaattgtta   420
cttacaataa aatttgaatc aatatccta atcaaggat cttaagacta gcacaattaa    480
aacatataac gtagaatatc tgaaataact cgaaaatatc tgaactaagt tagtagtttt   540
aaaatataat cccggtttgg accgggcagt atgtacttca atacttgtgg gttttgacga   600
ttttggatcg gattgggcgg gccagccaga ttgatctatt acaaatttca cctgtcaacg   660
ctaactccga acttaatcaa agattttgag ctaaggaaaa ctaatcagtg atcacccaaa   720
gaaacattc gtgataatt gtttgctttc catggcagca aaacaaatag gacccaaata    780
ggaatgtcaa aaaaagaaa gacacgaaac gaagtagtat aacgtaacac acaaaaataa    840
actagagata ttaaaaacac atgtccacac atggatacaa gagcatttaa ggagcagaag   900
gcacgtagtg gttagaaggt atgtgatata attaatcggc ccaaatagat tggtaagtag   960
tagccgtcta tatcatccat actcatcata acttcaacct                        1000
```

<210> SEQ ID NO 177
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0374

<400> SEQUENCE: 177

```
aagacacccg taaatgttgt catgtagaag aaactagaaa cgttaaacgc atcaaatcaa     60
gaaattaaat tgaaggtaat ttttaacgcc gcctttcaaa tattcttcct aggagaggct   120
acaagacgcg tatttctttc gaattctcca aaccattacc attttgatat ataataccga   180
catgccgttg ataaagtttg tatgcaaatc gttcattggg tatgagcaaa tgccatccat   240
tggttcttgt aattaaatgg tccaaaaata gtttgttccc actactagtt actaatttgt   300
atcactctgc aaaataatca tgatataaac gtatgtgcta tttctaatta aaactcaaaa   360
gtaatcaatg tacaatgcag agatgaccat aaaagaacat taaaacacta cttccactaa   420
atctatgggg tgccttggca aggcaattga ataaggagaa tgcatcaaga tgatatagaa   480
aatgctattc agtttataac attaatgttt tggcggaaaa ttttctatat attagacctt   540
tctgtaaaaa aaaaaaaatg atgtagaaaa tgctattatg tttcaaaaat ttcgcactag   600
tataatacgg aacattgtag tttacactgc tcattaccat gaaaaccaag gcagtatata   660
ccaacattaa taaactaaat cgcgattct agcaccccca ttaattaatt ttactattat    720
acattctctt tgcttctcga aataataaac ttctctatat cattctacat aataaataag   780
aaagaaatcg acaagatcta aatttagatc tattcagctt tttcgcctga gaagccaaaa   840
ttgtgaatag aagaaagcag tcgtcatctt cccacgtttg gacgaaataa acataacaa    900
taataaaata ataaatcaaa tatataaatc cctaatttgt ctttattact ccacaatttt   960
```

```
ctatgtgtat atatataccc acctctctct tgtgtatttg                        1000
```

<210> SEQ ID NO 178
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0377

<400> SEQUENCE: 178

```
tataaaccat tcctataaca ccatatttaa acataacaat gaattgcttg gatttcaaac    60
tttattaaat ttggatttta aattttaatt tgattgaatt ataccccctt aattggataa   120
attcaaatat gtcaactttt tttttgtaag atttttttat ggaaaaaaaa attgattatt   180
cactaaaaag atgacaggtt acttataatt taatatatgt aaaccctaaa aagaagaaaa   240
tagtttctgt tttcacttta ggtcttatta tctaaacttc tttaagaaaa tcgcaataaa   300
ttggtttgag ttctaacttt aaacacatta atatttgtgt gctatttaaa aaataattta   360
caaaaaaaaa aacaaattga cagaaaatat caggttttgt aataagatat ttcctgataa   420
atatttaggg aatataacat atcaaaagat tcaaattctg aaaatcaaga atggtagaca   480
tgtgaaagtt gtcatcaata tggtccactt ttctttgctc tataacccaa aattgaccct   540
gacagtcaac ttgtacacgc ggccaaacct ttttataatc atgctattta tttccttcat   600
ttttattcta tttgctatct aactgatttt tcattaacat gataccagaa atgaatttag   660
atggattaat tcttttccat ccacgacatc tggaaacact tatctcctaa ttaaccttac   720
ttttttttta gtttgtgtgc tccttcataa aatctatatt gtttaaaaca aaggtcaata   780
aatataaata tggataagta taataaatct ttattggata tttctttttt taaaaaagaa   840
ataaatcttt tttggatatt ttcgtggcag catcataatg agagactacg tcgaaaccgc   900
tggcaaccac ttttgccgcg tttaattcct ttctgaggct tatataaata gatcaaaggg   960
gaaagtgaga tataatacag acaaaacaag agaaaaga                          998
```

<210> SEQ ID NO 179
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0380

<400> SEQUENCE: 179

```
acaagtacca ttcacttttt tacttttcaa tgtatacaat catcatgtga taaaaaaaaa    60
aatgtaacca atcaacacac tgagatacgg ccaaaaaatg gtaatacata aatgtttgta   120
ggttttgtaa tttaaatact ttagttaagt tatgatttta ttattttttgc ttatcactta   180
tacgaaatca tcaatctatt ggtatctctt aatcccgctt tttaatttcc accgcacacg   240
caaatcagca aatggttcca gccacgtgca tgtgaccaca tattgtggtc acagtactcg   300
tcctttttttt ttcttttgta atcaataaat ttcaatccta aaacttcaca cattgagcac   360
gtcggcaacg ttagctccta aatcataacg agcaaaaaag ttcaaattag ggtatatgat   420
caattgatca tcactacatg tctacataat taatatgtat tcaaccggtc ggtttgttga   480
tactcatagt taagtatata tgtgctaatt agaattagga tgaatcagtt cttgcaaaca   540
actacggttt catataatat gggagtgtta tgtacaaaat gaaagaggat ggatcattct   600
gagatgttat gggctcccag tcaatcatgt tttgctcgca tatgctatct tttgagtctc   660
```

```
ttcctaaact catagaataa gcacgttggt tttttccacc gtcctcctcg tgaacaaaag        720
tacaattaca ttttagcaaa ttgaaaataa ccacgtggat ggaccatatt atatgtgatc        780
atattgcttg tcgtcttcgt tttcttttaa atgtttacac cactacttcc tgacacgtgt        840
ccctattcac atcatccttg ttatatcgtt ttacttataa aggatcacga acaccaaaac        900
atcaatgtgt acgtcttttg cataagaaga aacagagagc attatcaatt attaacaatt        960
acacaagaca gcgagattgt aaagagtaa gagagagag                                999

<210> SEQ ID NO 180
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0381

<400> SEQUENCE: 180
cacggtcaaa gtattgctaa catggtcatt acattgaaaa agaaaattaa ttgtctttac         60
tcatgtttat tctatacaaa taaaaatatt aaccaaccat cgcactaaca aaatagaaat        120
cttattctaa tcacttaatt gttgacaatt aaatcattga aaaatacact taaatgtcaa        180
atattcgttt tgcatacttt tcaatttaaa tacatttaaa gttcgacaag ttgcgtttac        240
tatcatagaa aactaaatct cctaccaaag cgaaatgaaa ctactaaagc gacaggcagg        300
ttacataacc taacaaatct ccacgtgtca attaccaaga gaaaaaaga gaagataagc        360 ggaacacgtg gtagcacaaa aaagataatg tgatttaaat taaaaaacaa aaacaaagac        420
acgtgacgac ctgacgctgc aacatcccac cttacaacgt aataaccact gaacataaga        480
cacgtgtacg atcttgtctt tgttttctcg atgaaaacca cgtgggtgct caaagtcctt        540
gggtcagagt cttccatgat tccacgtgtc gttaatgcac caaacaaggg tactttcggt        600
attttggctt ccgcaaatta gacaaaacag cttttgtttt gattgatttt tctcttctct        660
ttttccatct aaattctctt gggctctta atttcttttt gagtgttcgt tcgagatttg        720
tcggagattt tttcggtaaa tgttgaaatt ttgtgggatt ttttttatt tctttattaa        780 actttttttt attgaattta taaaagggga aggtcgtcat taatcgaaga aatggaatct        840
tccaaaattt gatattttgc tgtttttcttg ggattttgaat tgctctttat catcaagaat        900
ctgttaaaat ttctaatcta aaatctaagt tgagaaaaag agagatctct aatttaaccg        960
gaattaatat tctccgaccg aagttattat gttgcaggct                            1000

<210> SEQ ID NO 181
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0384

<400> SEQUENCE: 181
tttaaaaaat tggataaaac accgataaaa attcacattt gcaaattta ttcagtcgga         60 atatatattt gaaacaagtt ttgaaatcca ttggacgatt aaaattcatt gttgagagga        120
taaatatgga tttgttcatc tgaaccatgt cgttgattag tgattgacta ccatgaaaaa        180
tatgttatga aaagtataac aactttgat aaatcacatt tattaacaat aaatcaagac        240
aaaatatgtc aacaataata gtagtagaag atattaattc aaattcatcc gtaacaacaa        300
```

| | |
|---|---|
| aaaatcatac cacaattaag tgtacagaaa aaccttttgg atatatttat tgtcgctttt | 360 |
| caatgatttt cgtgaaaagg atatatttgt gtaaaataag aaggatcttg acgggtgtaa | 420 |
| aaacatgcac aattcttaat ttagaccaat cagaagacaa cacgaacact tctttattat | 480 |
| aagctattaa acaaaatctt gcctattttg cttagaataa tatgaagagt gactcatcag | 540 |
| ggagtggaaa atatctcagg atttgctttt agctctaaca tgtcaaacta tctagatgcc | 600 |
| aacaacacaa agtgcaaatt cttttaatat gaaacaaca ataatatttc taatagaaaa | 660 |
| ttaaaaaggg aaataaaata ttttttttaaa atatacaaaa gaagaaggaa tccatcatca | 720 |
| aagttttata aaattgtaat ataatacaaa cttgtttgct tccttgtctc tccctctgtc | 780 |
| tctctcatct ctcctatctt ctccatatat acttcatctt cacacccaaa actccacaca | 840 |
| aaatatctct ccctctatct gcaaattttc caaagttgca tcctttcaat ttccactcct | 900 |
| ctctaatata attcacattt tcccactatt gctgattcat ttttttttgt gaattatttc | 960 |
| aaacccacat aaaaaaatct ttgtttaaat ttaaaacca | 999 |

<210> SEQ ID NO 182
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0385

<400> SEQUENCE: 182

| | |
|---|---|
| actcaacaat aggacaagcc aaaaaaattc caattattgt gttactctat tcttctaaat | 60 |
| ttgaacacta atagactatg acatatgagt atataatgtg aagtcttaag atattttcat | 120 |
| gtgggagatg aataggccaa gttggagtct gcaaacaaga agctcttgag ccacgacata | 180 |
| agccaagttg atgaccgtaa ttaatgaaac taatgtgtg tggttatata ttagggaccc | 240 |
| atggccatat acacaatttt tgtttctgtc gatagcatgc gtttatatat atttctaaaa | 300 |
| aaactaacat atttactgga tttgagttcg aatattgaca ctaatataaa ctacgtacca | 360 |
| aactacatat gtttatctat atttgattga tcgaagaatt ctgaactgtt ttagaaaatt | 420 |
| tcaatacact taacttcatc ttacaacggt aaaagaaatc accactagac aaacaatgcc | 480 |
| tcataatgtc tcgaaccctc aaactcaaga gtatacattt tactagatta gagaatttga | 540 |
| tatcctcaag ttgccaaaga attggaagct tttgttacca aacttagaaa cagaagaagc | 600 |
| cacaaaaaaa gacaagggaa gttaaagatt gaagtgatgc atttgtctaa gtgtgaaagg | 660 |
| tctcaagtct caactttgaa ccataataac attactcaca ctccctttt ttttcttttt | 720 |
| ttttcccaaa gtaccttttt taattccctc tataacccac tcactccatt ccctctttct | 780 |
| gtcactgatt caacacgtgg ccacactgat gggatccacc tttcctctta cccacctccc | 840 |
| ggtttatata aacccttcac aacacttcat cgctctcaaa ccaactctct cttctctctt | 900 |
| ctctcctctc ttctacaaga agaaaaaaaa cagagccttt acacatctca aaatcgaact | 960 |
| tactttaacc accaaatact gattgaacac acttgaaa | 998 |

<210> SEQ ID NO 183
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0396

<400> SEQUENCE: 183

-continued

```
catagtaaaa gtgaatttaa tcatactaag taaaataaga taaaacatgt tatttgaatt      60
tgaatatcgt gggatgcgta tttcggtatt tgattaaagg tctggaaacc ggagctccta     120
taacccgaat aaaaatgcat aacatgttct tccccaacga ggcgagcggg tcagggcact     180
agggtcattg caggcagctc ataaagtcat gatcatctag gagatcaaat tgtatgtcgg     240
ccttctcaaa attacctcta agaatctcaa acccaatcat agaacctcta aaaagacaaa     300
gtcgtcgctt tagaatgggt tcggtttttg gaaccatatt tcacgtcaat ttaatgttta     360
gtataatttc tgaacaacag aattttggat ttatttgcac gtatacaaat atctaattaa     420
taaggacgac tcgtgactat ccttacatta agtttcactg tcgaaataac atagtacaat     480
acttgtcgtt aatttccacg tctcaagtct ataccgtcat ttacggagaa agaacatctc     540
tgtttttcat ccaaactact attctcactt tgtctatata tttaaaatta agtaaaaaag     600
actcaatagt ccaataaaat gatgaccaaa tgagaagatg gttttgtgcc agattttagg     660
aaaagtgagt caaggtttca catctcaaat ttgactgcat aatcttcgcc attaacaacg     720
gcattatata tgtcaagcca attttccatg ttgcgtactt ttctattgag gtgaaaatat     780
gggtttgttg attaatcaaa gagtttgcct aactaatata actacgactt tttcagtgac     840
cattccatgt aaactctgct tagtgtttca tttgtcaaca atattgtcgt tactcattaa     900
atcaaggaaa aatatacaat tgtataattt tcttatattt taaaattaat tttgatgtat     960
taccccttta taaataggct atcgctacaa caccaataac                          1000
```

<210> SEQ ID NO 184
<211> LENGTH: 1514
<212> TYPE: DNA
<213> ORGANISM: Arabidopsis thaliana
<220> FEATURE:
<221> NAME/KEY: misc_feature
<223> OTHER INFORMATION: Ceres Promoter p13879

<400> SEQUENCE: 184

```
tttcgatcct cttcttttt aggtttcttg atttgatgat cgccgccagt agagccgtcg      60
tcggaagttt cagagattaa aaccatcacc gtgtgagttg gtagcgaatt aacggaaagt     120
ctaagtcaag attttttaaa aagaaattta tgtgtgaaaa gaagccgttg tgtatattta     180
tataatttag aaaatgtttc atcatttttaa ttaaaaaatt aataatttgt agaagaaaga     240 agcattttt atacataaat catttacctt ctttactgtg ttttctctca cttacttcat     300
ttttactttt ttacaaaaaa gtgaaaagta aattacgtaa ttggtaacat aaattcactt     360
taaatttgca tatgttttgt tttcttcgga aactatatcg aaaagcaaac ggaaagaact     420
tcacaaaaaa ccctagctaa ctaaagacgc atgtgttctt cttattcttc atatatcctc     480
tgtttcttgt gttctgtttt gagtcttaca ttttcaatat ctgactctga ttactatatc     540
taaaagggaa catgaagaac ttgagaccat gttaaactgt acaatgcctt caaacatggc     600
taactaaaga tacattagat ggctttacag tgtgtaatgc ttattatctt taggtttttt     660
aaatcccttg tattaagtta tttaccaaat tatgttcttg tactgcttat tggcttggtt     720
gttgtgtgct ttgtaaacaa caccctttggc tttatttcat cctttgtaaa cctactggtc     780
tttgttcagc tcctcttgga agtgagtttg tatgcctgga acgggtttta atggagtgtt     840
tatcgacaaa aaaaaaatgt agcttttgaa atcacagaga gtagttttat attcaaatta     900
catgcatgca actaagtagc aacaaagttg atatggccga gttggtctaa ggcgccagat     960
taaggttctg gtccgaaagg gcgtgggttc aaatcccact gtcaacattc tcttttctc    1020
```

```
aaattaatat ttttctgcct caatggttca ggcccaatta tactagacta ctatcgcgac    1080
taaaataggg actagccgaa ttgatccggc ccagtatcag ttgtgtatca ccacgttatt    1140
tcaaatttca aactaaggga taaagatgtc atttgacata tgagatattt ttttgctcca    1200
ctgagatatt tttctttgtc ccaagataaa atatcttttc tcgcatcgtc gtctttccat    1260
ttgcgcatta aaccaaaaag tgtcacgtga tatgtcccca accactacga attttaacta    1320
cagatttaac catggttaaa ccagaattca cgtaaaccga ctctaaacct agaaaatatc    1380
taaaccttgg ttaatatctc agcccccctta taaataacga gacttcgtct acatcgttct    1440
acacatctca ctgctcacta ctctcactgt aatcccttag atcttctttt caaatttcac    1500
cattgcactg gatg                                                     1514

<210> SEQ ID NO 185
<211> LENGTH: 1954
<212> TYPE: DNA
<213> ORGANISM: Arabidopsis thaliana
<220> FEATURE:
<221> NAME/KEY: misc_feature
<223> OTHER INFORMATION: Ceres Promoter p326

<400> SEQUENCE: 185
gtgggtaaaa gtatccttct ttgtgcattt ggtattttta agcatgtaat aagaaaaacc      60
aaaatagacg gctggtattt aataaaagga gactaatgta tgtatagtat atgatttgtg     120
tggaatataa taaagttgta aaatatagat gtgaagcgag tatctatctt ttgactttca     180
aaggtgatcg atcgtgttct ttgtgatagt tttggtcgtc ggtctacaag tcaacaacca     240
ccttgaagtt ttcgcgtctc ggtttcctct tcgcatctgg tatccaatag catacatata     300
ccagtgcgga aaatggcgaa gactagtggg cttgaaccat aaggtttggc cccaatacgg     360
attccaaaca acaagcctag cgcagtcttt tgggatgcat aagactaaac tgtcgcagtg     420
atagacgtaa gatatatcga cttgattgga atcgtctaag ctaataagtt taccttgacc     480
gtttatagtt gcgtcaacgt ccttatggag attgatgccc atcaaataaa cctgaaaatc     540
catcaccatg accaccataa actcccttgc tgccgctgct ttggcttgag caaggtgttt     600
ccttgtaaag ctccgatctt tggataaagt gttccacttt ttgcaagtag ctctgacccc     660
tctcagagat gtcaccggaa tcttagacag aacctcctct gccaaatcac ttggaagatc     720
ggacaatgtc atcattttttg caggtaattt ctccttcgtt gctgctttgg cttgagcacg     780
gtgcttcttt gtaaagctcc gatctttgga taagagcgga tcggaatcct ctaggaggtg     840
ccagtccctt gacctattaa tttatagaag gttttagtgt attttgttcc aatttcttct     900
ctaacttaac aaataacaac tgcctcatag tcatgggctt caaattttat cgcttggtgt     960
atttcgttat ttgcaaggcc ttggcccatt ttgagcccaa taactaaatc tagccttttc    1020
agaccggaca tgaacttcgc atattggcgt aactgtgcag ttttaccttt ttcggatcag    1080
acaagatcag atttagacca cccaacaata gtcagtcata tttgacaacc taagctagcc    1140
gacactacta aaaagcaaac aaaagaagaa ttctatgttg tcattttacc ggtggcaagt    1200
ggacccttct ataaaagagt aaagagacag cctgtgtgtg tataatctct aattatgttc    1260
accgacacaa tcacacaaac ccttctctaa tcacacaact tcttcatgat ttacgacatt    1320
aattatcatt aactctttaa attcactttta catgctcaaa aatatctaat ttgcagcatt    1380
aatttgagta ccgataacta ttattataat cgtcgtgatt cgcaatcttc ttcattagat    1440
gctgtcaagt tgtactcgca cgcggtggtc cagtgaagca aatccaacgg tttaaaacct    1500
```

```
tcttacatttt ctagatctaa tctgaaccgt cagatatcta gatctcattg tctgaacaca   1560
gttagatgaa actgggaatg aatctggacg aaattacgat cttacaccaa cccctcgac    1620 gagctcgtat atataaagct tatacgctcc tccttcacct tcgtactact actaccacca   1680
catttcttta gctcaacctt cattactaat ctccttttaa ggtatgttca cttttcttcg   1740
attcatactt tctcaagatt cctgcatttc tgtagaattt gaaccaagtg tcgattttg    1800 tttgagagaa gtgttgattt atagatctgg ttattgaatc tagattccaa tttttaattg   1860
attcgagttt gttatgtgtg tttatactac ttctcattga tcttgtttga tttctctgct   1920
ctgtattagg tttctttcgt gaatcagatc ggaa                               1954
```

<210> SEQ ID NO 186
<211> LENGTH: 2016
<212> TYPE: DNA
<213> ORGANISM: Arabidopsis thaliana
<220> FEATURE:
<221> NAME/KEY: misc_feature
<223> OTHER INFORMATION: Ceres Promoter p32449

<400> SEQUENCE: 186

```
gatcggcctt cttcaggtct tctctgtagc tctgttactt ctatcacagt tatcgggtat     60
ttgagaaaaa agagttagct aaaatgaatt tctccatata atcatggttt actacaggtt    120
tacttgattc gcgttagctt tatctgcatc caaagttttt tccatgatgt tatgtcatat    180
gtgataccgt tactatgttt ataactttat acagtctggt tcactggagt ttctgtgatt    240
atgttgagta catactcatt catcctttgg taactctcaa gtttaggttg tttgaattgc    300
ctctgttgtg atacttattg tctattgcat caatcttcta atgcaccacc ctagactatt    360
tgaacaaaga gctgtttcat tcttaaacct ctgtgtctcc ttgctaaatg gtcatgcttt    420
aatgtcttca cctgtctttc tcttctatag atatgtagtc ttgctagata gttagttcta    480
cagctctctt ttgtagtctt gttagagagt tagttgagat attacctctt aaaagtatcc    540
ttgaacgctt tccggttatg accaatttgt tgtagctcct tgtaagtaga acttactggg    600
accagcgaga cagtttatgt gaatgttcat gcttaagtgt cgaacgtatc tatctctact    660
atagctctgt agtcttgtta gacagttagt tttatatctc catttttttg tagtcttgct    720
agttgagata ttacctcttc tcttcaaagt atccttgaac gctcaccggt tatgaaatct    780
ctacactata gctctgtagt cttgctagat agttagttct ttagctctct ttttgtagcc    840 tagttctttta gctctccttt tgtagccttg ctacagagta agatgggata ttacctcctt    900
gaacgctctc cggttatgac caatttgttg tagctccttg taagtagaac ttaggataga    960
gtgagtcaac tttaagaaag aacctagtat gtggcataac cagattgcag gctctgtctc   1020
ggctacagta acgtaactct atagctcttt gttttgttca gaaagaacca gtgattggat   1080
gattcgtcct tagaaactgg acctaacaac agtcattggc tttgaaatca agccacaaca   1140
atgcctatat gaaccgtcca tttcattat ccgtttcaaa ccagcccatt acatttcgtc    1200
ccattgataa ccaaaagcgg ttcaatcaga ttatgtttta attttaccaa attctttatg   1260
aagtttaaat tatactcaca ttaaaaggat tattggataa tgtaaaaatt ctgaacaatt   1320
actgattttg gaaaattaac aaatattctt tgaaatagaa gaaaaagcct ttttccttt    1380 gacaacaaca tataaaatca tactcccatt aaaaagattt taatgtaaaa ttctgaatat   1440
aagatatttt ttacaacaac aaccaaaaat atttattttt ttccttttttt acagcaacaa   1500 gaaggaaaaa cttttttttt tgtcaagaaa agggagatt atgtaaacag ataaaacagg    1560
```

```
gaaataact  aaccgaactc  tcttaattaa  catcttcaaa  taaggaaaat  tatgatccgc    1620
atatttagga  agatcaatgc  attaaaacaa  cttgcacgtg  gaaagagaga  ctatacgctc    1680
cacacaagtt  gcactaatgg  tacctctcac  aaaccaatca  aaatactgaa  taatgccaac    1740
gtgtacaaat  tagggtttta  cctcacaacc  atcgaacatt  ctcgaaacat  tttaaacagc    1800
ctggcgccat  agatctaaac  tctcatcgac  caattttga   ccgtccgatg  gaaactctag    1860
cctcaaccca  aaactctata  taagaaatc   ttttccttcg  ttattgctta  ccaaatacaa    1920
accctagccg  ccttattcgt  cttcttcgtt  ctctagtttt  ttcctcagtc  tctgttctta    1980
gatcccttgt  agtttccaaa  tcttccgata  aggcct                                2016
```

```
<210> SEQ ID NO 187
<211> LENGTH: 667
<212> TYPE: DNA
<213> ORGANISM: Arabidopsis thaliana
<220> FEATURE:
<221> NAME/KEY: misc_feature
<223> OTHER INFORMATION: Ceres Promoter PD1367

<400> SEQUENCE: 187
acagttttct  tttctcatct  tacaacaagt  ttccaggagg  atagagacat  aaacgaagct     60
cggattgtat  cgttcttttt  agcttttatt  cacatccgaa  agtcctgtag  tttagattct    120
gttatcttgc  ggttttgagt  taatcagaaa  cagagtaatc  aatgtaatgt  tgcaggctag    180
atctttcatc  tttggaaatt  tgttttttc   tcatgcaatt  tctttagctt  gaccatgagt    240
gactaaaaga  tcaatcagta  gcaatgattt  gatttggcta  agagacattt  gtccacttgg    300
catcttgatt  tggatggtta  caacttgcaa  gacccaattg  gatacttgct  atgacaactc    360
caactcaaga  gtgtcgtgta  actaagaacc  ttgactaatt  tgtaatttca  atcccaagtc    420
atgttactat  atgtttttt   gtttgtatta  ttttctctcc  tacaattaag  ctctttgacg    480
tacgtaatct  ccggaaccaa  ctcctatatc  caccatttac  tccacgttgt  ctccaattat    540
tggacgttga  aacttgacac  aacgtaaacg  tatctacgtg  gttgattgta  tgtacatatg    600
tacaaacgta  cacctttctc  ctctttcact  tcatcacttg  gcttgtgaat  tcattaattc    660
ctgcgaa                                                                   667
```

```
<210> SEQ ID NO 188
<211> LENGTH: 1836
<212> TYPE: DNA
<213> ORGANISM: Oryza sativa
<220> FEATURE:
<221> NAME/KEY: misc_feature
<223> OTHER INFORMATION: Ceres Promoter p530c10

<400> SEQUENCE: 188
gcctctcgac  cacgagttta  gcacttgtgc  aacatatatg  cgtgcgatga  acatctactg     60
atgcgccatg  cgaattttag  cgttcgttca  tgacgcttcc  aacggcacag  aggctgagca    120
gcagcatgca  tgcatggctc  ttgtgaaaac  aaaaaaggtt  actggtaaat  gacatgctgc    180
tgtagctagc  tagcagaatg  caaggcccat  gcatatgcaa  tgctatgcga  caagtacagt    240
accagcatgt  atggtagcca  gctaactaat  ctatcagcag  aggcagcaag  ctcgtgcatg    300
gtgtgatgca  cttctctcca  gtaatctagt  ggtaattttc  acccaaagcg  ttgctcatat    360
ggacagtaat  tagtaatatt  accaaggttc  acaatcccgt  tacctgacca  aatactactc    420
acgaatggta  tctctggttt  tcgttaaaac  cgttggtaaa  ccagcaaaaa  tagacaaaat    480
```

```
ttgtcaaaat tttaaatttt agtttttttt ttttaactta gccgggaaac cttgaagttt     540
gtgctgtcga gctgtcctgg gaaggacggt tttggttggg attgtgaacc ctggttactg     600
cacttcattt ttgaacagat attagtgcaa cagacaaatg ccaacgcatt tttttctgtt     660
taccggcaag ctgaagcttt tacgatcccc atacagccgt tgctgcaaac ctgccaagaa     720
agagcagcag aaacaggtgt cattttgtgg tggaaagcca agtaaagtaa acagaagatg     780
gaagatagtg aggaccaggg agtgaggcag gggacacatg gcccacgcct ccctgcacat     840
tttcgtgtat aaatacaggt ggatgcatcg ctctcccagc atccatcggt tctctgctct     900
gttcatccat agagtttcct cctcttctcc tttagtgcaa ggtagagaag agcatgtgtg     960
tgtgtgtgtg tgtgtgaact gtgaagtgca gagtgcttct gtagttctgt gttatgtcca    1020
tagtgatctt gttaggattg ttgctatgga tgcatgatgt tatggttgat ctctgaatta    1080
cagtagggac ttttctgaga tctctggatt agtgggtggt gctaaatttt tttctggttg    1140
catcagcttg ggtttctggt attggtgtgg gttcttgctc tgaattttgg ttcagaatgt    1200
cgatttgttt gtgtttgttc tctgaagttg agagtagcta tgatccatcc agcacagaac    1260
tgcaggtcct gcctgccggc tgcatataca ggacatgcca ttttgcaagc tctgggctta    1320
tggtttctct tttggagttc ttcttcttgc atgatctgtg ttctctaaca aaggaagcaa    1380
gatttagcaa ctttattcag agacaagaaa aggatctggc aaccttttgt ttctgtttta    1440
tcctactcgt aaagattgtt atttaagcaa aaatttccca aaagttttaa atataatttc    1500
catgatgtgc cactctcatg tccttgaacc tggcactcat tatgggctcc tcagaagtgc    1560
tgtagctaat gtcactaatc ttttgtatct ttgttcatag tcttgtattt tatgatgctt    1620
atccctttgt gctttccatg tttgatgtcc aaatgtcatg gcaatgtttt tgacttctag    1680
tagggggtttt agtaccttt tgttagataa gtacatccaa attctgttta tttattcaaa    1740
aatcattctg tttattcact gaaaacattt gtccattcaa tggactcata aactgtctgt    1800
gttttttcagg cttgaggatc catctagaag atagca                              1836
```

<210> SEQ ID NO 189
<211> LENGTH: 3000
<212> TYPE: DNA
<213> ORGANISM: Oryza sativa
<220> FEATURE:
<221> NAME/KEY: misc_feature
<223> OTHER INFORMATION: Ceres Promoter pOsFIE2-2

<400> SEQUENCE: 189

```
gcttaacaca tgaactacca aaatatactg atcactttgt tctagtcata cataccttaa      60
gtcattttat tctgcagtgt ttggattgga gggagcattc tagcatccct tgggtcgttc     120
cagcaaatgt ggttctccaa agcagagtaa gcacaacaca gtattttagg ttatgtttcc     180
cctatctcgt cacggacagc tcacaagtta atgtgattta tctcactata gatacgaaga     240
acatggagta tcctacatcc aaaggaagtg cccatgaagt tgtggagcat cgctacgatt     300
tgtgaccaaa tttgggtgca tgtgggcaat cgtattacag ccaccctgtt gttgatctat     360
atcgactatt atccgacgat atttatcatt atattatgac tagttagttt gtagattttg     420
agagggcaac ataagaagca atccagctta acctgttatg ttcttgatgg tagattctag     480
ttcatgtgtt gaatctgttc tccctgctgt agaatgtatc gagttgctgc tctctactct     540
gtacttttag aatacctttt caatcatttg gagtcagctg attgttgtac tacttatacg     600
ccacctgatt agtcatgtca acaattaaac ttgagcactg gttaagttaa gagtggcctg     660
```

```
attgtagttg ataatcacat tttattcgta gacattgtat gctggatctt tatcagccac    720
cgtcagatca tcctctgtaa taaatcttca tcagacgtgt gtgccaatcg caaggaacac    780
gaaatgcatc cgaaatgtta ctctgagtta atcaatacta taattcttgg tcaaattaat    840
tatttatatc tataaagttt aaattaaatt taggaaaatg aattcatgca aatcttgtgg    900
taagttgtca atttcataaa aaatccagct tactactccc tttttaggag tgtgttgtgg    960
ctgcacactt ctgccttttg atatatacgg ttctattctc ggtgtactcc tttattatta   1020
ttaaaacaat cccagttact tggtaagtgc taatcacgaa tcaaagtcaa cataacaaat   1080
catgtgcgta cagctataac tcgattacac aaacaacaaa attcatattt gaacataaat   1140
ccagttgtag catatctggt agtataaagt tttttttttg tatagaagag ttttaatttc   1200
tgtaagtttt ggaaagcatt taatcctaga aattgtagtg tagctcaact aaaaaataaa   1260
tgaacttgaa tcgaaattgg gttgtatcat aaatctttac cactcaaacg aatatttatc   1320
ctaaaccaca aatgactctt ttcatcaagg aatgttttgt tttcagcatt ttaaaaaaaa   1380
acttttctaa tatggttttc atgttcgtt  cttttgaaat ttaacatcta tttaatttgc   1440
acggctccat aaattcaacg gatacatatt ctgataatt  actaaggagg catatatcgg   1500
ctctcttaat acaccgctt  gtttctcaaa atttattttg agttttgtct acacattctc   1560
aaggacggta caaacacact atagatgttc acaatttttt ttttctaaag ttgattgatg   1620
gacaaatgtt tgaacatata aacatataag cactgaatat ttgcttatgc aggaggtatt   1680
tatatcaagt tcgatacttt actaccatag tccctaggac actaaaatgc cttcaatgat   1740
ctgatgaagc ctaagagaga atattgatca gtggagcgac ttgcaactac acatggcaca   1800
agtagactag acacggtata tattcatatt aacttgttaa aattttacta cttaacagtt   1860
cacttgtggt gcatccatat caattcttac ttacacaata tttgtaaaaa caacctaaca   1920
ctataggatg acctagacaa cctttatgtc aatcacactt agaagatgat cgtctttta    1980
ataaataatg tgtactacac accatgctct ccatatagat caagatctac aaaccccttcc   2040
acttataaac cttaccacca aaaactcatt aagttgcttc atttatctat gctattaaga   2100
aaaaaactta tttcgtttat gccatttcta gaaatggcta gtcacactat tcacaatatt   2160
atataataaa taaaagtttc aaatattcat ccaccaaaaa tcatcaagtc gtgggactta   2220
tatgttaatt agagaagtcc ctttgggtgc aatcgatttt ggaaacccta aattttttct   2280
atacatagaa gagagagatg tctagttgca attgcttttg cgatgtgcca accacccttc   2340
tagcttttcat cccacgtctac ttaattgcca ttcttcttct tctttttctt cactattact  2400
acctcctatc ttagcgaatc ttcttcttct tcactattac tacctcccac cttagtgaat   2460
tcatcctcat tgttcacaat gacattgcta agttaactag gtatgctaag tacacaatta   2520
gaatataacc tagagccttt gtttccatca tacttaaaag atgacatttt tatatagata   2580
aagtgtgcta ctcacaaggc ttactatata tatgtatgat acacacaaac tccacaaccc   2640
aaaactcttt caagttgtgt ggcccatcta tgctattaaa aagcccattt agcccatcca   2700
acatgagaaa ccctagggtt ttttccctat aaaagatacc taggttattg ttgctttttcc   2760
accccgcccg ccgccgctcc ctattcctat ttaatcccat ctctcttcct catcaccgct   2820
ctcctctctc caggcaagag gtacgcactt tttgtttcgg atttgaaatc tttgcttcgt   2880
tttactatca ttggtcataa gttcttttttt gaagatgttt gagaataagt ttatcattga   2940
gattatcgtc acttgtgata ggaagtacgc aacctcaagc cggacaagac gtgagcaaag   3000
```

```
<210> SEQ ID NO 190
<211> LENGTH: 2023
<212> TYPE: DNA
<213> ORGANISM: Oryza sativa
<220> FEATURE:
<221> NAME/KEY: misc_feature
<223> OTHER INFORMATION: Ceres Promoter pOsMEA

<400> SEQUENCE: 190
gagagcagaa catagtagcc gctgttttct gggggtgcaa tttgtgcaag atcgctatcc      60
ttatggacca tgcaagcacc aagcaatatt aagccaggtc caacagcggt cttggggaat    120
tcagaaatga gcttaaaaac ctccttgagc tggccagctc agccaaggag gtccatcatg    180
catgtgcatg ctcaatactt ggaattattg caaaatgatc ggtcattgac tggaagactt    240
tgcgccttc ctcagccaac cttatgtggc tgcatgcata gagtaccaac aggaaggtag     300
cgtttgttgg aataaggttt gcatccagca tgtccttgta gagcttcaaa gcctcagcac    360
cttggcccat gaaggccata tccagctaat tgcattccat gagaccacat tcttgctatc    420
catactgttg aagtgaagat gctccgagct tcggaaatgc ttccacacta tgcatacatg    480
tcaatgagca ctgtcatgac ataaacattg ggccccaagt cctcctcagc gataatccta    540
tgcagccact ttcccaggga caaagctcca agctgtgcac acgctgaaag agagctagaa    600
atgatgattg gatttggtca cacgctaagt accagcattt gctcaaagag gcaattgcc    660
atctccgtcc agccattcta ggcataccct ggtattattg ctttccatga ttccgattcc    720
gtggtcttct atggcatcgc attgaaggcc ttccttgcag actccatatc atttaaccta    780
cagtacaata tggtaattgc tgtcgacact ggagaattcg cagtaaatcc agacttgaga    840
ggaccatgta agcattgatc aagcagttca ttcccaaaca gactatacgg gatcagtgcc    900
agtgctcgag tttggcttca attccaaggc catcaaccca ataaacagat taactgatga    960
accaaccatg caattcgccg agcaaacata gattaagcat tgtaggcaac caaatctgga   1020
ttctccatca agtcaaagag acgccatgca gaattccaca tccccgctgt atacaccgag   1080
atcaaccggt cagaacatgc tcatactccg ccaaccctct cttcagaaca tgctcatact   1140
ccgccaaccc tctcttctct gcaagaggca tcctccccaa ttccccattg ttatatctgt   1200
tgctggtaag accgttgcca gcgtggttgt gtcagaccga acagactctg cactcgccat   1260
cctcacgaac gactccaggg cctccgaacc aggaagcccg gccggccatc agcgtgttcc   1320
acataacggt atccggcgac tgcacagtgt cgaacacctt gcgtgcgtgg tcacctctgg   1380
acagcatgaa gcgtacaggc tacagcttgg ccaatgcgga cgccacgaac gtgtcggcgg   1440
cgtaacccgc gcgtgcagcg cgccgcgcgc gggctgcgga gtcggttgga gacgacacgc   1500
cgccgccatg agagcaatga gcgaggtggc ggcgaaggcg aaggagaagt agtcgaggca   1560
agcggaagag aaggcggcag cggagaaagc gatcggggcg gcggaggagg tgggtgggag   1620
ggagggacgc gtagcggagg tcggaggagg agggagctga ggtttccggg gcggggtcg    1680
agagggtagt gtacggaggc gagggacacg gcgaggatct ggtcgaggta gcgcagtgtg   1740
aaggaaagcg cgatgaggcg gagggcgccg gcgaagagcg gcgcggcgga tagcgggagg   1800
aggcggcgcc ggcggggtct catccgattg gaaacagatt gggaagggg aggggtagg    1860
aatacgtggc gtcggcagta ttaggtagag agagaaaccc tttccatcct tgtctcttta   1920
gccccgaagg agagagaaaa atcagaaaaa aaaaccctc cgcgtgtggg ggaagcagag    1980
ctccggacgc tggcgccgct cgcgccaccg caccgcacc gcc                      2023
```

<210> SEQ ID NO 191
<211> LENGTH: 2034
<212> TYPE: DNA
<213> ORGANISM: Oryza sativa
<220> FEATURE:
<221> NAME/KEY: misc_feature
<223> OTHER INFORMATION: Ceres Promoter pOsYp102

<400> SEQUENCE: 191

```
gaacgaccca aacgcgtaaa tggtggtact ggtttccctg ctttgccgag taccagcagc      60
cacgaagaac gttacacaat cgagtacaaa atctataaga gcaagtttaa tagcatagcc     120
aaatactacc tctaaatcat ctatagccaa tttaatagtt catttattca ataattactt     180
ataaacatat actacaatca ttaatatatg gtcttacttc ttatacacat aatattttgg     240
agtccgtgtt acagctggct ataaatataa gggattttgg ttggatgtgg tacatccctat    300
tataatgaat ctagacatga aacctgtcca aattcatcgt gctaggatac gccacatcta     360
accaaaatct cttatcttta gggatggaga gagtaataat taaatgaagc taggtagagt     420
ttcccggtca atacgcttgc gtgtgcttat aagagcatgg ccaacagttt cccgatactc     480
ttcccaatat cagttttgag gagttttgtt ggaaaaaatc gctccaacag tagacctaaa     540
tcaccctaa aagcttggcg tttccaaacc cgcatatttc gttctccact tgtagggaag      600
agactcggcg cccaatcctt caaccgcatg cacttcgcgc gcgctgtgtg aaaattttcc     660
taccaggttc ttctttgtgc gttcgtctac ctgtgagtca atccatcacg ccagcagcct     720
catcttcccc gcagctgtct gggaaagcag ccatggctcc cccaagcttc cccagcgtcg     780
acatttttttt ctcagcggca gcgccagacc catctccaac ccaattgggc ggaccttcgt    840
cggcgctccc ccagcaccac caccgactcg aatcggccgt cgcccctatt catctccaat     900
cgtccctcga ccctaccgca tcctgcagca cagcctgtct ctcgcgtcag actggcgctg     960
cgctccccc ggtaatgtgc aggcgacaaa ggccccatgc gatgcgacca gcagccggcg    1020
acaaccggag gtgcccagtc gctggccttc atcgaatcat cgtgcacctc ggtcggagtc    1080
gatttctgat tgttgctgct gctcaaatct ggagcttgct attgctgaga actgcttggt    1140
ggtggtactg gaaatttgtt gtttgctggc tgatgaaaac tgttgttctt tgctgctaaa    1200
aactgctgct tgctagtact gaaaagtact attgcagctg ctgaaatatc ttgctgcttg    1260
ctgctgaaaa cttcaagttg ttaacaccgt tcacactaaa aaagctgaaa ttttttttct    1320
gggctgaaaa ccccattgtt gatgattgca gaaccaatat ttttccatgt aaaatacagg    1380
agatcgtggt aataatcaag tgaaatatca ttttggggca atactcaga tcgtacctga     1440
agccaatgga acattgttc aatgcttaaa ctgtcagtta tgatgtcaaa gagattgatc     1500
actgaatgtc ctgaaaggag ccgtgaggag gatgcagcat tgcagcgtgc gcgagcgtga    1560
gtggaggaga ggaatgacga ttctgttggt agttgtcgat gtggcctact ttttttgttt    1620
tgaggattaa attttgggaa tctcttggag ataaaaggta ttctcatacc ttaaatcctt    1680
tttagagatc taaaaaaaat gatttagggg attgaatttt gggtggctgt tggtgatgct    1740
ctaagttgca catcctgggg aaaaaccctcc ctaatccatc agcaaaccga tcaaccaccc    1800
acgacaagtc gacgccaccg tttttttttt ctccctccta agtcctaacc ccacaaaaat    1860
cccgcgaact ttcgtctcac cacgcgccgc gtgcccccta caaataccaa acaacaccca    1920
ccacgtccac tcacaaacca cgcaggaaac ctcagaaaat caccgtacgc gacgcgggcc    1980
caagaaaacc ccgacagaaa ccgcgcagca gcaacaccac caccggcgtc ggag          2034
```

<210> SEQ ID NO 192
<211> LENGTH: 1877
<212> TYPE: DNA
<213> ORGANISM: Oryza sativa
<220> FEATURE:
<221> NAME/KEY: misc_feature
<223> OTHER INFORMATION: Ceres Promoter pOsYp285

<400> SEQUENCE: 192

```
ggcccgagtt aaacgatctt ccacgtgtca gcgaatccta gtcgttcgat gaatctgaat      60
ctgacttgtg gtggttggac ggccacgtgt taaaaagggg aaacgtccgc atcacccgat     120
gctgggacat ttgcaatttc gatccagctg tagattgacc agttgttact ctctttttt     180
taacaccata caaacgtaat actccctctg tcccaaaata taagtatttt ttttaacctc     240
ggttcagtct tcgaggtgct actttgacca ataatattta taaaaataag atgttttaaa     300
taaagagagt tgcatattat gatagctcgt ttaatgataa acaaagtacc atcaaattta     360
catgattaat cttttaatt tatttgctat taatagttaa aatttaaaaa gtttgacttc     420
acactgttct aaaaatactt atattttggg acggagggag tacacattag agcaggtaca     480
atagcagact agtagccagc tataaacata ttttaatgag ataaagatg agagagaaca     540
gcgggctaca gatctgtagc cagctgcagc acggactcca agacattgtg tgtgtatgac     600
aggtgggacc atatattaat agtacagtaa gtaactattg tatgaattgg ctattagatt     660
agctataggt gaattgtagc tagtagtggg ctatactatt gaacttactc ttatatctct     720
caatatctcc agaaaactag gacgatatat attgatatta acaaagtcat catagatatc     780
tcgctatcga catatatatt acctatcact gaaaaaataa ttaatcataa atgcaagcac     840
atatactacg ttcaacactg aatgtaggta gattggtaga cgggttccac cgcaagaaaa     900
gcattgcacc agtgaagaaa gaaacatcgg aatttgtatg tagtttgttg tttgatgaat     960
tcttttgatt aaaaaaaact aaaatcagag ttgattcagt taatggtgtt gcctacgata    1020
tacttccata tcatgatatc actgtagact atgaatcata tctttaatta aaactaaatc    1080
aagaaattaa gtatgagacc tcaactcaat gaagaatttc tagttgaaaa acattcctag    1140
tgtgcgttcg gatggaggta gggatcttct ctccgttcat ataaaaccgg atggttcatt    1200
agaacatgat taattaagca acagttaatc taaaaataaa ttaatatttt ttaagaaatt    1260
tttgtataga gatcttttga aaaaaataca ttggttagaa agcatactaa taaaagaga    1320
aaaataagaa catagtacta tagtagaaaa tgagaacttg gagtatttga gaggatggga    1380
aataagaaga ttaagaagat gcgtaaagtg aacggttaac gcatgattga ttaattaaat    1440
attaattatt ttaaatttgg aaaataaatt agtatgattt ttaagcaaca tatatatata    1500
tatatatata tatatagaaa aacatagttt tagaaaatat aagcgtgtaa acgatatgc    1560
aggaacgaaa cgttgagcat tcaaaatttc aaattgaaca tatgaatcaa gagagaataa    1620
aaaaagaggc cttctaggct ggcatggaca attggacatg ttttcaacta gggtttcaag    1680
cttcgagcat ccacttttgt ccttgcaaac tttatacggc aaggcccgtg aatctagccc    1740
cccacaccac cccacccgcc cgcgccgcgc ggccgcctcg cctcccctcc cttctcctcc    1800
tctccgcccc cgccgccagg ccgtccacct ccgccgtctc ctcccccatt cgcacccaag    1860
gcgctggcgc ggaaggc                                                    1877
```

<210> SEQ ID NO 193
<211> LENGTH: 1000
<212> TYPE: DNA
<213> ORGANISM: Arabidopsis thaliana

```
<220> FEATURE:
<221> NAME/KEY: misc_feature
<223> OTHER INFORMATION: Ceres Promoter PT0565

<400> SEQUENCE: 193
caccaaatat agtgttattt caatactaaa atggtgttat ggttggagat gccctaaaga      60
taaacatgac gagacacgag atttattaat ttcttgatca accataactt ataacttaa     120
tattaatttc acttaataat ttccaattaa gtgaatcttt acttcaccaa aagttcctaa     180
cgaactctta tttctagca tcaatattac catgaactag catcaatact atcatgaaaa     240
attcctactt cctatccaac tcttaataac aatgctagtc ttaacaatat tcatcaaaaa     300
cttgatatag accttctaac ttagccacga ctagtatcgg tgaataccaa aattaatgta     360
ttcatgagaa cttgagattt ctctaatgta ttcttgttac taaacaagta acaacactca     420
agaaatatca tgatcaaata ttttactcat aaactccata tttcacattt tgaaaatttt     480
aaacagcaaa tcacattgaa ttttcgtggt aaaagtattt aaaattgaaa atagcagct      540
cctgatttca atgtataaat ttatctttat atggtttatg tctccaactt attttaaaaa     600
agagagaaag agcacccaaa aggtgaccgt ttgaaattcg aatttatttc cgtttgaaat     660
tcgaattcaa aaaagtaaa ccgaaccgag tctcgttact gactgtcaca cattgtttcc      720
ctaaaagcta attaacccat acgtggcgta ataacagg tcagtgatca atactaaata      780
acagacatac acctttaaaa ttcgtgcacg ctccaaaaca aatctacac ttcaaaatca      840
acggtcacga tcattcctca aatttcaaaa aattatttaa cctcacttcc ttcgctttgt     900
ttttaaaacc tctctctctt tctctttctc tttcgccatt aaaactctgt ttccttttc      960
agagattctc agagaagatt cattttaccc taagaaaaaa                         1000

<210> SEQ ID NO 194
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0015

<400> SEQUENCE: 194
ttgagcctta ttgttgttat tgacttttag ccaatagaaa gagatggaaa ttcaataatt      60
atccacaaaa ttccaaatca ttggtgtaca aaaagatcta aggctgttat attttcaaaa    120
aagaaagaaa agaaatgcaa caaatatgga ttaaactgtg gtttgtaaat tgagctttgc    180
atgaaaactt tatcactatg atttcactac tccatatta ttgactaaag tggcactaat     240
gaatttctta atcatgaaat cttgtatcaa aaagtactaa aataaacatg acattggcaa    300
ttaggaaaat tctaaattag aaattagtaa aaatgaaagg tgaaagggaa agatgatgat    360
atgaattggt tggtgaccag gagaaatgta tcccgatttt tgcagacact ttcagtgtcc    420
ccattcatat aattatggcc cacctcgtta agatttttca ttcaccacca taacaagatc    480
taagcttaga tttcatgtaa ttaaacatat aatatacttg ccaatactat ctaataaagt    540
atacttaagc aaaaattatt actctagtgt aaggcgatga aatataagtt tagttgaaaa    600
tttatgtcga tataacaaag tataatgaat taagaccttg gttttcgatt aacaaactaa    660
ttaaacacta gttttgccta ataaaaccgg gaatcgtatt caaaaccgaa cgacaaaaca    720
agggacaagt tgagagacaa aaccaaatca gcatctttct tccagaaatg tcatgaccac    780
atgacgtcat cttgacccct cttccattgtg atatctgtgg ataaagcgca cgtgtttaat    840
```

```
tcacgaacct tcgtagtaac gaaaaatcca caactttcat attttttaat tacccactaa      900
actaaaacaa atttggaaaa acatgaaaaa cttttctttt ttttccaggt tcgtgaacct      960
cgtaccctct atataaacct cttaaccacc ttccacata                             999
```

```
<210> SEQ ID NO 195
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0087

<400> SEQUENCE: 195
```

```
tgaattgagt aaaatgtgtt ttcaaacagt taggtggtag aaggtaaagg taataacatc       60
atgatcttac taaagaatt gttgcatact aactatcaat attctcaaca acataatata       120
atgttttttt aggtaatttt ccattttaat tttttgtgat taaacaatta aacaactcga      180
atgatgatga taaaaaaaaa aaattaacaa ctcgaataag ttaaagtagc aatacacatg      240
tcgttcaatt caaccaataa agtaagactt atatttttaa gaagttgact aatagcttaa      300
taagttggaa aacttgtgta gtttcttaat tcccacgtgc agtaagaaat aaaaatgaaa      360
aaaattatta tatccttccc actctgcgac ttttcttta ttttatcaaa tattaaaaag       420
attcatatca cagtttacac attgaaatca taaacgataa ttatgtattt tgtaataaaa      480
agttagttct gaagctcata cttggatag tcgctagtcg ctaatatgct ccttgtaata       540
attaaagtca ctacgacgca cgtcaaagcc gatatttagg gcttaattga tgcgtgtttt     600
tcttttcata taatagtaat ataaattagt actaataaag tatgatggat ggttgagaca      660
gaaaagaaaa aagatgactg tatggtcatc attacaaaga agaatgtatt cttcatgttc      720
ttaagaataa taaaatgtca cttgtaaatc aagttggtaa gcattttgag aactttgttc      780
gatgcaacgt atgatgattt atgtagacaa aagataaaac cgtatcttca actattgcca      840
agaaaagata aaacctaatc tagtcagtct ctcaacataa atacaaccca atagccaaac      900
tgtgtccaat tcggagagaa actaaactaa aacaaaacac aaaagcccaa cataagccca      960 ataaaacccca ttttataaac agaacattac taacactca                            999
```

```
<210> SEQ ID NO 196
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0093

<400> SEQUENCE: 196
```

```
atgatgaaca ttctacatat ataattatta tgtttaagca cttagacagc ataaattctt       60
tctaattata taaatctaac cttgttacat tgtacatcta taaattactt gaagaaataa      120
cgagttctat ttcttttaa aaattaaaaa tactatacca tatctcagtg attaagttga       180
accaaaaggt acggaggaga aacaagcatt tgattcttcc ttatttatt ttattcatct       240 ctcactaatg atggtggaga aaaaagaaa atacctaaca aacaaatata tattgtcata      300
caaaaatatt tctatatttt tagttaatta gtttatattc ctcactttc agggcttata      360 taagaaagtg agcaaacaca aatcaaaatg cagcagcaaa tactatcatc acccatctcc      420
ttagttctat tttataattc ctcttctttt tgttcatagc tttgtaatta tagtcttatt      480
tctctttaag gctcaataag aggaggtact attactacac ttctctctac ttttacttgt      540
```

```
attttagcat taaaatccta aaatccgttt taaattcaaa aataaactta gagatgttta      600
atctcgattc ggttttttcgg ctttaggaga ataattatat gaaattagta tggatatctt    660
tactagtttc cattcaaatg attctgattt caatctaata ctctcactct ttaattaaac     720
tatatgtagt gtaatttcac actgttaaat ttctaccatg tcatgtatat tagagttgca     780
tagaaaattg taaacatcc atttgaattc gaatgaaaca aaatgtttta aaataaaatt      840 ttggtttta aagaaaaat ctaaaactga attatatcgt ttaaccaagt tgtaaaagtc       900
ataaaacgta gtatcttgta aatcgctctt ccacggtcca aatagacttc tagtaataaa    960
caagtaaaac taattttggt ttcttactaa ttttcacaga                          1000
```

<210> SEQ ID NO 197
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0108

<400> SEQUENCE: 197

```
ttagctgaac caggaaattg atctcttata ccagtttccg ggtttagatt ggtttgatgg      60
cgatttgatt aaacccccga aattttatgt cgtagttgtg catagtatta ttattctttg    120
cggacaatag acgtatcggg accaagttct gtagcaaaat tgtataagct taagtttgat    180
gaaatttaaa ggtaatcact aaaacccaaa tgggacaata aaccggtgaa gatttagagt    240
ttttaatttt gactcatgaa tctggagaaa gagccctcgt taaaaggagt gaatcaatcc    300 atagggaaa aagttttgtc ttttaaaaa ctaagaaccc aaaccttaat agaagcagct      360
caatgtgtga caactttcca ctggcactaa gataaagtga ctagcgatga gtgcaattat    420
tgaaatagta gatggtaaat attacataca agagtaaaaa tatctttatg tcaatgctta    480
attcagtgtt tctggttaac aagagaaact tctctaactt tcgtaattgg gtcttataaa    540 atttttatgca attatgattt tacccttta ctacttttca ttagctttca cgaatctatt    600
ttgacaagag aaatcattag aggtaaacat gcttttggt caagggcctt aacagttcca    660
ccaatcaagc tcaaaagttg tacttaaccg acatcttctg tgaaaacata taattacatg    720
tacaaatcaa aactaccta tgaaataaat agaaatattg cagttcattt ctaatttaac    780
ctcttcaact tttaaaacta tttacattc tttatgtcat ttctagtcat tttgatgcaa    840
attgtaccat ttatggatta tcttcacaaa tttttaagtt ggtgaaaact ttttggtggg    900
tagttaaaac ttgaaataga aatttacttt accaaaataa actaatgaaa agtaatcact    960
ccactcccta taataagatt tccaacgttc ccactaagc                          999
```

<210> SEQ ID NO 198
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0022

<400> SEQUENCE: 198

```
tagttccatt acaatttcca aatgatttgt tacaaagcta caagattatt cgaaatagga      60
tttcatccat aagagagaat ggtgtggtcg acgctacaat gttgatttat tggttgtggt    120
ttgcatcttg gggatgtcaa atcctaagtt tcaagttctt gtaaaaacgt tttcaggttt    180
```

```
ctttaatata ttttaatatt aatgtaaaaa gaaaagatat agcttttgta caaaaaaatt    240
tgtttaatca ctatgtagga ggatgcgatc aaattcatgg aatgatgtat tattagcttt    300
tctatcctca ctctaaaaac aatactatag tgagttaaat aatttgatca tttcaatgta    360
gattaaaatt ttattaaaag aagaaaaatt taaaagccta taacaaaata aaaaaggagg    420
ctcgaggtat gatgggtgta gcagaagagc tggcaacagc tatcgactga gtgattacga    480
actcagtact cagtgttctc agctcacaca ctcttttttt gttctctttc ttttggacag    540
ctttcatttt ctcttttctt ttttctattt tgtttcaaaa ttccatccat attaaaatag    600
gcctgatcat gagaataaag gaaatactaa tgatgagttt ctcaataatg caataagatg    660
caattattat gagctattta ctattgaaaa tgagcaaata aatgtcaaaa cacaatctgg    720
ttaagttaga gcaactccat tgtataggat tcatgtagtt tctaagaaaa caaaatgtat    780
taatatttta cttttacatc caaaaaacca acttatatga gtaatagaaa cgatcctaat    840
attaggaatt ttagagattt tctctcatct gtttcttaac ttttcaatat ttttatttt    900 taaaattgta tgagtttcta ctaagaaact actgctggag ttggtcttag cttcccaatg    960
cttctccacc tatatatatg catatctcct tcttaaaac                          999
```

<210> SEQ ID NO 199
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0080

<400> SEQUENCE: 199

```
aagcggcaat ttagtaagaa gtactcaaag tatcatttac caaaagtata tggttttggg     60
aagagttgtt agggatgtat tctttctaaa cagatgatat gacgatgttc ttgaaaacta    120
atgttaaaga cggaatctct ggcatcttca ctcgggagat atattaaacc gttgattgta    180
gttagccatg tacttagctt agtgcacaaa taatctgctg caagaaatct ttttctatta    240
taatatctct catttaaaca ttagaacata ttgtttaact tgttcttcta gaaataaaac    300
tgctaatttc ttatggtaaa ctattttcct ttagattgca caatcgaact cgaaaatcta    360
gtggagacta tgtgactatg tttatatata tgaaacctaa atcaaattat cccaataatt    420
gggagacaca aaagaaaaat tacgaaagaa acaggaaat caaatcaaaa gataaagaga    480
aggtaaaaaa aggcaagaag cactaatgtt taatatttat agttttctcc attaaagaaa    540
aagcgatgat gtgtgttctc atcttttgtg aaagtatata tattgctttt gcttttctca    600
aaagcaaaag actcatccaa caagaacaaa aaaaaaaact aaagctcaat ccaaaagacg    660
aagaatgcat tggatactac aacttctttt tcacttttct ttcaaattta caattatgat    720
tttcacaata cagtttattc aaaaataaat aaaaaaacga ggcatgaaaa taatgattat    780
cctcttcact tattaagcca ctcactataa gcagagcaac tccagaacat agtgagcccc    840
caaaacatta aagcatgatg atgtctaatg atgatgatct tcttcgttcc atttctctaa    900 attttttggga tttctgcgaa gacccttctt ctctttctct tctctgaact tcaagattcg    960
tgtcggacaa attttttgttt ttatttttct gatgttaca                          999
```

<210> SEQ ID NO 200
<211> LENGTH: 3000
<212> TYPE: DNA
<213> ORGANISM: Arabidopsis thaliana
<220> FEATURE:

<221> NAME/KEY: misc_feature
<223> OTHER INFORMATION: Ceres Promoter PR0924

<400> SEQUENCE: 200

```
atctataacg agttaacatg ttgccagttt gaatcaagaa gcttggatga tgaatgaatg      60
gatcggtttg tggtacaatt cttaaaattg tagtagagga gacagagaaa aaacatgata     120
agactttggt atttacaact tgacggagac aagacagtaa gccaaatctg tcacaaaaac     180
actcaaactc ttttctcagt gttttgagtt taaagagaga cttattcact tcccctttcg     240
taacacttat ttgtctccca accaaacagt ttctgtcctt tcccttgtcc tcccacgtgc     300
atctttatat ctcatgactt ttcgtttcta gatcttgaat aatgtcttag tggattaggt     360
ttgttgtcgg taaattaggt gaccgttttt ttcttatatt tggaagatcg cgggatgaag     420
cagatactga gtttcagggc atacacacct aatttgaaaa tcattgttag tccaatttca     480
ctttaatctt gtttacaaaa aaattgatct gaaaatgttg atgggataag taaaaatgta     540
agttttgcta gtagtcatga tataataata gcaaaaccag atcaattttg agcaaaagga     600
agaaacaaaa aacagatcga tcccacgagc aagactaagt gtaaagtggt tcccacaaga     660
gccatatgga tatggtcctt caacttttaa agcccattac ttcagtggtc gacccgacat     720
tacgccacga gtagtcacgc acgcacgact ccgttcacgt gacattcacg ttgatatttc     780
cccctctact ctcttctgct tggttgatct aaaaaacatg aagagaccaa cctaatttca     840
tattaatata tgatatagac ttcatactca acagtcactt tcgtaatcca aatccatatc     900
ttacgaaatt agttcttaat aaaggttgtg gattaagtta taatattgtg ttaagagtta     960
agacacagca tataaccttg taccaacagt gctttattct taaatggaaa caaaacatat    1020
gtcaatgtca agcatacagc taaaatatca ttatctaata ttaagagtaa aacaagataa    1080
ttaaaaattg aaacaacacc atatttttat agctttactt atcgtatttt tctagtcttc    1140
atggtaattg tgttgcttta ttttgtttat aaatgaattt ggttcgacca gatagtctaa    1200
tatcagtttt taaacactgg ttttaataaa atcatatgtc ggcaattcaa cctgttacgt    1260
tgtatgattg tatcctagtc aaataggga ggaggtacta gtcgtttcaa ttagtttacg    1320
taatcaatcc aaagaaacta taagctataa agatcctcaa tttgttggtt acaataaaaa    1380
caacagttgt caaatttat gtttataaaa agtaataact atgttccttc ccatatagag    1440
caaagtacct caggataggc aaaccgtact taatagccct tattcataat ttgatccaac    1500
tcttccccac aaaattgcaa ctgatgaagt caatacttgt atagtgagtc aagctataaa    1560
tgtctagtga tagttttgtc tcttaaaagg ttaacaaaag ttatgacaag ctgaaaaatc    1620
agagtttgct aggagtatta cttacagtta tcagtttaag tatcacattt atagtattgt    1680
atacaatgat tcttaaattc ccctttttcc gtgcgaaacc aaattttcta ttggaaacat    1740
agaatgtaaa caaaaatatg ggacgttgtc cgttccaaca ttaaccaaac ttgtctatta    1800
ctaatattcg tgttggtttg atgttggatg tctaaattcg ttgaatcatg tgtctcttga    1860
cgaaatatgc atcttcttat ttcttagtat agatgcactt tatcattctt ttagtacatg    1920
cttaattttt ttttttaaaa tatgttgatt gtcatattgc caaagtatg aattaaagac    1980
gcacatctaa cacaagttag cagccgtaaa tccttccata aatttatttt gcaagttttg    2040
ctcattatat aatgagcgga atttatgata taatcgtttg taataatgtt atgttttgat    2100
caaaatttga aattaaaagt aggtgagaac ttgttataca gtgtagataa ggtggatctt    2160
gaatataaaa ataaaattta taagatgtat ttaaagcaga aaagcataaa actttagata    2220
```

| | |
|---|---|
| aaataatgta aaaatgtgtt agcatcaatg ttgggatatt ggccgacccg aacttaatca | 2280 |
| atgtcggaag ccattacttc tctcccaaaa gacctttttc cttcggagaa ctaggaactt | 2340 |
| cctcactacc tttcgcttaa cgtgaaagcc ataaatttca tatattcata aaaatcagaa | 2400 |
| aatctaaaac tgtttagtat cacctgtttt tggtatagac tattggtttt gtgttacttc | 2460 |
| ctaaactata tgatttcgta cttcattgga tcttatagag atgaatattc gtaaaaagat | 2520 |
| aagttatctg gtgaaacgtt acttcagtca tgttgggtct agatttacat actactatga | 2580 |
| aacattttaa gataataatt atcctagcca actatatgtt ctatattatg ggccaagaag | 2640 |
| atatagaact aaaagttcag aatttaacga tataaattac tagtatattc taatacttga | 2700 |
| atgattactg ttttagttgt ttagaataaa tagtagcgtg ttggttaaga taccatctat | 2760 |
| ccacatctat atttgtgtgg gttacataaa atgtacataa tattatatac atatatatgt | 2820 |
| atattttga taaagccata tattactcct tgacctctgc ccccatttcc ttttactata | 2880 |
| aataggaata ctcatgatcc tctaattcag caatcaacac caacgaacac aacctttttcc | 2940 |
| aaagccaata ataaaagaac aaaagctttt agtttcatca aagacgaagc tgccttagaa | 3000 |

<210> SEQ ID NO 201
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0388

<400> SEQUENCE: 201

| | |
|---|---|
| agaagtattc acgcaccaag gttatatttg tagtgacata ttctacaatt atcacatttt | 60 |
| tctcttatgt ttcgtagtcg cagatggtca attttttcta taataatttg tccttgaaca | 120 |
| caccaaacctt tagaaacgat gatatatacc gtattgtcac gctcacaatg aaacaaacgc | 180 |
| gatgaatcgt catcaccagc taaaagccta aacaccatc ttagttttca ctcagataaa | 240 |
| aagattattt gtttccaacc tttctattga attgattagc agtgatgacg taattagtga | 300 |
| tagtttatag taaacaaat ggaagtggta ataaatttac acaacaaaat atggtaagaa | 360 |
| tctataaaat aagaggttaa gagatctcat gttatattaa atgattgaaa gaaaacaaa | 420 |
| ctattggttg atttccatat gtaatagtaa gttgtgatga aagtgatgac gtaattagtt | 480 |
| gtatttatag taaacaaat taaatggta aggtaaattt ccacaacaaa acttggtaaa | 540 |
| aatcttaaaa aaaaaaaaag aggtttagag atcgcatgcg tgtcatcaaa ggttcttttt | 600 |
| cactttaggt ctgagtagtg ttagactttg attggtgcac gtaagtgttt cgtatcgcga | 660 |
| tttaggagaa gtacgtttta cacgtggaca caatcaacgg tcaagatttc gtcgtccaga | 720 |
| tagaggagcg atacgtcacg ccattcaaca atctcctctt cttcattcct tcattttgat | 780 |
| tttgagtttt gatctgcccg ttcaaaagtc tcggtcatct gcccgtaaat ataagatga | 840 |
| ttatatttat ttatatcttc tggtgaaaga agctaatata aagcttccat ggctaatctt | 900 |
| gtttaagctt ctcttcttct tctctctcct gtgtctcgtt cactagtttt ttttcggggg | 960 |
| agagtgatgg agtgtgtttg ttgaatagtt ttgacgatca | 1000 |

<210> SEQ ID NO 202
<211> LENGTH: 283
<212> TYPE: DNA
<213> ORGANISM: Arabidopsis thaliana
<220> FEATURE:
<221> NAME/KEY: misc_feature
<223> OTHER INFORMATION: Ceres Promoter PD0901

<400> SEQUENCE: 202

```
caaagtattt gacaagccat atggttttgg atcaaaaagt cggtccaaaa ttaatgtttt      60
atgtgcaaga accgacccat tgtacacacg tgttaacatc ttcaagactt tcatctctat    120
ttttcttttg gtcattaaga tacccattga tccgaatctg ttacattccc acctactttt    180
ttaattttta ctatccactc caaattaaac acaaccgatg attttaataa ttggaagctt    240
tttaaaatat ttctccacgt gcctctttgt gtttgtctat ata                      283
```

<210> SEQ ID NO 203
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0623

<400> SEQUENCE: 203

```
aaagttattg acattttgaa aggaccgtaa atattaccaa aaaactgacg gagttaggat      60
cggccacgta gaaagggaca aagagagaac agtcacggac tcggccagac taagtatggg    120
cctgtctgaa tccaaactca gctaagttcc aaaagcataa agagagatgt gtaatgaaat    180
gaacgtattc tagaaacgaa agcaatgtta tgctttgttt ttgagccaca tgttttgggg    240
agatggagag aatcttttt acgttttaa cctaacccac ttggcacttg gccaaaaaag    300
tgagaagaaa ctgtggcgaa tgagtaggcc acgccatgga ctttgttcct tgtccttcaa    360
aagttaaatt tatgttatgc gtggggacaa tctaagcaac gtggttcctt taaatatcgc    420
agcttcctct tttacactt tggagcctac gtgttttgtt ttggaccggc caaatacacg    480
agtcagtcag tttagaaata atttggatgt ccaaaaatct tggagatcca aataaaataa    540
ttagcatgtt ttagttcata agaatatgaa atgtagataa actgtctata ttaattttc    600
catagaattg gcttttttatc gaggtgatgt acttaatgac tttgttgatt actactcgta    660
taacaataaa gaatatgata ctatgtgaga cttataatga atttggtgtg tgttaattaa    720
tccagttgaa acagttttaat aacaaatcag aataaaaatt gtagtaagaa aatttgaacg    780
ctgatccttc aacctagata gtgaaccttt caaatactat atgattcacg tgtaatgttt    840
ttgaccgttg gttattttg tgtgaactat attaacttat caatatcgaa aggctaaata    900
agtaaataac taaagaaag ttcaggaaac aactcgacct aatgacctat catttctgat    960
cacccgtcct ataaatacat acgtaagatc attcgttact                         1000
```

<210> SEQ ID NO 204
<211> LENGTH: 33
<212> TYPE: PRT
<213> ORGANISM: Artificial Sequence
<220> FEATURE:
<223> OTHER INFORMATION: Truncated version of Ceres CLONE ID no.
      100021733
<220> FEATURE:
<221> NAME/KEY: misc_feature
<223> OTHER INFORMATION: Ceres CLONE ID no. 100021733_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

```
<400> SEQUENCE: 204

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 205
<211> LENGTH: 33
<212> TYPE: PRT
<213> ORGANISM: Artificial Sequence
<220> FEATURE:
<223> OTHER INFORMATION: Truncated version of Ceres CLONE ID no. 1036726
<220> FEATURE:
<221> NAME/KEY: misc_feature
<223> OTHER INFORMATION: Ceres CLONE ID no. 1036726_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 205

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 206
<211> LENGTH: 33
<212> TYPE: PRT
<213> ORGANISM: Artificial Sequence
<220> FEATURE:
<223> OTHER INFORMATION: Truncated version of Ceres CLONE ID no. 1482731
<220> FEATURE:
<221> NAME/KEY: misc_feature
<223> OTHER INFORMATION: Ceres CLONE ID no. 1482731_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 206

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys

<210> SEQ ID NO 207
<211> LENGTH: 80
<212> TYPE: PRT
<213> ORGANISM: Artificial Sequence
<220> FEATURE:
<223> OTHER INFORMATION: Truncated version of Ceres CLONE ID no. 1554560
<220> FEATURE:
<221> NAME/KEY: misc_feature
```

```
<223> OTHER INFORMATION: Ceres CLONE ID no. 1554560_T
<220> FEATURE:
<221> NAME/KEY: misc_feature
<222> LOCATION: (17)..(78)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 207

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
                20                  25                  30

Ala Asn Leu Gly Leu Arg Phe Phe Leu Lys Val Phe Glu Ile Ala Pro
            35                  40                  45

Ser Ala Lys Gln Met Phe Ser Phe Leu Arg Asp Ser Asp Val Pro Leu
        50                  55                  60

Glu Lys Asn Pro Lys Leu Lys Thr His Ala Met Ser Val Phe Val Met
65                  70                  75                  80

<210> SEQ ID NO 208
<211> LENGTH: 77
<212> TYPE: PRT
<213> ORGANISM: Artificial Sequence
<220> FEATURE:
<223> OTHER INFORMATION: Truncated version of Ceres CLONE ID no. 1802327
<220> FEATURE:
<221> NAME/KEY: misc_feature
<223> OTHER INFORMATION: Ceres CLONE ID no. 1802327_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 208

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
                20                  25                  30

Gly Leu Arg Phe Phe Leu Lys Ile Phe Glu Ile Ala Pro Ser Ala Lys
            35                  40                  45

Gln Met Phe Ser Phe Leu Arg Asp Ser Asp Val Pro Leu Glu Lys Asn
        50                  55                  60

Pro Lys Leu Lys Asn His Ala Met Ser Val Phe Val Met
65                  70                  75

<210> SEQ ID NO 209
<211> LENGTH: 77
<212> TYPE: PRT
<213> ORGANISM: Artificial Sequence
<220> FEATURE:
<223> OTHER INFORMATION: Truncated version of Ceres CLONE ID no. 1876458
<220> FEATURE:
<221> NAME/KEY: misc_feature
<223> OTHER INFORMATION: Ceres CLONE ID no. 1876458_T
<220> FEATURE:
<221> NAME/KEY: misc_feature
<222> LOCATION: (14)..(75)
<223> OTHER INFORMATION: Pfam Name: Globin
```

-continued

```
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 209

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Thr His Ala Met Ser Val Phe Val Met
65                  70                  75

<210> SEQ ID NO 210
<211> LENGTH: 79
<212> TYPE: PRT
<213> ORGANISM: Artificial Sequence
<220> FEATURE:
<223> OTHER INFORMATION: Truncated version of Ceres CLONE ID no. 1879148
<220> FEATURE:
<221> NAME/KEY: misc_feature
<223> OTHER INFORMATION: Ceres CLONE ID no. 1879148_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 210

Met Ala Leu Ala Asp Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 211
<211> LENGTH: 33
<212> TYPE: PRT
<213> ORGANISM: Artificial Sequence
<220> FEATURE:
<223> OTHER INFORMATION: Truncated version of Ceres CLONE ID no. 1884696
<220> FEATURE:
<221> NAME/KEY: misc_feature
<223> OTHER INFORMATION: Ceres CLONE ID no. 1884696_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40
```

```
<400> SEQUENCE: 211

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 212
<211> LENGTH: 76
<212> TYPE: PRT
<213> ORGANISM: Artificial Sequence
<220> FEATURE:
<223> OTHER INFORMATION: Truncated version of Ceres CLONE ID no. 1916866
<220> FEATURE:
<221> NAME/KEY: misc_feature
<223> OTHER INFORMATION: Ceres CLONE ID no. 1916866_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 212

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75

<210> SEQ ID NO 213
<211> LENGTH: 33
<212> TYPE: PRT
<213> ORGANISM: Artificial Sequence
<220> FEATURE:
<223> OTHER INFORMATION: Truncated version of Ceres CLONE ID no. 1950105
<220> FEATURE:
<221> NAME/KEY: misc_feature
<223> OTHER INFORMATION: Ceres CLONE ID no. 1950105_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 213

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys
```

-continued

```
<210> SEQ ID NO 214
<211> LENGTH: 79
<212> TYPE: PRT
<213> ORGANISM: Artificial Sequence
<220> FEATURE:
<223> OTHER INFORMATION: Truncated version of Ceres CLONE ID no. 1990746
<220> FEATURE:
<221> NAME/KEY: misc_feature
<223> OTHER INFORMATION: Ceres CLONE ID no. 1990746_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 214

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 215
<211> LENGTH: 79
<212> TYPE: PRT
<213> ORGANISM: Artificial Sequence
<220> FEATURE:
<223> OTHER INFORMATION: Truncated version of Ceres CLONE ID no. 2033803
<220> FEATURE:
<221> NAME/KEY: misc_feature
<223> OTHER INFORMATION: Ceres CLONE ID no. 2033803_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 215

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 216
<211> LENGTH: 33
<212> TYPE: PRT
<213> ORGANISM: Artificial Sequence
<220> FEATURE:
```

<223> OTHER INFORMATION: Truncated version of Ceres CLONE ID no. 2034916
<220> FEATURE:
<221> NAME/KEY: misc_feature
<223> OTHER INFORMATION: Ceres CLONE ID no. 2034916_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 216

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 217
<211> LENGTH: 33
<212> TYPE: PRT
<213> ORGANISM: Artificial Sequence
<220> FEATURE:
<223> OTHER INFORMATION: Truncated version of Ceres CLONE ID no. 513071
<220> FEATURE:
<221> NAME/KEY: misc_feature
<223> OTHER INFORMATION: Ceres CLONE ID no. 513071_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 217

Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys

<210> SEQ ID NO 218
<211> LENGTH: 33
<212> TYPE: PRT
<213> ORGANISM: Artificial Sequence
<220> FEATURE:
<223> OTHER INFORMATION: Truncated version of Ceres CLONE ID no. 522921
<220> FEATURE:
<223> OTHER INFORMATION: Ceres CLONE ID no. 522921_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 218

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp

-continued

```
                 20                  25                  30

Lys

<210> SEQ ID NO 219
<211> LENGTH: 76
<212> TYPE: PRT
<213> ORGANISM: Artificial Sequence
<220> FEATURE:
<223> OTHER INFORMATION: Truncated version of Ceres CLONE ID no. 546001
<220> FEATURE:
<221> NAME/KEY: misc_feature
<223> OTHER INFORMATION: Ceres CLONE ID no. 546001_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 219

Met Thr Thr Thr Leu Glu Arg Gly Phe Ser Glu Glu Gln Glu Ala Leu
1               5                   10                  15

Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
        35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met
65                  70                  75

<210> SEQ ID NO 220
<211> LENGTH: 76
<212> TYPE: PRT
<213> ORGANISM: Artificial Sequence
<220> FEATURE:
<223> OTHER INFORMATION: Truncated version of Ceres CLONE ID no. 651581
<220> FEATURE:
<221> NAME/KEY: misc_feature
<223> OTHER INFORMATION: Ceres CLONE ID no. 651581_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 220

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Asp Leu Gly
            20                  25                  30

Leu Lys Leu Phe Ile Lys Ile Phe Glu Ile Ala Pro Thr Ala Lys Lys
        35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75
```

-continued

```
<210> SEQ ID NO 221
<211> LENGTH: 77
<212> TYPE: PRT
<213> ORGANISM: Artificial Sequence
<220> FEATURE:
<223> OTHER INFORMATION: Truncated version of Ceres CLONE ID no. 839727
<220> FEATURE:
<221> NAME/KEY: misc_feature
<223> OTHER INFORMATION: Ceres CLONE ID no. 839727_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 221

Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
            20                  25                  30

Gly Leu Arg Phe Phe Leu Lys Ile Phe Glu Ile Ala Pro Ser Ala Arg
        35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met
65                  70                  75

<210> SEQ ID NO 222
<211> LENGTH: 76
<212> TYPE: PRT
<213> ORGANISM: Artificial Sequence
<220> FEATURE:
<223> OTHER INFORMATION: Truncated version of Public GI ID no. 11095158
<220> FEATURE:
<221> NAME/KEY: misc_feature
<223> OTHER INFORMATION: Public GI ID no. 11095158_T
<220> FEATURE:
<221> NAME/KEY: misc_feature
<222> LOCATION: (13)..(76)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 222

Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
            20                  25                  30

Leu Lys Leu Phe Leu Lys Ile Phe Glu Ile Ala Pro Ser Ala Gln Lys
        35                  40                  45

Leu Phe Ser Phe Leu Lys Asp Ser Lys Val Pro Leu Glu Gln Asn Thr
    50                  55                  60

Lys Leu Lys Pro His Ala Met Ser Val Phe Leu Met
65                  70                  75

<210> SEQ ID NO 223
<211> LENGTH: 71
<212> TYPE: PRT
<213> ORGANISM: Artificial Sequence
<220> FEATURE:
```

<223> OTHER INFORMATION: Truncated version of Public GI ID no. 12963875
<220> FEATURE:
<221> NAME/KEY: misc_feature
<223> OTHER INFORMATION: Public GI ID no. 12963875_T
<220> FEATURE:
<221> NAME/KEY: misc_feature
<222> LOCATION: (8)..(69)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 223

Met Ser Ser Phe Ser Glu Glu Gln Glu Ala Leu Val Val Lys Ser Trp
1               5                   10                  15

Gly Ser Met Lys Lys Asp Ala Gly Glu Trp Gly Leu Lys Phe Phe Leu
            20                  25                  30

Lys Ile Phe Glu Ile Ala Pro Ser Ala Lys Lys Met Phe Ser Phe Leu
        35                  40                  45

Lys Asp Ser Asn Val Pro Leu Asp Gln Asn Pro Lys Leu Lys Ile His
    50                  55                  60

Ala Lys Ser Val Leu Val Met
65                  70

<210> SEQ ID NO 224
<211> LENGTH: 84
<212> TYPE: PRT
<213> ORGANISM: Artificial Sequence
<220> FEATURE:
<223> OTHER INFORMATION: Truncated version of Public GI ID no. 14701800
<220> FEATURE:
<221> NAME/KEY: misc_feature
<223> OTHER INFORMATION: Public GI ID no. 14701800_T
<220> FEATURE:
<221> NAME/KEY: misc_feature
<222> LOCATION: (21)..(82)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 224

Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met
            20                  25                  30

Lys Lys Asp Ser Ala Asn Ile Gly Leu Arg Phe Phe Leu Lys Ile Phe
        35                  40                  45

Glu Val Ala Pro Ser Ala Ser Gln Met Phe Ser Phe Leu Arg Asn Ser
    50                  55                  60

Asp Val Pro Leu Glu Lys Asn Pro Lys Leu Lys Thr His Ala Met Ser
65                  70                  75                  80

Val Phe Val Met

<210> SEQ ID NO 225
<211> LENGTH: 76
<212> TYPE: PRT
<213> ORGANISM: Artificial Sequence
<220> FEATURE:
<223> OTHER INFORMATION: Truncated version of Public GI ID no. 15226675
<220> FEATURE:
<221> NAME/KEY: misc_feature -continued

```
<223> OTHER INFORMATION: Public GI ID no. 15226675_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 225

Met Glu Ser Glu Gly Lys Ile Val Phe Thr Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75

<210> SEQ ID NO 226
<211> LENGTH: 76
<212> TYPE: PRT
<213> ORGANISM: Artificial Sequence
<220> FEATURE:
<223> OTHER INFORMATION: Truncated version of Public GI ID no. 15824736
<220> FEATURE:
<221> NAME/KEY: misc_feature
<223> OTHER INFORMATION: Public GI ID no. 15824736_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 226

Met Ala Thr Tyr Glu Gly Lys Val Phe Thr Glu Gln Glu Ala Leu
1               5                   10                  15

Val Val Lys Ser Trp Thr Val Met Lys Lys Lys Thr Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75

<210> SEQ ID NO 227
<211> LENGTH: 76
<212> TYPE: PRT
<213> ORGANISM: Artificial Sequence
<220> FEATURE:
<223> OTHER INFORMATION: Truncated version of Public GI ID no. 30909306
<220> FEATURE:
<221> NAME/KEY: misc_feature
<223> OTHER INFORMATION: Public GI ID no. 30909306_T
<220> FEATURE:
<221> NAME/KEY: misc_feature
<222> LOCATION: (13)..(74)
<223> OTHER INFORMATION: Pfam Name: Globin
```

```
        Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 227

Met Glu Ser Glu Gly Lys Ile Val Phe Thr Glu Glu Gln Glu Ala Leu
1               5                  10                  15

Val Val Lys Ser Trp Ser Val Met Lys Lys Asn Ser Ala Asp Leu Gly
            20                  25                  30

Leu Lys Leu Phe Ile Lys Ile Phe Glu Ile Ala Pro Thr Ala Lys Lys
        35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75

<210> SEQ ID NO 228
<211> LENGTH: 73
<212> TYPE: PRT
<213> ORGANISM: Artificial Sequence
<220> FEATURE:
<223> OTHER INFORMATION: Truncated version of Public GI ID no. 37903656
<220> FEATURE:
<221> NAME/KEY: misc_feature
<223> OTHER INFORMATION: Public GI ID no. 37903656_T
<220> FEATURE:
<221> NAME/KEY: misc_feature
<222> LOCATION: (10)..(71)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 228

Met Glu Gly Lys Val Phe Thr Glu Glu Gln Thr Leu Val Val Lys
1               5                  10                  15

Ser Trp Gly Val Met Lys Lys Asn Ala Ala Glu Leu Gly Leu Lys Phe
            20                  25                  30

Phe Leu Lys Ile Phe Glu Ile Ala Pro Ser Ala Gln Lys Leu Phe Ser
        35                  40                  45

Phe Leu Arg Asp Ser Asp Ile Pro Leu Glu Lys Asn Pro Lys Leu Lys
    50                  55                  60

Pro His Ala Met Ser Val Phe Val Met
65                  70

<210> SEQ ID NO 229
<211> LENGTH: 76
<212> TYPE: PRT
<213> ORGANISM: Artificial Sequence
<220> FEATURE:
<223> OTHER INFORMATION: Truncated version of Public GI ID no. 62548111
<220> FEATURE:
<221> NAME/KEY: misc_feature
<223> OTHER INFORMATION: Public GI ID no. 62548111_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

```
<400> SEQUENCE: 229

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75
```